US008710191B2

(12) United States Patent
Gladue et al.

(10) Patent No.: US 8,710,191 B2
(45) Date of Patent: Apr. 29, 2014

(54) ANTIBODIES TO CCR2

(75) Inventors: Ronald P. Gladue, Stonington, CT (US); Bradley T. Keller, Chesterfield, MO (US); Shinji Ogawa, Chesterfield, MO (US); Arvind Rajpal, San Francisco, CA (US); Laurie A. Tylaska, Preston, CT (US); Shelley Sims Belouski, Camarillo, CA (US); Larry L. Green, San Francisco, CA (US); Meina Liang, Fremont, CA (US)

(73) Assignees: Pfizer Inc., New York, NY (US); Amgen Fremont Inc., Thousand Oaks, CA (US)

( * ) Notice: Subject to any disclaimer, the term of this patent is extended or adjusted under 35 U.S.C. 154(b) by 255 days.

(21) Appl. No.: 13/059,702

(22) PCT Filed: Aug. 17, 2009

(86) PCT No.: PCT/US2009/004711
§ 371 (c)(1),
(2), (4) Date: Jul. 26, 2011

(87) PCT Pub. No.: WO2010/021697
PCT Pub. Date: Feb. 25, 2010

(65) Prior Publication Data
US 2011/0274696 A1 Nov. 10, 2011

Related U.S. Application Data

(60) Provisional application No. 61/189,357, filed on Aug. 18, 2008.

(51) Int. Cl.
*C07K 16/28* (2006.01)
*C07K 16/00* (2006.01)

(52) U.S. Cl.
USPC .............. 530/388.22; 530/388.15; 530/388.1; 530/387.1

(58) Field of Classification Search
None
See application file for complete search history.

(56) References Cited

U.S. PATENT DOCUMENTS

| | | | |
|---|---|---|---|
| 5,545,806 | A | 8/1996 | Lonberg et al. |
| 5,545,807 | A | 8/1996 | Surani et al. |
| 5,569,825 | A | 10/1996 | Lonberg et al. |
| 5,591,669 | A | 1/1997 | Krimpenfort et al. |
| 5,612,205 | A | 3/1997 | Kay et al. |
| 5,625,126 | A | 4/1997 | Lonberg et al. |
| 5,633,425 | A | 5/1997 | Lonberg et al. |
| 5,643,763 | A | 7/1997 | Dunn et al. |
| 5,661,016 | A | 8/1997 | Lonberg et al. |
| 5,721,367 | A | 2/1998 | Kay et al. |
| 5,770,429 | A | 6/1998 | Lonberg et al. |
| 5,789,215 | A | 8/1998 | Berns et al. |
| 5,789,650 | A | 8/1998 | Lonberg et al. |
| 5,814,318 | A | 9/1998 | Lonberg et al. |
| 5,916,771 | A | 6/1999 | Hori et al. |
| 5,939,598 | A | 8/1999 | Kucherlapati et al. |
| 5,985,615 | A | 11/1999 | Jakobovits et al. |
| 5,994,619 | A | 11/1999 | Stice et al. |
| 5,998,209 | A | 12/1999 | Jokobovits et al. |
| 6,075,181 | A | 6/2000 | Kucherlapati et al. |
| 6,091,001 | A | 7/2000 | Jakobovits et al. |
| 6,114,598 | A | 9/2000 | Kucherlapati et al. |
| 6,130,364 | A | 10/2000 | Jakobovits et al. |
| 6,150,584 | A | 11/2000 | Kucherlapati et al. |
| 6,162,963 | A | 12/2000 | Kucherlapati et al. |
| 7,202,343 | B2 | 4/2007 | Gudas et al. |
| 2004/0047860 | A1 | 3/2004 | Hiestand et al. |
| 2005/0025768 | A1 | 2/2005 | De Fougerolles et al. |
| 2006/0039913 | A1 | 2/2006 | Das et al. |
| 2006/0246069 | A1 | 11/2006 | Sugimura |

FOREIGN PATENT DOCUMENTS

| | | |
|---|---|---|
| WO | WO91/10741 | 7/1991 |
| WO | WO94/02602 | 2/1994 |
| WO | WO96/33735 | 10/1996 |
| WO | WO96/34096 | 10/1996 |
| WO | WO97/31949 | 9/1997 |
| WO | WO98/16654 | 4/1998 |
| WO | WO98/24893 | 6/1998 |
| WO | WO98/50433 | 11/1998 |
| WO | WO99/45031 | 9/1999 |
| WO | WO99/53049 | 10/1999 |
| WO | WO00/05265 | 2/2000 |
| WO | WO00/09560 | 2/2000 |
| WO | WO00/37504 | 6/2000 |
| WO | WO03/066830 | 8/2003 |
| WO | WO2006/013427 | 2/2006 |

OTHER PUBLICATIONS

Green (JIM 1999 231:11-23).*
Rudikoff et al. (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*

(Continued)

*Primary Examiner* — Sharon Wen
(74) *Attorney, Agent, or Firm* — Ropes & Gray LLP

(57) ABSTRACT

Provided are antibodies including human antibodies and antigen-binding portions thereof that specifically bind to CCR2, specifically human CCR2, and that may function to inhibit CCR2. Anti-CCR2 antibodies include those which bind to the first and/or second extracellular loops of CCR2. Also provided are human anti-CCR2 antibodies and antigen-binding portions thereof. Isolated heavy and light chain immunoglobulins derived from human anti-CCR2 antibodies and nucleic acid molecules encoding such immunoglobulins are provided. Methods of making human anti-CCR2 antibodies or antigen-binding portions, compositions comprising these antibodies or antigen-binding portions, methods of using the antibodies and antigen-binding portions, and compositions for diagnosis and treatment are provided. Also provided are gene therapy methods using nucleic acid molecules encoding the heavy and/or light immunoglobulin molecules that comprise the human anti-CCR2 antibodies or antigen binding portions thereof.

11 Claims, 22 Drawing Sheets

(56) References Cited

OTHER PUBLICATIONS

Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Abbadie et al., Impaired neuropathic pain responses in mice lacking the chemokine receptor CCR2, Proc. Natl. Acad. Sci. USA 100(13):7947-7952 (2003).
Ahad et al., Polymorphisms of chemokine and chemokine receptor genes in idiopathic immune-mediated posterior segment uveitis, Mol. Vis. 13:388-396 (2007).
Andjelkovic et al., Functional expression of CCR2 by human fetal astrocytes, J. Neurosci. Res. 70(2):219-31 (2002).
Babcook et al., A novel strategy for generating monoclonal antibodies from single, isolated lymphocytes producing antibodies of defined specificities, Proc. Natl. Acad. Sci. USA 93:7843-7848 (1996).
Baggiolini et al., Interleukin-8 and related chemotactic cytokines—CXC and CC chemokines, Adv. Imunol. 55:97-179 (1994).
Boring et al., Impaired monocyte migration and reduced type 1 (Th1) cytokine responses in C-C chemokine receptor 2 knockout mice, J. Clin Invest. 100(10):2552-2561 (1997).
Boring et al., Decreased lesion formation in CCR2-/- mice reveals a role for chemokines in the initiation of atherosclerosis, Nature 394(6696):894-897 (1998).
Bracke et al., CC-chemokine receptors in chronic obstructive pulmonary disease, Inflammation & Allergy—Drug Targets 6:75-79 (2007).
Charo et al., Molecular cloning and functional expression of two monocyte chemoattractant protein 1 receptors reveals alternative splicing of the carboxyl-terminal tails, Proc. Natl. Acad. Sci. USA 91:2752-2756 (1994).
Chung, Inflammatory mediators in chronic obstructive pulmonary disease, Current Drug Targets—Inflammation & Allergy 4(6):619-625 (2005).
Coelho et al., The influence of chemokine receptor CCR2 genotypes in the route to cervical carcinogenesis, Gyn. Obstet. Inv. 64(4):208-212 (2007).
Coelho et al., Protective role of the polymorphism CCR2-64I in the progression from squamous intraepithelial lesions to invasive cervical carcinoma, Gyn. Onc. 96:760-764 (2005).
Connor et al., Change in coreceptor use correlates with disease progression in HIV-1—infected individuals, J. Exp. Med. 185(4):621-628 (1997).
Dawson et al., Targeting monocyte chemoattractant protein-1 signalling in disease, Exp. Opin. Ther. Targets 7(1):35-48 (2003).
De Paolo et al., CC chemokine ligand 2 and its receptor regulate mucosal production of IL-12 and TGF-beta in high dose oral tolerance J. Immunol. 171(7):3560-3567 (2003).
Flory et al., Pulmonary granuloma formation in the rat is partially dependent on monocyte chemoattractant protein 1, Lab. Invest. 69:396-404 (1993).
Frade et al., Characterization of the CCR2 chemokine receptor: functional CCR2 receptor expression in B cells, J. Immunology 159(11):5576-5584 (1997).
Frade et al., The amino-terminal domain of the CCR2 chemokine receptor acts as coreceptor for HIV-1 infection, J. Clin. Invest. 100(3):497-502 (1997).
Furukawa et al., Anti-monocyte chemoattractant protein-1/monocyte chemotactic and activating factor antibody inhibits neointimal hyperplasia in injured rat carotid arteries, Circ. Res. 84(3):306-314 (1999).
Garcia-Vicuna et al., CC and CXC chemokine receptors mediate migration, proliferation, and matrix metalloproteinase production by fibroblast-like synoviocytes from rheumatoid arthritis patients, Arthritis Rheum.; 50(12):3866-3877) (2004).
Garcia-Zepeda et al., Human monocyte chemoattractant protein (MCP)-4 is a novel CC chemokine with activities on monocytes, eosinophils, and basophils induced in allergic and nonallergic inflammation that signals through the CC chemokine receptors (CCR)-2 and -3, J. Immunol. 157(12):5613-5626 (1996).
Gaupp et al., Experimental autoimmune encephalomyelitis (EAE) in CCR2(-/-) mice: susceptibility in multiple strains, Am. J. Pathol. 162(1):139-150(2003).
Gavrilin et al., Site-directed mutagenesis of CCR2 identified amino acid residues in transmembrane helices 1, 2, and 7 important for MCP-1 binding and biological functions, Biochem Biophys Res Commun. 327(2):533-40 (2005).
Gong et al., Monocyte chemotactic protein-2 (MCP-2) uses CCR1 and CCR2B as its functional receptors, J. Biol. Chem. 272(18):11682-11685 (1997).
Gong et al., An antagonist of monocyte chemoattractant protein 1 (MCP-1) inhibits arthritis in the MRL-Ipr mouse model, J. Exp. Med. 186(1):131-137 (1997).
Green and Jakobovits, Regulation of B cell development by variable gene complexity in mice reconstituted with human immunoglobulin yeast artificial chromosomes, J. Exp. Med. 188(3):483-495 (1998).
Green et al., Antigen-specific human monoclonal antibodies from mice engineered with human Ig heavy and light chain YACs, Nature Genetics 7(1):13-21 (1994).
Griffiths et al., Human anti-self antibodies with high specificity from phage display libraries, EMBO J. 12:725-734 (1993).
Griffiths et al., Isolation of high affinity human antibodies directly from large synthetic repertoires, EMBO J. 13(14):3245-3260 (1994).
Guo et al., Transplantation of monocyte CC-chemokine receptor 2-deficient bone marrow into ApoE3-Leiden mice inhibits atherogenesis, Arterioscler. Thromb. Vasc. Biol. 23(3):447-53 (2003).
Han et al. Expression of the monocyte chemoattractant protein-1 receptor CCR2 is increased in hypercholesterolemia. Differential effects of plasma lipoproteins on monocyte function, J. Lipid Res. 40:1053-1063 (1999).
Han et al., Role of the first extracellular loop in the functional activation of CCR2: The first extracellular loop contains distinct domains necessary for both agonist binding and transmembrane signaling, J. Biol. Chem. 274(45):32055-32062 (1999).
Hosaka et al., Expression of the chemokine superfamily in rheumatoid arthritis, Clin. Exp. Immunol. 97(3):451-457 (1994).
Huang et al., CCL2/CCR2 pathway mediates recruitment of myeloid suppressor cells to cancers, Cancer Lett. 252(1):86-92 (2007).
Jain et al., Engineering antibodies for clinical applications, Trends in Bio. 25(7):307-316 (2007).
Jimenez-Sainz et al., Signaling Pathways for Monocyte Chemoattractant Protein 1-Mediated Extracellular Signal-Regulated Kinase Activation, Mol. Pharmacol. 64(3):773-82 (2003).
Koch et al., Enhanced production of monocyte chemoattractant protein-1 in rheumatoid arthritis, J. Clin. Invest. 90(3):772-779 (1992).
Koga et al., Mutant MCP-1 therapy inhibits tumor angiogenesis and growth of malignant melanoma in mice, Biochem. Biophys. Res. Comm. 365:279-284 (2008).
Loberg, Targeting CCL2 with systemic delivery of neutralizing antibodies induces prostate cancer tumor regression in vivo, Cancer Res. 67(19):9417-9424 (2007).
Lon Berg et al., Fully human antibodies from transgenic mouse and phage display platforms, Curr. Op. Immun. 20(4):450-459 (2008).
Lu et al., CCR2 expression correlates with prostate cancer progression, J. Cell. Biochem 101(3):676-685 (2007).
Lu et al., Monocyte chemotactic protein-1 (MCP-1) acts as a paracrine and autocrine factor for prostate cancer growth and invasion, The Prostate 66(12):1311-1318 (2006).
Mellado et al., Chemokine receptor 2 blockade prevents asthma in a cynomolgus monkey model, J. Pharm. Exp. Ther. 324(2):769-775 (2008).
Mendez et al., Functional transplant of megabase human immunoglobulin loci recapitulates human antibody response in mice, Nature Genetics 15:146-156 (1997).
Miller and Krangel, Biology and biochemistry of the chemokines: a family of chemotactic and inflammatory cytokines, Crit. Rev. Immunol. 12:17-46 (1992).
Monteclaro et al., Molecular approaches to identifying ligand binding and signaling domains of C-C chemokine receptors, Meth. Enzy. 228:70-84 (1997).

(56) References Cited

OTHER PUBLICATIONS

Moore et al., Protection from Pulmonary Fibrosis in the Absence of CCR2 Signaling, J. Immunol. 167:4368-4377(2001).

Myers et al., Signal transduction and ligand specificity of the human monocyte chemoattractant protein-1 receptor in transfected embryonic kidney cells, J. Biol. Chem. 270(11):5786-5792 (1995).

Nissim et al., Antibody fragments from a 'single pot' phage display library as immunochemical reagents, EMBO J. 13:692-698 (ibid EMBO J. 13:3245) (1994).

Ogilvie et al., Eotaxin is a natural antagonist for CCR2 and an agonist for CCR5, Blood 97(7):1920-1924 (2001).

Oppenheim et al., Properties of the novel proinflammatory supergene "intercrine" cytokine family, Annu. Rev. Immunol. 9:617-648 (1991).

Rodriguez-Frade et al., CCR2, [Online] 2000, DOI: 10.1006/ rwcy. 2000.22002 Retrieved from the Internet: URL:http:// apresslp.gypi.net/apcyto/ Ipext.dll? f=objects&fn=c22002.pdf [retrieved on Dec. 2, 2009].

Saitoh et al., Viral envelope protein gp64 transgenic mouse facilitates the generation of monoclonal antibodies against exogenous membrane proteins displayed on baculovirus, J. Imm. Meth. 322(1-2)04-117 (2007).

Salcedo et al., Human endothelial cells express CCR2 and respond to MCP-1: direct role of MCP-1 in angiogenesis and tumor progression, Blood 96(1):34-40 (2000).

Schimmer et al., Streptococcal cell wall-induced arthritis: requirements for IL-4, IL-10, IFN-gamma, and monocyte chemoattractant protein-1, J. Immunol. 160:1466-1471 (1998).

Schwartz et al., A modern view of atherogenesis, Am. J. Cardiol. 71(6):9B-14B (1993).

Seki et al., CCR2 promotes hepatic fibrosis in mice, Hepatology 50(1):185-197 (2009).

Tsui et al., Generation, characterization and biological activity of CCL2 (MCP-1/JE) and CCL12 (MCP-5) specific antibodies, Human Antibodies 16(3-4):117-125 (2007).

Tsutsumi et al., The critical role of ocular-infiltrating macrophages in the development of choroidal neovascularization, J. Leuk. Biol. 74:25-32 (2003.

Vielhauer et al., Obstructive nephropathy in the mouse: progressive fibrosis correlates with tubulointerstitial chemokine expression and accumulation of CC chemokine receptor 2- and 5-positive leukocytes, J. Am. Soc. Nephrol. 12:1173-1187 (2001).

Widera et al., MCP-1 induces migration of adult neural stem cells, Eur. J. Cell. Biol. 83(8): 381-387(2004).

Wong et al., Organization and differential expression of the human monocyte chemoattractant protein 1 receptor gene. Evidence for the role of the carboxyl-terminal tail in receptor trafficking, J. Biol. Chem. 272:1038-1045 (1997).

Xue et al., A critical role for CCL2 and CCL3 chemokines in the regulation of polymorphonuclear neutrophils recruitment during corneal infection in mice, Imm. Cell Biol. 85:525-531 (2007).

Yang et al., Attenuated liver tumor formation in the absence of CCR2 with a concomitant reduction in the accumulation of hepatic stellate cells, macrophages and neovascularization, Int. J. Cancer 118:335-345 (2006).

Yeo et al., Chemokine gene polymorphisms in idiopathic anterior uveitis, Cytokine 35(1-2):29-35 (2006).

Zafiropoulos et al., Significant involvement of CCR2-64I and CXCL12-3a in the development of sporadic breast cancer, J. Med. Genet. 41:e59 (2009).

Feria and Diaz-Gonzalez, The CCR2 receptor as a therapeutic target, Expert Opin. Ther. Patents 16(1)49-57 (2006).

\* cited by examiner

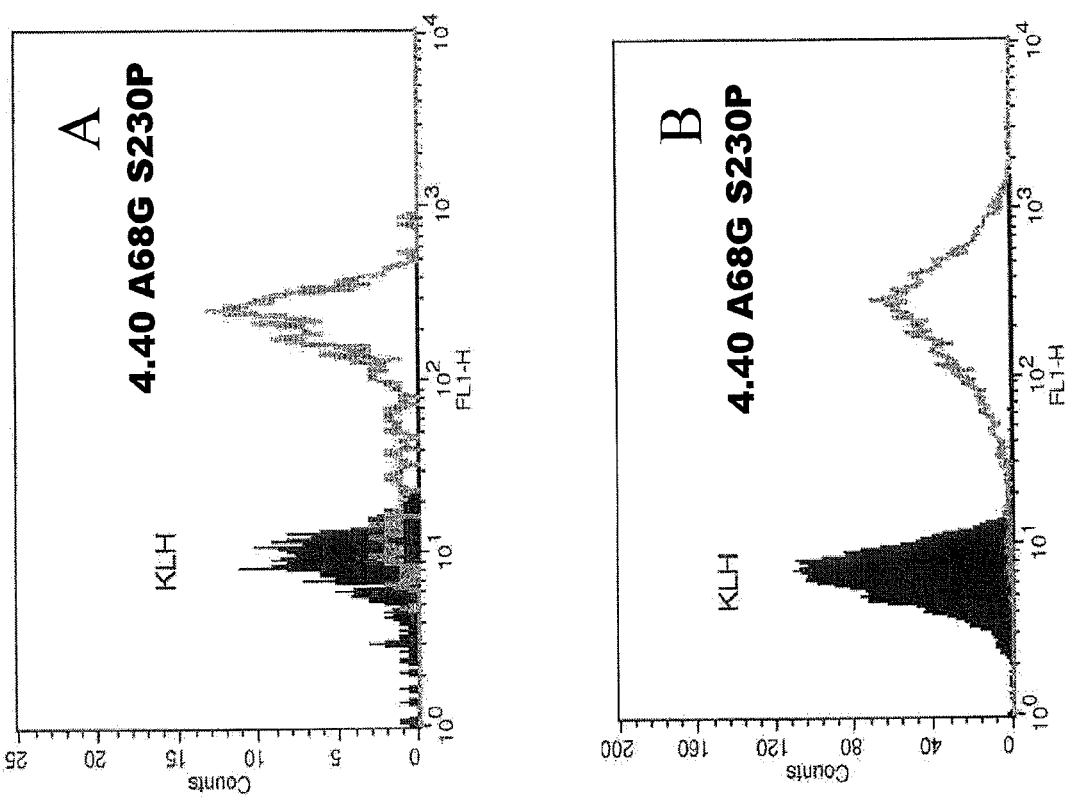

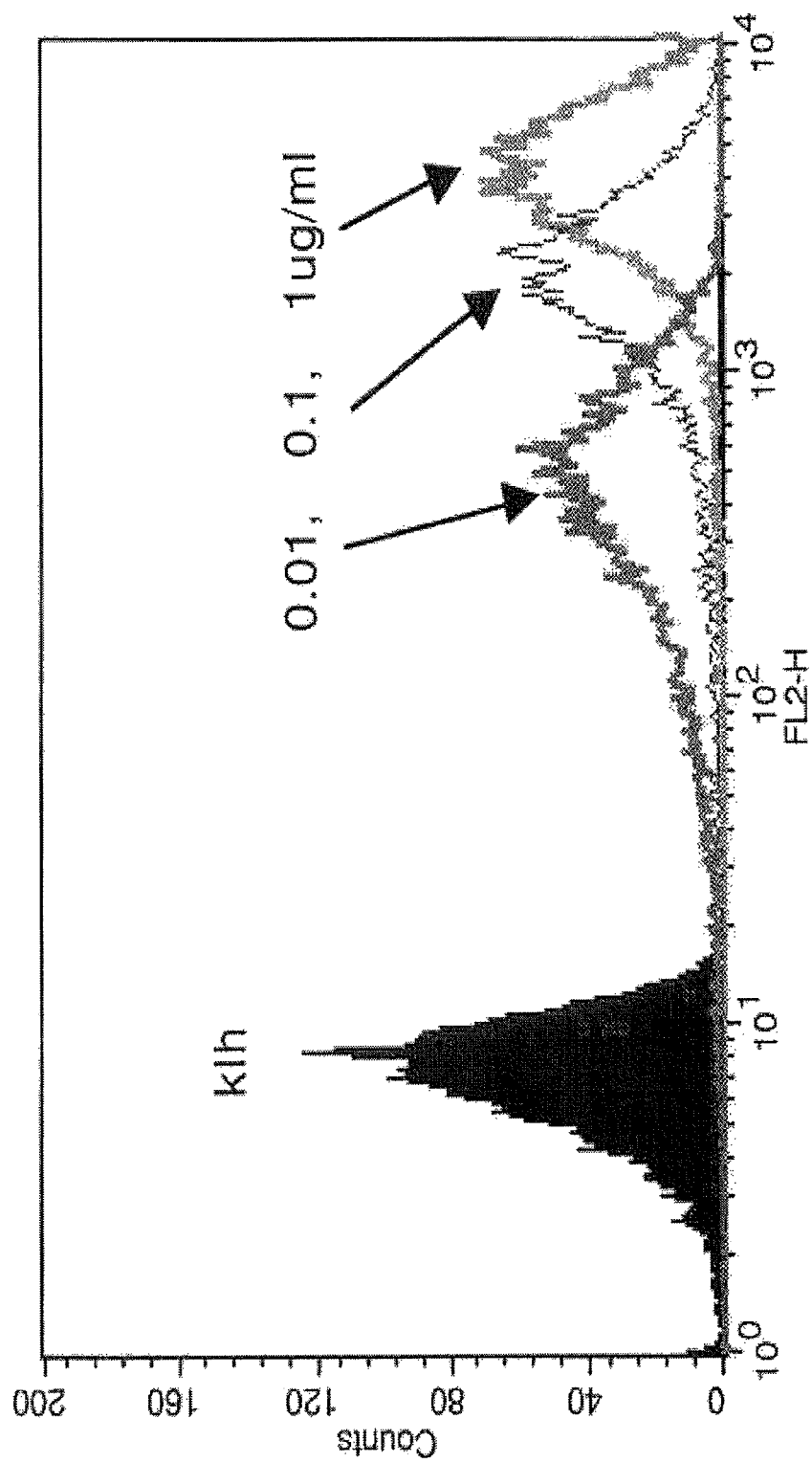

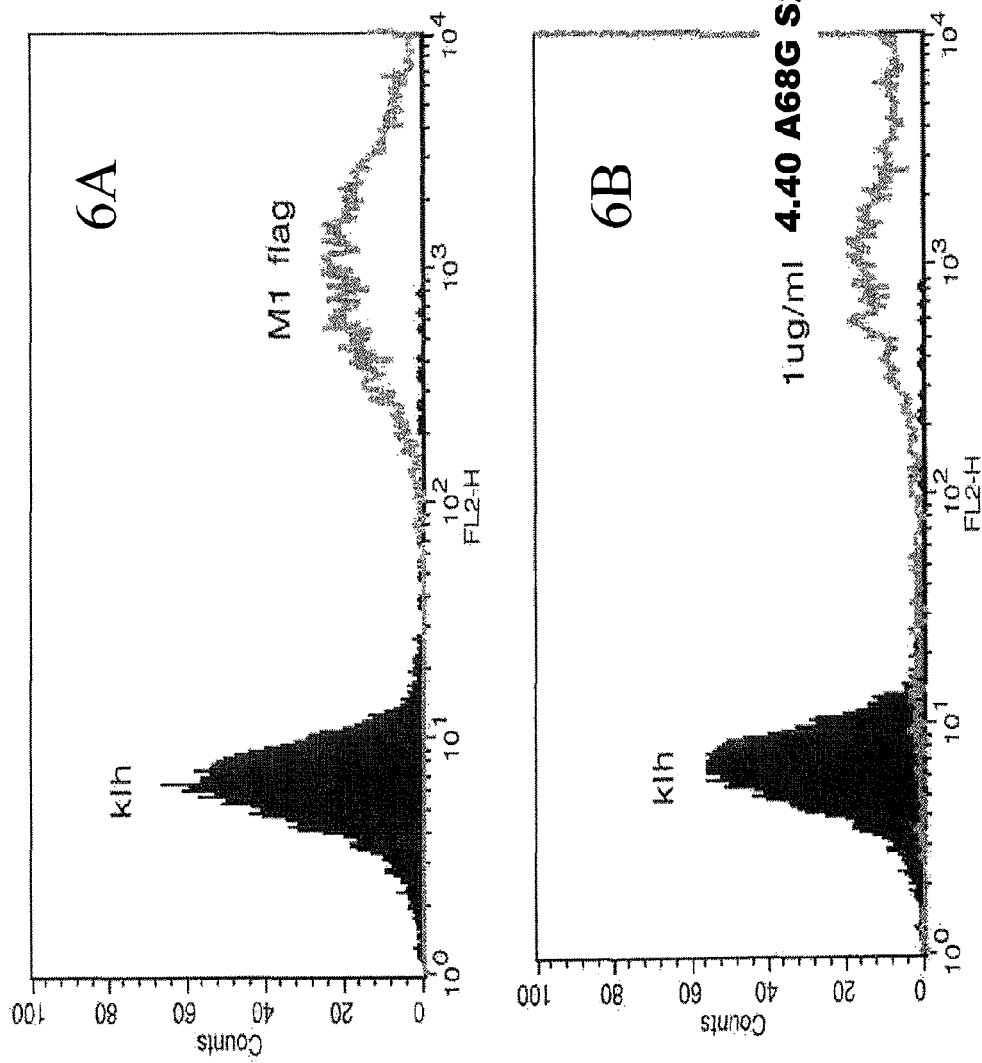
Figure 6A & B

Figure 17a

```
VH
Germline   QVQLVQSGAEVKKPGASVKVSCKASGYTFTSYYMHWVRQAPGQGLEWMGIINPSGGSTSYAQKFQG
4.22.3     ----------------------------------------I-----------M------T-----

Germline   RVTMTRDTSTSTVYMELSSLRSEDTAVYYCARE##YNWNY#AFDIWGQGTMVTVSS  SEQ ID NO:158
4.22.3     ---L-----------D----------------RW-K--FDV--------------

VL
Germline   DVVMTQSPLSLPVTLGQPASISCRSSQSLVYSDGNTYLNWFQQRPGQSPRRLIYKVSNWDS
4.22.3     -------------------------------P----------------L--------A Germline   GVPDRFSGSGSGTDFTLKISRVEAEDVGVYYCMQGTHWPITFGQGTRLEIK  SEQ ID NO:159
4.22.3     -------------------------------F---###-GRS---V-----
```

```
Germline   QVQLVESGGGVVQPGRSLRLSCAASGFTFSSYGMHWVRQAPGKGLEWVAVISYDGSNKYYADSVKG
4.40.2     ------------------------------------------L----K---------------

Germline   RFTISRDNSKNTLYLQMNSLRAEDTAVYYCAR##YNWNY##AFDIWGQGTMVTVSS  SEQ ID NO:160
4.40.2     --------------------------------DQAYWT-FD-------------
```

V_L

```
Germline   EIVLTQSPDFQSVTPKEKVTITCRASQSIGSSLHWYQQKPDQSPKLLIKYASQSFS
4.40.2     -------------------------------------------------------

Germline   GVPSRFSGSGSGTDFTLTINSLEAEDAATYYCHQSSSLPLTFGGGTKVEIK  SEQ ID NO:161
4.40.2     --------A-----------------------------------------
```

| | | |
|---|---|---|
| Germline | QVQLVESGGGVVQPGRSLRLSCAASGFTFSYGMHWVRQAPGKGLEWVAVISYDGSNKYYADSVKG | |
| 4.9.2 | ------------------------------------------------------GT---R---- | |
| Germline | RFTISRDNSKNTLYLQMNSLRAEDTAVYYCAR##YNWNY##AFDIWGQGTMVTVSS | SEQ ID NO:162 |
| 4.9.2 | -------K-------R---------DQAY-K-FD----- | |

V_L

| | | |
|---|---|---|
| Germline | DIQMTQSPSSLSASVGDRVTITCRASQSISSYLNWYQQKPGKAPKLLIYAASSLQS | |
| 4.9.2 | ----------------T--------------------------------------- | |
| Germline | GVPSRFSGSGSGTDFTLTISSLQPEDFATYYCQQSYSTPYTFGQGTKLEIK | SEQ ID NO:163 |
| 4.9.2 | ----------------------------NS-CS------- | |

```
Germline  QVQLVQSGAEVKKPGASVKVSCKASGYTFTSYYMHWVRQAPGQGLEWMGIINPSGGSTSYAQKFQG
4.39.3    ---------------------------------------I-----------M-----P------

Germline  RVTMTRDTSTSTVYMELSSLRSEDTAVYYCAR###YNWNY#AFDIWGQGTMVTVSS  SEQ ID NO:164
4.39.3    ----------D--------------F----ERW-K--FD----------------
```

V_L

```
Germline  DIVMTQSPDSLAVSLGERATINCKSSQSVLYSSNNKNYLAWYQQKPGQPPKLLIYWASTRES
4.39.3    ------------------------------------------------------------

Germline  GVPDRFSGSGSGTDFTLTISSLQAEDVAVYYCQQYYSTPWTFGQGTKVEIK  SEQ ID NO:165
4.39.3    --------------------------Q----------R------------
```

ANTIBODIES TO CCR2

CROSS-REFERENCE TO RELATED PATENTS AND PATENT APPLICATIONS

This application is a national stage filing under 35 U.S.C. 371 of International Application PCT/US2009/004711, filed Aug. 17, 2009, which claims the benefit of U.S. Provisional Patent Application No. 61/189,357, filed Aug. 18, 2008, the specifications of which are incorporated by reference herein in their entireties. International Application PCT/US2009/004711 was published under PCT Article 21(2) in English.

SEQUENCE LISTING

The instant application contains a Sequence Listing which has been submitted in ASCII format via EFS-Web and is hereby incorporated by reference in its entirety. Said ASCII copy, created on Jul. 26, 2011, is named "000659-0063-301_Sequence_Listing" and is 143,360 bytes in size.

JOINT RESEARCH AGREEMENT

The disclosure and claims herein were made as a result of activities undertaken within the scope of a joint research agreement between Pfizer Inc. and Abgenix Inc. that was in effect on or before the date the claimed subject matter was made.

BACKGROUND

Leukocyte infiltration into inflammatory sites is believed to be regulated by 8-10 kD proteins known as chemokines. These chemokines are classified into four groups, depending on the spacing of their N-terminal cysteine residues, designated CC, CXC, XC and CX3C. Chemokines can mediate a range of proinflammatory effects on leukocytes, such as triggering of chemotaxis, degranulation, synthesis of lipid mediators, and integrin activation (Oppenheim, J. J. et al., *Annu. Rev. Immunol.*, 9:617-648 (1991); Baggiolini, M., et al., *Adv. Imunol.*, 55:97-179 (1994); Miller, M. D. and Krangel, M. S., *Crit. Rev. Immunol.*, 12:17-46 (1992)).

One chemokine, Monocyte Chemotactic Protein 1 (MCP-1), also known as CCL2, acts upon monocytes, lymphocytes and dendritic cells, to induce chemotaxis, granule release, respiratory burst and cytokine release. Studies have suggested that MCP-1 is implicated in the pathology of diseases such as rheumatoid arthritis, atherosclerosis, granulomatous diseases, chronic obstructive pulmonary disease (COPD), obesity/diabetes, neuropathic pain, cancer, and multiple sclerosis (Koch, *J. Clin. Invest.* 90:772-79 (1992); Hosaka et al., *Clin. Exp. Immunol.* 97:451-457 (1994); Schwartz et al., *Am. J. Cardiol.* 71(6):9B-14B (1993); Schimmer et al., *J. Immunol.* 160:1466-1471 (1998); Flory et al., *Lab. Invest.* 69:396-404 (1993); Gong et al., *J. Exp. Med.* 186:131-137 (1997); Salcedo et al. *Blood* 96(1) 34-40 (2000); Bracke et al., *Inflammation & Allergy—Drug Targets* 6: 75-79 (2007); Chung Current Drug Targets—*Inflammation & Allergy* 4: 619-625 (2005).

CCR2 is a seven-transmembrane domain G-protein coupled chemotactic receptor which binds MCP-1 as well as other chemokines including CCL8 (MCP-2), CCL7 (MCP-3) and CCL13 (MCP-4) (Charo, I. F., et al., *Proc. Natl. Acad. Sci. USA* 91:2752-2756 (1994); Myers, S. J., et al., *J. Biol. Chem.* 270:5786-5792 (1995); Gong et al., *J. Biol Chem* 272:11682-11685 (1997); Garcia-Zepeda et al., *J. Immunol.* 157:5613-5626 (1996)). CCR2 is also known as CMKBR2 and CKR2. Two alternatively-spliced forms of the CCR2, CCR2A and CCR2B, have been cloned which differ in their C-termini (Wong et al (1997) *J. Biol. Chem.* 272:1038-1045). In signaling studies, both CCR2A and CCR2B mediate agonist-dependent calcium mobilization and adenylyl cyclase inhibition. CCR2 is expressed on monocytes, T cells, and dendritic cells, and interacts with chemokines secreted by endothelial cells, monocytes, and synovial fibroblasts.

The biological role of CCR2 has been probed through the use of CCR2 knockout mice (Boring et al., *J Clin Invest.* 100(10):2552-61 (1997); Boring et al., *Nature* 394(6696): 894-7 (1998); De Paolo et al., *J Immunol.* 171(7):3560-7 (2003); Gaupp et al., *Am J Pathol.* 162(1):139-50 (2003)). CCR2-/- mice have significant defects in both delayed-type hypersensitivity responses and production of Th1-type cytokines, and are generally less susceptible to developing experimental autoimmune encephalomyelitis (EAE). In addition to modulating immune responses, CCR2 is a co-receptor for HIV (Connor et al., *J. Exp. Med.* 185:621-628 (1997); Frade et al., *J Clin Invest.* 100(3):497-502 (1997)).

Due to the involvement of MCP-1 and its receptor CCR2 in undesirable immune responses, CCR2 antagonists may be promising therapeutic agents. However, few CCR2 antagonists have been described (see Ogilvie et al., *Blood* 97(7): 1920-4 (2001)). Thus, there is a need for novel and improved compositions that will bind CCR2 and block CCR2 signaling mediated by its ligand.

SUMMARY

Provided are isolated antibodies, or antigen-binding portions thereof, that specifically bind CCR2, particularly human CCR2, and may act as a CCR2 antagonist, and compositions comprising said antibodies or portions. Included are antibodies or antigen-binding portions that bind to CCR2 at an epitope other than the N-terminal portion or the third loop of CCR2. Such antibodies may bind to the first and/or second extracellular loops of CCR2.

Compositions comprising (i) the heavy and/or light chain, the variable domains thereof, or antigen-binding portions thereof, of said anti-CCR2 antibody, or nucleic acid molecules encoding them; and (ii) a pharmaceutically acceptable carrier are provided. The compositions may further comprise another component, such as a therapeutic agent or a diagnostic agent.

Diagnostic and therapeutic methods are also provided. Similarly, anti-CCR2 antibodies and portions thereof for the manufacture of medicaments to treat inflammatory and non-inflammatory disorders are provided.

Provided are vectors and host cells comprising the nucleic acid molecules, as well as methods of recombinantly producing the polypeptides encoded by the nucleic acid molecules. Isolated cell lines that produces an anti-CCR2 antibody or an antigen-binding portion thereof are also provided.

BRIEF DESCRIPTION OF THE DRAWINGS

FIGS. 1A, 1B, & 1C are graphs showing the binding of a CCR2 antibody to cells as assayed by FACS analysis. FIG. 1A is a graph illustrating binding of the AF-488 (ALEXA FLUOR® 488, Invitrogen) conjugated CCR2 antibody 4.40 A68G S230P to human whole blood monocytes compared to a KLH control antibody as assayed by FACS analysis. FIG. 1B is a graph illustrating binding of AF-488 conjugated CCR2 antibody 4.40 A68G S230P to 300-19 cells expressing human CCR2 as assayed by FACS analysis. FIG. 1C is a graph illustrating the binding of different concentrations of 4.40 A68G S230P antibody to CCR2 transfected 300-19 cells as detected with anti-human PE.

FIG. 3 illustrates the ability of the 4.40 A68G S230P antibody to inhibit the chemotaxis of THP-1 cells in response to the CCR2 ligand MCP-1 but not in response to the CCR1/CCR5 ligand MIP-1a.

FIGS. 6A & 6B illustrates the binding of 4.40 A68G S230P antibody to 300-19 cells expressing a chimeric receptor consisting of only the extracellular $1^{st}$ and $2^{nd}$ loops of CCR2 and the N terminus and third loop of CCR1.

FIGS. 17A-17D show an alignment of the germline amino acid sequences of the heavy and light chain variable regions compared to the respective 4.22.3, 4.40.2, 4.39.3 and 4.9.2 antibody heavy and light chain variable regions (only mismatches are shown for the 4.22.3, 4.40.2, 4.39.3 and 4.9.2 antibody). The CDRs are underlined and mismatched gap(s) are indicated by a pound sign (#).

DETAILED DESCRIPTION

Definitions and General Techniques

Figure 2:
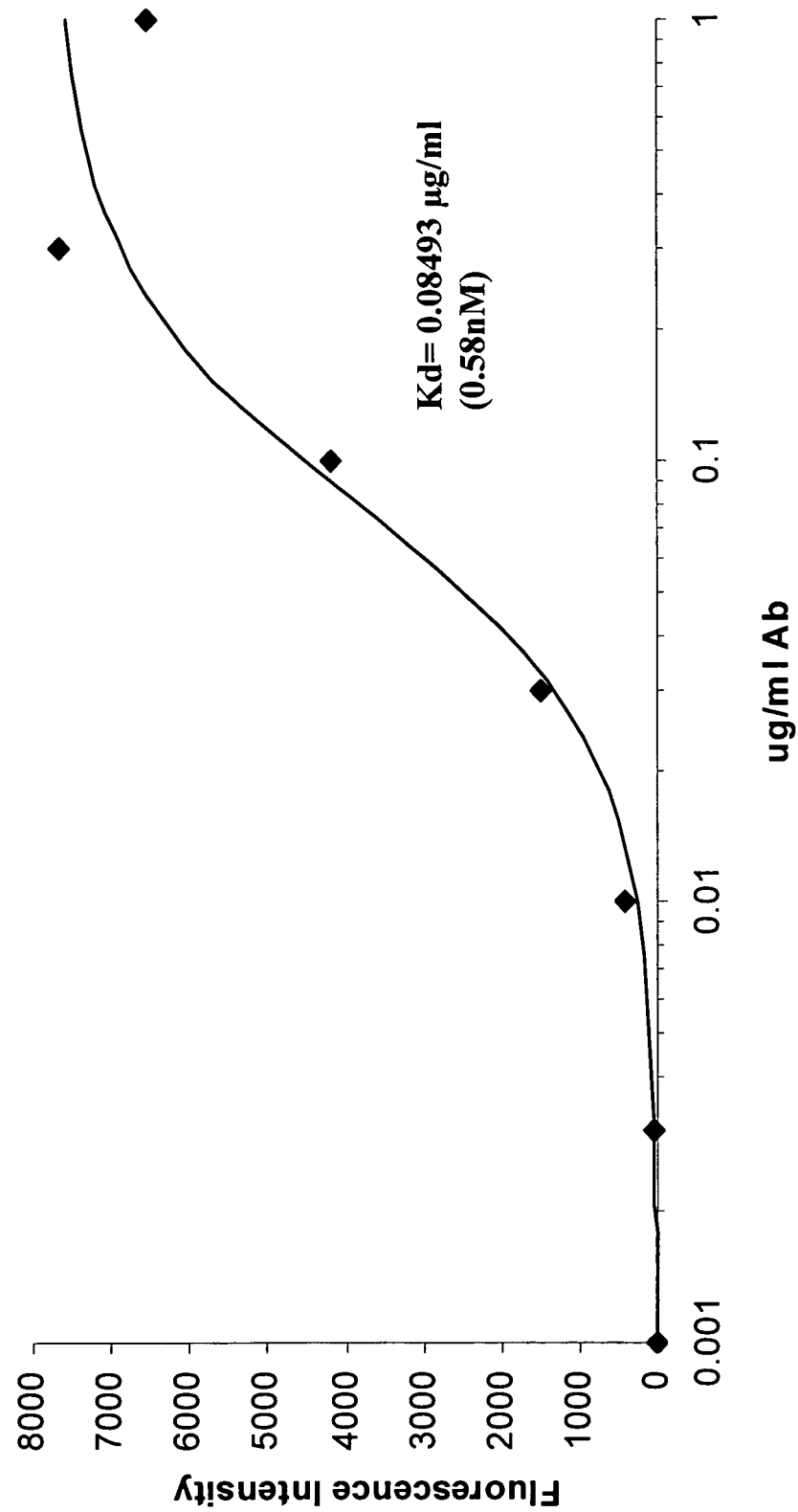
FIG. 2 illustrates the dose related binding of 4.40 A68G S230P antibody to CCR2 transfected 300-19 cells in a saturation binding assay.

Unless otherwise defined herein, scientific and technical terms used herein shall have the meanings that are commonly understood by those of ordinary skill in the art. Further, unless otherwise required by context, singular terms shall include pluralities and plural terms shall include the singular. All publications and other references mentioned herein are incorporated by reference in their entirety. Generally, nomenclature used in connection with, and techniques of, cell and tissue culture, molecular biology, immunology, microbiology, genetics, protein and nucleic acid chemistry, and hybridization described herein are those well known and commonly used in the art. In case of conflict, the present specification, including definitions, will control.

The methods and techniques are generally performed according to conventional methods well known in the art and as described in various general and more specific references that are cited and discussed throughout the present specification unless otherwise indicated. See, e.g., Sambrook et al., *Molecular Cloning: A Laboratory Manual*, second ed., Cold Spring Harbor Laboratory Press, Cold Spring Harbor, N.Y. (1989); Ausubel et al., *Current Protocols in Molecular Biology*, Greene Publishing Associates (1992); and Harlow and Lane, *Antibodies: A Laboratory Manual*, Cold Spring Harbor Laboratory Press, Cold Spring Harbor, N.Y. (1990), all of which are incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms, unless otherwise indicated, shall be understood to have the following meanings:

The term "polypeptide" encompasses native or artificial proteins, protein fragments and polypeptide analogs of a protein sequence. A polypeptide may be monomeric or polymeric.

The term "isolated protein," "isolated polypeptide" or "isolated antibody" is a protein, polypeptide or antibody that by virtue of its origin or source of derivation (1) is not associated with naturally associated components that accompany it in its native state, (2) is free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally-associated components by isolation, using protein purification techniques well known in the art.

Examples of isolated antibodies include an anti-CCR2 antibody that has been affinity purified using CCR2 or a portion thereof, an anti-CCR2 antibody that has been synthesized by a hybridoma or other cell line in vitro, and a human anti-CCR2 antibody derived from a transgenic mouse.

A protein or polypeptide is "substantially pure," "substantially homogeneous," or "substantially purified" when at least about 60 to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and may be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "antibody analog" as used herein refers to an antibody that comprises a segment that has substantial identity to a portion of an amino acid sequence and that has at least one of the following properties: (1) specific binding to CCR2 under suitable binding conditions, (2) ability to inhibit at least one biological activity of CCR2. Typically, antibody analogs comprise a conservative amino acid substitution (or insertion or deletion) with respect to the native sequence. Analogs typically are at least 20 or 25 amino acids long, at least 50, 60, 70, 80, 90, 100, 150 or 200 amino acids long or longer, and can often be as long as a full-length heavy chains or light chains of the antibodies. Some cases include antibody analogs with 1, 2, 3, 4, 5, 6, 7, 8, 9, 10, 11, 12, 13, 14, 15, 16 or 17 substitutions from the germline amino acid sequence.

In certain cases, amino acid substitutions to an anti-CCR2 antibody or antigen-binding portion thereof are those which: (1) reduce susceptibility to proteolysis, (2) reduce susceptibility to oxidation, (3) alter binding affinity for forming protein complexes, (4) add or remove glycosylation sites and (5) confer or modify other physicochemical or functional properties of such analogs, but still retain specific binding to CCR2. Analogs can include various muteins of a sequence other than the normally-occurring peptide sequence. For example, single or multiple amino acid substitutions, such as conservative amino acid substitutions, may be made in the normally-occurring sequence in a portion of the polypeptide outside the domain(s) forming intermolecular contacts. A conservative amino acid substitution should not substantially change the structural characteristics of the parent sequence; e.g., a replacement amino acid should not alter the anti-parallel β-sheet that makes up the immunoglobulin binding domain that occurs in the parent sequence, or disrupt other types of secondary structure that characterizes the parent sequence. In general, glycine and proline would not be used in an anti-parallel β-sheet. Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et al., *Nature* 354:105 (1991), incorporated herein by reference.

Where an "antibody" is referred to herein, it is normally understood that an antigen-binding portion thereof may also be used. An antigen-binding portion competes with the intact antibody for specific binding. See generally, *Fundamental Immunology*, Ch. 7 (Paul, W., ed., second ed. Raven Press, N.Y. (1989)) (incorporated by reference in its entirety for all purposes). Antigen-binding portions may be produced by recombinant DNA techniques or by enzymatic or chemical cleavage of intact antibodies. In some cases, antigen-binding portions include Fab, Fab', F(ab')$_2$, Fd, Fv, dAb, and complementarity determining region (CDR) fragments, single-chain antibodies (e.g., scFv), chimeric antibodies, diabodies and polypeptides that contain at least a portion of an antibody that is sufficient to confer specific antigen binding to the polypeptides.

From N-terminus to C-terminus, both the mature light and heavy chain variable domains of an antibody comprise the regions FR1, CDR1, FR2, CDR2, FR3, CDR3 and FR4. The assignment of amino acids to each domain herein is in accordance with the definitions of Kabat, *Sequences of Proteins of Immunological Interest* (National Institutes of Health, Bethesda, Md. (1987 and 1991)); Chothia & Lesk, *J. Mol. Biol.* 196:901-917 (1987); or Chothia et al., *Nature* 342:878-883 (1989).

As used herein, an antibody that is referred to by number is the same as a monoclonal antibody that is obtained from the hybridoma of the same number. For example, monoclonal antibody 4.40 is the same antibody as one obtained from hybridoma 4.40, or a subclone thereof. Sequential subclones are designated for example 4.40.1, 4.40.2, and 4.40.3, and have substantially the same sequences and functionality.

As used herein, an Fd fragment means an antibody fragment that consists of the $V_H$ and $C_H1$ domains; an Fv fragment consists of the $V_L$ and $V_H$ domains of a single arm of an antibody; and a dAb fragment (Ward et al., *Nature* 341:544-546 (1989)) consists of a $V_H$ domain.

In some cases, the antibody is a single-chain antibody (e.g., scFv) in which $V_L$ and $V_H$ domains are paired to form a monovalent molecules via a synthetic linker that enables them to be made as a single polypeptide chain. (See, e.g., Bird et al., *Science* 242:423-426 (1988) and Huston et al., *Proc. Natl. Acad. Sci. USA* 85:5879-5883 (1988).) In some cases, the antibodies are diabodies, i.e., are bivalent antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites. (See, e.g., Holliger P. et al., *Proc. Natl. Acad. Sci. USA* 90:6444-6448 (1993), and Poljak R. J. et al., *Structure* 2:1121-1123 (1994).) In some cases, one or more CDRs from an antibody herein may be incorporated into a molecule either covalently or noncovalently to make it an immunoadhesin that specifically binds to CCR2. In such cases, the CDR(s) may be incorporated as part of a larger polypeptide chain, may be covalently linked to another polypeptide chain, or may be incorporated noncovalently. In cases having one or more binding sites, the binding sites may be identical to one another or may be different.

As used herein, the term "human antibody" means any antibody in which the variable and constant domain sequences are human sequences. The term encompasses antibodies with sequences derived from human genes, but which have been changed, e.g., to decrease possible immunogenicity, increase affinity, eliminate cysteines that might cause undesirable folding, etc. The term encompasses such antibodies produced recombinantly in non-human cells, which might impart glycosylation not typical of human cells. These antibodies may be prepared in a variety of ways, as described herein.

The term "chimeric antibody" as used herein means an antibody that comprises regions from two or more different antibodies. In one case, one or more of the CDRs of the chimeric antibody are derived from a human anti-CCR2 antibody. In another case, all of the CDRs are derived from human anti-CCR2 antibodies. In another case, the CDRs from more than one human anti-CCR2 antibodies are combined in a chimeric antibody. For instance, a chimeric antibody may comprise a CDR1 from the light chain of a first human anti- CCR2 antibody, a CDR2 from the light chain of a second human anti-CCR2 antibody and a CDR3 from the light chain of a third human anti-CCR2 antibody, and CDRs from the heavy chain may be derived from one or more other anti-CCR2 antibodies. Further, the framework regions may be derived from one of the anti-CCR2 antibodies from which one or more of the CDRs are taken or from one or more different human antibodies.

In some cases, a chimeric antibody is a humanized anti-CCR2 antibody. A humanized anti-CCR2 antibody comprises the amino acid sequence of one or more framework regions and/or the amino acid sequence from at least a portion of the constant region of one or more human anti-CCR2 antibodies and CDRs derived from a non-human anti-CCR2 antibody.

Fragments or analogs of antibodies or immunoglobulin molecules can be readily prepared by those of ordinary skill in the art following the teachings of this specification. Preferred amino- and carboxy-termini of fragments or analogs occur near boundaries of functional domains.

The term "surface plasmon resonance," as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.). For further descriptions, see Jonsson U. et al., *Ann. Biol. Clin.* 51:19-26 (1993); Jonsson U. et al., *Biotechniques* 11:620-627 (1991); Jonsson B. et al., *J. Mol. Recognit.* 8:125-131 (1995); and Johnsson B. et al., *Anal. Biochem.* 198:268-277 (1991).

The term "$K_D$" refers to the equilibrium dissociation constant of a particular antibody-antigen interaction. An antibody is said to specifically bind an antigen when the dissociation constant is ≤1 mM, ≤100 nM, or ≤10 nM. In certain cases, the $K_D$ is 1 pM to 500 pM. In other cases, the $K_D$ is between 500 pM to 1 µM, 1 µM to 100 nM, or 100 mM to 10 nM.

The term "epitope" includes any protein determinant capable of specific binding to an immunoglobulin or T-cell receptor or otherwise interacting with a molecule. Epitopic determinants generally consist of chemically-active surface groupings of molecules such as amino acids or carbohydrate or sugar side chains and generally have specific three dimensional structural characteristics, as well as specific charge characteristics. An epitope may be "linear" or "conformational." In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another. Once a desired epitope on an antigen is determined, it is possible to generate antibodies to that epitope, e.g., using the techniques described in the present specification. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to CCR2, e.g., the antibodies compete for binding to the antigen. A high throughput process for "binning" antibodies based upon their cross-competition is described in International Patent Application No. WO 03/48731.

As used herein, the twenty conventional amino acids and their abbreviations follow conventional usage. See *Immunology—A Synthesis* (second Edition, E. S. Golub and D. R. Gren, Eds., Sinauer Associates, Sunderland, Mass. (1991)), incorporated herein by reference.

The term "polynucleotide" as referred to herein means a polymeric form of nucleotides of at least 10 bases in length, either ribonucleotides or deoxyribonucleotides or a modified form of either type of nucleotide. The term includes single and double stranded forms.

The term "isolated polynucleotide" as used herein means a polynucleotide of genomic, cDNA, or synthetic origin or some combination thereof, which by virtue of its origin the "isolated polynucleotide" (1) is not associated with all or a portion of a polynucleotides with which the "isolated polynucleotide" is found in nature, (2) is operably linked to a polynucleotide to which it is not linked in nature, or (3) does not occur in nature as part of a larger sequence.

The term "naturally occurring nucleotides" as used herein includes deoxyribonucleotides and ribonucleotides. The term "modified nucleotides" as used herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoroamidate, and the like. See e.g., LaPlanche et al., *Nucl. Acids Res.* 14:9081 (1986); Stec et al., *J. Am. Chem. Soc.* 106:6077 (1984); Stein et al., *Nucl. Acids Res.* 16:3209 (1988); Zon et al., *Anti-Cancer Drug Design* 6:539 (1991); Zon et al., *Oligonucleotides and Analogues: A Practical Approach*, pp. 87-108 (F. Eckstein, Ed., Oxford University Press, Oxford England (1991)); U.S. Pat. No. 5,151,510; Uhlmann and Peyman, *Chemical Reviews* 90:543 (1990), the disclosures of which are hereby incorporated by reference. An oligonucleotide can include a label for detection, if desired.

"Operably linked" sequences include both expression control sequences that are contiguous with the gene of interest and expression control sequences that act in trans or at a distance to control the gene of interest. The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, means a nucleic acid molecule capable of transporting another nucleic acid to which it has been linked. In some cases, the vector is a plasmid, i.e., a circular double stranded piece of DNA into which additional DNA segments may be ligated. In some cases, the vector is a viral vector, wherein additional DNA segments may be ligated into the viral genome. In some cases, the vectors are capable of autonomous replication in a host cell into which they are introduced (e.g., bacterial vectors having a bacterial origin of replication and episomal mammalian vectors). In other cases, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The term "recombinant host cell" (or simply "host cell"), as used herein, means a cell into which a recombinant expression vector has been introduced. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

The term "percent sequence identity" in the context of nucleotide sequences means the residues in two sequences that are the same when aligned for maximum correspondence. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Methods Enzymol.* 183:63-98 (1990); Pearson, *Methods Mol. Biol.* 132:185-219 (2000); Pearson, *Methods Enzymol.* 266:227-258 (1996); Pearson, *J. Mol. Biol.* 276:71-84 (1998); incorporated herein by reference). Unless otherwise specified, default parameters for a particular program or algorithm are used. For instance, percent sequence identity between nucleotide sequences can be determined using FASTA with its default parameters (a word size of 6 and the NOPAM factor for the scoring matrix) or using Gap with its default parameters as provided in GCG Version 6.1, incorporated herein by reference.

A reference to a nucleotide sequence encompasses its complement unless otherwise specified. Thus, a reference to a nucleic acid having a particular sequence should be understood to encompass its complementary strand, with its complementary sequence.

As used herein, the terms "percent sequence identity" and "percent sequence homology" are used interchangeably.

The term "substantial similarity" or "substantial sequence similarity," when referring to a nucleic acid or fragment thereof, means that when optimally aligned with appropriate nucleotide insertions or deletions with another nucleic acid (or its complementary strand), there is nucleotide sequence identity in at least about 85%, at least about 90%, and at least about 95%, 96%, 97%, 98% or 99% of the nucleotide bases, as measured by any well-known algorithm of sequence identity, such as FASTA, BLAST or Gap, as discussed above.

As applied to polypeptides, the term "substantial identity" means that two peptide sequences, when optimally aligned, such as by the programs GAP or BESTFIT using default gap weights as supplied with the programs, share at least 70%, 75% or 80% sequence identity, at least 90% or 95% sequence identity, and at least 97%, 98% or 99% sequence identity. In certain cases, residue positions that are not identical differ by conservative amino acid substitutions. A "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity may be adjusted upwards to correct for the conservative nature of the substitution. Means for making this adjustment are well-known to those of skill in the art. See, e.g., Pearson, *Methods Mol. Biol.* 243:307-31 (1994). Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., *Science* 256:1443-45 (1992), incorporated herein by reference. A "moderately conservative" replacement is any change having a nonnegative value in the PAM250 log-likelihood matrix.

Sequence identity for polypeptides is typically measured using sequence analysis software. Protein analysis software matches sequences using measures of similarity assigned to various substitutions, deletions and other modifications, including conservative amino acid substitutions. For instance, GCG contains programs such as "Gap" and "Bestfit" which can be used with default parameters as specified by the programs to determine sequence homology or sequence identity between closely related polypeptides, such as homologous polypeptides from different species of organisms or between a wild type protein and a mutein thereof. See, e.g., GCG Version 6.1 (University of Wisconsin, Wis.). Polypeptide sequences also can be compared using FASTA using default or recommended parameters, see GCG Version 6.1. FASTA (e.g., FASTA2 and FASTA3) provides alignments and percent sequence identity of the regions of the best overlap between the query and search sequences (Pearson, *Methods Enzymol.* 183:63-98 (1990); Pearson, *Methods Mol. Biol.* 132:185-219 (2000)). Another preferred algorithm when comparing a sequence to a database containing a large number of sequences from different organisms is the computer program BLAST, especially blastp or tblastn, using default parameters as supplied with the programs. See, e.g., Altschul et al., *J. Mol. Biol.* 215:403-410 (1990); Altschul et al., *Nucleic Acids Res.* 25:3389-402 (1997).

CCR2 is a seven-transmembrane domain protein, and accordingly it has six loops. Loops 1, 3 and 5, counting from the extracellular N-terminus, are intracellular loops, while loops 2, 4 and 6 are extracellular. The first, second and third extracellular loops of CCR2 refer to loops 2, 4 and 6, respectively.

Throughout this specification and claims, the word "comprise," or variations such as "comprises" or "comprising," will be understood to imply the inclusion of a stated integer or group of integers but not the exclusion of any other integer or group of integers.

Human Anti-CCR2 Antibodies and Characterization Thereof

In some cases, human anti-CCR2 antibodies are provided. In some cases, human anti-CCR2 antibodies are produced by immunizing a non-human transgenic animal, e.g., a rodent, whose genome comprises human immunoglobulin genes so that the transgenic animal produces human antibodies. In some cases, the anti-CCR2 antibodies and antigen-binding portions include, but are not limited to, antibodies or antigen-binding portions (i) which bind to the first or second extracellular loop of CCR2, or both; (ii) which do not bind to the N-terminal end or the third extracellular loop of CCR2 or both; or (iii) which do both (i) and (ii). In another case, human anti-CCR2 antibodies that bind to a polypeptide comprising the amino acid sequence of SEQ ID NO:128 or SEQ ID NO:129 are provided. In another case, human anti-CCR2 antibodies bind to a polypeptide comprising an amino acid sequence 80, 85, 90, 95, 96, 97, 98, or 99% identical to SEQ ID NO:128 or SEQ ID NO:129. In another case, the anti-CCR2 antibodies and antigen-binding portions include, but are not limited to, antibodies or antigen-binding portions which bind to the third extracellular loop of CCR2.

The $V_H$, $V_\kappa$, $V_\lambda$ genes are classified into families on the basis of sequence homology. Two $V_H$, $V_\kappa$, or $V_\lambda$ genes belong to the same family if they share the same nucleotide sequence at more than 80% of the positions. An anti-CCR2 antibody may comprise a human kappa light chain ($V_\kappa$) or a human lambda light chain ($V_\lambda$) or an amino acid sequence derived there from. In some cases comprising a lambda light chain, the light chain variable domain ($V_L$) utilizes a human $V_\lambda 1$, $V_\lambda 2$, $V_\lambda 3$, $V_\lambda 4$, $V_\lambda 5$, $V_\lambda 6$, $V_\lambda 7$, $V_\lambda 8$, $V_\lambda 9$, or $V_\lambda 10$ family gene (Williams S. C. et al. *J. Mol. Bio.* 264:220-232 (1996)).

In some cases comprising a kappa light chain, the light chain variable domain ($V_L$) utilizes a human $V_K I$, $V_K II$, $V_K III$, $V_K IV$, $V_K V$, or $V_K VI$ family gene (Cox J. P. L., et al., *Eur. J. Immunol* 24:827-836 (1994)), preferably a $V_K I$, $V_K II$, $V_K IV$, or $V_K VI$ family gene, preferably a $V_K I$ or $V_K VI$ family gene. In some cases, the light chain germline sequence is selected from human $V_K$ sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8. In certain cases, this light chain human germline gene is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6. In certain cases, the light chain utilizes a human $V_K I$ O12, $V_K II$ A1, a $V_K IV$ B3 or a $V_K VI$ A26 germline gene.

An anti-CCR2 antibody may comprise a heavy chain variable domain ($V_H$) that utilizes a human $V_H 1$, $V_H 2$, $V_H 3$, $V_H 4$, $V_H 5$, $V_H 6$ or $V_H 7$ family gene. In particular examples, this heavy chain human germline gene is selected from VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81. In certain cases, the heavy chain utilizes a human $V_H I$ 1-46 or a $V_H III$ 3-30 gene.

In particular cases, the light chain variable region and/or heavy chain variable region comprises a framework region or at least a portion of a framework region (e.g., containing 2 or 3 subregions, such as FR2 and FR3). In certain cases, at least FRL1, FRL2, FRL3, or FRL4 is fully human. In other examples, at least FRH1, FRH2, FRH3, or FRH4 is fully human. In some cases, at least FRL1, FRL2, FRL3, or FRL4 is a germline sequence (e.g., human germline) or comprises human consensus sequences for the particular framework (readily available at the sources of known human Ig sequences described herein). In other examples, at least FRH1, FRH2, FRH3, or FRH4 is a germline sequence (e.g., human germline) or comprises human consensus sequences for the particular framework.

In some cases, the $V_L$ of the CCR2 antibody comprises one or more amino acid substitutions, deletions, and/or insertions relative to the germline amino acid sequence of the human gene. In some cases, the $V_L$ of the anti-CCR2 antibody comprises 1, 2, 3, 4, 5, 6, 7, 8, 9, or 10 amino acid substitutions relative to the germline amino acid sequence. In some cases, one or more of those substitutions, deletions, and/or insertions is in a CDR of the light chain. In some cases, the amino acid substitutions, deletions and/or insertions relative to germline are at one or more of the same positions as the substitution, deletion and/or insertion relative to germline in any one or more of the $V_L$ of antibodies 4.40, 4.9, 4.22, 4.39 or 4.40 A68G S230P. For example, the $V_L$ of an anti-CCR2 antibody may contain one or more amino acid substitutions, deletions, and/or insertions compared to germline found in the $V_L$ of antibody 4.40. In some cases, the amino acid changes are at one or more of the same positions, but involve a different substitution, deletion and/or insertion compared to germline. In some cases, substitution may represent conservative amino acid substitutions at such position(s) relative to the amino acid in the reference antibody. For example, if a particular position in one of these antibodies is substituted relative to germline and is glutamate, one may substitute aspartate at that position. Similarly, if an amino acid substitution compared to germline is serine, one may conservatively substitute threonine for serine at that position.

In some cases, the light chain of the human anti-CCR2 antibody comprises the variable domain ($V_L$) amino acid sequence of antibody 4.40 (SEQ ID NO:101); 4.9 (SEQ ID NO:29); 4.22 (SEQ ID NO:65); 4.39 (SEQ ID NO:194); or 4.40 A68G S230P (SEQ ID NO:113); or said amino acid sequence having up to 1, 2, 3, 4, 5, 6, 7, 8, 9, or 10 conservative amino acid substitutions and/or a total of up to 3 non-conservative amino acid substitutions. In some cases, the light chain may comprise CDR1, CDR2 and CDR3 independently selected from the light chain CDR1, CDR2 and CDR3, respectively of the light chain of antibody 4.40, 4.9, 4.22, 4.39 or 4.40 A68G S230P, or CDRs each having less than 4 or less than 3 conservative amino acid substitutions and/or a total of three or fewer non-conservative amino acid substitutions. In some cases, the light chain of the anti-CCR2 antibody comprises a light chain CDR1, CDR2, and CDR3, each of which is independently selected from the light chain CDR1, CDR2 and CDR3 regions of monoclonal antibody 4.40 (SEQ ID NO:100); 4.9 (SEQ ID NO:28); 4.22 (SEQ ID NO:64); 4.39 (SEQ ID NO:193); or 4.40 A68G S230P (SEQ ID NO:112). In certain cases, the light chain of the anti-CCR2 antibody comprises the light chain CDR1, CDR2 and CDR3 of an antibody comprising the amino acid sequence of the $V_L$ region of an antibody selected from 4.40 (SEQ ID NO:101); 4.9 (SEQ ID NO:29); 4.22 (SEQ ID NO:65); 4.39 (SEQ ID NO:194); or 4.40 A68G S230P (SEQ ID NO:113); or said CDRs each having less than 4 or less than 3 conservative amino acid substitutions and/or a total of three or fewer non-conservative amino acid substitutions. Sequence identifiers are listed for the CDRs of certain antibodies in Table 8.

With regard to the heavy chain, in some cases, the variable domain ($V_H$) utilizes a human $V_H$ 3-30, or $V_H$ 1-46 gene sequence. In some cases, the $V_H$ sequence of the anti-CCR2 antibody contains one or more amino acid substitutions, deletions and/or insertions (additions) relative to the germline amino acid sequence. In some cases, the variable domain of the heavy chain comprises 1, 2, 3, 4, 5, 6, 7, 8, 9, 10, 11, 12, 13, 14, 15, 16, or 17 substitutions, deletions and/or insertions from the germline amino acid sequence. In some cases, the substitution is a non-conservative substitution compared to the germline amino acid sequence. In some cases, the substitution, deletion and/or insertion are in a CDR of the heavy chain. In some cases, the amino acid substitution, deletion and/or insertion are made at one or more of the same positions as the mutations from germline in any one or more of the $V_H$ of antibodies 4.40, 4.22, 4.39 or 4.9. In other cases, the amino acid substitution, deletion and/or insertion are at one or more of the same positions but involve a different substitution, deletion and/or insertion than in the reference antibody. In some cases the antibody comprises a heavy chain CDR3 having the amino acid sequence of SEQ ID NO:202 or SEQ ID NO:203.

In some cases, the heavy chain comprises the $V_H$ amino acid sequence of antibody 4.40 (SEQ ID NO:83); 4.22 (SEQ ID NO:47); 4.9 (SEQ ID NO:11); 4.39 (SEQ ID NO:176); or said $V_H$ amino acid sequence having up to 1, 2, 3, 4, 6, 8, or 10 conservative amino acid substitutions and/or a total of up to 3 non-conservative amino acid substitutions. In some cases, the heavy chain comprises the amino acid sequence from the beginning of the CDR1 to the end of the CDR3 of any one of the foregoing antibodies.

a non-canonical cysteine. The substitution can be made in a CDR or framework region of a variable domain or in the constant domain of an antibody. In some cases, the cysteine is canonical.

Another type of amino acid substitution that may be made is to change any potential proteolytic sites in the antibody. Such sites may occur in a CDR or framework region of a variable domain or in the constant domain of an antibody. Substitution of cysteine residues and removal of proteolytic sites may decrease the risk of any heterogeneity in the antibody product and thus increase its homogeneity. Another type of amino acid substitution is to eliminate asparagine-glycine pairs, which form potential deamidation sites, by altering one or both of the residues. In some cases, amino acid substitution are used to insert or remove a glycosylation site. In some cases, the C-terminal lysine of the heavy chain of the anti-CCR2 antibody may be proteolytically or genetically removed. In various cases, the heavy and light chains of the anti-CCR2 antibodies may optionally include a signal sequence.

In one aspect, the antibodies are produced by a hybridoma.

Table 1 lists the sequence identifiers (SEQ ID NOs) of the nucleic acids encoding the full-length, and variable domain-comprising portions, of heavy and light chains, and the corresponding deduced amino acid sequences of exemplary antibodies.

TABLE 1

HUMAN ANTI-CCR2 ANTIBODIES

SEQUENCE IDENTIFIER (SEQ ID NO:)

| Monoclonal Antibody | Variable Domain Comprising Portion | | | | Full Length | | | |
|---|---|---|---|---|---|---|---|---|
| | Heavy ($V_H$) | | Light ($V_L$) | | Heavy | | Light | |
| | Protein | DNA | Protein | DNA | Protein | DNA | Protein | DNA |
| 4.40.2 | 83 | 74 | 101 | 92 | 82 | 73 | 100 | 91 |
| 4.40.2 A68G S230P | 83 | 74 | 113 | 110 | 116 | 115 | 112 | 109 |
| 4.9.2 | 11 | 2 | 29 | 20 | 10 | 1 | 28 | 19 |
| 4.22.3 | 47 | 38 | 65 | 56 | 46 | 37 | 64 | 55 |
| 4.39.3 | 176 | 167 | 194 | 185 | 175 | 166 | 193 | 184 |

In some cases, the heavy chain comprises the heavy chain CDR1, CDR2 and CDR3 of antibody 4.40, 4.22, 4.39 or 4.9 or said CDRs each having less than 8, less than 6, less than 4, or less than 3 conservative amino acid substitutions and/or a total of three or fewer non-conservative amino acid substitutions.

In some cases, the heavy chain CDRs are independently selected from the CDRs of antibodies 4.40, 4.22, 4.39 or 4.9. In another case, the heavy chain comprises CDRs independently selected from two or more $V_H$ regions selected from 4.40 (SEQ ID NO:83); 4.22 (SEQ ID NO:47); 4.39 (SEQ ID NO:176) or 4.9 (SEQ ID NO:11). In another case, the antibody comprises a light chain as disclosed above and a heavy chain as disclosed above. In a further case, the light chain CDRs and the heavy chain CDRs are from the same antibody.

One type of amino acid substitution that may be made is to change one or more cysteines in the antibody, which may be chemically reactive, to another residue, such as, without limitation, alanine or serine. In one case, there is a substitution of Also provided are heavy and/or light chain variants of certain of the above-listed human anti-CCR2 antibodies, comprising one or more amino acid substitutions. To designate the variants, the first letter is the one letter symbol for the amino acid of the naturally-occurring antibody chain, the number refers to the position of the amino acid (wherein position one is the N-terminal amino acid), and the second letter is the one letter symbol for the variant amino acid. In some cases, heavy chain variants are provided. One such heavy chain variant is a hinge region stabilizing mutation to reduce formation of half-monomer (Angal, S. et al. *Molecular Immunology* 30:105-108 (1993)). One such hinge stabilizing mutation of the 4.40 antibody heavy chain variant has a proline substitution for serine at position 230 of SEQ ID NO:82. The DNA sequence encoding the S230P variant has a CCA codon beginning at position 688 of SEQ ID NO:115.

Also provided are variant light chains of monoclonal antibody 4.40. A68G is a 4.40 light chain variant, represented by SEQ ID NO:113, in which residue 68 is a glycine residue. In the DNA sequence, the A68G 4.40 variant is encoded by SEQ ID NO:109, in which the codon beginning at position 252 is GGG.

In other cases, antibodies containing combinations of amino acid variants can be produced. An example of a combination of variants is the anti-CCR2 antibody 4.40 A68G S230P, which comprises the light chain substitution A68G and the heavy chain substitution S230P in the context of the 4.40 antibody. Further combinations of a variant heavy chain and a variant light chain of 4.40 are included.

In one case, the anti-CCR2 antibody is 4.40, 4.22, 4.39, 4.40 A68G S230P or 4.9. In still further cases, included are antibodies comprising variable domain amino acid sequences with more than 80%, more than 85%, more than 90%, more than 95%, more than 96%, more than 97%, more than 98% or more than 99% sequence identity to an variable domain amino acid sequence of any of the above-listed human anti-CCR2 antibodies.

Class and Subclass of Anti-CCR2 Antibodies

The class and subclass of anti-CCR2 antibodies may be determined by any method known in the art. In general, the class and subclass of an antibody may be determined using antibodies that are specific for a particular class and subclass of antibody. Such antibodies are commercially available. The class and subclass can be determined by ELISA, or Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

In some cases, the anti-CCR2 antibody is a monoclonal antibody. The anti-CCR2 antibody can be an IgG, an IgM, an IgE, an IgA, or an IgD molecule. In one case, the anti-CCR2 antibody is an IgG, belonging to, e.g., an IgG1, IgG2, IgG3, or IgG4 subclass. In another case, the anti-CCR2 antibody is an IgG4. In still another case, the antibody is an IgG4 isoallotype (Ellison J. and Hood L., *PNAS* 79:1984-1988 (1982); & Brusco A. et al., *Eur J. Immunogenticsl* 25:349-355 (1998)).

Binding Affinity of Anti-CCR2 Antibodies to CCR2

In some cases, the anti-CCR2 antibodies bind to CCR2 with high affinity.

In some cases, the anti-CCR2 antibodies bind with high affinity to the first extracellular loop of CCR2, to the second extracellular loop of CCR2, or to an epitope formed by both the $1^{st}$ and $2^{nd}$ extracellular loops.

In a related case, the anti-CCR2 antibodies bind to a polypeptide consisting of the amino acid sequence set forth in SEQ ID NO:128 or in SEQ ID NO:129.

In some cases, the anti-CCR2 antibodies do not bind to the third extracellular loop of CCR2 or to the N-terminal domain of CCR2.

In another case, the anti-CCR2 antibodies do not bind to a peptide consisting of the sequence set forth in SEQ ID NO:127 or in SEQ ID NO:130. In another case, the anti-CCR2 antibody binds to the first and/or second extracellular loops of CCR2, with a $K_D$ of about $2 \times 10^{-7}$ M or less, with a $K_D$ of about $2 \times 10^{-8}$ M or less, with a $K_D$ of about $2 \times 10^{-9}$ M or less, with a $K_D$ of about $1 \times 10^{-9}$ M or less, with a $K_D$ of about $9 \times 10^{-10}$ M or less, with a $K_D$ of about $8 \times 10^{-10}$ M or less, with a $K_D$ of about $7 \times 10^{-10}$ M or less, with a $K_D$ of about $6 \times 10^{-10}$ M or less, with a $K_D$ of $5 \times 10^{-10}$ M or less, with a $K_D$ of about $4 \times 10^{-10}$ M or less, with a $K_D$ of about $3 \times 10^{-10}$ M or less, or with a $K_D$ of about $2 \times 10^{-10}$ M or less. In certain cases, the antibody binds to CCR2, or to the first and/or second extracellular loops of CCR2, with substantially the same $K_D$ as an antibody selected from 4.40, 4.9, 4.22, 4.39 or 4.40 A68G S230P. In still another case, the antibody binds to CCR2, or to the first and/or second extracellular loops of CCR2, with substantially the same $K_D$ as an antibody that comprises a heavy chain variable domain having the amino acid sequence of the $V_H$ region found in SEQ ID NO:83, SEQ ID NO:11, SEQ ID NO:176 or SEQ ID NO:47. In still another case, the antibody binds to CCR2 with substantially the same $K_D$ as an antibody that comprises the CDRs of a light chain variable domain having the amino acid sequence of the $V_L$ region found in SEQ ID NO:101, SEQ ID NO:113, SEQ ID NO:29, SEQ ID NO:194 or SEQ ID NO:65, or that comprises the CDRs of a heavy chain variable domain having the amino acid sequence the $V_H$ region found in SEQ ID NO:83, SEQ ID NO:11, SEQ ID NO:176 or SEQ ID NO:47.

In some cases, the anti-CCR2 antibody may have a low dissociation rate constant ($k_{off}$). In some cases, the anti-CCR2 antibody may bind to CCR2, or more preferably to the first and/or second extracellular loops of CCR2, with a $k_{off}$ of $1.0 \times 10^{-3}$ s-1 or lower, a $k_{off}$ of $5.0 \times 10^{-4}$ s$^{-1}$ or lower or a $k_{off}$ of $2 \times 10^{-4}$ s$^{-1}$ or lower. In some cases, the $k_{off}$ may be substantially the same as an antibody described herein, including an antibody selected from 4.40, 4.9, 4.22, 4.39 and 4.40 A68G S230P. In some cases, the antibody may bind to CCR2, or to the first and/or second extracellular loops of CCR2, with substantially the same $k_{off}$ as an antibody that comprises the CDRs of a heavy chain, or the CDRs of a light chain, from an antibody selected from 4.40, 4.9 and 4.40 A68G S230P. In some cases, the antibody may bind to CCR2, or to the first and/or second extracellular loops of CCR2, with substantially the same $k_{off}$ as an antibody that comprises (i) a heavy chain variable domain having the amino acid sequence of the $V_H$ region found in SEQ ID NO:83, or SEQ ID NO:11, (ii) a light chain variable domain having the amino acid sequence of the $V_L$ region found in SEQ ID NO:101, SEQ ID NO:113, SEQ ID NO:29, or (iii) both (i) and (ii). In still another case, the antibody may bind to CCR2, or to the first and/or second extracellular loops of CCR2, with substantially the same $k_{off}$ as an antibody that comprises the CDRs of a light chain variable domain having the amino acid sequence of the $V_L$ region found in SEQ ID NO:101, SEQ ID NO:113, or SEQ ID NO:29; and the CDRs of a heavy chain variable domain having the amino acid sequence of the $V_H$ region found in SEQ ID NO:83 or SEQ ID NO:11.

The binding affinity and dissociation rate of an anti-CCR2 antibody to CCR2 can be determined by methods known in the art. The binding affinity can be measured by ELISAs, RIAs, flow cytometry, surface plasmon resonance, such as BIACORE™. The dissociation rate can be measured by surface plasmon resonance. One can determine whether an antibody has substantially the same $K_D$ as an anti-CCR2 antibody by using methods known in the art. Example 5 exemplifies a method for determining affinity constants of anti-CCR2 monoclonal antibodies.

Identification of CCR2 Epitopes Recognized by Anti-CCR2 Antibodies

Provided are human anti-CCR2 monoclonal antibodies that binds to CCR2 and may compete or cross-compete with and/or binds the same epitope as: (a) an antibody selected from 4.40, 4.9, 4.22, 4.39 and 4.40 A68G S230P; (b) an antibody that comprises a heavy chain variable domain having an amino acid sequence of the variable domain found in SEQ ID NO:83, SEQ ID NO:11, SEQ ID NO:176 or SEQ ID NO:47, (c) an antibody that comprises a light chain variable domain having an amino acid sequence of the variable domain found in SEQ ID NO:101, SEQ ID NO:113, SEQ ID NO:29, SEQ ID NO:194, or SEQ ID NO:65, or (d) an antibody that comprises both a heavy chain variable domain as defined in (b) and a light chain variable domain as defined in (c). If two antibodies reciprocally compete with each other for binding to CCR2, they are said to cross-compete.

One can determine whether an antibody binds to the same epitope, competes or cross-competes for binding with an anti-CCR2 antibody provided herein by using methods known in the art. In one case, one allows the anti-CCR2 antibody provided herein to bind to CCR2 under saturating conditions and then measures the ability of the test antibody to bind to CCR2. If the test antibody is able to bind to CCR2 at the same time as the provided anti-CCR2 antibody, then the test antibody binds to a different epitope as the anti-CCR2 antibody. However, if the test antibody is not able to bind to CCR2 at the same time, then the test antibody binds to the same epitope, an overlapping epitope, or an epitope that is in close proximity to the epitope bound by the human anti-CCR2 antibody provided herein. To determine if a test antibody cross-competes with a reference antibody, the experiment is conducted reversing the antibodies, i.e., one allows the test antibody to bind to CCR2 and then measures the ability of the anti-CCR2 antibody provided herein to bind CCR2. These experiments can be performed using ELISA, RIA, BIACORE™, or flow cytometry (FACS).

Inhibition of CCR2 Activity by Anti-CCR2 Antibody

In some cases, provided are anti-CCR2 antibodies that inhibit CCR2-mediated signaling. In other cases, provided are anti-CCR2 antibodies that inhibit MCP-1, MCP-2, MCP-3, and/or MCP-4 mediated signaling through CCR2. In other cases, provided are anti-CCR2 antibodies that inhibit the binding of MCP-1 MCP-2, MCP-3 and/or MCP-4 to CCR2. In one case, the CCR2 is human CCR2. In some cases, the CCR2 is human CCR2A, CCR2B or both. In still another case, the anti-CCR2 antibody is a human antibody.

The $IC_{50}$ of an anti-CCR2 antibody can be measured in ligand binding assays such as ELISA, RIA, or related assays and cell-based assays such as chemotaxis assays of cells expressing CCR2. In various cases, the antibody or an antigen-binding portion thereof inhibits ligand binding between MCP-1 and CCR2 with an $IC_{50}$ of no more than 5 µg/ml, no more than 1 µg/ml, no more than 0.5 µg/ml, or no more than 0.20 µg/ml as measured by an ELISA assay.

In another case, an anti-CCR2 antibody that reduces activation of CCR2 in the presence of CCR2 ligands such as MCP-1 (CCL2), MCP-2, MCP-3, and/or MCP-4 is provided. In one case, the anti-CCR2 antibody may inhibit CCR2 ligand induced (i) G-protein activation, (ii) adenylate cyclase activation, (iii) mitogen-activated protein kinases (MAPKs) activation, (iv) cytosolic calcium mobilization, (v) ERK phosphorylation, (vi) chemotaxis, or (vii) actin polymerization. One can determine whether an anti-CCR2 antibody can prevent, inhibit or reduce activation of CCR2 in the presence of MCP-1 by determining the GTP/GDP ratio of G-proteins in cells labeled with radiolabeled GTP, by measuring GTPgS incorporation, by measuring cytosolic calcium influx using calcium chromophores, or by measuring the phosphorylation state of MAPKs in a cell. Assays for detecting CCR2 activation and/or MCP-1 binding to CCR2 are described, for example, in Gabrilin et al., *Biochem Biophys Res Commun.* 327(2):533-40 (2005), and Jimenez-Sainz et al., *Mol Pharmacol.* 64(3):773-82 (2003).

In one case, one would determine the levels of CCR2 activation using a chemotaxis assay. In some cases, the $IC_{50}$, measured using a chemotaxis assay, is no more than 5 µg/ml, no more than 1 µg/ml, no more than 0.5 µg/ml, or no more than 0.20 µg/ml. Example 10 exemplifies one type of assay that measures inhibition of CCR2 by an anti-CCR2 antibody by monitoring calcium mobilization.

In another aspect, contacting a cell with the antibody may result in a down regulation of cell surface CCR2 expression after incubation with the antibody. In some cases, the incubation can be a short time period (e.g., 4 hours) or a longer time period (e.g., 24 hours). A down regulation of cell surface CCR2 expression can be measured using Western blotting, ELISA, or FACS analysis. In particular cases, contacting a cell with the antibody may result in at least a 6% decrease, at least a 10% decrease, at least a 20% decrease, at least a 30% decrease, or at least a 50% decrease of cell surface CCR2 expression as measured by Western blotting or ELISA.

In another aspect, the antibody reduces MCP-1 induced pERK phosphorylation. A down regulation of MCP-1 induced pERK phosphorylation can be measured using Western blotting, ELISA, or FACS analysis. In particular cases, the antibody produces at least a 6% decrease, at least a 10% decrease, at least a 20% decrease, at least a 30% decrease, or at least a 50% decrease of MCP-1 induced pERK phosphorylation as measured by FACS analysis.

Inhibition of Chemotaxis In Vivo with Anti-CCR2 Antibodies

According to some cases, provided are anti-CCR2 antibodies that inhibit the chemotaxis of immune cells in viva Immune cells whose chemotaxis is inhibited include peripheral blood mononuclear cells, THP cells, monocytes, memory T lymphocytes, dendritic cells, basophils, natural killer cells and adoptively transferred CCR2+ cells. In one case, the anti-CCR2 antibody inhibits immune cell chemotaxis in response to one or more of MCP-1, MCP-2, MCP-3 and MCP-4. In one case, the chemokine is MCP-1. In still another case, the chemokine is MCP-3. The anti-CCR2 antibody may inhibit chemotaxis to sites of inflammation or injury.

According to some cases, also provided are anti-CCR2 antibodies that inhibit the chemotaxis of non-immune cells, including but not limited to, fibroblast-like synoviocytes (FLS) (see Garcia-Vicuna et al., *Arthritis Rheum.* 50(12):3866-77 (2004)), adult neural stem cells (see Widera et al., *Eur J Cell Biol.* 83(8):381-7 (2004)) and human fetal astrocytes (see Andjelkovic et al., *J Neurosci Res.* 70(2):219-31 (2002)).

In one case, the antibody inhibits cell chemotaxis as compared to the chemotaxis of cells in an untreated animal. In another case, the anti-CCR2 antibody reduces chemotaxis by at least 30%, 35%, 40%, 45%, 50%, 55%, 60%, 65%, 70%, 75%, 80%, 85%, 90%, 95% or 100%. In one case, the inhibition of chemotaxis is measured at least 1 hour after the animals have started treatment with the antibody. In another case, the inhibition of chemotaxis is measured at least 7 days after the animals have started treatment with the antibody. In another case, the anti-CCR2 antibody results in chemotaxis inhibition of at least 10% to 100%.

Species and Molecular Selectivity

In another aspect, the anti-CCR2 antibodies demonstrate both species and molecular selectivity. In some cases, the anti-CCR2 antibody binds to human and cynomolgus CCR2. The anti-CCR2 antibody may bind to additional CCR2 of non-human primate species. In some cases, the anti-CCR2 antibody does not bind to mouse or rat CCR2. Following the teachings of the specification, one may determine the species selectivity for the anti-CCR2 antibody using methods well known in the art. For instance, one may determine the species selectivity using Western blot, flow cytometry, ELISA, immunoprecipitation or RIA. In one case, one may determine the species selectivity using flow cytometry. In another case, one may determine species specificity by assessing the ability of the antibody to inhibit MCP-1 functional responses using cells from that species. This may include chemotaxis, actin polymerization, calcium mobilization, etc.

In another case, the anti-CCR2 antibody has a selectivity for the polypeptide consisting of the amino acid sequence set forth in SEQ ID NO:126 (human CCR2B) over the polypeptide consisting of the amino acid sequence set forth in SEQ ID NO:131 (human CCR5). In another case, the anti-CCR2 antibody has selectivity for CCR2 over CCR5 of at least 2-fold, at least 5 fold, at least 10 fold, at least 25 fold, at least 50 fold, or at least 100 fold. In another case, the human anti-CCR2 antibodies bind to a polypeptide comprising an amino acid sequence 80, 85, 90, 95, 96, 97, 98, or 99% identical to SEQ ID NO:126.

In another case, the anti-CCR2 antibody may have a selectivity for the polypeptide consisting of the amino acid sequence set forth in SEQ ID NO:125 (human CCR2A) over the polypeptide consisting of the amino acid sequence set forth in SEQ ID NO:131 (human CCR5) of at least 2-fold, at least 5 fold, at least 10 fold, at least 25 fold, at least 50 fold, or at least 100-fold. In another case, the human anti-CCR2 antibodies bind to a polypeptide comprising an amino acid sequence 80, 85, 90, 95, 96, 97, 98, or 99% identical to SEQ ID NO:125.

One can determine the selectivity of the anti-CCR2 antibody for CCR2 using methods well known in the art following the teachings of the specification. For instance one can determine the selectivity using Western blot, flow cytometry, ELISA, immunoprecipitation or RIA, and/or functional assays such as chemotaxis, calcium mobilization, or actin polymerization.

Methods of Producing Antibodies and Antibody Producing Cell Lines

Immunization

In some cases, human antibodies are produced by immunizing a non-human, transgenic animal comprising within its genome some or all of human immunoglobulin heavy chain and light chain loci with a CCR2 antigen. In one case, the non-human animal is a XENOMOUSE™ animal. (Amgen Fremont, Inc. (formerly Abgenix, Inc.), Fremont, Calif.).

XENOMOUSE™ mice are engineered mouse strains that comprise large fragments of human immunoglobulin heavy chain and light chain loci and are deficient in mouse antibody production. See, e.g., Green et al., Nature Genetics 7:13-21 (1994) and U.S. Pat. Nos. 5,916,771, 5,939,598, 5,985,615, 5,998,209, 6,075,181, 6,091,001, 6,114,598, 6,130,364, 6,162,963 and 6,150,584. See also WO 91/10741, WO 94/02602, WO 96/34096, WO 96/33735, WO 98/16654, WO 98/24893, WO 98/50433, WO 99/45031, WO 99/53049, WO 00/09560, and WO 00/037504.

In another aspect, provided is a method for making anti-CCR2 antibodies from non-human, non-mouse animals by immunizing non-human transgenic animals that comprise human immunoglobulin loci with a CCR2 antigen. One can produce such animals using the methods described in the above-cited documents. The methods disclosed in these documents can be modified as described in U.S. Pat. No. 5,994,619, which is hereby incorporated by reference. U.S. Pat. No. 5,994,619 describes methods for producing novel cultured inner cell mass (CICM) cells and cell lines, derived from pigs and cows, and transgenic CICM cells into which heterologous DNA has been inserted. CICM transgenic cells can be used to produce cloned transgenic embryos, fetuses, and offspring. The '619 patent also describes methods of producing transgenic animals that are capable of transmitting the heterologous DNA to their progeny. In preferred cases the non-human animals are mammals, particularly rats, sheep, pigs, goats, cattle or horses.

XENOMOUSE™ mice produce an adult-like human repertoire of fully human antibodies and generate antigen-specific human antibodies. In some cases, the XENOMOUSE™ mice contain approximately 80% of the human antibody V gene repertoire through introduction of germline configuration fragments of the human heavy chain loci and kappa light chain loci. In other cases, XENOMOUSE™ mice further contain approximately all of the human lambda light chain locus. See Mendez et al., Nature Genetics 15:146-156 (1997), Green and Jakobovits, J. Exp. Med. 188:483-495 (1998), and WO 98/24893, the disclosures of which are hereby incorporated by reference.

In another case, the antibodies are generated using VELOCIMOUSE™ technology (Regeneron Pharmaceuticals, Tarrytown, N.Y.) for immediate generation of genetically altered mice directly from modified embryonic stem (ES) cells (Poueymirou W. T., et al., Nature Biotechnology 25:91-99 (2007)).

In some cases, the non-human animal comprising human immunoglobulin genes are animals that have a human immunoglobulin "minilocus." In the minilocus approach, an exogenous Ig locus is mimicked through the inclusion of individual genes from the Ig locus. Thus, one or more $V_H$ genes, one or more $D_H$ genes, one or more $J_H$ genes, a mu constant domain, and a second constant domain (preferably a gamma constant domain) are formed into a construct for insertion into an animal. This approach is described, inter alia, in U.S. Pat. Nos. 5,545,807, 5,545,806, 5,569,825, 5,625,126, 5,633,425, 5,661,016, 5,770,429, 5,789,650, 5,814,318, 5,591,669, 5,612,205, 5,721,367, 5,789,215, and 5,643,763, hereby incorporated by reference.

In another aspect, a method for making humanized anti-CCR2 antibodies is provided. In some cases, non-human animals are immunized with a CCR2 antigen as described herein under conditions that permit antibody production. Antibody-producing cells are isolated from the animals, and nucleic acids encoding the heavy and light chains of an anti-CCR2 antibody of interest are isolated. These nucleic acids are subsequently engineered using techniques known to those of skill in the art and as described further below to reduce the amount of non-human sequence, i.e., to humanize the antibody to reduce the immune response in humans In some cases, the CCR2 antigen is isolated and/or purified CCR2. In one case, the CCR2 antigen is human CCR2. In some cases, the CCR2 antigen is a fragment of CCR2. In some cases, the CCR2 fragment is an extracellular loop, the N-terminal domain or the C-terminal end of CCR2. In certain cases, the CCR2 fragment comprises the first or second extracellular loop of CCR2. In other cases, the CCR2 fragment comprises the amino acid sequence set forth in SEQ ID NO:128 or SEQ ID NO:129.

In other cases, the CCR2 fragment does not comprise the third extracellular loop or the N-terminal domain of CCR2.

In other cases, the CCR2 fragment does not comprise the amino acid sequence set forth in SEQ ID NO:127 or SEQ ID NO:130. In some cases, the CCR2 fragment comprises at least one epitope of CCR2. In other cases, the CCR2 antigen is a cell that expresses or over expresses CCR2 or an immunogenic fragment thereof on its surface. In some cases, the CCR2 antigen is a CCR2 fusion protein. In some cases, the CCR2 is a synthetic peptide immunogen.

Immunization of animals can be by any method known in the art. See, e.g., Harlow and Lane, Antibodies: A Laboratory Manual, New York: Cold Spring Harbor Press, 1990. Methods for immunizing non-human animals such as mice, rats, sheep, goats, pigs, cattle and horses are well known in the art. See, e.g., Harlow and Lane, supra, and U.S. Pat. No. 5,994, 619. In one case, the CCR2 antigen is administered with an adjuvant to stimulate the immune response. Exemplary adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. If a polypeptide is being administered, the immunization schedule will involve two or more administrations of the polypeptide, spread out over several weeks. Example 1 exemplifies a method for producing anti-CCR2 monoclonal antibodies in XENOMOUSE™ mice.

Production of Antibodies and Antibody-Producing Cell Lines

After immunization of an animal with a CCR2 antigen, antibodies and/or antibody-producing cells can be obtained from the animal. In some cases, anti-CCR2 antibody-containing serum is obtained from the animal by bleeding or sacrificing the animal. The serum may be used as it is obtained from the animal, an immunoglobulin fraction may be obtained from the serum, or the anti-CCR2 antibodies may be purified from the serum.

In some cases, antibody-producing immortalized cell lines are prepared from cells isolated from the immunized animal. After immunization, the animal is sacrificed and peripheral blood, lymph node and/or splenic B cells are immortalized by any means known in the art. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. See, e.g., Harlow and Lane, supra. If fusion with myeloma cells is used, the myeloma cells preferably do not secrete immunoglobulin polypeptides (a non-secretory cell line). Immortalized cells are screened using CCR2, a portion thereof, or a cell expressing CCR2. In one case, the CCR2 portion (i) comprises the first and/or second extracellular loops of CCR2; (ii) comprises the amino acid sequence set forth in SEQ ID NO:128 and/or SEQ ID NO:129; (iii) does not comprise the third extracellular loop and/or the N-terminal domain of CCR2; (iv) does not comprise the amino acid sequence set forth in SEQ ID NO:127 and/or SEQ ID NO:130; or (v) combinations thereof. In one case, the initial screening is performed using an enzyme-linked immunoassay (ELISA) or a radioimmunoassay. An example of ELISA screening is provided in WO 00/37504, incorporated herein by reference.

Anti-CCR2 antibody-producing cells, e.g., hybridomas, are selected, cloned and further screened for desirable characteristics, including robust growth, high antibody production and desirable antibody characteristics, as discussed further below. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

In one aspect, the immunized animal is a non-human animal that expresses human immunoglobulin genes and the splenic B cells are fused to a myeloma cell line from the same species as the non-human animal. In an exemplary case, the immunized animal is a XENOMOUSE™ mouse and the myeloma cell line is a non-secretory mouse myeloma. In one case, the myeloma cell line is P3-X63-Ag8.653 (American Type Culture Collection). See, e.g., Example 1.

Screening the immortalized antibody-producing cells to identify an antibody directed to the first and/or second extracellular loop of CCR2 may be achieved by testing if the antibodies produced by the cell bind to a peptide comprising the amino acid sequence of the first or second extracellular loop of CCR2. Alternatively or in combination, antibodies produced by the cell may be tested for binding to chimeric chemokine receptors which have primarily the sequence of another chemokine receptor but sequences of the first and/or second extracellular loops of CCR2. See Example 8, which exemplifies the use of chimeras to map the epitope of anti-CCR2 antibodies. In a complementary case, antibodies produced by the cell which are known to bind to CCR2 may be tested for binding to chimeric chemokine receptors which have primarily the sequence of CCR2 but which lack the wild type first and/or second extracellular loops of CCR2, e.g., have the first and/or second extracellular loops from another cytokine receptor or contain mutations in one or both of these extracellular loops.

In another aspect, provided are cells and cell lines (including hybridomas) that produce a human anti-CCR2 antibody. In one case, the human anti-CCR2 antibody produced by the cell, cell line or hybridoma is an antagonist of CCR2. In still another case, the human anti-CCR2 antibody (i) binds to the first and/or second extracellular loops of CCR2; (ii) binds to the amino acid sequence set forth in SEQ ID NO:128 and/or SEQ ID NO:129; (iii) does not bind to the third extracellular loop and/or the N-terminal domain of CCR2; (iv) does not bind to the amino acid sequence set forth in SEQ ID NO:127 and/or SEQ ID NO:130; or (v) combinations thereof. In another case, the human anti-CCR2 antibody produced by the cell, cell line or hybridoma does not bind to the third extracellular loop with high affinity, does not bind to the N-terminal domain of CCR2 with high affinity, or does not bind to either with high affinity.

In still another aspect, a transgenic animal is immunized with CCR2, primary cells, e.g., spleen or peripheral blood cells, are isolated from an immunized transgenic animal and individual cells producing antibodies specific for the desired antigen are identified. For example, polyadenylated mRNA from each individual cell is isolated and reverse transcription polymerase chain reaction (RT-PCR) is performed using sense primers that anneal to variable region sequences, e.g., degenerate primers that recognize most or all of the FR1 regions of human heavy and light chain variable region genes and anti-sense primers that anneal to constant or joining (J) region sequences. cDNAs of the heavy and light chain variable domains are then cloned and expressed in any suitable host cell, e.g., a myeloma cell, as chimeric antibodies with respective immunoglobulin constant regions, such as the heavy chain and κ or λ constant domains. See Babcook, J. S. et al., *Proc. Natl. Acad. Sci. USA* 93: 7843-48 (1996), incorporated herein by reference. Anti-CCR2 antibodies may then be identified and isolated as described herein.

In another aspect, phage display techniques can be used to provide libraries containing a repertoire of antibodies with varying affinities for CCR2. Primary B cells can be used directly as a source of DNA. The mixture of cDNAs obtained from B cell, e.g., derived from spleens, is used to prepare an expression library, for example, a phage display library transfected into *E. coli*. The resulting cells are tested for immunoreactivity to CCR2. Techniques for the identification of high affinity human antibodies from such libraries are described by Griffiths et al., *EMBO J.* 13:3245-3260 (1994); Nissim et al., ibid, pp. 692-698 and by Griffiths et al., ibid, 12:725-734, which are incorporated by reference. Ultimately, clones from the library are identified that produce binding affinities of a desired magnitude for the antigen and the DNA encoding the product responsible for such binding is recovered and manipulated for standard recombinant expression. Phage display libraries may also be constructed using previously manipulated nucleotide sequences and screened in a similar fashion. In general, the cDNAs encoding heavy and light chains are independently supplied or linked to form Fv analogs for production in the phage library.

The phage library is then screened for the antibodies with the highest affinities for CCR2 and the genetic material recovered from the appropriate clone. Further rounds of screening can increase affinity of the original antibody isolated.

Nucleic Acids, Vectors, Host Cells, and Recombinant Methods of Making Antibodies Nucleic Acids Also encompassed are nucleic acid molecules encoding anti-CCR2 antibodies or antigen-binding portions thereof. In some cases, different nucleic acid molecules encode the heavy chain and the light chain of an anti-CCR2 immunoglobulin. In other cases, the same nucleic acid molecule encodes a heavy chain and a light chain of an anti-CCR2 immunoglobulin. In one case, the nucleic acid encodes a CCR2 antibody, or antigen-binding portion thereof.

In some cases, the nucleic acid molecule encoding the variable domain of the light chain ($V_L$) comprises a human $V_K1$, $V_K2$, $V_K3$, $V_K4$, $V_K5$ or $V_K6$ gene family segment, and a $J_K1$, $J_K2$, $J_K4$, or $J_K5$ gene segment with or without mutations from the germline.

In some cases, the nucleic acid molecule encoding the light chain, encodes an amino acid sequence comprising 1, 2, 3, 4, 5, 6, 7, 8, 9, or 10 substitutions from the germline amino acid sequence(s). In some cases, the nucleic acid molecule comprises a nucleotide sequence that encodes a $V_L$ amino acid sequence comprising 1, 2, 3, 4, 5, 6, 7, 8, 9, or 10 conservative amino acid substitutions and/or 1, 2, or 3 non-conservative substitutions compared to germline $V_K$, and $J_K$ sequences. Substitutions may be in the CDRs, the framework regions, or in the constant domain.

In some cases, the nucleic acid molecule encodes a $V_L$ amino acid sequence comprising one or more variants compared to germline sequence that are identical to the variations found in the $V_L$ of one of the antibodies 4.40, 4.9, 4.22, 4.39 or 4.40 A68G S230P. In some cases, the nucleic acid encodes a VL amino acid sequence comprising a mutation in one or more of the same positions as mutations from germline in a CCR2 antibody provided herein but that comprises a different substitution, in some cases a conservative substitution, compared to the substitution in the provided antibody.

In some cases, the nucleic acid molecule encodes at least three amino acid substitutions compared to the germline sequence found in the $V_L$ of one of the antibodies 4.40, 4.9, 4.22, 4.39 or 4.40 A68G S230P.

In some cases, the nucleic acid molecule comprises a nucleotide sequence that encodes the $V_L$ amino acid sequence of monoclonal antibody 4.40 (SEQ ID NO:101), 4.9 (SEQ ID NO:29), 4.22 (SEQ ID NO:65), 4.39 (SEQ ID NO:194) or 4.40 A68G S230P (SEQ ID NO:113), or a variant or portion thereof. In some cases, the nucleic acid encodes an amino acid sequence comprising the light chain CDRs of one of said above-listed antibodies. In some cases, said portion is a contiguous portion comprising CDR1-CDR3.

In some cases, the nucleic acid molecule encodes a $V_L$ amino acid sequence that is at least 70%, 75%, 80%, 85%, 90%, 95%, 97%, 98% or 99% identical to a $V_L$ amino acid sequence of any one of a $V_L$ region of antibodies 4.40, 4.9, 4.22. 4.39 or 4.40 A68G S230P, or an amino acid sequence of a $V_L$ region of any one of SEQ ID NO:101, SEQ ID NO:113, SEQ ID NO:29, SEQ ID NO:194 or SEQ ID NO:65. Nucleic acid molecules include nucleic acids encoding the $V_L$ region found in SEQ ID NO:101, SEQ ID NO:113, SEQ ID NO:29 or SEQ ID NO:65.

In another case, the nucleic acid encodes a full-length light chain of an antibody selected from 4.40, 4.9, 4.22, 4.39 or 4.40 A68G S230P, or a light chain comprising the amino acid sequence of SEQ ID NO:100, SEQ ID NO:112, SEQ ID NO:64, SEQ ID NO:193 or SEQ ID NO:28, or said light chain sequence comprising a mutation, such as one disclosed herein.

In still another case, the nucleic acid molecule encodes the variable domain of the heavy chain ($V_H$) that comprises a human 3-30 or 1-46 $V_H$ gene sequence or a sequence derived there from. In various cases, the nucleic acid molecule utilizes a human 3-30 $V_H$ gene sequence, a human D1-7 gene sequence and a human $J_H3B$ gene sequence; a human 1-46 $V_H$ gene sequence, a human D1-7 gene sequence and a human $J_H3B$ gene sequence; or sequence derived from the human genes.

In some cases, the nucleic acid molecule encodes an amino acid sequence comprising 1, 2, 3, 4, 5, 6, 7, 8, 9, 10, 11, 12, 13, 14, 15, 16, 17 or 18 mutations compared to the germline amino acid sequence of the human V, D or J genes. In some cases, said mutations are in the $V_H$ region. In some cases, said mutations are in the CDRs.

In some cases, the nucleic acid molecule encodes an amino acid sequence comprising one or more amino acid mutations compared to the germline sequence that are identical to amino acid mutations found in the $V_H$ of monoclonal antibody 4.40, 4.22, 4.39 or 4.9. In some cases, the nucleic acid encodes at least three amino acid mutations compared to the germline sequences that are identical to at least three amino acid mutations found in one of the above-listed monoclonal antibodies.

In some cases, the nucleic acid molecule comprises a nucleotide sequence that encodes at least a portion of the $V_H$ amino acid sequence of a monoclonal antibody selected from 4.40 (SEQ ID NO:83), 4.22 (SEQ ID NO:47), 4.39 (SEQ ID NO:176) or 4.9 (SEQ ID NO:11), a variant thereof, or said sequence having conservative amino acid mutations and/or a total of three or fewer non-conservative amino acid substitutions. In various cases the sequence encodes one or more CDRs, a CDR3 region, all three CDRs, a contiguous portion including CDR1-CDR3, or the entire $V_H$ region, with or without a signal sequence.

In some cases, the nucleic acid molecule comprises a nucleotide sequence that encodes the amino acid sequence of one of SEQ ID NO:82, SEQ ID NO:46, SEQ ID NO:10, SEQ ID NO:175 or SEQ ID NO:116, or said sequence having a signal sequence. In some preferred cases, the nucleic acid molecule comprises at least a portion of the nucleotide sequence of SEQ ID NO:73 or SEQ ID NO:115, or said sequence having a signal sequence. In some cases, said portion encodes the $V_H$ region (with or without a signal sequence), a CDR3 region, all three CDRs, or a contiguous region including CDR1-CDR3.

In some cases, the nucleic acid molecule encodes a $V_H$ amino acid sequence that is at least 70%, 75%, 80%, 85%, 90%, 95%, 97%, 98% or 99% identical to the $V_H$ amino acid sequences of any one of $V_H$ region of antibodies 4.40, 4.9, 4.22, 4.39 or 4.40 A68G S230P, or an amino acid sequence of a $V_H$ region of any one of SEQ ID NO:83, SEQ ID NO:47, SEQ ID NO:176 or SEQ ID NO:11. Also included are nucleic acids encoding the amino acid sequence of 4.40 (SEQ ID NO:83), 4.22 (SEQ ID NO:47), 4.39 (SEQ ID NO:176) or 4.9 (SEQ ID NO:11), or to a $V_H$ region thereof, or that has the nucleotide sequence of SEQ ID NO:74, SEQ ID NO:38, SEQ ID NO:167, SEQ ID NO:2 or that encodes a $V_H$ region thereof.

In another case, the nucleic acid encodes a full-length heavy chain of an antibody selected from 4.40, 4.22, 4.9, 4.39, or 4.40 A68G S230P, or a heavy chain having the amino acid sequence of SEQ ID NO:10, SEQ ID NO:46, SEQ ID NO:82, SEQ ID NO:175 or SEQ ID NO:116, with or without a signal sequence, or a heavy chain comprising a mutation, such as one of the variants discussed herein. Further, the nucleic acid may comprise the nucleotide sequence of SEQ ID NO:1, SEQ ID NO:37, SEQ ID NO:73, SEQ ID NO:166 or SEQ ID NO:115, or a nucleic acid molecule encoding a heavy chain comprising a mutation, such as one of the variants discussed herein.

A nucleic acid molecule encoding the heavy or light chain of an anti-CCR2 antibody or portions thereof can be isolated from any source that produces such antibody. In various cases, the nucleic acid molecules are isolated from a B cell isolated from an animal immunized with CCR2 or from an immortalized cell derived from such a B cell that expresses an anti-CCR2 antibody. Methods of isolating mRNA encoding an antibody are well-known in the art. See, e.g., Sambrook et al. The mRNA may be used to produce cDNA for use in the polymerase chain reaction (PCR) or cDNA cloning of antibody genes. In one case, the nucleic acid molecule is isolated from a hybridoma that has as one of its fusion partners a human immunoglobulin-producing cell from a non-human transgenic animal. In other cases, the human immunoglobulin producing cell is isolated from a XENOMOUSE™ animal. In another case, the human immunoglobulin-producing cell is from a non-human, non-mouse transgenic animal, as described herein. In another case, the nucleic acid is isolated from a non-human, non-transgenic animal. The nucleic acid molecules isolated from a non-human, non-transgenic animal may be used, e.g., for humanized antibodies.

In some cases, a nucleic acid encoding a heavy chain of an anti-CCR2 antibody comprises a nucleotide sequence encoding a $V_H$ domain joined in-frame to a nucleotide sequence encoding a heavy chain constant domain from any source. Similarly, a nucleic acid molecule encoding a light chain of an anti-CCR2 antibody can comprise a nucleotide sequence encoding a $V_L$ domain joined in-frame to a nucleotide sequence encoding a light chain constant domain from any source.

In a further aspect, nucleic acid molecules encoding the variable domain of the heavy ($V_H$) and/or light ($V_L$) chains are "converted" to full-length antibody genes. In one case, nucleic acid molecules encoding the $V_H$ or $V_L$ domains are converted to full-length antibody genes by insertion into an expression vector already encoding heavy chain constant ($C_H$) or light chain constant ($C_L$) domains, respectively, such that the $V_H$ segment is operatively linked to the $C_H$ segment(s) within the vector, and/or the $V_L$ segment is operatively linked to the $C_L$ segment within the vector. In another case, nucleic acid molecules encoding the $V_H$ and/or $V_L$ domains are converted into full-length antibody genes by linking, e.g., ligating, a nucleic acid molecule encoding a $V_H$ and/or $V_L$ domains to a nucleic acid molecule encoding a $C_H$ and/or $C_L$ domain using standard molecular biological techniques. Nucleotide sequences of human heavy and light chain immunoglobulin constant domain genes are known in the art. See, e.g., Kabat et al., *Sequences of Proteins of Immunological Interest*, 5th Ed., NIH Publ. No. 91-3242, 1991. Nucleic acid molecules encoding the full-length heavy and/or light chains may then be expressed from a cell into which they have been introduced and the anti-CCR2 antibody isolated.

The nucleic acid molecules may be used to recombinantly express anti-CCR2 antibodies. The nucleic acid molecules also may be used to produce chimeric antibodies, bispecific antibodies, single chain antibodies, immunoadhesins, diabodies, mutated antibodies and antibody derivatives, as described further below. If the nucleic acid molecules are derived from a non-human, non-transgenic animal, the nucleic acid molecules may be used for antibody humanization, also as described herein.

In some cases, nucleic acids encoding a full-length heavy chain or a full-length light chain wherein the nucleotide sequence encoding the constant region amino acid sequence contain one or more mutations compared to a germline human constant region sequence are provided. For example, the nucleic acid may encode an amino acid substitution that improves a property of the antibody, by adding or removing a glycosylation site or encoding a substitutions that improves the stability or half-life of the antibody. The nucleic acid also may contain "silent" mutations to add or remove a restriction enzyme site, for example to facilitate cloning of the nucleic acid into a particular expression vector.

Vectors

Vectors are provided comprising nucleic acid molecules that encode the heavy chain and/or light chain of an anti-CCR2 antibody or an antigen-binding portions thereof. Also provided are vectors comprising nucleic acid molecules encoding fusion proteins, modified antibodies, antibody fragments, and probes thereof.

In some cases, the anti-CCR2 antibodies or antigen-binding portions are expressed by inserting DNAs encoding partial or full-length light and/or heavy chains, obtained as described herein, into expression vectors such that the genes are operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. In some instances the antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human $C_H$ or $C_L$ immunoglobulin sequence, with appropriate restriction sites engineered so that any $V_H$ or $V_L$ sequence can be inserted and expressed, as described herein. In such vectors, splicing usually occurs between the splice donor site in the inserted J region and the splice acceptor site preceding the human C domain, and also at the splice regions that occur within the human $C_H$ exons. Polyadenylation and transcription termination occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. No. 5,168,062, U.S. Pat. No. 4,510,245 and U.S. Pat. No. 4,968,615. Methods for expressing antibodies in plants, including a description of promoters and vectors, as well as transformation of plants is known in the art. See, e.g., U.S. Pat. No. 6,517,529, incorporated herein by reference. Methods of expressing polypeptides in bacterial cells or fungal cells, e.g., yeast cells, are also well known in the art.

In addition to the antibody chain genes and regulatory sequences, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, incorporated herein by reference). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification), the neo gene (for G418 selection), and the glutamate synthetase (GS) gene.

Non-Hybridoma Host Cells and Methods of Recombinantly Producing Protein

Nucleic acid molecules encoding anti-CCR2 antibodies and vectors comprising these nucleic acid molecules can be used for transfection of a suitable mammalian, plant, bacterial, insect or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455, incorporated herein by reference). Methods of transforming plant cells are well known in the art, including, e.g., Agrobacterium-mediated transformation, biolistic transformation, direct injection, electroporation and viral transformation. Methods of transforming bacterial, insect cells, and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NSO cells, NSO cells, SP2 cells, HEK-293T cells, NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as Sf9 or Sf21 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Plant host cells include, e.g., *Nicotiana, Arabidopsis*, duckweed, corn, wheat, potato, etc. Bacterial host cells include *E. coli* and *Streptomyces* species. Yeast host cells include *Schizosaccharomyces pombe, Saccharomyces cerevisiae* and *Pichia pastoris*.

Further, expression of antibodies from production cell lines can be enhanced using a number of known techniques. For example, the glutamine synthetase gene expression system (the GS system) is a common approach for enhancing expression under certain conditions. The GS system is discussed in whole or part in connection with European Patent Nos. 216 846, 256 055, 323 997 and 338 841.

It is likely that antibodies expressed by different cell lines or in transgenic animals will have different glycosylation from each other. However, all antibodies encoded by the nucleic acid molecules provided herein, or comprising the amino acid sequences provided herein are part of the instant disclosure, regardless of the glycosylation of the antibodies.

Transgenic Animals and Plants

Anti-CCR2 antibodies also can be produced transgenically through the generation of a mammal or plant that is transgenic for the immunoglobulin heavy and light chain sequences of interest and production of the antibody in a recoverable form there from. In connection with the transgenic production in mammals, anti-CCR2 antibodies can be produced in, and recovered from, the milk of goats, cows, or other mammals. See, e.g., U.S. Pat. Nos. 5,827,690, 5,756,687, 5,750,172, and 5,741,957, incorporated herein by reference. In some cases, non-human transgenic animals that comprise human immunoglobulin loci are immunized with CCR2 or an immunogenic portion thereof, as described herein. Methods for making antibodies in plants are described, e.g., in U.S. Pat. Nos. 6,046,037 and 5,959,177, incorporated herein by reference.

In some cases, non-human transgenic animals or plants are produced by introducing one or more nucleic acid molecules encoding an anti-CCR2 antibody into the animal or plant by standard transgenic techniques. See Hogan and U.S. Pat. No. 6,417,429, supra. The transgenic cells used for making the transgenic animal can be embryonic stem cells or somatic cells or a fertilized egg. The transgenic non-human organisms can be chimeric, nonchimeric heterozygotes, and nonchimeric homozygotes. See, e.g., Hogan et al., *Manipulating the Mouse Embryo: A Laboratory Manual* second ed., Cold Spring Harbor Press (1999); Jackson et al., *Mouse Genetics and Transgenics: A Practical Approach*, Oxford University Press (2000); and Pinkert, *Transgenic Animal Technology: A Laboratory Handbook*, Academic Press (1999), all incorporated herein by reference. In some cases, the transgenic non-human animals have a targeted disruption and replacement by a targeting construct that encodes a heavy chain and/or a light chain of interest. In one case, the transgenic animals comprise and express nucleic acid molecules encoding heavy and light chains that specifically bind to CCR2, and preferably (i) bind to the first and/or second extracellular loops of CCR2; (ii) which do not bind to the N-terminal end or the third extracellular loop of CCR2 or both; or (iii) both. In one case, the transgenic animals comprise and express nucleic acid molecules encoding heavy and light chains that specifically bind to human CCR2. In some cases, the transgenic animals comprise nucleic acid molecules encoding a modified antibody such as a single-chain antibody, a chimeric antibody or a humanized antibody. The anti-CCR2 antibodies may be made in any transgenic animal. In one case, the non-human animals are mice, rats, sheep, pigs, goats, cattle or horses. The non-human transgenic animal expresses said encoded polypeptides in blood, milk, urine, saliva, tears, mucus and other bodily fluids.

Phage Display Libraries

A method is provided for producing an anti-CCR2 antibody or antigen-binding portion thereof comprising the steps of synthesizing a library of human antibodies on phage, screening the library with CCR2 or a portion thereof, isolating phage that bind CCR2, and obtaining the antibody from the phage. By way of example, one method for preparing the library of antibodies for use in phage display techniques comprises the steps of immunizing a non-human animal comprising human immunoglobulin loci with CCR2 or an antigenic portion thereof to create an immune response, extracting antibody-producing cells from the immunized animal; isolating RNA encoding heavy and light chains of antibodies from the extracted cells, reverse transcribing the RNA to produce cDNA, amplifying the cDNA using primers, and inserting the cDNA into a phage display vector such that antibodies are expressed on the phage. Recombinant anti-CCR2 antibodies may be obtained in this way.

Recombinant anti-CCR2 human antibodies can be isolated by screening a recombinant combinatorial antibody library. The library may be a scFv phage display library, generated using human $V_L$ and $V_H$ cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., *Bio/Technology* 9:1370-1372 (1991); Hay et al., *Hum. Antibod. Hybridomas* 3:81-85 (1992); Huse et al., *Science* 246:1275-1281 (1989); McCafferty et al., *Nature* 348: 552-554 (1990); Griffiths et al., *EMBO J.* 12:725-734 (1993); Hawkins et al., *J. Mol. Biol.* 226:889-896 (1992); Clackson et al., *Nature* 352:624-628 (1991); Gram et al., *Proc. Natl. Acad. Sci. USA* 89:3576-3580 (1992); Garrad et al., *Bio/Technology* 9:1373-1377 (1991); Hoogenboom et al., *Nuc. Acid Res.* 19:4133-4137 (1991); and Barbas et al., *Proc. Natl. Acad. Sci. USA* 88:7978-7982 (1991), all incorporated herein by reference.

In one case, to isolate and produce human anti-CCR2 antibodies with the desired characteristics, a human anti-CCR2 antibody as described herein is first used to select human heavy and light chain sequences having similar binding activity toward CCR2, using the epitope imprinting methods described in PCT Publication No. WO 93/06213, incorporated herein by reference. The antibody libraries used in this method may be scFv libraries prepared and screened as described in PCT Publication No. WO 92/01047, McCafferty et al., *Nature* 348:552-554 (1990); and Griffiths et al., *EMBO J.* 12:725-734 (1993), all incorporated herein by reference. The scFv antibody libraries can be screened using human CCR2 as the antigen.

Once initial human $V_L$ and $V_H$ domains are selected, "mix and match" experiments are performed, in which different pairs of the initially selected $V_L$ and $V_H$ segments are screened for CCR2 binding to select preferred $V_L/V_H$ pair combinations. Additionally, to further improve the quality of the antibody, the $V_L$ and $V_H$ segments of the preferred $V_L/V_H$ pair(s) can be randomly mutated, preferably within the CDR3 region of $V_H$ and/or $V_L$, in a process analogous to the in vivo somatic mutation process responsible for affinity maturation of antibodies during a natural immune response. This in vitro affinity maturation can be accomplished by amplifying $V_H$ and $V_L$ domains using PCR primers complimentary to the $V_H$ CDR3 or $V_L$ CDR3, respectively, which primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be re-screened for binding to CCR2.

Following screening and isolation of an anti-CCR2 antibody from a recombinant immunoglobulin display library, nucleic acids encoding the selected antibody can be recovered from the display package (e.g., from the phage genome) and subcloned into other expression vectors by standard recombinant DNA techniques. If desired, the nucleic acid can further be manipulated to create other antibody forms, as described herein. To express a recombinant human antibody isolated by screening of a combinatorial library, the DNA encoding the antibody is cloned into a recombinant expression vector and introduced into a mammalian host cells, as described herein.

Class Switching

Another aspect provides a method for converting the class or subclass of an anti-CCR2 antibody to another class or subclass. In some cases, a nucleic acid molecule encoding a $V_L$ or $V_H$ that does not include sequences encoding $C_L$ or $C_H$ is isolated using methods well-known in the art. The nucleic acid molecule then is operatively linked to a nucleotide sequence encoding a $C_L$ or $C_H$ from a desired immunoglobulin class or subclass. This can be achieved using a vector or nucleic acid molecule that comprises a $C_L$ or $C_H$ chain, as described herein. For example, an anti-CCR2 antibody that was originally IgM can be class switched to an IgG. Further, the class switching may be used to convert one IgG subclass to another, e.g., from IgG1 or IgG2 to IgG4. Another method for producing an antibody comprising a desired isotype comprises the steps of isolating a nucleic acid encoding a heavy chain of an anti-CCR2 antibody and a nucleic acid encoding a light chain of an anti-CCR2 antibody, isolating the sequence encoding the $V_H$ region, ligating the $V_H$ sequence to a sequence encoding a heavy chain constant domain of the desired isotype, expressing the light chain gene and the heavy chain construct in a cell, and collecting the anti-CCR2 antibody with the desired isotype.

Deimmunized Antibodies

In another aspect, the antibody may be deimmunized to reduce its immunogenicity using the techniques described in, e.g., PCT Publication Nos. WO98/52976 and WO00/34317 (incorporated herein by reference).

Mutated Antibodies

In another aspect, the nucleic acid molecules, vectors and host cells may be used to make mutated anti-CCR2 antibodies. The antibodies may be mutated in the variable domains of the heavy and/or light chains, e.g., to alter a binding property of the antibody. For example, a mutation may be made in one or more of the CDRs to increase or decrease the $K_D$ of the antibody for CCR2, to increase or decrease $k_{off}$, or to alter the binding specificity of the antibody. Techniques in site-directed mutagenesis are well-known in the art. See, e.g., Sambrook et al. and Ausubel et al., supra. In another case, one or more mutations are made at an amino acid residue that is known to be changed compared to the germline in monoclonal antibody 4.40, 4.9, 4.22, 4.39 or 4.40 A68G S230P. The mutations may be made in a CDR or framework region of a variable domain, or in a constant domain. In one case, the mutations are made in a variable domain. In some cases, one or more mutations are made at an amino acid residue that is known to be changed compared to the germline in a CDR or framework region of a variable domain of an amino acid sequence selected from SEQ ID NO:11, SEQ ID NO:47, SEQ ID NO:83, SEQ ID NO:176, SEQ ID NO:29, SEQ ID NO:65, SEQ ID NO:101, SEQ ID NO:194 or SEQ ID NO:113.

In another aspect, the framework region is mutated so that the resulting framework region(s) have the amino acid sequence of the corresponding germline gene. A mutation may be made in a framework region or constant domain to increase the half-life of the anti-CCR2 antibody. See, e.g., PCT Publication No. WO 00/09560, incorporated herein by reference. A mutation in a framework region or constant domain also can be made to alter or reduce the immunogenicity of the antibody, to provide a site for covalent or non-covalent binding to another molecule, to add or remove one or more glycosylation sites or to alter such properties as complement fixation, FcR binding and antibody-dependent cell-mediated cytotoxicity (ADCC). A single antibody may have mutations in any one or more of the CDRs or framework regions of the variable domain or in the constant domain.

In some cases, there are from 1 to 8, including any number in between, amino acid mutations in either the $V_H$ or $V_L$ domains of the mutated anti-CCR2 antibody compared to the anti-CCR2 antibody prior to mutation. In any of the above, the mutations may occur in one or more CDRs. Further, any of the mutations can be conservative amino acid substitutions. In some cases, there are no more than 5, 4, 3, 2, or 1 amino acid change in the constant domains.

Modified Antibodies

In another aspect, a fusion antibody or immunoadhesin may be made that comprises all or a portion of an anti-CCR2 antibody linked to another polypeptide. In one case, only the variable domains of the anti-CCR2 antibody are linked to the polypeptide. In still another case, the $V_H$ domain of an anti-CCR2 antibody is linked to a first polypeptide, while the $V_L$ domain of an anti-CCR2 antibody is linked to a second polypeptide that associates with the first polypeptide in a manner such that the $V_H$ and $V_L$ domains can interact with one another to form an antigen binding site. In still another case, the $V_H$ domain is separated from the $V_L$ domain by a linker such that the $V_H$ and $V_L$ domains can interact with one another (see below under Single Chain Antibodies). The $V_H$-linker-$V_L$ antibody is then linked to the polypeptide of interest. The fusion antibody is useful for directing a polypeptide to a CCR2-expressing cell or tissue. The polypeptide may be a therapeutic agent, such as a toxin, chemokine or other regulatory protein, or may be a diagnostic agent, such as an enzyme that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody.

To create a single chain antibody (scFv), the $V_H$- and $V_L$-encoding DNA fragments are operatively linked to another fragment encoding a flexible linker, e.g., encoding the amino acid sequence (Gly$_4$-Ser)$_3$, such that the $V_H$ and $V_L$ sequences can be expressed as a contiguous single-chain protein, with the $V_L$ and $V_H$ domains joined by the flexible linker. See, e.g., Bird et al., *Science* 242:423-426 (1988); Huston et al., *Proc. Natl. Acad. Sci. USA* 85:5879-5883 (1988); McCafferty et al., *Nature* 348:552-554 (1990). The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to CCR2 and to another molecule.

In another aspect, other modified antibodies may be prepared using anti-CCR2 antibody encoding nucleic acid molecules. For instance, "Kappa bodies" (Ill et al., *Protein Eng.* 10: 949-57 (1997)), "Minibodies" (Martin et al., *EMBO J.* 13: 5303-9 (1994)), "Diabodies" (Holliger et al., *Proc. Natl. Acad. Sci. USA* 90: 6444-6448 (1993)), or "Janusins" (Traunecker et al., *EMBO J.* 10:3655-3659 (1991) and Traunecker et al., *Int. J. Cancer* (Suppl.) 7:51-52 (1992)) may be prepared using standard molecular biological techniques following the teachings of the specification.

Bispecific antibodies or antigen-binding fragments can be produced by a variety of methods including fusion of hybridomas or linking of Fab' fragments. See, e.g., Songsivilai & Lachmann, *Clin. Exp. Immunol.* 79: 315-321 (1990), Kostelny et al., *J. Immunol.* 148:1547-1553 (1992). In addition, bispecific antibodies may be formed as "diabodies" or "Janusins." In some cases, the bispecific antibody binds to two different epitopes of CCR2. In some cases, the bispecific antibody has a first heavy chain and a first light chain from monoclonal antibody 4.40, 4.9 or 4.40 A68G S230P and an additional antibody heavy chain and light chain. In some cases, the additional light chain and heavy chain also are from one of the above-identified monoclonal antibodies, but are different from the first heavy and light chains.

In some cases, the modified antibodies described herein are prepared using one or more of the variable domains or CDRs from a human anti-CCR2 monoclonal antibody provided herein.

Derivatized and Labeled Antibodies

An anti-CCR2 antibody or antigen-binding portion can be derivatized or linked to another molecule (e.g., another peptide or protein). In general, the antibodies or portion thereof are derivatized such that the CCR2 binding is not affected adversely by the derivatization or labeling. Accordingly, the antibodies and antibody portions are intended to include both intact and modified forms of the human anti-CCR2 antibodies described herein. For example, an antibody or antibody portion can be functionally linked (by chemical coupling, genetic fusion, noncovalent association or otherwise) to one or more other molecular entities, such as another antibody (e.g., a bispecific antibody or a diabody), a detection agent, a cytotoxic agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Another type of derivatized antibody is a labeled antibody. Useful detection agents with which an antibody or antigen-binding portion may be derivatized include fluorescent compounds, including fluorescein, fluorescein isothiocyanate, rhodamine, phycoerythrin, 5-dimethylamine-1-napthalene-sulfonyl chloride, lanthanide phosphors and the like. An antibody can also be labeled with enzymes that are useful for detection, such as horseradish peroxidase, β-galactosidase, luciferase, alkaline phosphatase, glucose oxidase and the like. When an antibody is labeled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody can also be labeled with biotin, and detected through indirect measurement of avidin or streptavidin binding. An antibody can also be labeled with a predetermined polypeptide epitope recognized by a secondary reporter (e.g., leucine zipper pair sequences, binding sites for secondary antibodies, metal binding domains, epitope tags). In some cases, labels are attached by spacer arms of various lengths to reduce potential steric hindrance.

An anti-CCR2 antibody can also be labeled with a radiolabeled amino acid. The radiolabel can be used for both diagnostic and therapeutic purposes. For instance, the radiolabel can be used to detect CCR2-expressing tumors by X-ray or other diagnostic techniques. Further, the radiolabel can be used therapeutically as a toxin for cancerous cells or tumors. Examples of labels for polypeptides include, but are not limited to, the following radioisotopes or radionuclides—$^{3}$H, $^{14}$C, $^{15}$N, $^{35}$S, $^{90}$Y, $^{99}$Tc, $^{111}$In, $^{125}$I and $^{131}$I.

An anti-CCR2 antibody can also be derivatized with a chemical group such as polyethylene glycol (PEG), a methyl or ethyl group, or a carbohydrate group. These groups are useful to improve the biological characteristics of the antibody, e.g., to increase serum half-life or to increase tissue binding.

In some cases, the anti-CCR2 antibody can be labeled with a paramagnetic, radioactive or fluorogenic ion or moiety that is detectable upon imaging.

In some cases, the paramagnetic ion is chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). In other cases, the radioactive ion is iodine123, technetium99, indium111, rhenium188, rhenium186, copper67, iodine131, yttrium90, iodine125, astatine211, and gallium67. In other cases, the anti-CCR2 antibody is labeled with an X-ray imaging agent such as lanthanum (III), gold (III) lead (II) and bismuth (III).

Pharmaceutical Compositions and Kits

Compositions comprising a human anti-CCR2 antibody with antagonist properties are provided. Such compositions are useful to treat a condition in which CCR2 has a role, including, but not limited to, liver fibrosis, renal fibrosis, pulmonary fibrosis, psoriasis; inflammatory disorders, allergic disorders, autoimmune diseases, graft rejection disorders, atherosclerosis, obesity, HIV infection, neuropathic pain, inflammation associated with ischemia, stenosis and restenosis, cancer, sepsis, scleroderma, and diabetes. In some cases, the treatment is of liver fibrosis mediated by hepatitis C virus (HCV), hepatitis B virus (HBV), non-alcohol steatohepatitis (NASH), and/or alcohol induced steatohepatitis (ASH). In some cases, the subject is in need of a reduction of leukocyte infiltration into tissues, such as tissues that are the sites of inflammatory responses. In some cases, the subject of treatment is a human. In other cases, the subject is a veterinary subject. Examples of tissues in need of reduced inflammation or reduced leukocyte infiltration include but are not limited to, connective tissue, cartilage, liver, lung, kidney, neural tissue including brain, spinal cord, and peripheral neural tissue, heart, blood vessels, esophagus, stomach, small intestine, large intestine, colon, prostate, pancreas, urinary tract, ovaries, breasts, uterus, testis, penis, bone, muscle, thyroid gland, adrenal gland, pituitary, adipose tissue, bone marrow, blood, thymus, spleen, lymph nodes, skin, eye, ear or nose. In one case, the tissues are tissues having mucosal surfaces.

As used herein, "pharmaceutically acceptable carrier" means any and all solvents, dispersion media, coatings, antibacterial and antifungal agents, isotonic and absorption delaying agents, and the like that are physiologically compatible. Some examples of pharmaceutically acceptable carriers merely by way of illustration, are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

The compositions may be in a variety of forms, for example, liquid, semi-solid and solid dosage forms, such as liquid solutions (e.g., injectable and infusible solutions), dispersions or suspensions, tablets, pills, powders, liposomes and suppositories. The form depends on the intended mode of administration and therapeutic application. Typical compositions are in the form of injectable or infusible solutions, such as compositions similar to those used for passive immunization of humans. The preferred mode of administration is parenteral (e.g., intravenous, subcutaneous, intraperitoneal, intramuscular). In one case, the antibody is administered by intravenous infusion or injection. In still another case, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the anti-CCR2 antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies may be administered by a variety of methods known in the art, although for many therapeutic applications, the preferred route/mode of administration is subcutaneous, intramuscular, or intravenous infusion. As will be appreciated by the skilled artisan, the route and/or mode of administration will vary depending upon the desired results. Other modes of administration include intraperitoneal, intrabronchial, transmucosal, intraspinal, intrasynovial, intraaortic, intranasal, ocular, otic, topical and buccal, and intratumor.

In certain cases, the active compound of the antibody compositions may be prepared with a carrier that will protect the antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems* (J. R. Robinson, ed., Marcel Dekker, Inc., New York, 1978).

Additional active compounds also can be incorporated into the compositions. In certain cases, an inhibitory anti-CCR2 antibody is co-formulated with and/or co-administered with one or more additional therapeutic, diagnostic, or prophylactic agents. Therapeutic agents include, without limitation, an anti-CCR2 antibody with a different fine specificity, antibodies that bind other targets, photosensitizers, androgen, estrogen, nonsteroidal anti-inflammatory agents, antihypertensive agents, analgesic agents, antidepressants, antibiotics, anti-cancer agents, anesthetics, anti-emetics, anti-infectants, contraceptives, anti-diabetic agents, steroids, anti-allergy agents, chemotherapeutic agents, anti-migraine agents, agents for smoking cessation, anti-viral agents, immunosuppressants, thrombolytic agent, cholesterol-lowering agents and anti-obesity agents.

Therapeutic agents also include peptide analogues that inhibit CCR2, antibodies or other molecules that bind to MCP-1, MCP-2, MCP-3 or MCP-4 and prevent their binding to CCR2, and agents that inhibit CCR2 expression. In one case, the additional agents that inhibit CCR2 expression comprise an antisense nucleic acid capable of hybridizing to a CCR2 mRNA, such as a hairpin RNA or siRNA. Sequence-specific nucleic acids capable of inhibiting gene function by RNA interference are well-known in the art. Such combination therapies may require lower dosages of the inhibitory anti-CCR2 antibody as well as the co-administered agents, thus avoiding possible toxicities or complications associated with the various monotherapies.

In certain specific cases, the therapeutic agent(s) that is co-formulated with and/or co-administered with an inhibitory anti-CCR2 antibody is an antimicrobial agent. Antimicrobial agents include antibiotics (e.g. antibacterial), antiviral agents, antifungal agents, and anti-protozoan agents. Non-limiting examples of antimicrobial agents are sulfonamides, trimethoprim-sulfamethoxazole, quinolones, penicillins, and cephalosporins.

In certain specific cases, the therapeutic agent(s) that is co-formulated with and/or co-administered with an inhibitory anti-CCR2 antibody and a chemokine antagonist, a CCR2 antagonist, a MCP-1 antagonist or a CCR5 antagonist. The CCR2 antagonist or a MCP-1 antagonist include, but are not limited to: antibodies directed to MCP-1 (U.S. Pat. No. 7,202,343, US2005/0025768, US2006/0039913, US2006/0246069, & US2004/004/0047860); tetrahydropyranyl cyclopentyl benzylamide compounds (US2006/0116421); heterrarylpperdine compounds (US2005/0250781); piperidi- nyl cyclopentyl aryl benzylamide compounds (US2006/0173013); cyclic amine compounds (U.S. Pat. No. 6,140,349 & U.S. Pat. No. 6,476,054); cyclopentyl compounds (US2002/0049222 & U.S. Pat. No. 6,545,023); tetrahydropyranyl cyclopentyl tetrahydorpyridopypridine compounds (US2004/0167156, U.S. Pat. No. 6,812,234 & U.S. Pat. No. 7,230,008); aminocyclopentyl fused heterotricyclicamide compounds (US2007/0004714); piperidinyl-alpha-aminoamide compounds (US2005/0250814); substituted pyrazole compounds (WO06/88813); tetrahydropyranyl cyclopentyl heterocyclic amide compounds (US2006/0178363); 7 and 8 membered heterocyclic cyclopentyl benzylamide compounds (US2006/0183731); benzoxazinyl-amidocyclopentyl-heterocyclic compounds (US2006/0069088); 3-aminocyclopentanecarboxamide compounds (US2007/0149532); nitrogen containing heterocyclic compounds (US2007/0155713); triazolyl phenyl bensenesulonamide compounds (WO08/10934); substituted pyrrolinde derivates (US2004/0186140); substituted benzamide and substituted phenylcarbamate derivatives (U.S. Pat. No. 7,087,604); substituted cycloalkylamine compounds (US2005/0054626); substituted bicycloalkylamine compounds (US2005/0227960); pyrrolidinone and pyrrolidine-thione compounds (US2003/0149081, U.S. Pat. No. 6,727,275 & U.S. Pat. No. 6,936,633); mercaptoimidazole compounds (US2007/0244138); substituted dipiperidine compounds (US2007/0197590); phenylamino substituted quaternary salt compounds (US2006/0293379); bicyclic and bridged nitrogen heterocycles (US2006/0074121); 3-aminocyclopentanecarboxamide compounds (US2006/0020133); 3-(4-heteroarylcyclohexylamino)cyclopentanecarboxamide compounds (US2005/0267146); triazolo compounds (U.S. Pat. No. 6,492,364); heteroaryl sulfonamide compounds (US2006/0173019); aryl sulfonamides (U.S. Pat. No. 6,939,885); bis-aryl sulfonamides (U.S. Pat. No. 7,227,035 & US2004/0167113); substituted benzamide compounds (U.S. Pat. No. 6,821,964); substituted diazepam compounds (US2007/0249589); Triazaspiro[5.5]undecane derivatives (US2005/267114); substituted piperidinecarboxamide compounds (US2003/0114443 & U.S. Pat. No. 6,562,978); benzazepine derivatives (US2004/0235822 & U.S. Pat. No. 7,262,185);

In selected cases the chemokine antagonist co-formulated or co-administered with the CCR2 antibodies is SELZENTRY™ (Maraviroc), which is chemically described as 4,4-difluoro-N-{(1S)-3-[exo-3-(3-isopropyl-5-methyl-4H-1,2,4-triazol-4-yl)-8-azabicyclo[3.2.1]oct-8-yl]-1-phenylpropyl}cyclohexanecarboxamide:

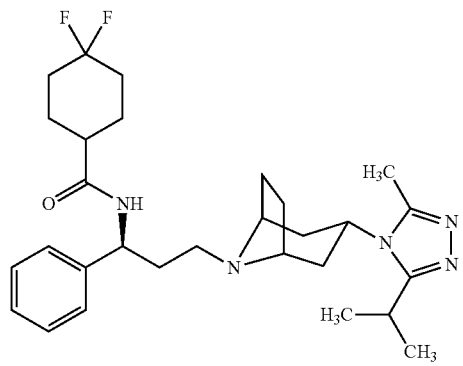 [SMILES: Cc1nnc(C(C)C)n1C1CC2CCC(C1)N2CC[C@H](NC(=O)C1CCC(F)(F)CC1)c1ccccc1]

In certain specific cases, the therapeutic agent(s) that is co-formulated with and/or co-administered with an inhibitory anti-CCR2 antibody is a CB-1 receptor antagonist. As used herein, the term "CB-1 receptor" refers to a G-protein coupled type 1 cannabinoid receptor. The term "antagonist" includes both full antagonists and partial antagonists, as well as inverse agonists. The CB-1 receptor antagonist may be selective to the CB-1 receptor. "CB-1 receptor selective" means that the compound has little or no activity to antagonize the cannabinoid-2 receptor (CB-2). The CB-1 antagonist may be at least about 10 fold selective for the CB-1 receptor in comparison to the CB-2 receptor. For example, the inhibitory concentration (IC50) for antagonizing the CB-1 receptor is about 10 or more times lower than the IC50 for antagonizing the CB-2 receptor. Suitable CB-1 receptor antagonists include compounds disclosed in U.S. Pat. Nos. 5,462,960; 5,596,106; 5,624,941; 5,747,524; 6,017,919; 6,028,084; 6,432,984; 6,476,060; 6,479,479; 6,518,264; and 6,566,356; U.S. Patent Publication Nos. 2003/0114495; 2004/0077650; 2004/0092520; 2004/0122074; 2004/0157838; 2004/0157839; 2004/0214837; 2004/0214838; 2004/0214855; 2004/0214856; 2004/0058820: 2004/0235926; 2004/0259887; 2005/0080087; 2005/0026983 and 2005/0101592; PCT Patent Publication Nos. WO 03/075660; WO 02/076949; WO 01/029007; WO 04/048317; WO 04/058145; WO 04/029204; WO 04/012671; WO 03/087037; WO 03/086288; WO 03/082191; WO 03/082190; WO 03/063781; WO 04/012671; WO 04/013120; WO 05/020988; WO 05/039550; WO 05/044785; WO 05/044822; and WO 05/049615: PCT Patent Application Serial Nos. PCT/IB2004/004050 filed on Dec. 6, 2004; PCT/IB2004/004017 filed on Dec. 6, 2004; PCT/IB2004/004023 filed on Dec. 6, 2004; and PCT/IB2004/004019 filed on Dec. 6, 2004; and U.S. Provisional Application Nos. 60/523,937 filed on Nov. 21, 2003; 60/529,908 filed on Dec. 16, 2003; 60/529,909 filed on Dec. 16, 2003; 60/529,910 filed on Dec. 16, 2003; 60/530,012 filed on Dec. 16, 2003; and 60/564,648 filed on Apr. 21, 2004. All of the above patents and patent applications are incorporated herein by reference. Preferred CB-1 receptor antagonists for use in the methods include: rimonabant (SR141716A also known under the tradename Acomplia™) is available from Sanofi-Synthelabo or can be prepared as described in U.S. Pat. No. 5,624,941; N-(piperidin-1-yl)-1-(2,4-dichlorophenyl)-5-(4-iodophenyl)-4-methyl-1H-pyrazole-3-carboxamide (AM251) is available from Tocris™, Ellisville, Mo.; [5-(4-bromophenyl)-1-(2,4-dichloro-phenyl)-4-ethyl-N-(1-piperidinyl)-1H-pyrazole-3-carboxamide] (SR147778) which can be prepared as described in U.S. Pat. No. 6,645,985; N-(piperidin-1-yl)-4,5-diphenyl-1-methylimidazole-2-carboxamide, N-(piperidin-1-yl)-4-(2,4-dichlorophenyl)-5-(4-chlorophenyl)-1-methylimidazole-2-carboxamide, N-(piperidin-1-yl)-4,5-di-(4-methylphenyl)-1-methylimidazole-2-carboxamide, N-cyclohexyl-4,5-di-(4-methylphenyl)-1-methylimidazole-2-carboxamide, N-(cyclohexyl)-4-(2,4-dichlorophenyl)-5-(4-chlorophenyl)-1-methylimidazole-2-carboxamide, and N-(phenyl)-4-(2,4-dichlorophenyl)-5-(4-chlorophenyl)-1-methylimidazole-2-carboxamide which can be prepared as described in PCT Patent Publication No. WO 03/075660; the hydrochloride, mesylate and besylate salt of 1-[9-(4-chloro-phenyl)-8-(2-chloro-phenyl)-9H-purin-6-yl]-4-ethylamino-piperidine-4-carboxylic acid which can be prepared as described in U.S. Patent Publication No. 2004/0092520; 1-[7-(2-chloro-phenyl)-8-(4-chloro-phenyl)-2-methyl-pyrazolo[1,5-a][1,3,5]triazin-4-yl]-3-ethylamino-azetidine-3-carboxylic acid amide and 1-[7-(2-chloro-phenyl)-8-(4-chloro-phenyl)-2-methyl-pyrazolo[1,5-a][1,3,5]triazin-4-yl]-3-methylamino-azetidine-3-carboxylic acid amide which can be prepared as described in U.S. Patent Publication No. 2004/0157839; 3-(4-chloro-phenyl)-2-(2-chloro-phenyl)-6-(2,2-difluoro-propyl)-2,4,5,6-tetrahydro-pyrazolo[3,4-c]pyridin-7-one, 2-(2-chloro-phenyl)-3-(4-ethyl-phenyl)-5-(2,2,2-trifluoro-ethyl)-4,5-dihydro-2H-pyrrolo[3,4-c]pyrazol-6-one, and 2-(2-chloro-phenyl)-3-(4-isopropyl-phenyl)-5-(2,2,2-trifluoro-ethyl)-4,5-dihydro-2H-pyrrolo[3,4-c]pyrazol-6-one which can be prepared as described in U.S. Patent Publication No. 2004/0214855; 3-(4-chloro-phenyl)-2-(2-chloro-phenyl)-7-(2,2-difluoro-propyl)-6,7-dihydro-2H,5H-4-oxa-1,2,7-triaza-azulen-8-one which can be prepared as described in U.S. Patent Publication No. 2005/0101592; 2-(2-chloro-phenyl)-6-(2,2,2-trifluoro-ethyl)-3-(4-trifluoromethyl-phenyl)-2,6-dihydro-pyrazolo[4,3-d]pyrimidin-7-one which can be prepared as described in U.S. Patent Publication No. 2004/0214838; (S)-4-chloro-N-{[3-(4-chloro-phenyl)-4-phenyl-4,5-dihydro-pyrazol-1-yl]-methylamino-methylene}-benzenesulfonamide (SLV-319) and (S)—N-{[3-(4-chloro-phenyl)-4-phenyl-4,5-dihydro-pyrazol-1-yl]-methylamino-methylene}-4-trifluoromethyl-benzenesulfonamide (SLV-326) which can be prepared as described in PCT Patent Publication No. WO 02/076949; N-piperidino-5-(4-bromophenyl)-1-(2,4-dichlorophenyl)-4-ethylpyrazole-3-carboxamide which can be prepared as described in U.S. Pat. No. 6,432,984; 1-[bis-(4-chloro-phenyl)-methyl]-3-[(3,5-difluoro-phenyl)-methanesulfonyl-methylene]-azetidine which can be prepared as described in U.S. Pat. No. 6,518,264; 2-(5-(trifluoromethyl)pyridin-2-yloxy)-N-(4-(4-chlorophenyl)-3-(3-cyanophenyl)butan-2-yl)-2-methylpropanamide which can be prepared as described in PCT Patent Publication No. WO 04/048317; 4-{[6-methoxy-2-(4-methoxyphenyl)-1-benzofuran-3-yl]carbonyl}benzonitrile (LY-320135) which can be prepared as described in U.S. Pat. No. 5,747,524; 1-[2-(2,4-dichlorophenyl)-2-(4-fluorophenyl)-benzo[1,3]dioxole-5-sulfonyl]-piperidine which can be prepared as described in WO 04/013120; and [3-amino-5-(4-chlorophenyl)-6-(2,4-dichlorophenyl)-furo[2,3-b]pyridin-2-yl]-phenyl-methanone which can be prepared as described in WO 04/012671.

In certain specific cases, the therapeutic agent(s) that is co-formulated with and/or co-administered with an inhibitory anti-CCR2 antibody is an angiogenic factor. Angiogenic factors include, but are not limited to, basic fibroblast growth factor, acidic fibroblast growth factor, vascular endothelial growth factor, angiogenin, transforming growth factor α and β tumor necrosis factor, angiopoietin, platelet-derived growth factor, placental growth factor, hepatocyte growth factor, and proliferin.

In certain specific cases, the therapeutic agent(s) that is co-formulated with and/or co-administered with an inhibitory anti-CCR2 antibody is an thrombolytic agent. Thrombolytic agents include, but are not limited to, urokinase plasminogen activator, urokinase, streptokinase, inhibitors of α2-plasmin inhibitor, and inhibitors of plasminogen activator inhibitor-1, angiotensin converting enzyme (ACE) inhibitors, spironolactone, tissue plasminogen activator (tPA), an inhibitor of interleukin 1β-converting enzyme, anti-thrombin III, and the like.

In certain specific cases, the therapeutic agent(s) that is co-formulated with and/or co-administered with an inhibitory anti-CCR2 antibody is an anti-obesity agent. Anti-obesity agents include, but are not limited to, an apo-B/MTP inhibitor, a 11β-hydroxy steroid dehydrogenase-1 inhibitor, peptide $YY_{3-36}$ or an analog thereof, a MCR-4 agonist, a CCK-A agonist, a monoamine reuptake inhibitor, a sympathomimetic agent, a $β_3$ adrenergic receptor agonist, a dopamine agonist, a melanocyte-stimulating hormone receptor analog, a 5-HT2c receptor agonist, a melanin concentrating hormone antagonist, leptin, a leptin analog, a leptin receptor agonist, a galanin antagonist, a lipase inhibitor, a bombesin agonist, a neuropeptide-Y receptor antagonist, a thyromimetic agent, dehydroepiandrosterone or analog thereof, a glucocorticoid receptor antagonist, an orexin receptor antagonist, a glucagon-like peptide-1 receptor agonist, a ciliary neurotrophic factor, a human agouti-related protein antagonist, a ghrelin receptor antagonist, a histamine 3 receptor antagonist or inverse agonist, and a neuromedin U receptor agonist.

In certain specific cases, the therapeutic agent(s) that is co-formulated with and/or co-administered with an inhibitory anti-CCR2 antibody is a agent which inhibits the recruitment and/or adhesion of neutrophils and/or mononuclear cells to a site of vascular injury. Such therapeutic agents can, for example, inhibit the activity (e.g., binding activity, signaling activity) of a cell surface molecule through which cellular adhesion, chemotaxis and/or homing are mediated. For example, antagonists of cellular adhesion molecules (e.g., integrins (e.g., β1, β2, β3, β4, β5, β6, β7, β8 integrins), selectins (e.g., E-selectin, P-selectin, L-selectin), cadherins (e.g., E-, P-, N-cadherins) and immunoglobulin superfamily adhesion molecules (e.g., LFA-2, LFA-3, CD44)) and antagonists of cytokine receptors (e.g., antagonists of chemokine receptor function) can be co-formulated with and/or co-administered with an inhibitory anti-CCR2 antibody. In addition, agents which bind to ligands of cellular adhesion molecules or cytokines or chemokines and inhibit the binding of ligand to receptors expressed on neutrophils and/or mononuclear cells can also be co-formulated with and/or co-administered with an inhibitory anti-CCR2 antibody.

In certain specific cases, the therapeutic agent(s) that is co-formulated with and/or co-administered with an inhibitory anti-CCR2 antibody is an cardiac therapeutic agent. Exemplary therapeutic agents intended to treat cardiac disorders include, but are not limited to, growth factors, angiogenic agents, calcium channel blockers, antihypertensive agents, inotropic agents, antiatherogenic agents, anti-coagulants, β-blockers, anti-arrhythmia agents, cardiac glycosides, anti-inflammatory agents, antibiotics, antiviral agents, antifungal agents and agents that inhibit protozoan infections, and antineoplastic agents.

In certain specific cases, the cardiac therapeutic agent(s) that is co-formulated with and/or co-administered with an inhibitory anti-CCR2 antibody is a calcium channel blocker. Calcium channel blockers include, but are not limited to, dihydropyridines such as nifedipine, nicardipine, nimodipine, and the like; benzothiazepines such as dilitazem; phenylalkylamines such as verapamil; diarylaminopropylamine ethers such as bepridil; and benzimidole-substituted tetralines such as mibefradil.

In certain specific cases, the cardiac therapeutic agent(s) that is co-formulated with and/or co-administered with an inhibitory anti-CCR2 antibody is an antihypertensive agent. Antihypertensive agents include, but are not limited to, diuretics, including thiazides such as hydroclorothiazide, furosemide, spironolactone, triamterene, and amiloride; antiadrenergic agents, including clonidine, guanabenz, guanfacine, methyldopa, trimethaphan, reserpine, guanethidine, guanadrel, phentolamine, phenoxybenzamine, prazosin, terazosin, doxazosin, propanolol, methoprolol, nadolol, atenolol, timolol, betaxolol, carteolol, pindolol, acebutolol, labetalol; vasodilators, including hydralizine, minoxidil, diazoxide, nitroprusside; and angiotensin converting enzyme inhibitors, including captopril, benazepril, enalapril, enalaprilat, fosinopril, lisinopril, quinapril, ramipril; angiotensin receptor antagonists, such as losartan; and calcium channel antagonists, including nifedine, amlodipine, felodipine XL, isadipine, nicardipine, benzothiazepines (e.g., diltiazem), and phenylalkylamines (e.g. verapamil).

In certain specific cases, the cardiac therapeutic agent(s) that is co-formulated with and/or co-administered with an inhibitory anti-CCR2 antibody is an anti-coagulant. Anticoagulants include, but are not limited to, heparin, warfarin, hirudin, tick anti-coagulant peptide, low molecular weight heparins such as enoxaparin, dalteparin, and ardeparin, ticlopidine, danaparoid, argatroban, abciximab and tirofiban.

In certain specific cases, the cardiac therapeutic agent(s) that is co-formulated with and/or co-administered with an inhibitory anti-CCR2 antibody is an antiarrhythmic agent. Antiarrhythmic agents include, but are not limited to, sodium channel blockers (e.g., lidocaine, procainamide, encainide, flecanide, and the like), beta adrenergic blockers (e.g., propranolol), prolongers of the action potential duration (e.g., amiodarone), and calcium channel blockers (e.g., verpamil, diltiazem, nickel chloride, and the like). Delivery of cardiac depressants (e.g., lidocaine), cardiac stimulants (e.g., isoproterenol, dopamine, norepinephrine, etc.), and combinations of multiple cardiac agents (e.g., digoxin/quinidine to treat atrial fibrillation) is also of interest.

In certain specific cases, the cardiac therapeutic agent(s) that is co-formulated with and/or co-administered with an inhibitory anti-CCR2 antibody is an agent for treating congestive heart failure. Agents for treating congestive heart failure include, but are not limited to, a cardiac glycoside, inotropic agents, a extracellular loop diuretic, a thiazide diuretic, a potassium ion sparing diuretic, an angiotensin converting enzyme inhibitor, an angiotensin receptor antagonist, a nitro vasodilator, a phosphodiesterase inhibitor, a direct vasodilator, an α1-adrenergic receptor antagonist, a calcium channel blocker, and a sympathomimetic agent.

In certain specific cases, the cardiac therapeutic agent(s) that is co-formulated with and/or co-administered with an inhibitory anti-CCR2 antibody is an agent suitable for treating cardiomyopathies, such as but not limited to, dopamine, epinephrine, norepinephrine, and phenylephrine.

Also included are compositions for inhibiting viral infection, and in particular HIV-infection, in a mammal comprising an amount of an antibody in combination with an amount of an antiviral agent, wherein the amounts of the anti-CCR2 antibody and of antiviral agent are together effective in inhibiting viral replication, viral infection of new cells or viral loads. Many antiviral agents are presently known in the art, including nucleoside analogues (e.g., AZT, 3TC, and ddI), protease inhibitors and chemokine receptor antagonists may inhibit HIV infection but not viral infections.

In another aspect, the anti-CCR2 antibody or fragment thereof may be co-administered with other therapeutic agents, such as antiinflammatory drugs or molecules, to a patient who has a inflammatory disorder, such as arthritis, atherosclerosis or multiple sclerosis. In one aspect, methods for the treatment of the inflammatory disorder in a mammal comprising administering to said mammal a therapeutically effective amount of a compound in combination with an antiinflammatory agent are provided. Antiinflammatory agents include, but are not limited to, any known nonsteroidal antiinflammatory agent such as, salicylic acid derivatives (aspirin), para-aminophenol derivatives (acetaminophen), indole and indene acetic acids (indomethacin), heteroaryl acetic acids (ketorolac), arylpropionic acids (ibuprofen), anthranilic acids (mefenamic acid), enolic acids (oxicams) and alkanones (nabumetone) and any known steroidal antiinflammatory agent which include corticosteriods and biologically active synthetic analogs with respect to their relative glucocorticoid (metabolic) and mineralocorticoid (electrolyte-regulating) activities. In another case, the anti-CCR2 antibody is administered in combination with a non-steroidal anti-inflammatory drug such as aspirin (Bayer, Bufferin), ibuprofen (Motrin, Advil), naproxen sodium (Aleve), ketoprofen (Orudis KT), indomethacin (Indocin), etodolac (Lodine), diclofenac sodium (Voltaren), rofecoxib (Vioxx), celecoxib (Celebrex), nabumetone (Relafen) or in combination with a steroid such as prednisone, prednisolone, dexamethasone, beclomethasone, budesonide, fluticasone or triamcinolone.

Additionally, other drugs used in the therapy of inflammation include but are not limited to antagonists such as all histamine and bradykinin receptor antagonists, leukotriene and prostaglandin receptor antagonists, and platelet activating factor receptor antagonists. In still another case, the antibody or combination therapy is administered along with radiotherapy, chemotherapy, photodynamic therapy, surgery or other immunotherapy treatment i.e. therapy targeting the immune system. In yet still another case, the antibody will be administered with another antibody. For example, the anti-CCR2 antibody may be administered with an antibody or other agent that is known to inhibit inflammation, e.g., an antibody or agent that inhibits alpha-4 integrin (US2004/0009169) or IL-8 receptor (US2004/0037830). Additional antibodies that may be coadministered with the anti-CCR2 antibodies are described in U.S. Pat. Nos. 6,696,550; 6,406,865; 6,352,832; and 6,084,075, the contents of which are incorporated by reference herein.

The compositions may include a "therapeutically effective amount" or a "prophylactically effective amount" of an antibody or antigen-binding portion. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount may be less than the therapeutically effective amount.

Dosage regimens can be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the anti-CCR2 antibody or portion thereof and the particular therapeutic or prophylactic effect to be achieved, and (b) the limitations inherent in the art of compounding such an antibody for the treatment of sensitivity in individuals.

An exemplary, non-limiting range for a therapeutically or prophylactically-effective amount of an antibody or antibody portion is 0.025 to 50 mg/kg, 0.1 to 50 mg/kg, 0.1-25, 0.1 to 10 or 0.1 to 3 mg/kg. In one case, the antibody is administered in a formulation as a sterile aqueous solution having a pH that ranges from about 5.0 to about 6.5 and comprising from about 1 mg/ml to about 200 mg/ml of antibody, from about 1 millimolar to about 100 millimolar of histidine buffer, from about 0.01 mg/ml to about 10 mg/ml of polysorbate 80 or polysorbate 20, from about 100 millimolar to about 400 millimolar of a non-reducing sugar selected from but not limited to trehalose or sucrose, from about 0.01 millimolar to about 1.0 millimolar of disodium EDTA dihydrate and optionally comprise a pharmaceutically acceptable antioxidant in addition to a chelating agent. Suitable antioxidants include, but are not limited to, methionine, sodium thiosulfate, catalase, and platinum. For example, the composition may contain methionine in a concentration that ranges from 1 mM to about 100 mM, and in particular, is about 27 mM. In some cases, a formulation contains 5 mg/ml of antibody in a buffer of 20 mM sodium citrate, pH 5.5, 140 mM NaCl, and 0.2 mg/ml polysorbate 80. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Another aspect provides kits comprising an anti-CCR2, or antigen-binding portion, or a composition comprising such an antibody or antigen-binding fragment. A kit may include, in addition to the antibody or composition, diagnostic or therapeutic agents. A kit can also include instructions for use in a diagnostic or therapeutic method, as well as packaging material such as, but not limited to, ice, dry ice, STYROFOAM™, foam, plastic, cellophane, shrink wrap, bubble wrap, cardboard and starch peanuts. In one case, the kit includes the antibody or a composition comprising it and a diagnostic agent that can be used in a method described herein. In still another case, the kit includes the antibody or a composition comprising it and one or more therapeutic agents that can be used in a method described herein.

Compositions and kits for inhibiting cancer in a mammal comprising an amount of an antibody in combination with an amount of a chemotherapeutic agent, wherein the amounts of the compound, salt, solvate, or prodrug, and of the chemotherapeutic agent are together effective in inhibiting abnormal cell growth are provided. Many chemotherapeutic agents are presently known in the art. In some cases, the chemotherapeutic agent is selected from the group consisting of mitotic inhibitors, alkylating agents, anti-metabolites, intercalating antibiotics, chemokine inhibitors, cell cycle inhibitors, enzymes, topoisomerase inhibitors, biological response modifiers, anti-hormones, e.g., anti-androgens, and anti-angiogenesis agents.

Diagnostic Methods of Use

In another aspect, diagnostic methods are provided. The anti-CCR2 antibodies can be used to detect CCR2 in a biological sample in vitro or in vivo. In one case, a method is provided for diagnosing the presence or location of an CCR2-expressing cells in a subject in need thereof, comprising the steps of injecting the antibody into the subject, determining the expression of CCR2 in the subject by localizing where the antibody has bound, comparing the expression in the subject with that of a normal reference subject or standard, and diagnosing the presence or location of the cells. The anti-CCR2 antibodies may also be used as a marker for inflammation and/or for the infiltration of immune cells, such as monocytes, into a tissue.

The anti-CCR2 antibodies can be used in a conventional immunoassay, including, without limitation, an ELISA, an RIA, flow cytometry, tissue immunohistochemistry, Western blot or immunoprecipitation. The anti-CCR2 antibodies may be used to detect CCR2 from humans. In another case, the anti-CCR2 antibodies may be used to detect CCR2 from cynomolgus monkeys or rhesus monkeys. In another case, the anti-CCR2 antibodies may be used to detect CCR2 from rodents, such as mice and rats.

Also provided is a method for detecting CCR2 in a biological sample comprising contacting the biological sample with an anti-CCR2 antibody and detecting the bound antibody. In one case, the anti-CCR2 antibody is directly labeled with a detectable label. In another case, the anti-CCR2 antibody (the first antibody) is unlabeled and a second antibody or other molecule that can bind the anti-CCR2 antibody is labeled. As is well known to one of skill in the art, a second antibody is chosen that is able to specifically bind the particular species and class of the first antibody. For example, if the anti-CCR2 antibody is a human IgG, then the secondary antibody could be an anti-human-IgG. Other molecules that can bind to antibodies include, without limitation, Protein A and Protein G, both of which are available commercially, e.g., from Pierce Chemical Co.

Suitable labels for the antibody or secondary antibody have been disclosed supra, and include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S or $^{3}$H.

In other cases, CCR2 can be assayed in a biological sample by a competition immunoassay utilizing CCR2 standards labeled with a detectable substance and an unlabeled anti-CCR2 antibody. In this assay, the biological sample, the labeled CCR2 standards and the anti-CCR2 antibody are combined and the amount of labeled CCR2 standard bound to the unlabeled antibody is determined. The amount of CCR2 in the biological sample is inversely proportional to the amount of labeled CCR2 standard bound to the anti-CCR2 antibody.

One can use the immunoassays disclosed above for a number of purposes. For example, the anti-CCR2 antibodies can be used to detect CCR2 in cultured cells. In one case, the anti-CCR2 antibodies are used to determine the amount of CCR2 on the surface of cells that have been treated with various compounds. This method can be used to identify compounds that modulate CCR2 protein levels. According to this method, one sample of cells is treated with a test compound for a period of time while another sample is left untreated. If the total CCR2 expression is to be measured, the cells are lysed and the total CCR2 expression is measured using one of the immunoassays described herein. The total CCR2 expression in the treated versus the untreated cells is compared to determine the effect of the test compound.

A preferred immunoassay for measuring total CCR2 expression is flow cytometry or immunohistochemistry. If the cell surface CCR2 expression is to be measured, the cells are not lysed, and the cell surface levels of CCR2 are measured using one of the immunoassays described herein. A preferred immunoassay for determining cell surface levels of CCR2 includes the steps of labeling the cell surface proteins with a detectable label, such as biotin or $^{125}$I, immunoprecipitating the CCR2 with an anti-CCR2 antibody and then detecting the labeled CCR2.

Another immunoassay for determining the localization of CCR2, e.g., cell surface levels, is by using immunohistochemistry. An immunoassay to detect cell surface levels of CCR2 includes binding of an anti-CCR2 antibody labeled with an appropriate fluorophore, such as fluorescein or phycoerythrin, and detecting the primary antibody using flow cytometry. In another case, the anti-CCR2 antibody is unlabeled and a second antibody or other molecule that can bind the anti-CCR2 antibody is labeled. Methods such as ELISA, RIA, flow cytometry, Western blot, immunohistochemistry, cell surface labeling of integral membrane proteins and immunoprecipitation are well known in the art. See, e.g., Harlow and Lane, supra. In addition, the immunoassays can be scaled up for high throughput screening in order to test a large number of compounds for either activation or inhibition of CCR2.

The anti-CCR2 antibodies also can be used to determine the levels of CCR2 in a tissue or in cells derived from the tissue. In some cases, the tissue is a diseased tissue. In some cases, the tissue is a tissue biopsy. In some cases of the method, a tissue or a biopsy thereof is excised from a patient. The tissue or biopsy is then used in an immunoassay to determine, e.g., total CCR2 expression, cell surface levels of CCR2 or localization of CCR2 by the methods discussed above. Such methods can be used to determine whether a tissue expresses high levels of CCR2, which could be indicative that the tissue is a target for treatment with anti-CCR2 antibody.

The antibodies also can be used in vivo to identify tissues and organs that express CCR2. In some cases, the anti-CCR2 antibodies are used to identify CCR2-expressing cells.

The method comprises the steps of administering a detectably labeled anti-CCR2 antibody or a composition comprising them to a patient in need of such a diagnostic test and subjecting the patient to imaging analysis to determine the location of the CCR2-expressing tissues. Imaging analysis is well known in the medical art, and includes, without limitation, X-ray analysis, magnetic resonance imaging (MRI) or computed tomography (CT). The antibody can be labeled with any agent suitable for in vivo imaging, for example a contrast agent, such as barium, which can be used for X-ray analysis, or a magnetic contrast agent, such as a gadolinium chelate, which can be used for MRI or CT. Other labeling agents include, without limitation, radioisotopes, such as $^{99}$Tc. In another case, the anti-CCR2 antibody will be unlabeled and will be imaged by administering a second antibody or other molecule that is detectable and that can bind the anti-CCR2 antibody. In another case, a biopsy is obtained from the patient to determine whether the tissue of interest expresses CCR2.

In some cases, the detectably labeled anti-CCR2 comprises a fluorophore. In certain cases, the fluorophore is selected from the group consisting of a near-infrared fluorescent dye, dinitrophenyl, fluorescein and derivatives thereof, rhodamine, derivatives of rhodamine, phycoerythrin, phycocyanin, allophycocyanin, o-phthaldehyde and fluorescamine, TEXAS RED™, RHODAMINE GREEN™, OREGON GREEN™, CASCADE BLUE™, phycoerythrin, CY3™, CY5™, CY2™, CY7™, coumarin, infrared 40, MR 200, IRD 40, ALEXA FLUOR™, Tetramethylrhodamine, PACIFIC BLUE™, SYBR™, and BODIPY™. In another case, the flourophore includes one of the following compounds with their emission maxima indicated in nm in brackets, CY2™ (506), GFP (Red Shifted) (507), YO-PRO®-1 (509), YOYO®-1 (509), Calcein (517), FITC (518), FLUORX® (519), ALEXA® (520), Rhodamine 110 (520), 5-FAM (522), OREGON GREEN® 500 (522), OREGON GREEN® 488 (524), RIBOGREEN® (525), RHODAMINE GREEN® (527), Rhodamine 123 (529), MAGNESIUM GREEN® (531), CALCIUM GREEN® (533), TO-PRO®-1 (533), TOTO®-1 (533), JOE (548), BODIPY® 530/550 (550), Dil (565), BODIPY® (568), BODIPY® 558/568 (568), BODIPY® 564/570 (570), CY3® (570), ALEXA® 546 (570), TRITC (572), MAGNESIUM ORANGE® (575), Phycoerythrin R&B (575), Rhodamine Phalloidin (575), CALCIUM ORANGE® (576), Pyronin Y (580), Rhodamine B (580), TAMRA (582), RHODAMINE RED® (590), CY3.5® (596), ROX (608), CALCIUM CRIMSON™ (615), ALEXA® 594 (615), TEXAS RED™ (615), Nile Red (628), YO-PRO®-3 (631), YOYO®-3 (631), R-phycocyanin (642), C-Phycocyanin (648), TO-PRO®-3 (660), TOTO®-3 (660), DiD DilC(5) (665), CY5™ (670), Thiadicarbocyanine (671) and Cy5.5™ (694).

Therapeutic Methods of Use

In another aspect, provided are methods for inhibiting CCR2 activity by administering an anti-CCR2 antibody to a patient in need thereof. Any of the types of antibodies described herein may be used therapeutically. In various cases, the anti-CCR2 antibody is a human, chimeric or humanized antibody. In some cases, the antibody, or antigen-binding portion thereof, binds to the first and/or second extracellular loop of CCR2. The antibody, or antigen-binding portion thereof, preferably does not bind to the third extracellular loop or to the N-terminal domain of CCR2.

In still another case, the CCR2 is human and the patient is a human patient. Alternatively, the patient may be a mammal that expresses a CCR2 that the anti-CCR2 antibody cross-reacts with. The antibody may be administered to a non-human mammal expressing CCR2 with which the antibody cross-reacts for veterinary purposes or as an animal model of human disease. Such animal models may be useful for evaluating the therapeutic efficacy of antibodies.

In one aspect, methods are provided for treating, aiding in the treatment, preventing or aiding in the prevention of, a CCR2-mediated disorder in a subject by administering to the subject a therapeutically-effective amount of an anti-CCR2 antibody. As used herein, the term "a CCR2-mediated disorder" is intended to include diseases and other disorders in which the presence of high levels of CCR2 expression or activity in a subject suffering from the disorder have been shown to be, or are suspected of being, either responsible for the pathophysiology of the disorder or a factor that contributes to a worsening of the disorder. Such disorders may be evidenced, for example, by an increase in the levels of CCR2 on the cell surface in the affected cells or tissues of a subject suffering from the disorder, or by an increase in a CCR2-mediated activity in a cell type, such as in a basophil, monocyte or lymphocyte, that contributes to the pathology of the disorder or that contributes to the worsening of the disorder or by an increase in the level of CCR2 ligands, such as MCP-1, at an inflammatory site. The increase in CCR2 expression may be detected, for example, using an anti-CCR2 antibody. An increase in CCR2 activity may be detected by an increase in activation of G-protein, F-actin polymerization or increased chemotaxis of CCR2-expressing cells, such as chemotaxis in response to MCP-1 or other CCR2 ligands.

In one aspect, the CCR2-mediated disorder is characterized by fibrosis. The term "fibrosis" as used herein refers to a pathological condition characterized by excessive deposition and metabolism of fibrotic material (e.g., extracellular matrix) in response to tissue damage. In many cases, fibrosis represents a normal repair process (i.e., wound healing) gone awry due to chronic or excessive tissue insult leading to fibroblast or stellate cell activation and proliferation and collagen accumulation. Fibrosis conditions include fibroproliferative disorders that are associated with vascular diseases, such as cardiac disease, cerebral disease, and peripheral vascular disease, as well as all the main tissues and organ systems such as the eye, skin, kidney, lung, gut and liver (Wynn, *Nature Reviews* 4:583-594 (2004); Bataller, R and Brenner, D., *J. Clin. Invest.* 115:209-218 (2005)). Other sources are chemotherapeutic drugs, radiation-induced fibrosis, and injuries and burns. While fibrosis conditions cover a wide group of pathologies, it is believed that for most of these conditions, the general mechanisms leading to fibrotic tissue accumulation have many elements in common. Often the condition is initiated in response to an influx of inflammatory cells and perpetuated by the subsequent cytokine signaling pathways between the infiltrating cells (e.g., macrophages, T cells) and resident cells within the tissue (e.g., stellate, myofibroblast or Kupffer cells). For example, MCP-1 has been shown to play a role in several diseases of the lung (Rose C E Jr, Sung S S, Fu S M. *Microcirculation* 10:273-288 (2003)) and CCR2 deficient mice are protected from development of lung fibrosis (Moore B B, et al. Protection from Pulmonary Fibrosis in the Absence of CCR2 Signaling. *J. Immunol.* 167: 4368-4377 (2001)), suggesting a key role of this receptor in the lung. Similarly, pericytes are a key fibrogenic cell type involved in the development of scleroderma and PDGF receptor tyrosine kinase inhibitors (RTKI) have been shown to slow the proliferation of pericytes and suppress skin lesions in patients with this progressive disease. In the kidney, leukocyte infiltration plays a major role in mediating tubulointerstitial inflammation and fibrosis in chronic kidney disease. Vielhauer and colleagues have established that in a mouse model of obstructive nephropathy, expression of CCR2 and CCR5 on accumulating macrophages and $CD3^+$ lymphocytes correlates with progressive fibrosis at sites of tissue damage (Vielhauer V, et al. *J. Am. Soc. Nephrol.* 12:1173-1187 (2001)).

As used herein the term "fibrosis" is also used synonymously with "fibroblast accumulation and collagen deposition". Fibroblasts are connective tissue cells, which are dispersed in connective tissue throughout the body. Fibroblasts secrete a nonrigid extracellular matrix containing type I and/or type III collagen. In response to an injury to a tissue, nearby fibroblasts or stellate cells migrate into the wound, proliferate, and produce large amounts of collagenous extracellular matrix. Collagen is a fibrous protein rich in glycine and proline that is a major component of the extracellular matrix and connective tissue, cartilage, and bone. Collagen molecules are triple-stranded helical structures called α-chains, which are wound around each other in a ropelike helix. Collagen exists in several forms or types; of these, type I, the most common, is found in skin, tendon, and bone; and type III is found in skin, blood vessels, and internal organs. Exemplary fibrosis conditions include, but are not limited to, lung diseases associated with fibrosis, e.g., idiopathic pulmonary fibrosis, radiation induced fibrosis, chronic obstructive pulmonary disease (COPD), scleroderma, bleomycin induced pulmonary fibrosis, chronic asthma, silicosis, asbestos induced pulmonary fibrosis, acute lung injury and acute respiratory distress (including bacterial pneumonia induced, trauma induced, viral pneumonia induced, ventilator induced, non-pulmonary sepsis induced, and aspiration induced); chronic nephropathies associated with injury/fibrosis (kidney fibrosis), e.g., lupus, diabetes, scleroderma, glomerular nephritis, focal segmental glomerular sclerosis, IgA nephropathy, hypertension, allograft, Lupus, and Alport; gut fibrosis, e.g., scleroderma, and radiation induced gut fibrosis; liver fibrosis, e.g., cirrhosis, alcohol induced liver fibrosis, nonalcoholic steatohepatitis (NASH), biliary duct injury, primary biliary cirrhosis, infection or viral induced liver fibrosis (e.g. chronic HCV infection), and autoimmune hepatitis; head and neck fibrosis, e.g., radiation induced; corneal scarring, e.g., LASIX™, corneal transplant, and trabeculectomy; hypertrophic scarring and keloids, e.g., burn induced and surgical; and other fibrotic diseases, e.g., sarcoidosis, scleroderma, spinal cord injury/fibrosis, myelofibrosis, vascular restenosis, atherosclerosis, Wegener's granulomatosis, mixed connective tissue disease, and Peyronie's disease.

In one aspect, the CCR2-mediated disorder is characterized by pathological inflammation. The term "pathological inflammation" as used herein refers to an inappropriate and/or chronic inflammation associated with disorders including, but not limited to, asthma, atherosclerosis, AIDS dementia, diabetes, inflammatory bowel disease, rheumatoid arthritis, transplant rejection, graft versus host disease, multiple sclerosis (especially to inhibit further demyelination), tumors, tumor metastasis, nephritis, atopic dermatitis, psoriasis, myocardial ischemia and chronic prostatitis, obesity, metabolic syndrome. Such inflammation is characterized by a heightened response of inflammatory cells, including infiltrating leukocytes. Over time, such pathological inflammation often results in damage to tissue in the region of inappropriate inflammation. Accordingly, provided are methods of treating a subject having pathological inflammation comprising administering to the subject a therapeutically effective amount of an antibody or antigen-binding portion thereof which binds to and inhibits CCR2.

The antibody or an antigen-binding fragments thereof, can also be used to treat disorders in which activation of the CCR2 by binding of chemokines, including MCP-1, MCP-2, MCP-3 and MCP-4, is implicated.

The antagonistic anti-CCR2 antibodies or antigen-binding fragments thereof (e.g., 4.40 and/or 4.9 or antigen-binding fragments thereof) can be used to treat inflammatory or allergic diseases and conditions, including respiratory allergic diseases such as asthma, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis), chronic obstructive pulmonary disease, anaphylaxis or hypersensitivity responses, drug allergies (e.g., to penicillin, cephalosporins), insect sting allergies, inflammatory bowel diseases, such as Crohn's disease and ulcerative colitis, spondyloarthropathies, scleroderma, psoriasis and inflammatory dermatoses such as dermatitis, eczema, atopic dermatitis, allergic contact dermatitis, urticaria, vasculitis (e.g., necrotizing, cutaneous, and hypersensitivity vasculitis).

The antagonistic anti-CCR2 antibodies or antigen-binding fragments thereof (e.g., 4.40 and/or 4.9 or antigen-binding fragments thereof) can be used to treat autoimmune diseases. Examples of autoimmune disorders include, but are not limited to, Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitus, and autoimmune inflammatory eye disease.

In certain cases, the autoimmune disease treated with the antagonistic anti-CCR2 antibodies is Rheumatoid Arthritis (RA). A TH1 disorder, RA is a common human autoimmune disease with a prevalence of about 1% among Caucasians (Harris, B. J. et al., 1997, In Textbook of Rheumatology 898-932), currently affecting 2.5 million Americans. RA is characterized by chronic inflammation of the synovial joints and infiltration by activated T cells, macrophages and plasma cells, leading to a progressive destruction of the articular cartilage. It is the most severe form of joint disease.

In still another aspect, the autoimmune disease treated with the antagonistic anti-CCR2 antibodies is Multiple Sclerosis (MS). MS, also a TH1 disorder, is the most common central nervous system (CNS) demyelinating disease, affecting 350,000 (0.1%) individuals in North America and 1.1 million worldwide. In general, MS is considered to be an autoimmune disease mediated in part by proinflammatory CD4 T (Th1) cells and monocytes that recognize specific myelin polypeptides in association with MHC class II molecules expressed on antigen (Ag) presenting cells (APC).

The antagonistic anti-CCR2 antibodies or antigen-binding fragments thereof (e.g., 4.40 and/or 4.9 or antigen-binding fragments thereof) can be used to treat human type I or insulin-dependent diabetes mellitus (IDDM), a disease characterized by autoimmune destruction of the beta cells in the pancreatic islets of Langerhans. The depletion of beta cells results in an inability to regulate levels of glucose in the blood. In humans a long presymptomatic period precedes the onset of diabetes. During this period there is a gradual loss of pancreatic beta cell function. The development of disease is implicated by the presence of autoantibodies against insulin, glutamic acid decarboxylase, and the tyrosine phosphatase IA2 (IA2).

The antagonistic anti-CCR2 antibodies or antigen-binding fragments thereof (e.g., 4.40 and/or 4.9 or antigen-binding fragments thereof) also can be used to treat neuropathic pain. Mice lacking the CCR2 have been shown to have reduced neuropathic pain (Abbadie et al., *Proc Natl Acad Sci USA*. 100(13): 7947-52 (2003)). As used herein, the term "neuropathic pain" means pain resulting from injury to a nerve. Neuropathic pain is distinguished from nociceptive pain, which is the pain caused by acute tissue injury involving small cutaneous nerves or small nerves in muscle or connective tissue. Pain involving a nociceptive mechanism usually is limited in duration to the period of tissue repair and generally is alleviated by available analgesic agents or opioids as described in Myers, Regional Anesthesia 20:173-184 (1995). Neuropathic pain typically is long-lasting or chronic and often develops days or months following an initial acute tissue injury. Neuropathic pain can involve persistent, spontaneous pain as well as allodynia, which is a painful response to a stimulus that normally is not painful. Neuropathic pain also can be characterized by hyperalgesia, in which there is an accentuated response to a painful stimulus that usually is trivial, such as a pin prick.

The antagonistic anti-CCR2 antibodies are useful in alleviating neuropathic pain resulting from a disorder of peripheral nerve, dorsal root ganglia, spinal cord, brainstem, thalamus or cortex. The method is useful in alleviating neuropathic pain regardless of the etiology of the pain. For example, a method can be used to alleviate neuropathic pain resulting from a peripheral nerve disorder such as neuroma; nerve compression; nerve crush, nerve stretch or incomplete nerve transsection; mononeuropathy or polyneuropathy. A method also can be used to alleviate neuropathic pain resulting from a disorder such as dorsal root ganglion compression; inflammation of the spinal cord; contusion, tumor or hemisection of the spinal cord; tumors of the brainstem, thalamus or cortex; or trauma to the brainstem, thalamus or cortex The antagonistic anti-CCR2 antibodies or antigen-binding fragments thereof (e.g., 4.40 and/or 4.9 or functional fragments thereof) can be also be used to treat atherosclerosis. Atherosclerotic plaque develops over several decades and involves inflammatory cell infiltration, smooth muscle cell proliferation, accumulation of extracellular matrix, fibrous cap formation, and angiogenesis. (Bayes-Genis et al. *Circ. Res.* 86:125-130 (2000)). Chemotaxis is involved in the early development of atherosclerosis. Cell populations migrate toward the inner part of the vascular wall and originate the neointima, which leads to the formation of an atherosclerotic plaque. For example, monocyte chemotaxis is induced by monocyte chemoattractant protein 1 (MCP-1), which is expressed early in the development of atherosclerosis in the injured arterial wall. (Furukawa et al. *Circ. Res.* 84:306-314 (1999); Han et al. *J. Lipid Res.* 40:1053 (1999)). Transplantation of bone marrow from CCR2−/− mice, but not from CCR2+/+ mice, into ApoE3-Leiden mice, a mouse strain susceptible for diet-induced atherosclerosis, decreases atherogenesis, suggesting that MCP-1 signaling through CCR2 contributes to atherosclerosis (Guo et al. (2003) *Arterioscler Thromb Vasc Biol.;* 23(3):447-53). Accordingly, the CCR2 antagonist antibodies and in particular the antagonist antibodies which bind to the first and/or second extracellular loop of CCR2, may be administered to a subject to reduce the incidence of, to treat, or to aid in the treatment of atherosclerosis.

The antagonistic anti-CCR2 antibodies or antigen-binding fragments thereof (e.g., 4.40 and/or 4.9 or antigen-binding fragments thereof) also can be used to treat obesity. In obesity, adipose tissue has been demonstrated to contain large numbers of monocytes. These monocytes may contribute either to fat deposition or the development of various sequelae commonly associated with Obesity commonly termed metabolic syndrome. Metabolic syndrome includes such alterations as the development of diabetes.

The antagonistic anti-CCR2 antibodies or antigen-binding fragments thereof (e.g., 4.40 and/or 4.9 or antigen-binding fragments thereof) can be also be used to treat stenosis or restenosis of the vasculature, particularly of the arteries, e.g., the coronary artery, such as stenosis or restenosis which results from vascular intervention (e.g., surgical, therapeutic or mechanical intervention), as well as neointimal hyperplasia. For example, restenosis, which typically produces a narrowing of the lumenal opening of the vessel, can result from vascular injury including, but not limited to, that produced by vascular graft procedures, angioplasty, including angioplasty performed by balloon, atherectomy, laser or other suitable method (e.g., percutaneous translumenal coronary angioplasty (PTCA)), stent placement (e.g., mechanical or biological endovascular stent placement), vascular bypass procedures or combinations thereof, as well as other procedures used to treat stenotic or occluded blood vessels.

The antagonistic anti-CCR2 antibodies or antigen-binding fragments thereof (e.g., 4.40 and/or 4.9 or antigen-binding fragments thereof) also can be used to treat graft rejection (e.g., in transplantation), including allograft rejection or graft-versus-host disease, and organ transplant-associated arteriosclerosis.

Antibodies and antigen-binding fragments thereof which are antagonists of CCR2 can be used as therapeutics for HIV infection. HIV-1 and HIV-2 are the etiologic agents of acquired immunodeficiency syndrome (AIDS) in humans. AIDS results in part from the depletion of CD4$^+$ T lymphocytes in HIV infected individuals. HIV-1 infects primarily T lymphocytes, monocytes/macrophages, dendritic cells and, in the central nervous system, microglia. All of these cells express the CD4 glycoprotein, which serves as a receptor for HIV-1 and HIV-2. Efficient entry of HIV into target cells is dependent upon binding of the viral exterior envelope glycoprotein, gp120, to the amino-terminal CD4 domain.

Furthermore, CCR2 has been shown to act as a co-receptor for HIV-1 (Frade et al. (1997) *J Clin Invest.;* 100(3):497-502). After virus binding, the HIV-1 envelope glycoproteins mediate the fusion of viral and host cell membranes to complete the entry process. Membrane fusion directed by HIV-1 envelope glycoproteins expressed on the infected cell surface leads to cell-cell fusion, resulting in syncytia.

Antibodies and antigen-binding fragments thereof which are antagonists of CCR2 can be used as therapeutics for the treatment of a variety of ophthalmology conditions including Age Related Macular Degeneration (AMD), Uveitis, and Corneal Infections.

Age Related Macular Degeneration (AMD)

CCR2 has been shown to play role in the recruitment of macrophages in the development of choroidal neovascularization (CNV) that is observed in age related macular degeneration patients, as well as in angioid streaks, high myopia, ocular histoplasmosis patients (Tsutsumi, C. et al. *Journal of Leukocyte Biology* 74:25-32, 2003).

Uveitis

An association between single nucleotide polymorphisms of CCR2 and its ligand (MCP-1) has been demonstrated in patients with acute idiopathic anterior uveitis (Yeo, T K, et al. *Cytokine* 35:29-35 2006) and idiopathic immune-mediated posterior segment uveitis Ahad, M A, et al. *Mol Vis* 13:388-396 2007)

Corneal Infections (Bacterial):

CCL2 has been shown to play a role in the regulation of polymorphonuclear neutrophils (PMNs) recruitment during corneal infection (Xue, M. L, et al. *Immunology and Cell Biology* 85:525-531 2007). While PMNs are essential for eliminating bacteria and promoting wound healing in the cornea the persistence of these cells may result in chronic inflammatory disease.

Antibodies and antigen-binding fragments thereof which are antagonists of CCR2 can be used as therapeutics for the treatment of a variety of solid tumors and cancers, including chronic lymphocytic leukemia, chronic myelocytic leukemia, multiple myeloma, malignant myeloma, Hodgkin's disease, and carcinomas of the prostate, bladder, breast, cervix, colon, lung, liver or stomach solid tumors and cancers.

Prostate Cancer

MCP-1 has been shown to act as a paracrine and autocrine factor for prostate cancer growth and invasion (Lu, Y. et al. *The Prostate* 66:1311-1318, 2006) and CCR2 expression has been shown to correlate with prostate cancer progression (Lu, Y. et al. *Journal of cellular biochemistry* 101:676-685, 2007). Systemic delivery of neutralizing anti-MCP-1 antibodies has been shown to induce prostate cancer tumor regression in mice (Loberg, R. D., *Cancer Res* 67:9417-9424 2007).

Breast Cancer

Tumor associated macrophages are thought to play a critical role in tumor immune surveillance and development and the activation and recruitment of lymphocytes are regulated by chemokines including MCP-1. A significant association has been demonstrated for CCR2 polymorphism in breast cancer (Zafiropoulos, A., N. et al. *Journal of medical genetics* 41:e59 2009). The CCL2/CCR2 pathway has also been shown to play a pivotal role in the recruitment to cancers, including breast, ovarian and gastric cancers, of myeloid suppressor cells, which promote tumor progression, angiogenesis and vasculoangiogenesis (Huang, B., et al. *Cancer letters* 252:86-92, 2007).

Melanoma

Blocking of MCP-1 function has also been shown to inhibit the recruitment of tumor associated macrophages and prevent tumor angiogenesis and growth in malignant melanoma in mice (Koga, M. et al. *Biochemical and biophysical research communications* 365:279-284, 2008).

Liver Cancer

Blocking of CCR2 has been shown to reduce trafficking of hepatic stellate cells, a main source of matrix metalloproteinase 2, which facilitates neovavascularization during liver tumor formation (Yang, X. et al. *International journal of cancer* 118:335-345, 2006).

Cervical Cancer

CCR2 has been shown to play a role in macrophage recruitment leading to tumor angiogenesis in the development of cervical neoplasia from squamous intraepithelial lesions (Coelho, A., et al. *Gynecologic oncology* 96:760-764, 2005; Coelho, A., et al. *Gynecologic and obstetric investigation* 64:208-212, 2007).

Ovarian Cancer

The CCL2/CCR2 pathway has also been shown to play a pivotal role in the recruitment to cancers, including breast, ovarian and gastric cancers, of myeloid suppressor cells, which promote tumor progression, angiogenesis and vasculoangiogenesis (Huang, B., et al. *Cancer letters* 252:86-92, 2007).

The antibody may be administered once or multiple times. The antibody may be administered from four times daily to once every six months or longer. The administering may be on a schedule such as three times daily, twice daily, once daily, once every two days, once every three days, once weekly, once every two weeks, once every month, once every two months, once every three months and once every six months. The antibody may also be administered continuously via a minipump. The antibody may be administered via a mucosal, buccal, intranasal, inhalable, intravenous, subcutaneous, intramuscular, parenteral, intratumor or topical route. The antibody may be administered locally or systemically.

The antibody may be administered once, at least twice or for at least the period of time until the condition is treated, palliated or cured. The antibody will generally be administered as part of a pharmaceutical composition as described herein. The dosage of antibody will generally be in the range of 0.1-100 mg/kg, 0.5-50 mg/kg, 1-20 mg/kg, or 1-10 mg/kg. The serum concentration of the antibody may be measured by any method known in the art.

The examples below are for illustration only and are not to be construed as limiting the scope in any manner.

EXAMPLE 1

Generation of Hybridomas Producing Anti-CCR2 Antibody

Eight to ten week old XENOMOUSE™ mice that produce human IgG2 and IgG4 antibodies were immunized in their hind footpads with 300-19 cells transfected with CCR2B (Genbank MN000648, SEQ ID NO:204) ($10^7$ cells/dose/mouse in TITERMAX™ Gold Adjuvant, Sigma, Catalog #T2684, lot #K1599; prepare 50/50 volume). The mice received five to nine booster injections in Aluminium Phosphate Gel Adjuvant (Catalog #1452-250, batch #8937, HCl Biosector (5 ul/mouse/boost)) and qCpG (IMMUNEASY™ Mouse Adjuvant) (Catalog #303101; lot #11551249; Qiagen (15 ul/mouse/boost)) over a three to eight week period. Four days before fusion, the mice were given a final injection in PBS. The spleen and lymph node lymphocytes from immunized mice were collected and fused with the non-secretory myeloma P3-X63-Ag8.653 cell line. The fused cells were subjected to HAT selection as previously described (Galfre and Milstein, *Methods Enzymol.* 73:3-46 (1981)). A panel of hybridomas all secreting CCR2-specific human antibodies was recovered. A number of antibodies were identified for binding to CCR2 as assessed by FACS analysis. Hybridomas were selected for further study, some of which are listed in Table 6.

The hybridomas indicated in Table 2 were deposited under terms in accordance with the Budapest Treaty with the American Type Culture Collection (ATCC), 10801 University Blvd., Manassas, Va. 20110-2209. The hybridomas have been assigned the following accession numbers:

TABLE 2

| Antibody | Mouse Hybridoma Cell Line Designation | Strain Designation | ATCC Designation | Deposit Date |
|---|---|---|---|---|
| 4.9.3 | PF11-4.9.3 | LN 15923 | PTA-6979 | Sep. 16, 2005 |
| 4.22.3 | PF11-4.22.3 | LN 15924 | PTA-6980 | Sep. 16, 2005 |
| 4.40.3 | PF11-4.40.3 | LN 15925 | PTA-6981 | Sep. 16, 2005 |
| 7.123.1 | PF11-7.123.1 | LN 15931 | PTA-7341 | Jan. 25, 2006 |
| 8.19.1.1 | PF11-8.19.1.1 | LN 15932 | PTA-7342 | Jan. 25, 2006 |

EXAMPLE 2

Sequencing of Anti-CCR2-Antibodies

To analyze the structure of antibodies produced, nucleic acids were cloned that encode heavy and light chain variable domain containing fragments from hybridomas producing anti-CCR2 monoclonal antibodies. The light chains and the light chains of the CCR2 antibodies were cloned and sequence verified as exemplified for the 4.40.2 antibody as follows:

Poly(A)$^+$ mRNA was isolated using an RNEASY™ MINI KIT (Qiagen) and cDNA synthesized from the mRNA with the ADVANTAGE RT-for-PCR kit (BD Biosciences) using oligo(dT) priming. The oligo(dT) primed cDNA was amplified for clone 4.40.2 using the primers listed in Table 3. Amplification was achieved using the PFUULTRA HIGH-FIDELITY Polymerase (Stratagene) and a PTC-200 DNA Engine (MJ Research) with cycling as follows: 2' at 95° C.; 25× (20" at 95° C., 30" at 55° C., 30" at 72° C.); 10' at 72° C. PCR amplicons were cloned into the heavy and light chain expression vectors. Vectors were then transformed into MAX EFFICIENCY DH5α chemically competent cells (Invitrogen) using the standard protocol. Clones were sequence verified using Grills 16$^{th}$ BDTv3.1/dGTP chemistry (Applied Biosystems Inc) and a 3730xl DNA Analyzer (Applied Biosystems Inc). From the nucleotide sequence and predicted amino acid sequence of the antibodies, the gene usage was identified for each antibody chain. Alignments to the "V Base sequence directory" (MRC Centre for Protein Engineering, Cambridge, UK; Tomlinson, et al., J. Mol. Biol., 227, 776-798 (1992); Hum. Mol. Genet., 3, 853-860 (1994); EMBO J., 14, 4628-4638 (1995)) were made using MACVECTOR™ and GENEWORKS™ software programs (Oxford Molecular Group, Campbell, Calif., USA).

TABLE 3

Variable Domain Primers Designed for Amplifying 4.40.2 (5' to 3')

| CCR2_440_VH_G2_F VH3.30 | CAGGTGCAGCTGGTGGAGTCTGG (SEQ ID NO: 147) |
|---|---|
| CCR2_440_VH_G2_R JH3b | GAAGAGACGGTGACCATTGTCCCTT (SEQ ID NO: 148) |
| CCR2_440_VL_K_F A26 | GAAATTGTGCTGACTCAGTCTCCAG AC (SEQ ID NO: 149) |
| CCR2_440_VL_K_R JK4 | GTTTGATCTCCACCTTGGTCCCTC (SEQ ID NO: 150) |

Table 4 sets forth the gene utilization of selected hybridoma antibody clones.

TABLE 4

Heavy and Light Chain Gene Utilization

| | Heavy Chain Germline | | | Kappa Light Chain Germline | |
|---|---|---|---|---|---|
| Clone | $V_H$ | $D_H$ | $J_H$ | Vκ | Jκ |
| 4.9.3 | VH3-30 | D1-7 | JH3B | O12 | JK2 |
| 4.22.3 | VH1-46 | D1-7 | JH3B | A1 | JK5 |
| 4.39.3 | VH1-46 | D1-7 | JH3B | B3 | JK1 |
| 4.40.3 | VH3-30 | D1-7 | JH3B | A26 | JK4 |

Hybridoma clones were generated in IgG4 mice and once the sequences were obtained the variable domains were cloned into IgG1, IgG2, and IgG4 format expression vectors for comparison.

EXAMPLE 3

Mutagenesis of Anti-CCR2-Antibodies

Reversion to Germline Sequence in Light Chain Variable Region

The alanine residue at position 68 in the light chain of CCR2 4.40.2 was reverted to the germline residue, glycine, by site-directed mutagenesis as follows. The point mutation in the codon for amino acid residue 68 was changed using the primers in Table 5. Site-directed mutagenesis was performed using a QUIKCHANGE™ II Site-Directed Mutagenesis kit (Stratagene) with the standard protocol including the following modifications to cycling: 2' at 96° C.; 16× (50" at 96° C., 10" at 68° C.); 10' at 68° C. Mutagenized vector was transformed into XL1-Blue supercompetent cells. To verify that mutagenesis was successful, clones were sequenced using Grills 16$^{th}$ BDTv3.1/dGTP chemistry (Applied Biosystems Inc.) and a 3730xl DNA Analyzer (Applied Biosystems Inc.).

TABLE 5

Mutagenesis Primers (5' to 3')

| CCR2_440_VK_G68A_F | GGCAGTGGATCTGGGACAGATTTCACC (SEQ ID NO: 151) |
|---|---|
| CCR2_440_VK_G68A_R | GGTGAAATCTGTCCCAGATCCACTGCC (SEQ ID NO: 152) |

*Changed nucleotide is bolded and underlined.

The resulting antibody was designated 4.40 A68G (SEQ ID NO:112), having a glycine at position 68 of the light chain variable region.

Generation of IgG4 Heavy Chain Constant Region with Hinge-Stabilizing Mutation

The IgG4 heavy chain constant regions were isolated from a pCON-G4(pro) (Lonza, Basel, Switzerland) derived IgG4 expression vector, which has a hinge region stabilizing mutation from germline, Serine to Proline at amino acid 230 (Angal, S. et al. *Molecular Immunology* 30:105-108 (1993)), in the context of the IgG4 L309 allotype (Brusco A. et al., *Eur J. Immunogenticsl* 25:349-355 (1998)).

A silent mutation (Lys, AAG→AAA) was introduced by PCR mutagenesis into the 11$^{th}$ nucleotide residue of the G4 CH1 exon of pCON-G4(pro) vector, to remove an ApaI recognition site to facilitate subcloning, using the following amplification primers:

G4_Forward
(SEQ ID NO: 153)
ttatgctgggcccagctctgtcccacaccgcggtcacatggcaccacct ctcttgcaGCTTCCACCAAAGGCCCATCCGTCTTCCCCC (Hybridizing bases in CAPS (mutation of residue #11 of CH1 is BOLDED); Non-hybridizing bases in lowercase)

G4_Reverse:
(SEQ ID NO: 154)
tcatattctctagaTCATTTACCCAGAGACAGGGAGAGG (Hybridizing bases in CAPs. Non-hybridizing bases with XbaI site in lowercase)

Amplification was achieved using Expand Hi-Fi Polymerase (Roche) and a PTC-200 DNA ENGINE™ (MJ Research) with thermal cycling as follows: 3' at 95° C.; 22× (20" at 95° C., 30" at 58° C., 2'10" at 72° C.

Another silent mutation (Thr, ACC→ACA) was introduced by PCR mutagenesis at nucleotide residue 209 of the G4 CH1 exon of the pCON-G4(pro) vector to remove a BstEII site in order to facilitate use of that enzyme for subcloning variable regions into the expression vector using the following primers:

G4delBst_F
(SEQ ID NO: 155)
CAGCGTGGTGACAGTGCCCTCCAGCAG

G4delBst_R
(SEQ ID NO: 156)
CTGCTGGAGGGCACTGTCACCACGCTG.

Amplification was achieved using the QUIKCHANGE™ Site-Directed Mutagenesis Kit (Stratagene) and a PTC-200 DNA Engine (MJ Research) with thermal cycling as follows: 1' at 96° C.; 14× (50" at 96° C., 15'48" at 68° C.); 10' at 72° C.

The resulting IgG4 constant region comprising the hinge region mutation and the two silent mutations, referred to as S230P, was then subcloned as an ApaI/XbaI fragment into the ApaI/XbaI sites of a DHFR antibody expression vector. The heavy chain variable region of the 4.40.2 antibody was then cloned into the expression vector comprising the G4 S230P constant region resulting in a full-length heavy chain construct. The 4.40 derived antibody having the light chain variable region A68G germline substitution and the heavy chain hinge region S230P substitution was designated 4.40 A68G S230P having the light chain amino sequence of SEQ ID NO:112 and the heavy chain amino acid sequence of SEQ ID NO:116.

Supernatants from cells transfected with the expression vectors were collected and purified by standard Protein A affinity chromatography to isolate recombinant immunoglobulins. These proteins were then characterized by SDS-PAGE, light scatter, and spectrophotometry.

EXAMPLE 4

In Vitro Binding

FIG. 1 shows the in vitro binding of AF-488 conjugated antibody 4.40 A68G S230P to human monocytes in whole blood (FIG. 1A), to CCR2-transfected 300-19 cells (FIG. 1B), and binding of different concentrations of 4.40 A68G S230P antibody to CCR2-transfected 300-19 cells as detected with anti-human PE (FIG. 1C). Briefly, 1 million cells in a volume of 100 ul were stained with the test antibody using Dulbecco's Phosphate Buffered Saline, containing 2% heat inactivated Fetal Bovine Serum and 0.002% Sodium Azide. Fifteen minutes later, a secondary detection antibody was added. After 30 minutes, cells were washed in buffer, resuspended in 500 ul and assessed for staining on a FACS CALIBUR. A total of 10,000 events per tube were assessed. The mean channel fluorescent intensity was assessed for each concentration of antibody as an indicator for the magnitude of staining.

EXAMPLE 5

Determination of Affinity Constants ($K_D$) of Anti-CCR2 Monoclonal Antibodies

Figure 6C:
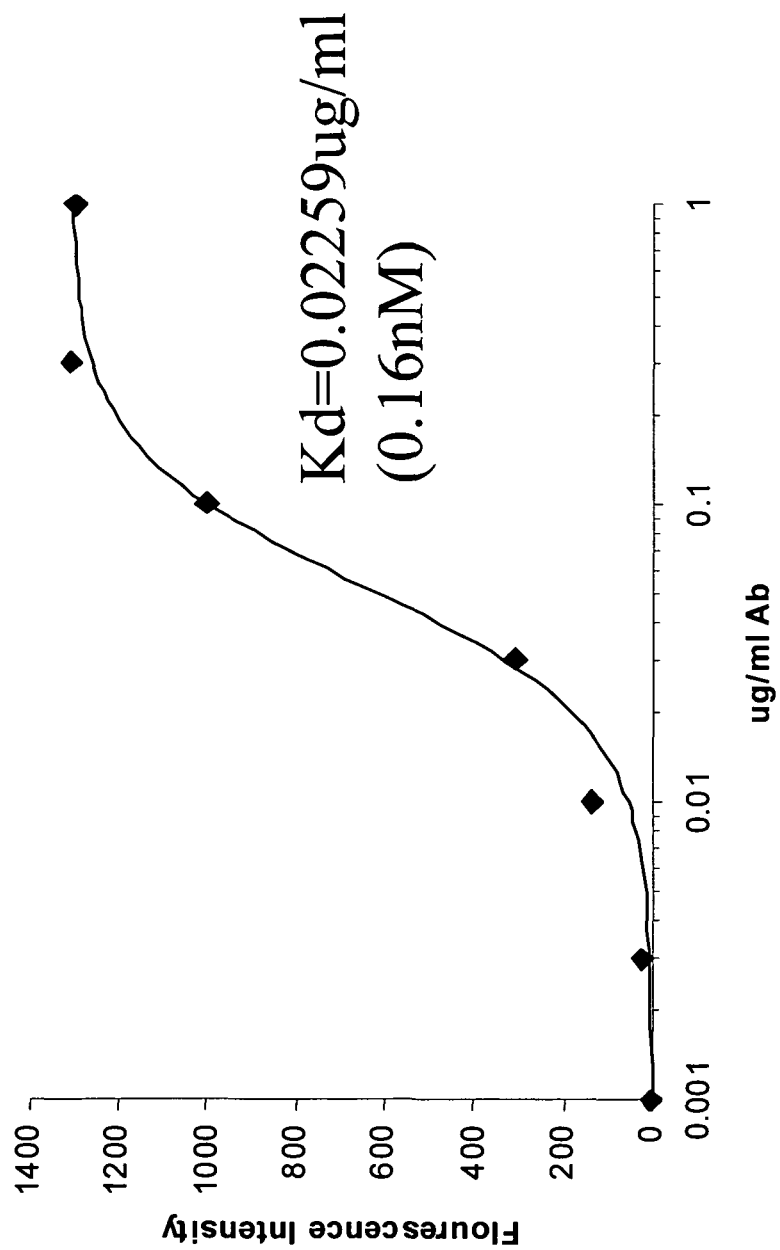
FIG. 6C depicts a saturation binding assay of 4.40 A68G S230P to the chimeric receptor transfected 300-19 cells as measured by FACS analysis.

To assess the $K_D$ of the antibodies for the CCR2, antibody binding to 300-19 cells expressing CCR2 was assessed by FACS in a 3 hour assay. Briefly, using a buffer of Dulbecco's Phosphate Buffered Saline containing 2% heat inactivated Fetal Bovine Serum, 0.002% Sodium Azide and 0.005 mg/ml Cytochalasin-B (Sigma 6762), 1 million cells in a volume of 100 ul were stained with the test antibody. Fifteen minutes later, a secondary detection antibody, R-Phycoerythrin conjugated Affini-pure F(ab') fragment Donkey anti-human IgG H+L (Jackson 709-116-149), was added. Tubes were gently shaken for 3 hours at room temperature. After 2 washes in buffer, cells were resuspended in 500 ul of buffer and assessed on a FACS CALIBUR™. A total of 10,000 events per tube were assessed. The mean channel fluorescent intensity was assessed for each concentration of antibody as an indicator for the magnitude of staining. These binding studies demonstrated that the 4.40 A68G S230P antibody binds to human CCR2 on transfected cells with a $K_D$ of 0.085 ug/mL (0.58 nM) (FIG. 2). When saturation binding was assessed on cells expressing a CCR2/CCR5 chimera receptor having the first and second extracellular loops of the CCR2 (see Example 7), a similar concentration curve and $K_D$ ($K_D$=0.023 ug/mL (0.16 nM)) were obtained as shown in FIG. 6C.

EXAMPLE 6

Inhibition of MCP-1 induced Chemotaxis

Human anti-CCR2 antibodies were evaluated for their ability to inhibit the chemotaxis of THP-1 monocytes (ATCC #TIB 202), in response to the CCR2 ligand, MCP-1 (CCL2). Chemotaxis was conducted in 96 well chemotaxis chambers purchased from NeuroProbe, Inc. (Gaithersburg, Md.) as previously described (see Gladue R P et al., *J Biol Chem* 278: 40473-40480 (2003)). Briefly, CCL2 was diluted in RPMI 1640 medium (Roswell Park Memorial Institute) containing 0.1% BSA, and then added to the bottom wells of the chamber. A filter with 5 μm pores (Neuroprobe) was placed between the upper and lower wells of the chamber. THP-1 cells were then added to the top chamber ($8 \times 10^5$) in the presence or absence of various concentrations of the test antibodies. The apparatus was incubated for 3 hrs in a 5% $CO_2$ humidified incubator at 37° C. After the incubation period, the non-migrating cells were removed from the upper chamber and the top of the filter was wiped. 2 mM cold EDTA was then added to the upper wells, and the chemotaxis chamber was incubated at 4° C. for 20 minutes. The EDTA was then removed and the 96 well microtiter plate was centrifuged at 800×g for 10 minutes. The filter was then removed, the culture medium discarded, and 0.2% FDA was added to the plates. The plates were then incubated for 1.5 hours at 37° C. until a yellow color developed. The number of migrating cells was quantified by reading the intensity of the color on a microtiter plate reader at 490 nm. As shown in Table 6, several antibodies that inhibited THP1 chemotaxis to different degrees were identified.

TABLE 6

Inhibition of MCP-1-induced THP-1 Chemotaxis

| Antibody Clone | IC50 (ug/ml) |
|---|---|
| 4.40.3 | 0.137 |
| 4.22.3 | 0.138 |
| 4.39.3 | 0.139 |
| 4.9.2 | 0.198 |
| 4.6.3 | 0.400 |
| 4.48.3 | 0.491 |
| 4.41.1 | 0.521 |
| 4.3.1 | 0.618 |
| 4.52.1 | 0.641 |
| 4.59.2 | 1.020 |
| 4.24.3 | 2.264 |

Figure 3:
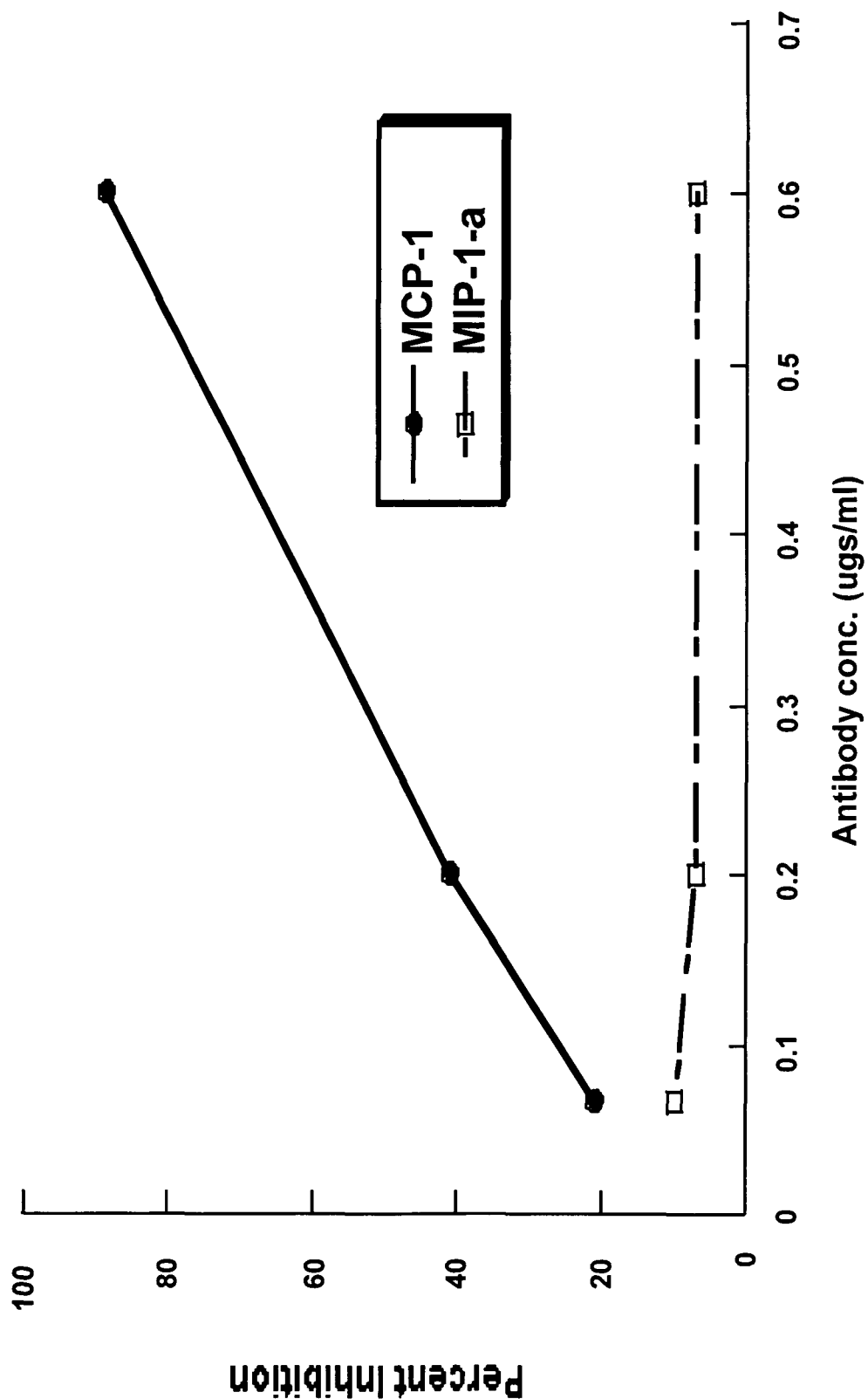

Similarly, the antibody 4.40 A68G S230P inhibited chemotaxis of THP-1 monocytes in response to MCP-1 (IC50=0.148 ug/ml) but not the CCR1/CCR5 ligand MIP-1, as shown in FIG. 3.

Primary Monocyte Chemotaxis

Figure 4:
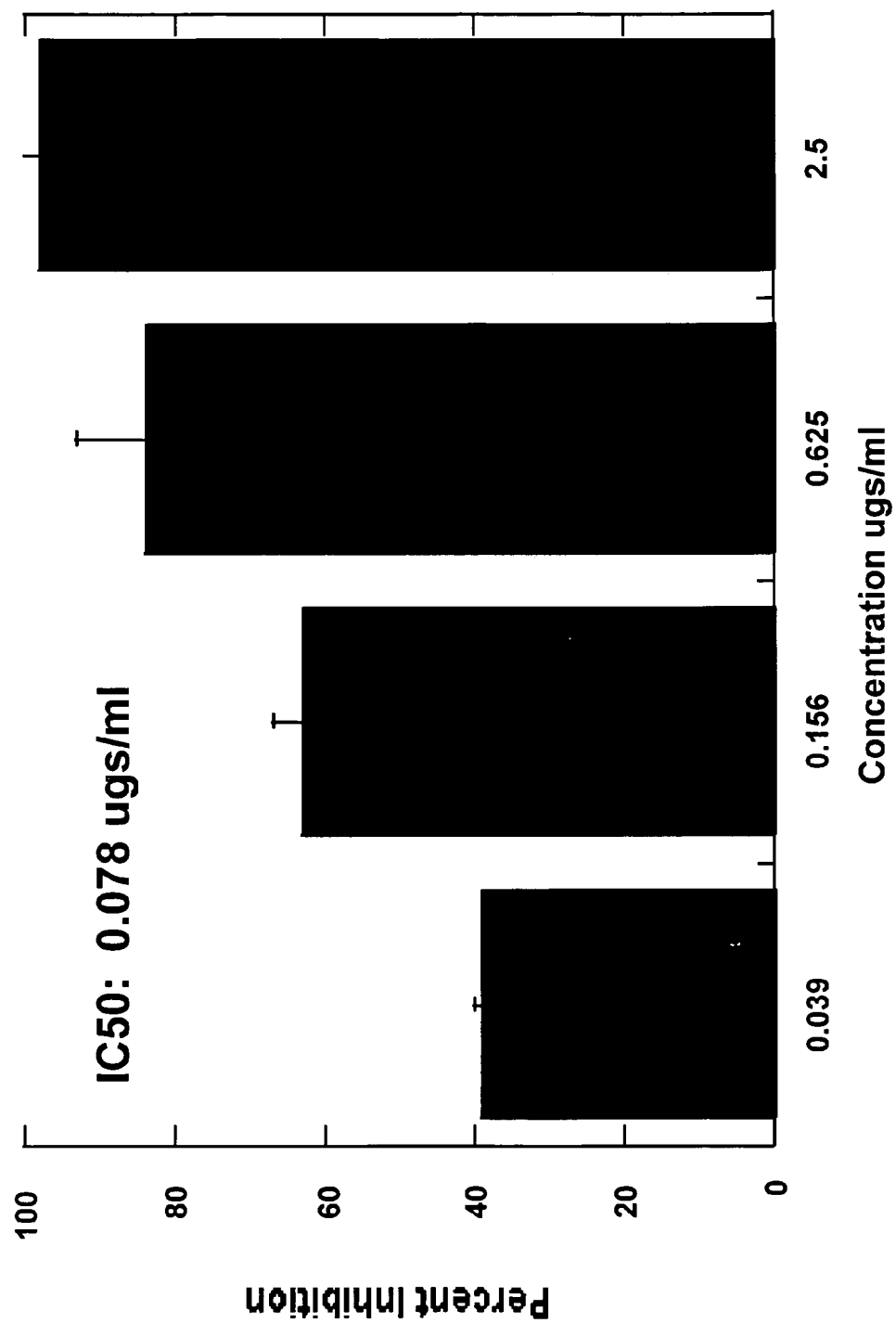
FIG. 4 illustrates the ability of the 4.40 A68G S230P antibody to inhibit the chemotaxis of primary human monocytes in response to MCP-1.

Heparinized human whole blood was layered over ACCUSPIN HISTOPAQUE 1077 tubes (Sigma; St. Louis, Mo.) and spun down. The mononuclear cell fraction was collected and washed 3× with PBS, red blood cells (RBC's) were lysed with water, and the cells were resuspended at $4 \times 10^6$/ml in RPMI (Gibco; Grand Isle, N.Y.) with 0.1% BSA (Sigma) and 10 mM HEPES (Gibco). Antibody dilutions or KLH control were added to 0.25 nM MCP-1 (Peprotech; Rocky Hill, N.J.) and 30 ul were placed in the bottom of a 48 well Boyden chamber (Neuroprobe; Gaithersburg, Md.); negative control was media alone. A 5 um PVP-free filter (Neuroprobe) was placed over this and the chamber sealed. Isolated mononuclear cells were incubated with antibody dilutions or KLH control for 30 minutes at room temperature. Then 50 ul were added to the upper wells. The chamber was incubated for 90 minutes at 37° C. in a 5% $CO_2$ humidified incubator. After incubation, the cells were aspirated out of the upper wells, the top of the filter was wiped, air-dried, stained with DIFF-QUIK™ (Dade-Behring; Newark, Del.), and the number of migrating cells in 6 fields were counted. The inhibition of chemotaxis of primary isolated human monocytes in response to MCP-1 by antibody 4.40 A68G S230P is shown in FIG. 4.

Further, as exemplified with the 4.40 antibody, no inhibition of THP-1 cells was observed to the CCR1/CCR5 ligand MIP-1a (FIG. 3).

EXAMPLE 7

CCR2/CCR1 Chimera Construction

Antibodies that inhibited MCP-1-induced chemotaxis were tested for binding to CCR2 chimeras to map their epitopes. This was accomplished by assessing the binding of the antibodies to 300-19 cells expressing different receptor chimeras consisting of extracellular loop ($1^{st}$, $2^{nd}$ and/or $3^{rd}$) and N-terminal substitutions of the CCR2 with portions of the CCR1 (M=CCR2, R=CCR1).

Construction of Chimera Receptor MRRR

The MRRR chimeric receptor (N-terminus of CCR2 (M), $1^{st}$, $2^{nd}$, and $3^{rd}$ extracellular loop of CCR1 (R)) was constructed using the QUIKCHANGE® Site-Directed mutagenesis kit from Stratagene and the following mutagenesis primers to mutate the first ApaL restriction enzyme site in wild type human CCR1, cloned into the expression vector pcDNA3 (Invitrogen, Carlsbad, Calif.) to a BamHI site using the following primers:

```
sense primer 40A:
                                        (SEQ ID NO: 132)
CGAGAGGGCCTTTGGGATCCAACTGCTGCC anti-sense primer 40B:
                                        (SEQ ID NO: 133)
GGCAGCAGTTGGATCCCAAAGGCCCTCTCG
```

The chimeric receptor containing a FLAG-tagged MMRR chimera (N-terminus and $1^{st}$ extracellular loop of CCR2, $2^{nd}$ and $3^{rd}$ extracellular loops of CCR1) cloned into pCMV-1 derived expression vector (Pharmacia; Piscataway, N.J.) was provided by Israel Charo of the J. David Gladstone Institutes. The construction of the MMRR chimera (referred to as "2211" by the authors) is described in Monteclaro F. S. et al. (*Methods in Enzymology* 228:70-84 (1997)). The first ApaL site in the chimera was mutated to a BamH1 site using the following mutagenesis primers:

```
Sense primer: 41A:
                                        (SEQ ID NO: 134)
GCAAATTGGGATCCAACTCCTGCC Anti-sense primer: 41B:
                                        (SEQ ID NO: 135)
GGCAGGAGTTGGATCCCAATTTGC.
```

Each resulting mutated clone was cut with NdeI and BamHI. The fragment containing the vector from the CCR1/pcDNA3 BamHI mutant and the 632 basepair NdeI/BamHI fragment containing just the CCR2 N-terminus from the mutated MMRR/pCMV1 plasmid were gel isolated and ligated together resulting in the MRRR/pcDNA3 chimera.

The BamHI site in the MRRR chimera was mutated back to an ApaL site using the following mutagenesis primers:

```
Sense primer 41C:
                                        (SEQ ID NO: 136)
GCAAATTGGGGCCCAACTGCTGCC Anti-sense primer 41D:
                                        (SEQ ID NO: 137)
GGCAGCAGTTGGGCCCCAATTTGC.
```

The complete MRRR fragment was PCR amplified using sense primer 66C (SEQ ID NO:138) homologous to the FLAG tag region of the vector and anti-sense primer 66D (SEQ ID NO:139) homologous to the 3' end of CCR1 and containing a HindIII site.

```
Sense primer 66C
                                        (SEQ ID NO: 138)
CTCTTGTGCCAGGGTGTGGTCTCCGA Anti-sense primer 66D
                                        (SEQ ID NO: 139)
GATCGAAGCTTTCAGAACCCAGCAGAGAGTTCATG
```

Figure 5:
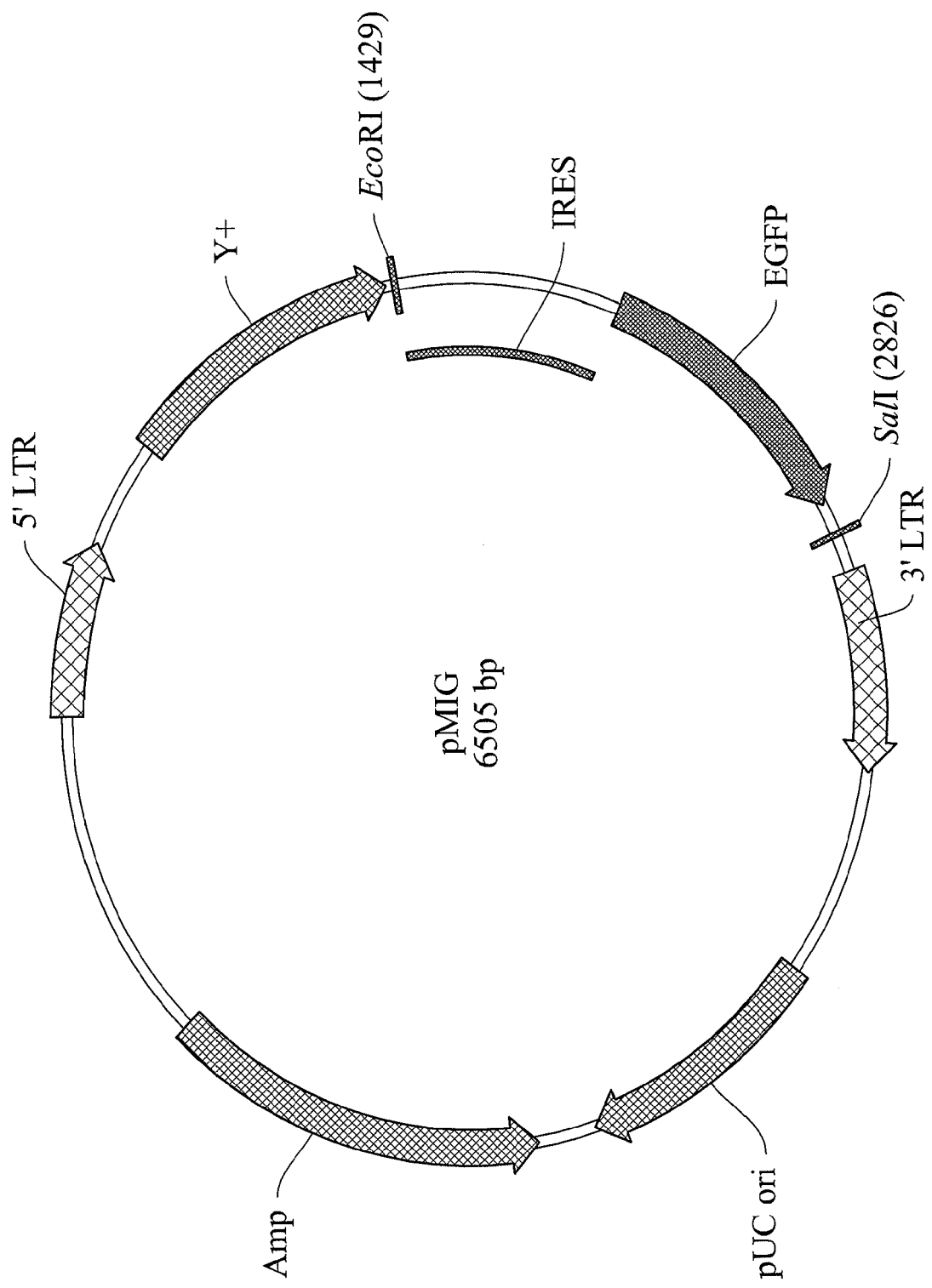
FIG. 5 shows the plasmid map of a retroviral vector for expression of the CCR1/CCR2 chimeras.

This fragment was then subcloned into the PfIMI and HindIII sites of a pMIG (Van Parijs, L. et al., *Immunity* 11:281-188 (1999)) derived retroviral construct (FIG. 5), replacing an inserted gene (a mouse/human chimera) that was preceded by a FLAG tag followed by the Sal1 site and had the internal ribosomal entry site-enhanced green fluorescent protein site (IRESEGFP) removed.

Construction of Chimera Receptor RRRM and RMMR

The RRRM (N-terminus, $1^{st}$ and $2^{nd}$ extracellular loops of CCR1, and $3^{rd}$ extracellular loop CCR2) and RMMR (N-terminus and $3^{rd}$ extracellular loop CCR1, and $2^{nd}$ and $3^{rd}$ extracellular loops of CCR2) chimeric receptors were made using a two step PCR method.

For the RRRM chimera, the third loop of human wild type CCR2 was first PCR amplified using the following primers:

```
Sense chimeric primer 89A:
                                        (SEQ ID NO: 140)
GACTATACTTATTTCTGTTTTCATTGTCATTCTCCTGAACACC Anti-sense primer 81B:
                                        (SEQ ID NO: 141)
CGCCAAGCTTCATTATAAACCAGCCGAGA.
```

The wild type human CCR2 was cloned into retroviral-derived expression vector pMIG as a template. The N-terminal region through the second extracellular loop was PCR amplified using the following primers:

```
Sense primer 89C:
                                        (SEQ ID NO: 142)
ACGCGTCGACGAAACTCCAAACACCACAGAG Anti-sense chimeric primer 89B:
                                        (SEQ ID NO: 143)
GTTCAGGAGAATGACAATGAAAACAGAAATAAGTATAGTC,
``` and wild type CCR1 was cloned into the expression vector pcDNA3 as a template.

These fragments were gel purified, combined and PCR-amplified together using the 5' and 3' end primers: 89C (SEQ ID NO:142) and 81B (SEQ ID NO:141). The resulting fragment was ligated into the SalI/HindII sites of the retroviral vector, pMIG containing an N-terminal FLAG tag and having the IRESEGFP removed.

Construction of the Chimera Receptor RMMR

The CCR1 third extracellular loop through the cytoplasmic tail was PCR-amplified using wild type CCR1 cloned into the expression vector pcDNA3 as a template and the following primers:

Sense chimeric primer 85A:

(SEQ ID NO: 144)
TCATTCTCCTGAACACCTTCCAAGACTTCCTGTTCACCCA

Anti-sense primer 78D:

(SEQ ID NO: 145)
GCCAAGCTTCCAGTGTGATGGATATCTGA, which hybridizes to an area of the vector 3' of the insert in the wild type CCR1/pcDNA3 plasmid.

A second fragment was PCR-amplified containing the N-terminus of CCR1 and an area containing the first and second extracellular loops of CCR2 using a FLAG tagged RMMM/pcDNA3 plasmid obtained from Israel Charo of the J. David Gladstone Institutes as a template. The construction of the RMMM chimera construct (referred to as "2111" by the authors) is described in Monteclaro, F. S. et al. (*Methods in Enzymology* 228:70-84 (1997)). The primers used were sense primer 66C (SEQ ID NO:138), which hybridizes to the FLAG tag and the anti-sense chimeric primer 85B:

(SEQ ID NO: 146)
TGGGTGAACAGGAAGTCTTGGAAGGTGTTCAGGAGAATGA.

These two fragments were gel purified, combined and PCR-amplified together using the 5' and 3' end primer: 66C (SEQ ID NO:138) and 78D (SEQ ID NO:144). This final fragment was digested with PflMI and HindIII and ligated into the pMIG retroviral vector containing a N-terminal FLAG tag and having the IRESEGFP removed.

Chimera Expression

Retrovirus was produced from each chimera construct and used to transduce 300-19 cells. Expression was determined by FACS analysis using anti-FLAG epitope antibody M1 (Sigma; St. Louis, Mo., catalog #F3040).

EXAMPLE 8

Epitope Mapping

Figure 7:
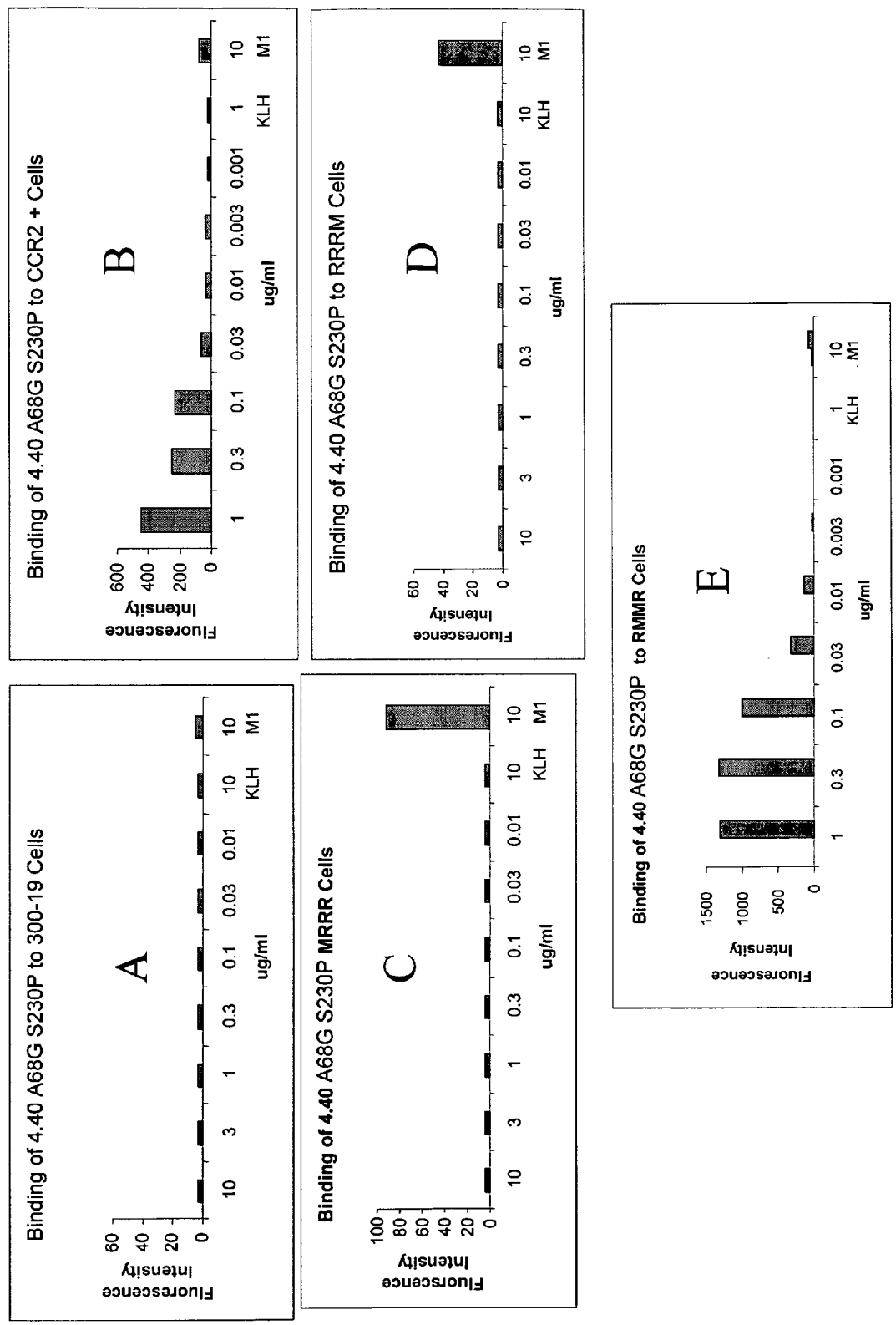
FIG. 7 shows saturation binding analysis (3 hr saturation curve) of the 4.40 A68G S230P antibody on (A) 300-19 control cells; (B) transfected 300-19 cells expressing full length CCR2; (C) transfected 300-19 cells expressing flag-tagged (M1) MRRR chimera [N terminus of CCR2 (M) flag tagged to ensure receptor expression and the loop regions of CCR1 (R)]; (D) transfected 300-19 cells expressing flag-tagged (M1) RRRM chimera [N terminus and $1^{st}$ and $2^{nd}$ loop of CCR1 (R) flag tagged to ensure receptor expression and the $3^{rd}$ loop of CCR2 (M)]; and (E) transfected 300-19 cells expressing flag-tagged (M1) RMMR chimera [N terminus and 3rd loop of CCR1 (R) flag tagged to ensure receptor expression and the $1^{st}$ and 2nd loop of CCR2 (M)].

Binding of antibodies to the CCR2/CCR1 chimeric receptors was assessed using FACS analysis. All receptors were tagged at the N-terminus with FLAG and also stained with the anti-FLAG antibody M1 such that receptor expression could be confirmed. FIGS. 6A & B illustrate the FACS staining of FLAG on the N-terminus with M1 antibody (FIG. 6A) as compared to the staining of 4.40 (FIG. 6B). FIG. 6C illustrates a saturation binding curve of the 4.40 A68G S230P antibody on RMMR chimera transfected 300-19 cells. Saturation binding of the 4.40 A68G S230P antibody to 300-19 cells not transfected with CCR2 showed no binding at concentrations up to 10 ug/mL (FIG. 7A) while 300-19 cells transfected with fully human CCR2 displayed dose-dependent binding at concentrations above 0.01 ug/mL (FIG. 7B). Moreover, saturation binding of the 4.40 A68G S230P antibody to chimeric receptors expressing only the N-terminus of CCR2 (MRRR) together with the 3 loop regions of CCR1 (FIG. 7C) or the 3rd extracellular loop of CCR2 with the N-terminus and $1^{st}$ and $2^{nd}$ loop regions of CCR1 (RRRM) failed to exhibit any significant binding at concentrations up to 10 ug/mL (FIG. 7D). By contrast, saturation binding of the 4.40 A68G S230P antibody to chimeric receptors expressing the N-terminus and $3^{rd}$ loop region of CCR1 and the $1^{st}$ and $2^{nd}$ loop regions of CCR2 (RMMR) showed significant dose-dependent binding at concentrations above 0.001 ug/mL (FIG. 7E). Receptor expression on all of these receptor transfectants was confirmed by assessing the staining of FLAG on the N-terminus with an M1 antibody (Sigma #F3040).

TABLE 7

| | Epitope mapping | | | | | |
|---|---|---|---|---|---|---|
| Clone | Full Length CCR2 (MMMM) | N-terminus of CCR2 (MRRR) | $1^{st}$, $2^{nd}$, and $3^{rd}$ loops of CCR2 (RMMM) | $1^{st}$ and $2^{nd}$ loops of CCR2 (RMMR) | Chemotaxis IC50 (μg/ml) | Epitope |
| 4.40.2 | + | − | + | + | 0.130 | $1^{st}/2^{nd}$ loop |
| 4.9.2 | + | − | + | + | 0.198 | $1^{st}/2^{nd}$ loop |
| 4.52.3 | + | + | − | | 0.642 | N-terminus |
| 4.22.3 | + | − | + | − | 0.137 | $3^{rd}$ loop |
| 4.6.3 | + | + | + | | 0.400 | complex* |
| 4.48.3 | + | + | + | | 0.491 | complex |
| 4.3.1 | + | + | + | | 0.618 | complex |
| 4.59.2 | + | + | + | | 1.020 | complex |
| 4.41.1 | + | − | − | | 0.521 | complex |
| 4.24.3 | + | − | − | | 2.264 | complex |
| 4.39.3 | + | − | − | − | 0.139 | complex |

*Complex = binds to wild type but does not bind to the chimeras

Peptide ELISA

Figure 8:
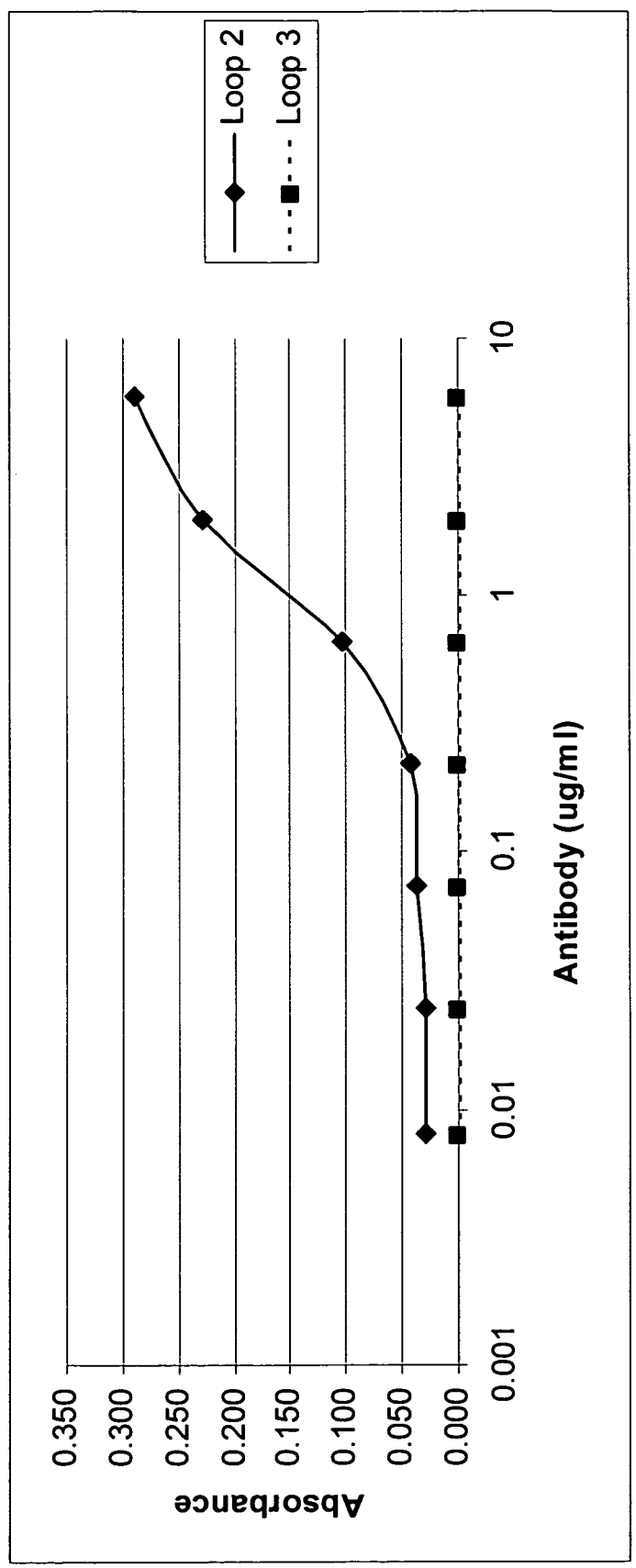
FIG. 8 shows binding of the 4.40 A68G S230P antibody to either loop 2 or loop 3 peptide regions of CCR2 as assessed in a capture ELISA.

In addition, epitope binding to the first and/or second loop of CCR2 was also assessed using a peptide ELISA. A Reacti-Bind NEUTRAVIDIN™ Coated, High Binding Capacity ELISA plate (Pierce; Rockford, Ill.) was washed 3× with PBS/0.05% Tween20 and then coated with 100 ul/well of 6 ug/ml biotinylated CCR2 loop 2 (SEQ ID NO:129) or loop 3 (SEQ ID NO:130) peptide (AnaSpec; San Jose, Calif.). The plate was incubated for 1 hour and then washed 3×. The CCR2 antagonist antibody 4.40.3 A68G S230P or other primary antibody, diluted in PBS/0.1% BSA/0.05% Tween20, was then added to the plate in serial dilution and incubated for 1 hour, as were other controls. The plate was washed 3× and 100 ul/well HRP-Mouse anti-Human IgG4 secondary antibody (Zymed; So. San Francisco, Calif.) was added to all the wells at 1:5000 dilution and incubated for 1 hour. The plate was washed 3× and TMB substrate was added to all the wells and incubated for ~30 minutes. The color reaction was stopped with 2M $H_2SO_4$ and the absorbance reading was measured on a plate reader at 450 nM (FIG. 8). Antibodies, including antibodies 4.9 and 4.40, were identified that bound to the second extracellular loop peptide of the receptor and did not bind to the third loop.

EXAMPLE 9

Binding Selectivity

Figure 9:
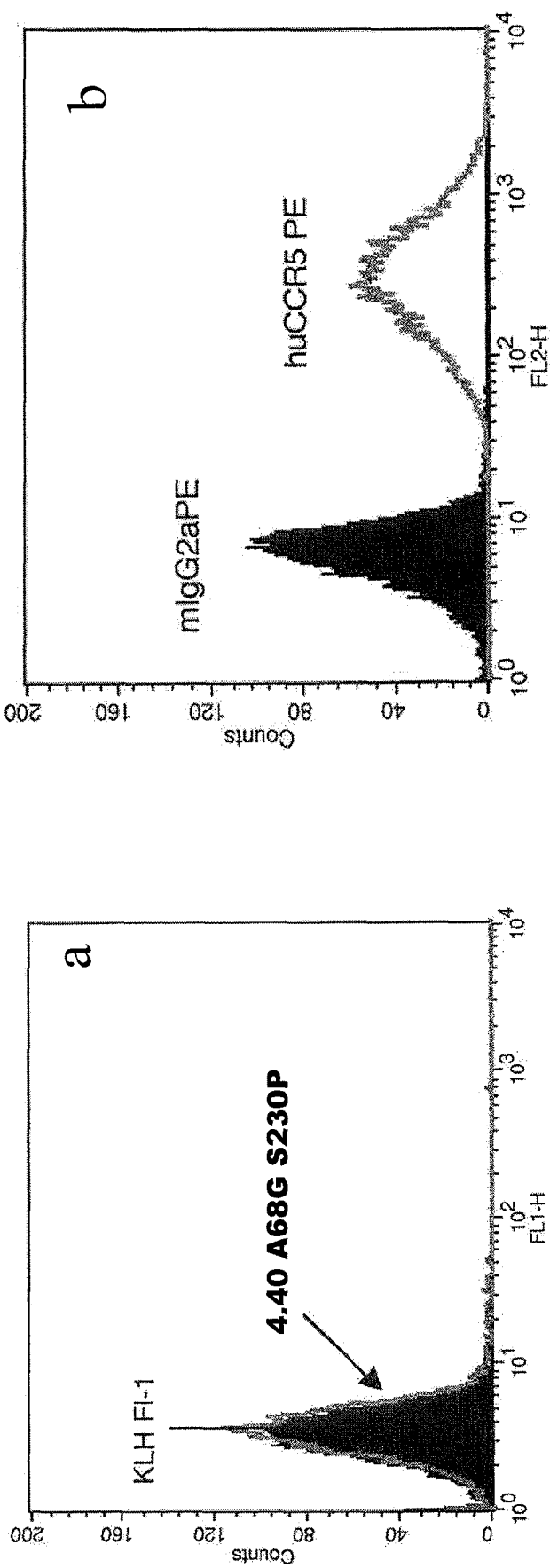
FIG. 9 shows two graphs illustrating the FACS immunostaining of 300-19 cells expressing recombinant CCR5, with either the AF-488 conjugated 4.40.3 A68G S230P antibody (panel A) or with an anti-CCR5 antibody (panel B).

The selectivity of the 4.40 A68G S230P antibody for human CCR2 was confirmed by the absence of binding to a closely related chemokine receptor, CCR5, as shown in FIG. 9 and by the lack of inhibition of chemotaxis induced by the CCR5/CCR1 ligand MIP-1a (FIG. 3). An anti-CCR5 antibody (Pharmingen, catalog #555992) bound to cells expressing CCR5 (FIG. 9b) while the CCR2 antibody 4.40.3 A68G S230P showed no binding to these same cells (FIG. 9a). For these studies, 300.19 cells engineered to express CCR5 were incubated with either the CCR2 selective antibody, 4.40 A68G S230P, or the CCR5-selective antibody for 30 minutes. Cells were then washed in FACS buffer (0.02% sodium azide, 2% heat inactivated fetal bovine serum in PBS) and analyzed for cell surface expression using a flow cytometer using standard methods.

EXAMPLE 10

Calcium Mobilization

Figure 10:
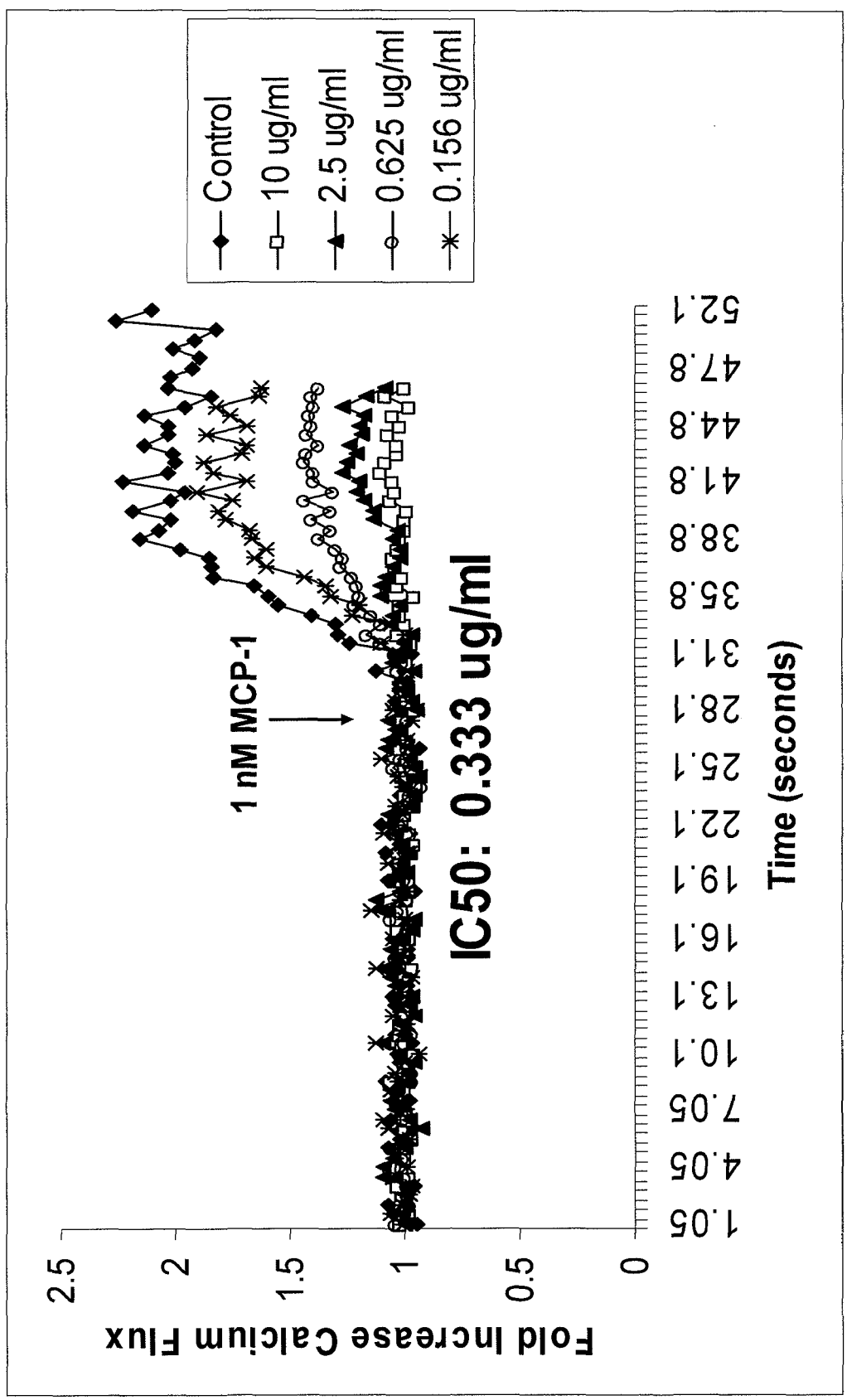
FIG. 10 illustrates the inhibition of MCP-1 induced activity by 4.40 A68G S230P antibody as assessed by calcium mobilization on CCR2 transfected 300-19 cells.

To determine if antibody 4.40 acts as a functional antagonist on CCR2 and does not possess any significant agonist properties, the effects of 4.40.3 on calcium mobilization of CCR2 transfected 300-19 cells was tested as previously described (Gladue R P et al., *J Biol Chem* 278:40473-40480 (2003)). Human CCR2 transfected 300-19 cells were spun down and resuspended at $2 \times 10^6$ cells/ml with PTI buffer (HBSS (Gibco, Grand Island, N.Y.) with 10 mM Hepes (Gibco) and 4.0 mM $CaCl_2$ (Sigma; St. Louis, Mo.)). The cells were loaded with 2 ul of indo-1 AM (Molecular Probes; Eugene, Oreg.) per ml (2 uM final) and incubated for 25 minutes at 37° C. The cells were then washed 2× with PTI buffer and suspended at $1 \times 10^7$/ml. Several concentrations of the antibody or appropriate controls were added to the cells and incubated for 30 minutes at room temperature. To a 1 mm square cuvette (Sarstedt; Germany), 1.8 ml of pre-warmed PTI buffer were added along with 200 ul of the cell suspension. The cells were excited and fluorescence was measured using equipment from Photon Technology Corporation International (PTI; Lawrenceville, N.J.). The machine was paused and 20 ul of 100 nM MCP-1 (Peprotech; Rocky Hill, N.J.) was added. After the response, the following reagents were added in this order to release and chelate total calcium: 20 ul of 18% Triton X-100; 20 ul of 3M Tris pH 8.5; 20 ul of 0.5M EGTA pH 8.5 (all from Sigma). The antibody 4.40 inhibited the ability of MCP-1 to induce calcium mobilization in a dose-responsive manner (FIG. 10). Similar results were obtained with the 4.40 A68G S230P antibody.

EXAMPLE 11

Inhibition of Chemotaxis Towards CCL2 and CCL7

Figure 11:
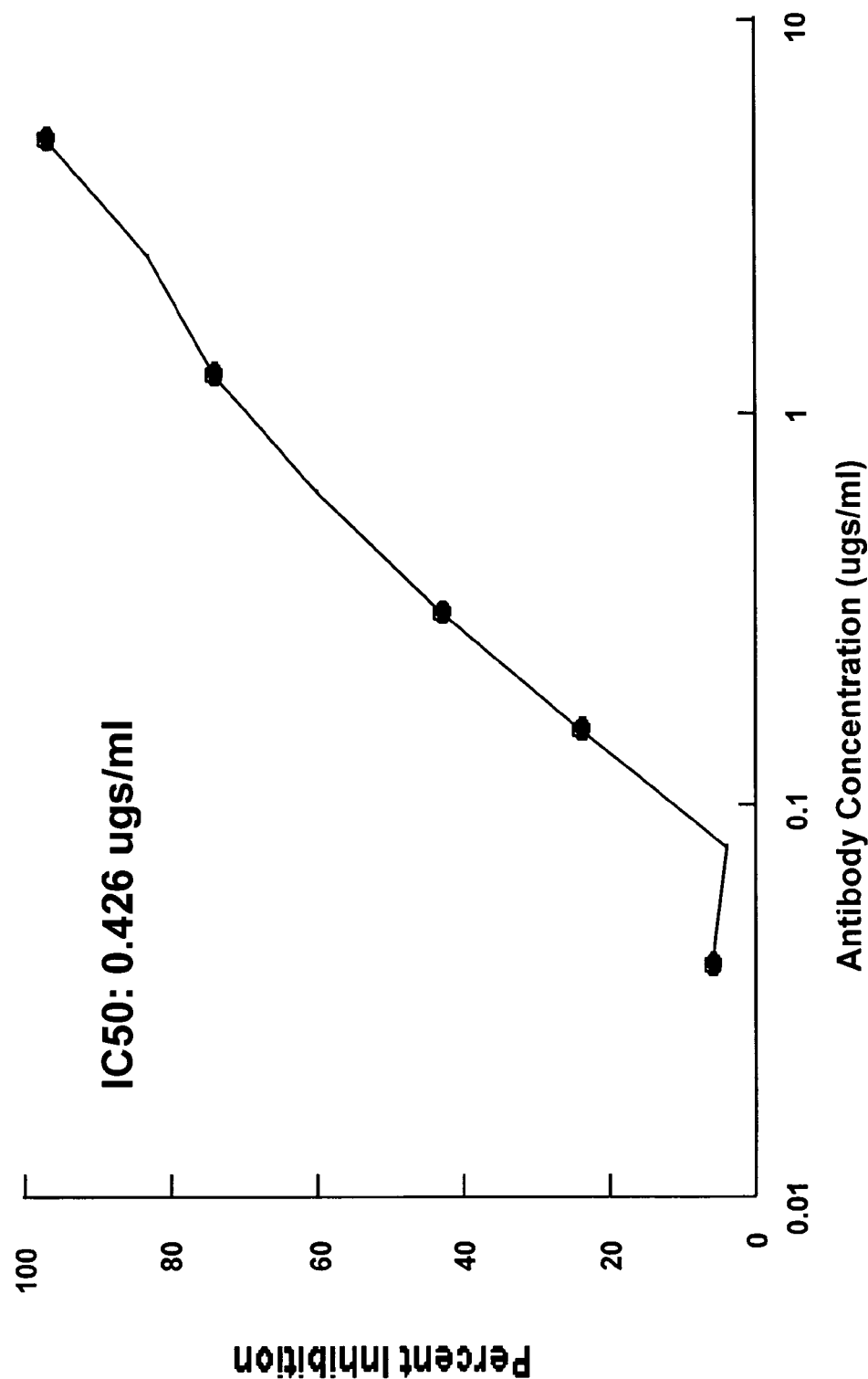
FIG. 11 demonstrates the inhibition of MCP-3 induced chemotaxis of CCR2 transfected 300-19 cells by the 4.40 A68G S230P antibody.

To determine if the inhibition of chemotaxis by the 4.40 A68G S230P antibody is specific for MCP-1 or if it also applies to other CCR2 ligands, chemotaxis of THP-1 cells towards MCP-1(CCL2) was compared to that towards CCL3 (MIP-1a) as was shown in FIG. 3. In addition the migration of CCR2 transfected 300-19 cells toward another CCR2 ligand, CCL7 (MCP-3) in the presence of antibody 4.40 A68G S230P was also assessed using a similar chemotaxis assay as described in Example 6. While the 4.40 A68G S230P antibody inhibits chemotaxis towards both known CCR2 ligands, CCL2 (FIG. 3) and CCL7 (FIG. 11), FIG. 3 shows it does not block chemotaxis towards the CCR1/CCR5 ligand, CCL3 (MIP-1a).

EXAMPLE 12

Actin Polymerization in Monocytes

Human Whole Blood Actin Polymerization

Figure 12:
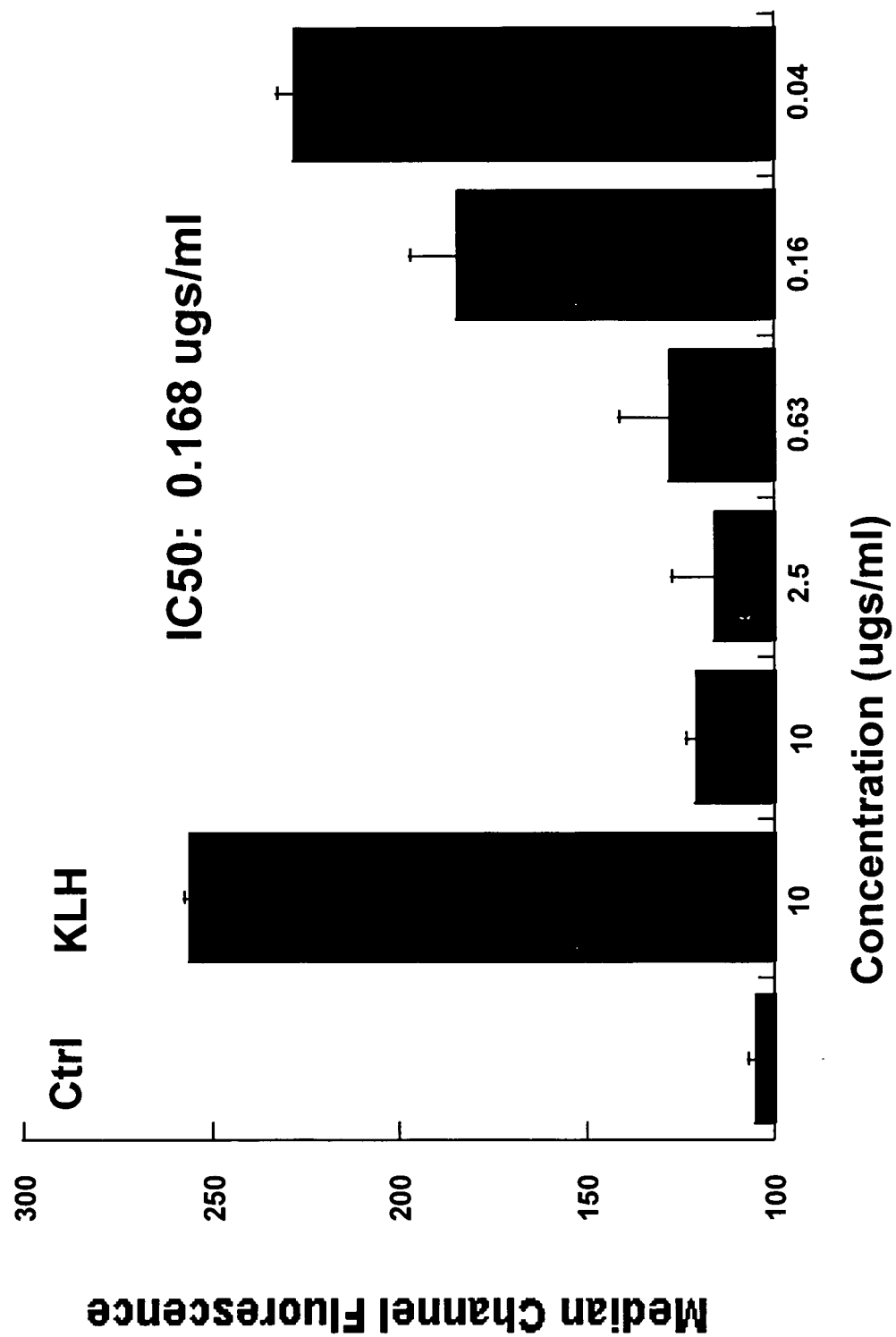
FIG. 12 illustrates the inhibition of human monocyte actin polymerization in response to MCP-1 in whole blood by the 4.40 A68G S230P antibody.

Monoclonal Antibody 4.40 A68G S230P also was tested for its ability to inhibit actin polymerization in human whole blood as shown in FIG. 12. Blood was collected in EDTA vacutainer tubes (VWR; Boston, Mass.) and then incubated with dilutions of antibody or KLH control for 30 minutes at room temperature. Buffer control or 10 µl of 100 nM MCP-1 (Peprotech; Rocky Hill, N.J.) were added to a 48 well Corning plate (VWR). 100 µl of blood was then added with gentle mixing and incubated for 40 seconds after which the reaction was stopped with 0.8 ml of stop/lyse reagent (10% of FACS lysing solution (Becton Dickinson; San Jose, Calif.), 20% of 16% paraformaldehyde (Electron Microscopy Sciences; Ft. Wash., Pa.), and 70% of $H_2O$). The plate was incubated for 10 minutes at room temperature, spun down, and cells were transferred to a 96 well round bottom polypropylene plate, and washed 2× with PBS. 100 µl of PBS were added per well. Then 50 µl of staining reagent were added (10% of a 5 mg/ml lysophosphotidylcholine (Sigma) in 10×HBSS, 80% of the 16% paraformaldehyde, and 10% of 6.6 uM NBD phallacidin (Molecular Probes; Eugene, Oreg.)). The cells were stained for one hour at room temperature in the dark. After incubation, cells were washed 2× with PBS containing 2% fetal bovine serum (Hyclone, Logan Utah) and the fluorescence was quantified on a FACSCAN (Becton Dickinson) gated on monocytes. As shown in FIG. 12, antibody 4.40 A68G S230P inhibited actin polymerization with an $IC_{50}$ of 0.168 ug/ml.

Cynomolgus Monkey Whole Blood Actin Polymerization

Figure 13:
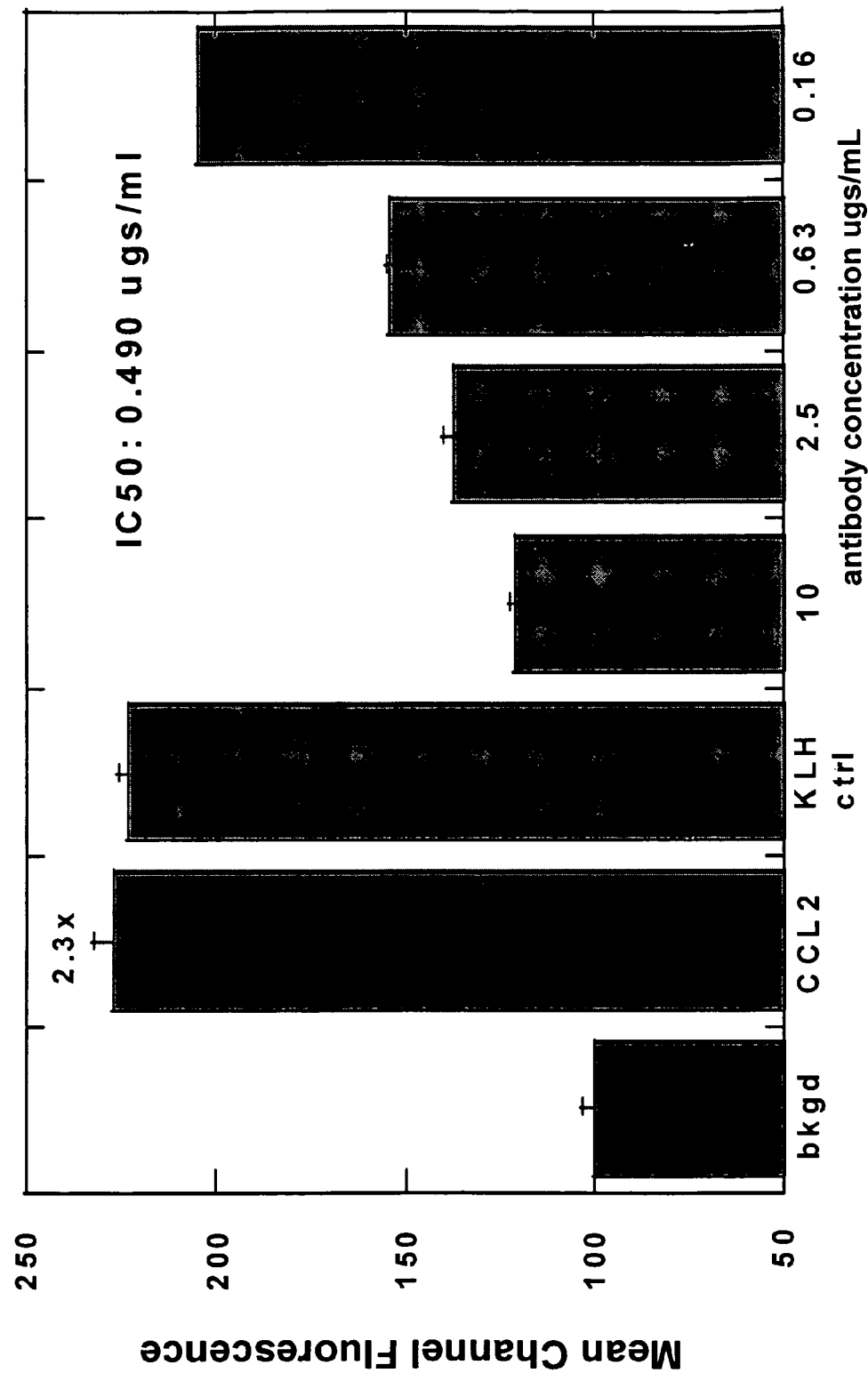
FIG. 13 illustrates the inhibition of monocyte actin polymerization in female cynomolgus monkey response to MCP-1 in whole blood by the 4.40 A68G S230P antibody.

Blood was collected in EDTA vacutainer tubes (VWR; Boston, Mass.) and then incubated with dilutions of antibody or isotype control for 30 minutes at room temperature. During this time 10 ul of 100 nM MCP-1 (Peprotech; Rocky Hill, N.J.; final concentration 10 nM) or buffer control (HBSS with no $Ca^{+2}$ or $Mg^{+2}$ (Gibco; Grand Island, N.Y.) and 0.2% BSA (Sigma; St. Louis, Mo.)) were added to a 48 well Corning plate (VWR). 100 ul of blood was then added with gentle mixing and incubated for 40 seconds. The reaction was stopped with 0.8 ml of stop/lyse reagent (10% of FACS lysing solution (Becton Dickinson; San Jose, Calif.), 20% of 16% paraformaldehyde (Electron Microscopy Sciences; Ft. Wash., Pa.), and 70% of $H_2O$). The plate was incubated for 10 minutes, spun down, and washed 2× with PBS. The cells were then stained for one hour at room temperature in the dark with staining reagent (10% of a 5 mg/ml lysophosphotidylcholine (Sigma) in 10×HBSS, 80% of the 16% paraformaldehyde, and 10% of 6.6 uM NBD phallacidin (Molecular Probes; Eugene, Oreg.)). After incubation, cells were washed 2× with PBS containing 2% fetal bovine serum (Hyclone, Logan Utah) and the fluorescence was quantified on a FACSCAN (Becton Dickinson) gated on activated monocytes. As shown in FIG. 13, antibody 4.40 A68G S230P inhibited whole blood actin polymerization in the cynomolgus monkey with an $IC_{50}$ of 0.49 ug/ml.

EXAMPLE 13

Collagen I mRNA Quantification Assay

Figure 14:
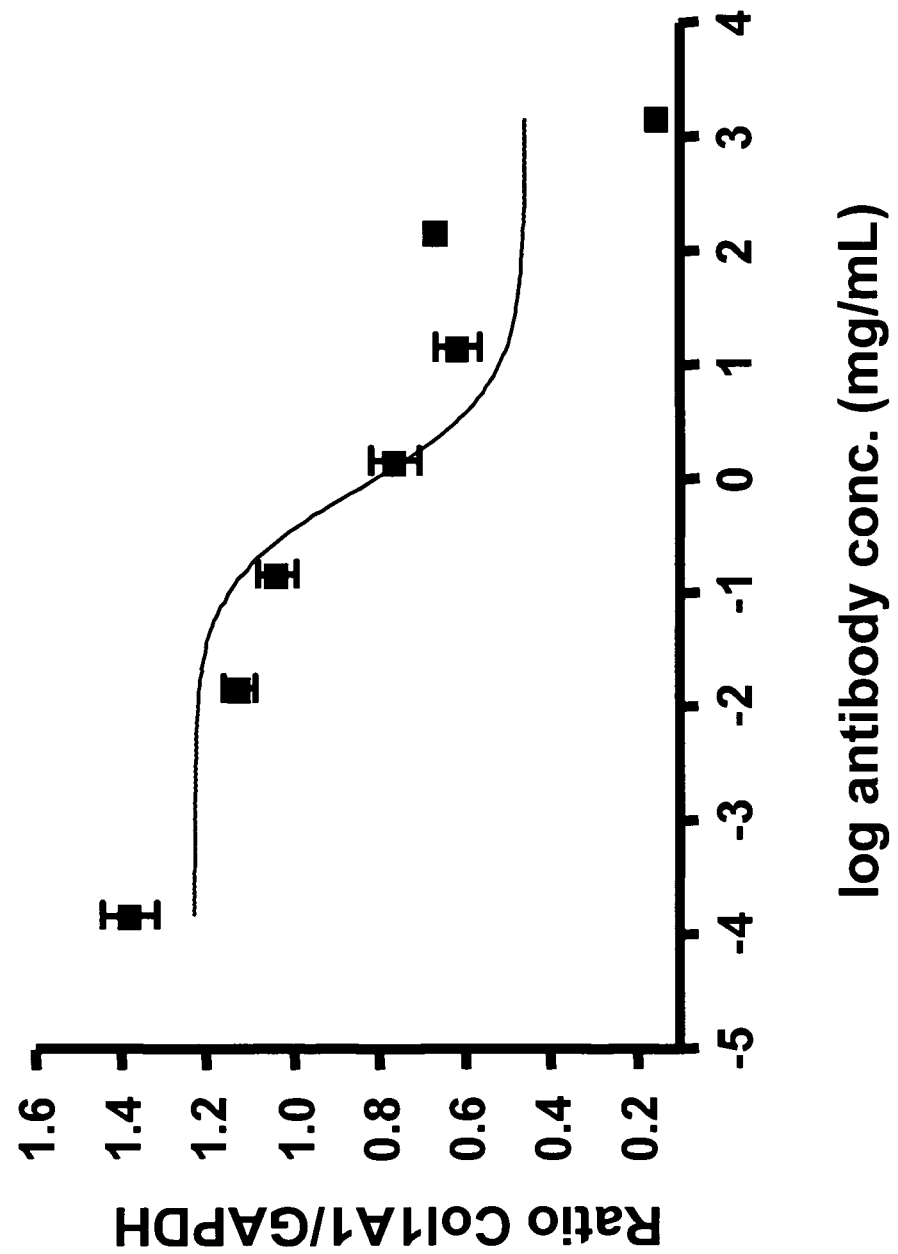
FIG. 14 shows the dose-dependent inhibition of collagen 1 mRNA synthesis in the hHSC cell line, LI90, by the 4.40 A68G S230P antibody.

Human hepatic stellate cell line, LI-90 (JCRB Cellbank, Japan), was grown in flasks containing DME medium supplemented with 10% deactivated FBS, 100 U/ml Penicillin/100 ug/ml Streptomycin and 2 mM L-Gln (Invitrogen) at 37° C. in a 5% CO2 humidified incubator. Cells were grown in 96-well tissue culture plates at 20,000 cells/well for 3 days and treated with 1000 nM of MCP-1 (PeproTech) and various concentrations of 4.40 A68G S230P for 48 hours at 37° C. The culture medium was removed and the cells were lysed by addition of 100 ul of lysing buffer supplied with QUANTIGENE™ Expression Kit (Panomics). The branched DNA assay was performed following the manufacturer's instructions. Briefly, samples of total RNA were loaded on a 96-well microtiter plate containing hybridization buffer and 50 fmol/ul of Col1A1/GAPDH probe set. The captured mRNAs were hybridized to branched DNA molecules that contained alkaline phosphatase molecules by incubating at 46° C. for 60 min. After further incubation with the chemiluminescent substrate at 46° C. for 30 min, luminescence was quantified with a luminometer (ARVOsx, Perkin Elmer; Mass., USA). The ratio of the luminescence of Col1A1 against GAPDH was calculated, and the data was analyzed by Prism 4.0 software to determine $IC_{50}$ values (GraphPad). As shown in FIG. 14, 4.40 A68G S230P inhibited collagen IAI mRNA synthesis in LI90 cells induced by MCP-1 with an $IC_{50}$ value of 0.89 μg/mL (6.2 nM).

EXAMPLE 14 pERK Phosphorylation

Figure 15:
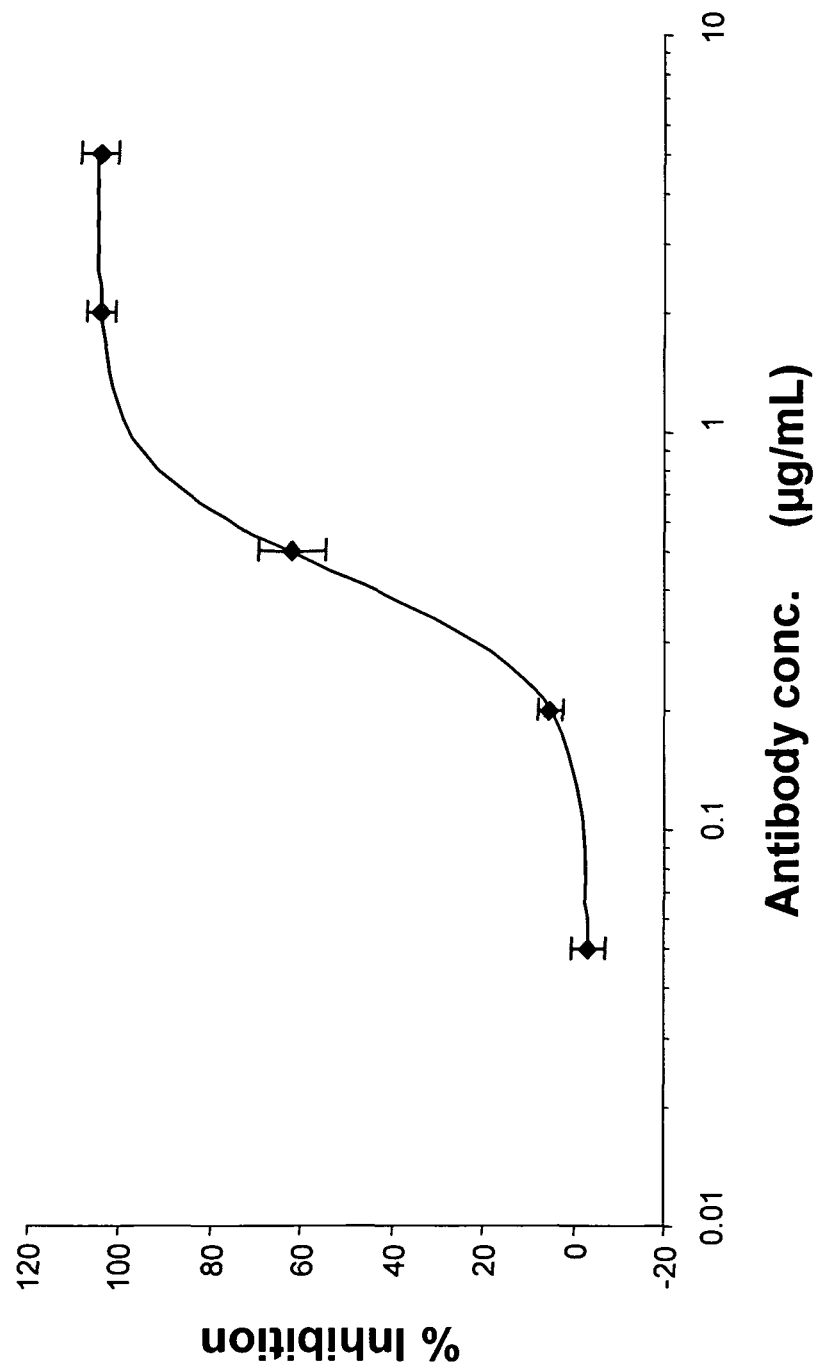
FIG. 15 demonstrates the dose-dependent inhibition of pERK phosphorylation in human whole blood at 10 nM MCP-1 by the 4.40 A68G S230P antibody.

Human whole blood was freshly isolated from healthy volunteers. FACS analysis indicated a high level of phosphorylation of extracellular signal-regulated kinase (pERK) in CD14+ monocytes 6 min after addition of MCP-1. 4.40 A68G S230P inhibited MCP-1 induced pERK phosphorylation in whole blood in a dose-dependent manner (FIG. 15). pERK phosphorylation in monocytes following ex vivo stimulation with MCP-1 can be utilized as a mechanism biomarker, thereby facilitating PK/PD and translational pharmacology. The $IC_{50}$ and $IC_{90}$ values obtained for the 4.40 A68G S230P antibody in this whole blood assay were 0.44 μg/mL (2.9 nM) and 0.89 μg/ml (6.1 nM), respectively.

EXAMPLE 15

Murine Acute Hepatitis Model

Figure 16:
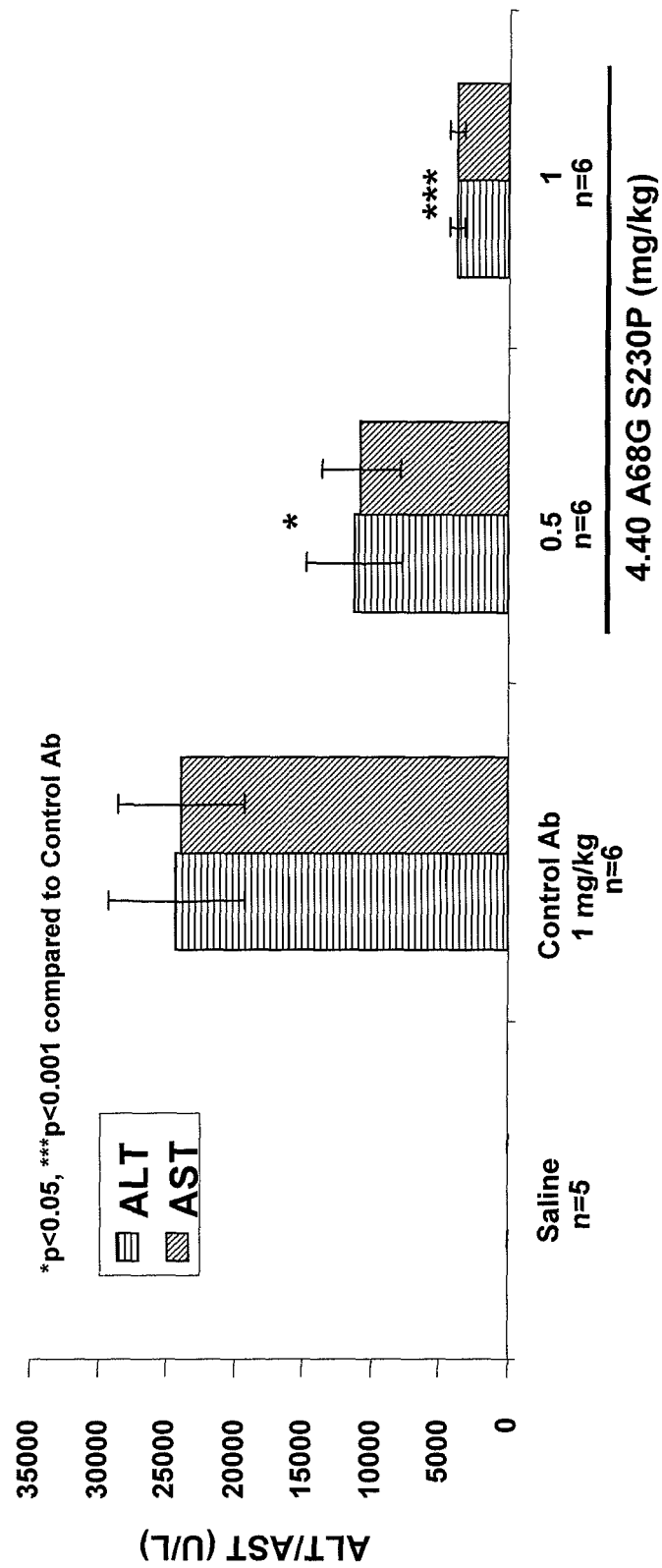
FIG. 16 shows the decrease of plasma alanine transaminase (ALT) and aspartate aminotransferase (AST) activities in human CCR2 knock-in mice by the 4.40 A68G S230P antibody 24 hours after a single ConA injection.

Efficacy of the 4.40 A68G S230P antibody was also examined using an acute mouse ConA model of hepatitis. For this study, transgenic mice were used in which mouse CCR2 had been replaced by human CCR2 since the 4.40 A68G S230P antibody does not recognize the rodent CCR2. The animals were given a single intraperitoneal injection of the mAb at 0.1, 0.3 or 1.0 mg/kg in saline. An $IgG_4$ isotype control antibody was administered to a separate group. Thirty minutes later the animals were given an i.v. tail vein injection (0.1 mL) of 15 mg/kg ConA in pyrogen-free saline. A control group was given saline without ConA. After 24 hours, blood samples were obtained and plasma liver enzymes analyzed. As shown in FIG. 16, ALT and AST were markedly elevated in the control antibody group with values close to 25,000 U/L. By contrast, mice treated with 0.5 and 1.0 mg/kg 4.40 A68G S230P showed a significant reduction of their plasma liver enzymes by approximately 50% and 80%, respectively.

EXAMPLE 17

Therapeutic Effects in Animal Disease Models

Inflammation

The therapeutic effects of the human anti-CCR2 antibodies or antigen-binding fragments thereof, including the 4.40 and 4.9 antibodies, are tested using in vivo mammalian models of inflammation. Leukocyte infiltration is monitored upon intradermal injection of a chemokine, such as MCP-1, and an antibody or fragment thereof reactive with mammalian CCR2, such as the 4.40 antibody, into a suitable animal, such as rabbit, mouse, rat, guinea pig or rhesus macaque (see e.g., Van Damme, J. et al., *J. Exp. Med.* 176:59-65 (1992); Zachariae, C. O. C. et al., *J. Exp. Med.* 171:2177-2182 (1990); Jose, P. J. et al., *J. Exp. Med.* 179: 881-887 (1994)). Skin biopsies are assessed histologically for infiltration of leukocytes (e.g., eosinophils and granulocytes). It is expected that the antagonistic anti-CCR2 antibodies will decrease infiltration of leukocyte compared to control animals.

Multiple Sclerosis

The therapeutic effects of the antibodies or fragments thereof, including the 4.40 and 4.9 antibodies, are tested using in vivo mammalian models of multiple sclerosis. Experimental autoimmune encephalomyelitis (EAE) is a T cell-mediated inflammatory disease of the central nervous system (CNS) that serves as an animal model for multiple sclerosis (MS) (see Steinman L, *Neuron* 24:511-514 (1999)). On day 0 and day 7 post-immunization (p.i.) with encephalitogenic $MOG_{35-55}$ peptide, C57/J 129 and/or C57BU6 mice are sensitized for active EAE by subcutaneous (s.c.) injection (two sites, dorsal flank) with a total of 600 μg of encephalitogenic $MOG_{35-55}$ emulsified in incomplete Freund's adjuvant (IFA; Difco, Detroit, Mich.), containing 70 μg of *Mycobacterium tuberculosis*, H37Ra (Difco). On day 0 and day 2 p.i., each mouse also receives 500 ng of pertussis toxin (PTX; List Biological Laboratories, Campbell, Calif.) intravenously (i.v.) via a tail vein. Some animals also receive an escalated dosage of anti-CCR2 antagonistic antibodies, such as the 4.40 antibody. Animals are assessed daily for clinical signs and evaluated according to the following scale: grade 0, no abnormalities; grade 1, weak tail; grade 2, limp tail and weakness in hind-limbs; grade 3, hind-limb paraparesis; grade 4, tetraplegia; and grade 5, moribund or death.

In addition, light microscopy studies are performed on glutaraldehyde/osmium-fixed tissue samples from the optic nerve, cerebrum, cerebellum, and spinal cord. The tissue samples are dehydrated and embedded in epoxy resin from which 1-μm sections are cut and stained with toluidine blue. Inflammation, demyelination, Wallerian degeneration (WD), and remyelination are scored on a scale of 0 to 5, as described previously (Cannella et al., *Proc Natl Acad Sci USA* 95:10100-10105 (1998)). It is expected that mice treated with anti-CCR2 antagonistic antibodies will exhibit reduced signs of clinical abnormalities, inflammation, demyelination and WD over control animals. It is further expected that such reduction will occur in a dosage-dependent manner.

Neuropathic Pain

The therapeutic effects of the antibodies or fragments thereof, including the 4.40 and 4.9 antibodies, are tested using in vivo mammalian models of neuropathic pain. C57BL mice are divided into two groups. The experimental group is administered anti-CCR2 antagonistic antibodies daily, such as the 4.40 antibody, via tail vein injection while a second group is not administered the antibody. The two groups are tested at time intervals after the initiation of treatment in the following assays:

Rota-Rod.

Initially, mice are trained on the rota-rod for 3 min at a speed of 10 rpm. For testing, the speed is set at 10 rpm for 60 s and subsequently accelerated to 600 rpm. The time taken for mice to fall after the beginning of the acceleration is recorded.

Hot Plate.

Mice are habituated to the hot-plate apparatus with temperature set at 45° C. for 2 min. Subsequently, mice are placed on the hot-plate and the temperature is sequentially changed to 52.5° C. and 55.5° C. (cutoff set at 30 s) each and then to 58.5° C. (cutoff set at 20 s). The time when mice either lick their paws or jump is recorded.

Formalin Test.

For 4 days before testing, mice are acclimated for 2 hours every day on the test platform. On the day of the study, mice are placed for 1 hour on the test platform and subsequently are administered 10 µl of 2% formalin in the plantar surface of the left paw. The time mice spend either licking or lifting the injected paw is recorded over 2-minute periods at 5-minute intervals for 50 min.

Thermal and Mechanical Stimulation.

Thermal sensitivity is assessed by measuring paw withdrawal latencies to a radiant heat stimulus (Hargreaves et al., *Pain* 32:77-88 (1988)). Mechanical sensitivity is determined with calibrated von Frey filaments by using the up-and-down paradigm (Chaplan et al., *J. Neurosci. Methods* 53, 55-63 (1994)).

Nerve Injury.

Mice are anesthetized with a mixture of ketamine (50 mg/kg, i.m.) and medetomidine (1 mg/kg, i.m.). An incision is made just below the hip bone, parallel to the sciatic nerve. The nerve is exposed and any adhering tissue is removed from the nerve. A tight ligature with 6-0 silk suture thread around one-third to one-half of the diameter of the sciatic nerve is made. Muscles are closed with suture thread and the wound, with wound clips. The response of the mice to mechanical stimulation is tested before and up to 15 days after nerve injury.

It is expected that the mice treated with anti-CCR2 antagonistic antibodies will exhibit reduced signs neuropathic pain compared to control mice.

TABLE 8

CDR Sequences (SEQ ID NO:)

| Antibody | $V_H$ CDR1 | $V_H$ CDR2 | $V_H$ CDR3 | $V_L$ CDR1 | $V_L$ CDR2 | $V_L$ CDR3 |
|---|---|---|---|---|---|---|
| 4.9 | 12 | 13 | 14 | 30 | 31 | 32 |
| 4.22 | 48 | 49 | 50 | 66 | 67 | 68 |
| 4.40 | 84 | 85 | 86 | 102 | 103 | 104 |
| 4.39 | 177 | 178 | 179 | 195 | 196 | 197 |

We claim:

1. An isolated human monoclonal antibody or an antigen-binding portion thereof that specifically binds to human CCR2, comprising a heavy chain variable ($V_H$) domain amino acid sequence comprising
   a $V_H$ CDR1 as set forth in SEQ ID NO:84, a $V_H$ CDR2 as set forth in SEQ ID NO:85, and a $V_H$ CDR3 as set forth in SEQ ID NO:86; and a light chain variable ($V_L$) domain amino acid sequence comprising a $V_L$ CDR1 as set forth in SEQ ID NO:102, a $V_L$ CDR2 as set forth in SEQ ID NO:103, and a $V_L$ CDR3 as set forth in SEQ ID NO:104.

2. The isolated human monoclonal antibody or antigen-binding portion thereof according to claim 1, comprising the heavy chain variable ($V_H$) domain amino acid sequence selected from the group consisting of: SEQ ID NO:83, SEQ ID NO:83 having a conservative amino acid substitution, SEQ ID NO:83 having a germline amino acid substitution compared to SEQ ID NO:160, and an amino acid sequence at least 90% identical to SEQ ID NO:83.

3. The isolated human monoclonal antibody or an antigen-binding portion thereof according to claim 1, comprising the light chain variable ($V_L$) domain amino acid sequence selected from the group consisting of:
   SEQ ID NO:101, SEQ ID NO:113, SEQ ID NO:101 having a conservative amino acid substitution, SEQ. ID NO: 113 having a conservative amino acid substitution, SEQ ID NO:101 having a germline amino acid substitution compared to SEQ ID NO:161, SEQ ID NO:113 having a germline amino acid substitution compared to SEQ ID NO: 161, an amino acid sequence at least 90% identical to SEQ ID NO:101, and an amino acid sequence at least 90% identical to SEQ ID NO:113.

4. An isolated human monoclonal antibody or an antigen-binding portion that specifically binds to CCR2, comprising: heavy chain CDR1, CDR2 and CDR3 from the heavy chain of a monoclonal antibody produced by the hybridoma designated ATCC Accession No. PTA-6981; and light chain CDR1, CDR2 and CDR3 from the light chain of the monoclonal antibody produced by the hybridoma designated ATCC Accession No. PTA-6981.

5. The isolated human monoclonal antibody or antigen binding portion according to claim 1, the antibody having the heavy chain and the light chain selected from the group consisting of:
   a) the heavy chain having an amino acid sequence of SEQ NO:82 and the light chain having an amino acid sequence of SEQ ID NO:100
   and
   b) the heavy chain having an amino acid sequence of SEQ ID NO:116 and the light chain having an amino acid sequence of SEQ ID NO:112.

6. The isolated human monoclonal antibody or antigen-binding portion according to claim 1, wherein the heavy chain amino acid sequence is SEQ ID NO:116 and the light chain amino acid sequence is SEQ ID NO:112.

7. The isolated human monoclonal antibody or antigen-binding portion according to claim 1, further comprising one or more $V_H$ FR1, FR2, FR3 or FR4 and/or $V_L$ FR1, FR2, FR3 or FR4 amino acid sequence of an antibody heavy or light chain sequence selected from the group consisting of: SEQ ID NO:82, SEQ ID NO:100, SEQ ID NO: 116, and SEQ ID NO:112.

8. The isolated human monoclonal antibody or antigen-binding portion according to claim 7, further comprising a heavy chain constant domain.

9. The isolated human monoclonal antibody or antigen-binding portion according to claim 8, further comprising a light chain constant domain.

10. A pharmaceutical composition comprising the antibody or antigen-binding portion according to claim 1 and a pharmaceutically acceptable carrier.

11. An isolated human monoclonal antibody or an antigen-binding portion thereof that specifically binds to human CCR2, comprising the heavy chain variable ($V_H$) domain amino acid sequence of SEQ ID NO:83 and the light chain variable ($V_L$) domain amino acid sequence of SEQ ID NO:113.

* * * * *

UNITED STATES PATENT AND TRADEMARK OFFICE
CERTIFICATE OF CORRECTION

| | | |
|---|---|---|
| PATENT NO. | : 8,710,191 B2 | Page 1 of 1 |
| APPLICATION NO. | : 13/059702 | |
| DATED | : April 29, 2014 | |
| INVENTOR(S) | : Gladue et al. | |

It is certified that error appears in the above-identified patent and that said Letters Patent is hereby corrected as shown below:

In the Specification:

Column 52, in TABLE 2, in the line that begins with 4.22.3 under the Antibody column, replace "PTA-6980" with -- PTA-6981 --.

Column 52, in TABLE 2, in the line that begins with 4.40.3 under the Antibody column, replace "PTA-6981" with -- PTA-6980 --.

In the Claims:

Column 183, claim 4, line 66, replace "PTA-6981" with -- PTA-6980 --.

Column 184, claim 4, line 29, replace "PTA-6981" with -- PTA-6980 --.

Signed and Sealed this
Fifth Day of August, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,710,191 B2                                                      Page 1 of 1
APPLICATION NO.   : 13/059702
DATED             : April 29, 2014
INVENTOR(S)       : Gladue et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 416 days.

Signed and Sealed this

Twenty-ninth Day of September, 2015

Michelle K. Lee
*Director of the United States Patent and Trademark Office*

SEQUENCE LISTING

<160> NUMBER OF SEQ ID NOS: 203

<210> SEQ ID NO 1
<211> LENGTH: 1350
<212> TYPE: DNA
<213> ORGANISM: Homo sapiens

<400> SEQUENCE: 1

```
caggtgcagc tggtggagtc tgggggaggc gtggtccagc ctggagggtc cctgagactc      60
tcctgtgcag cctctggatt caccttcagt agttatggca tgcactgggt ccgccaggct     120
ccaggcaagg ggctggagtg ggtggcagtt caaacatatg atggaagaaa taaatactat     180
gcagactccg tgaagggccg attcaccatc tccagagaca attccaagaa aacgttgtat     240
ctgcaaatga acagactgag agctgaggac acggctgtgt attattgtgc gagagatcag     300
gcgtactgga agtactttga tgcttttgat atctggggcc aagggacaat ggtcaccgtc     360
tcttcagctt ccaccaaggg cccatccgtc ttccccctgg cgcctgctc  caggagcacc     420 tccgagagca gccgccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660
gagtccaaat atggtccccc atgcccatca tgcccagcac ctgagttcct ggggggacca     720
tcagtcttcc tgttccccc  aaaacccaag gacactctca tgatctcccg gacccctgag     780
gtcacgtgcg tggtggtgga cgtgagccag gaagacccc  aggtccagtt caactggtac     840
gtggatggcg tggaggtgca taatgccaag acaaagccgc gggaggagca gttcaacagc     900
acgtaccgtg tggtcagcgt cctcaccgtc ctgcaccagg actggctgaa cggcaaggag     960
tacaagtgca aggtctccaa caaaggcctc ccgtcctcca tcgagaaaac catctccaaa    1020
gccaaagggc agccccgaga gccacaggtg tacaccctgc ccccatccca ggaggagatg    1080
accaagaacc aggtcagcct gacctgcctg gtcaaaggct tctaccccag cgacatcgcc    1140
gtggagtggg agagcaatgg gcagccggag aacaactaca agaccacgcc tcccgtgctg    1200
```

```
gactccgacg gctccttctt cctctacagc aggctaaccg tggacaagag caggtggcag   1260
gaggggaatg tcttctcatg ctccgtgatg catgaggctc tgcacaacca ctacacacag   1320
aagagcctct ccctgtctct gggtaaatga                                    1350
```

<210> SEQ ID NO 2
<211> LENGTH: 366
<212> TYPE: DNA
<213> ORGANISM: Homo sapiens

<400> SEQUENCE: 2

```
caggtgcagc tggtggagtc tgggggaggc gtggtccagc ctgggaggtc cctgagactc    60
tcctgtgcag cctctggatt caccttcagt agttatggca tgcactgggt ccgccaggct   120
ccaggcaagg ggctggagtg ggtggcagtt caaacatatg atggaagaaa taaatactat   180
gcagactccg tgaagggccg attcaccatc tccagagaca attccaagaa acgttgtat   240 ctgcaaatga acagactgag agctgaggac acggctgtgt attattgtgc gagagatcag   300
gcgtactgga agtactttga tgcttttgat atctggggcc aagggacaat ggtcaccgtc   360
tcttca                                                              366
```

<210> SEQ ID NO 3
<211> LENGTH: 15
<212> TYPE: DNA
<213> ORGANISM: Homo sapiens

<400> SEQUENCE: 3

```
agttatggca tgcac                                                     15
```

<210> SEQ ID NO 4
<211> LENGTH: 51
<212> TYPE: DNA
<213> ORGANISM: Homo sapiens

<400> SEQUENCE: 4

```
gttcaaacat atgatggaag aaataaatac tatgcagact ccgtgaaggg c             51
```

<210> SEQ ID NO 5
<211> LENGTH: 39
<212> TYPE: DNA
<213> ORGANISM: Homo sapiens

<400> SEQUENCE: 5

```
gatcaggcgt actggaagta ctttgatgct tttgatatc                           39
```

<210> SEQ ID NO 6
<211> LENGTH: 90
<212> TYPE: DNA
<213> ORGANISM: Homo sapiens

<400> SEQUENCE: 6

```
caggtgcagc tggtggagtc tgggggaggc gtggtccagc ctgggaggtc cctgagactc    60
tcctgtgcag cctctggatt caccttcagt                                     90
```

<210> SEQ ID NO 7
<211> LENGTH: 42
<212> TYPE: DNA
<213> ORGANISM: Homo sapiens

<400> SEQUENCE: 7

```
tgggtccgcc aggctccagg caaggggctg gagtgggtgg ca                       42
```

<210> SEQ ID NO 8
<211> LENGTH: 96
<212> TYPE: DNA
<213> ORGANISM: Homo sapiens

<400> SEQUENCE: 8
cgattcacca tctccagaga caattccaag aaaacgttgt atctgcaaat gaacagactg    60
agagctgagg acacggctgt gtattattgt gcgaga                              96

<210> SEQ ID NO 9
<211> LENGTH: 33
<212> TYPE: DNA
<213> ORGANISM: Homo sapiens

<400> SEQUENCE: 9
tggggccaag ggacaatggt caccgtctct tca                                 33

<210> SEQ ID NO 10
<211> LENGTH: 449
<212> TYPE: PRT
<213> ORGANISM: Homo sapiens

<400> SEQUENCE: 10

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Gln Thr Tyr Asp Gly Arg Asn Lys Tyr Tyr Ala Asp Ser Val
    50                  55                  60

Lys Gly Arg Phe Thr Ile Ser Arg Asp Asn Ser Lys Lys Thr Leu Tyr
65                  70                  75                  80

Leu Gln Met Asn Arg Leu Arg Ala Glu Asp Thr Ala Val Tyr Tyr Cys
                85                  90                  95

Ala Arg Asp Gln Ala Tyr Trp Lys Tyr Phe Asp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270
```

```
Pro Glu Val Gln Phe Asn Trp Tyr Val Asp Gly Val Glu Val His Asn
        275                 280                 285
Ala Lys Thr Lys Pro Arg Glu Glu Gln Phe Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
        340                 345                 350
Leu Pro Pro Ser Gln Glu Glu Met Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
            420                 425                 430
Ala Leu His Asn His Tyr Thr Gln Lys Ser Leu Ser Leu Ser Leu Gly
        435                 440                 445
Lys

<210> SEQ ID NO 11
<211> LENGTH: 122
<212> TYPE: PRT
<213> ORGANISM: Homo sapiens

<400> SEQUENCE: 11

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Gln Thr Tyr Asp Gly Arg Asn Lys Tyr Tyr Ala Asp Ser Val
    50                  55                  60
Lys Gly Arg Phe Thr Ile Ser Arg Asp Asn Ser Lys Lys Thr Leu Tyr
65                  70                  75                  80
Leu Gln Met Asn Arg Leu Arg Ala Glu Asp Thr Ala Val Tyr Tyr Cys
                85                  90                  95
Ala Arg Asp Gln Ala Tyr Trp Lys Tyr Phe Asp Ala Phe Asp Ile Trp
            100                 105                 110
Gly Gln Gly Thr Met Val Thr Val Ser Ser
        115                 120

<210> SEQ ID NO 12
<211> LENGTH: 5
<212> TYPE: PRT
<213> ORGANISM: Homo sapiens

<400> SEQUENCE: 12

Ser Tyr Gly Met His
1               5

<210> SEQ ID NO 13
```

```
<211> LENGTH: 17
<212> TYPE: PRT
<213> ORGANISM: Homo sapiens

<400> SEQUENCE: 13

Val Gln Thr Tyr Asp Gly Arg Asn Lys Tyr Tyr Ala Asp Ser Val Lys
1               5                   10                  15

Gly

<210> SEQ ID NO 14
<211> LENGTH: 13
<212> TYPE: PRT
<213> ORGANISM: Homo sapiens

<400> SEQUENCE: 14

Asp Gln Ala Tyr Trp Lys Tyr Phe Asp Ala Phe Asp Ile
1               5                   10

<210> SEQ ID NO 15
<211> LENGTH: 30
<212> TYPE: PRT
<213> ORGANISM: Homo sapiens

<400> SEQUENCE: 15

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser
                20                  25                  30

<210> SEQ ID NO 16
<211> LENGTH: 14
<212> TYPE: PRT
<213> ORGANISM: Homo sapiens

<400> SEQUENCE: 16

Trp Val Arg Gln Ala Pro Gly Lys Gly Leu Glu Trp Val Ala
1               5                   10

<210> SEQ ID NO 17
<211> LENGTH: 32
<212> TYPE: PRT
<213> ORGANISM: Homo sapiens

<400> SEQUENCE: 17

Arg Phe Thr Ile Ser Arg Asp Asn Ser Lys Lys Thr Leu Tyr Leu Gln
1               5                   10                  15

Met Asn Arg Leu Arg Ala Glu Asp Thr Ala Val Tyr Tyr Cys Ala Arg
                20                  25                  30

<210> SEQ ID NO 18
<211> LENGTH: 11
<212> TYPE: PRT
<213> ORGANISM: Homo sapiens

<400> SEQUENCE: 18

Trp Gly Gln Gly Thr Met Val Thr Val Ser Ser
1               5                   10

<210> SEQ ID NO 19
<211> LENGTH: 645
<212> TYPE: DNA
<213> ORGANISM: Homo sapiens

<400> SEQUENCE: 19
```

```
gacatccaga tgacccagtc tccatcctcc ctgtctacat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacaatt ccccgtgcag ttttggccag   300
gggaccaagc tggagatcaa cgaactgtg gctgcaccat ctgtcttcat cttcccgcca   360
tctgatgagc agttgaaatc tggaactgcc tctgttgtgt gcctgctgaa gaacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttag                   645

<210> SEQ ID NO 20
<211> LENGTH: 321
<212> TYPE: DNA
<213> ORGANISM: Homo sapiens

<400> SEQUENCE: 20
gacatccaga tgacccagtc tccatcctcc ctgtctacat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacaatt ccccgtgcag ttttggccag   300
gggaccaagc tggagatcaa a                                             321

<210> SEQ ID NO 21
<211> LENGTH: 33
<212> TYPE: DNA
<213> ORGANISM: Homo sapiens

<400> SEQUENCE: 21
cgggcaagtc agagcattag cagctattta aat                                 33

<210> SEQ ID NO 22
<211> LENGTH: 21
<212> TYPE: DNA
<213> ORGANISM: Homo sapiens

<400> SEQUENCE: 22
gctgcatcca gtttgcaaag t                                              21

<210> SEQ ID NO 23
<211> LENGTH: 27
<212> TYPE: DNA
<213> ORGANISM: Homo sapiens

<400> SEQUENCE: 23
caacagagtt acaattcccc gtgcagt                                        27

<210> SEQ ID NO 24
<211> LENGTH: 69
<212> TYPE: DNA
<213> ORGANISM: Homo sapiens

<400> SEQUENCE: 24
```

```
gacatccaga tgacccagtc tccatcctcc ctgtctacat ctgtaggaga cagagtcacc    60
atcacttgc                                                            69
```

<210> SEQ ID NO 25
<211> LENGTH: 45
<212> TYPE: DNA
<213> ORGANISM: Homo sapiens

<400> SEQUENCE: 25

```
tggtatcagc agaaaccagg gaaagcccct aagctcctga tctat                    45
```

<210> SEQ ID NO 26
<211> LENGTH: 96
<212> TYPE: DNA
<213> ORGANISM: Homo sapiens

<400> SEQUENCE: 26

```
ggggtcccat caaggttcag tggcagtgga tctgggacag atttcactct caccatcagc    60
agtctgcaac ctgaagattt tgcaacttac tactgt                              96
```

<210> SEQ ID NO 27
<211> LENGTH: 30
<212> TYPE: DNA
<213> ORGANISM: Homo sapiens

<400> SEQUENCE: 27

```
tttggccagg ggaccaagct ggagatcaaa                                     30
```

<210> SEQ ID NO 28
<211> LENGTH: 214
<212> TYPE: PRT
<213> ORGANISM: Homo sapiens

<400> SEQUENCE: 28

Asp Ile Gln Met Thr Gln Ser Pro Ser Ser Leu Ser Thr Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Ser Pro Cys
                85                  90                  95

Ser Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Lys Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 29
<211> LENGTH: 107
<212> TYPE: PRT
<213> ORGANISM: Homo sapiens

<400> SEQUENCE: 29

Asp Ile Gln Met Thr Gln Ser Pro Ser Ser Leu Ser Thr Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Ser Pro Cys
                85                  90                  95

Ser Phe Gly Gln Gly Thr Lys Leu Glu Ile Lys
            100                 105

<210> SEQ ID NO 30
<211> LENGTH: 11
<212> TYPE: PRT
<213> ORGANISM: Homo sapiens

<400> SEQUENCE: 30

Arg Ala Ser Gln Ser Ile Ser Ser Tyr Leu Asn
1               5                   10

<210> SEQ ID NO 31
<211> LENGTH: 7
<212> TYPE: PRT
<213> ORGANISM: Homo sapiens

<400> SEQUENCE: 31

Ala Ala Ser Ser Leu Gln Ser
1               5

<210> SEQ ID NO 32
<211> LENGTH: 9
<212> TYPE: PRT
<213> ORGANISM: Homo sapiens

<400> SEQUENCE: 32

Gln Gln Ser Tyr Asn Ser Pro Cys Ser
1               5

<210> SEQ ID NO 33
<211> LENGTH: 23
<212> TYPE: PRT
<213> ORGANISM: Homo sapiens

<400> SEQUENCE: 33

Asp Ile Gln Met Thr Gln Ser Pro Ser Ser Leu Ser Thr Ser Val Gly
1               5                   10                  15

Asp Arg Val Thr Ile Thr Cys

<210> SEQ ID NO 34
<211> LENGTH: 15
<212> TYPE: PRT
<213> ORGANISM: Homo sapiens

<400> SEQUENCE: 34

Trp Tyr Gln Gln Lys Pro Gly Lys Ala Pro Lys Leu Leu Ile Tyr
1               5                   10                  15

<210> SEQ ID NO 35
<211> LENGTH: 32
<212> TYPE: PRT
<213> ORGANISM: Homo sapiens

<400> SEQUENCE: 35

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 36
<211> LENGTH: 10
<212> TYPE: PRT
<213> ORGANISM: Homo sapiens

<400> SEQUENCE: 36

Phe Gly Gln Gly Thr Lys Leu Glu Ile Lys
1               5                   10

<210> SEQ ID NO 37
<211> LENGTH: 1350
<212> TYPE: DNA
<213> ORGANISM: Homo sapiens

<400> SEQUENCE: 37
caggtgcagc tggtgcagtc tggggctgag gtgaagaagc ctggggcctc agtgaaggtt      60
tcctgcaagg catctggata caccttcacc agctactata tgcactggat acgacaggcc     120
cctggacaag gcttgagtg gatgggaatg atcaaccta gtggtggtag cacaacctac       180
gcacagaagt tccagggcag agtcaccttg accaggggaca cgtccacgag cacagtctac    240
atggacctga gcagcctgag atctgaggac acggccgtat attactgtgc gagagagaga    300
tggtataagt ggaacttcga tgtttttgat atctgggggcc aagggacaat ggtcaccgtc    360
tcttcagctt ccaccaaggg cccatccgtc ttccccctgg cgccctgctc caggagcacc    420
tccgagagca cagccgccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacg    600
aagacctaca cctgcaacgt agatcacaag cccagcaaca ccaaggtgga caagagagtt    660
gagtccaaat atggtccccc atgcccatca tgcccagcac ctgagttcct ggggggacca    720
tcagtcttcc tgttccccc aaaacccaag gacactctca tgatctcccg gacccctgag    780
gtcacgtgcg tggtggtgga cgtgagccag gaagacccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa   1020

```
gccaaagggc agccccgaga gccacaggtg tacaccctgc ccccatccca ggaggagatg    1080
accaagaacc aggtcagcct gacctgcctg gtcaaaggct tctacccag cgacatcgcc    1140 gtggagtggg agagcaatgg gcagccggag aacaactaca agaccacgcc tcccgtgctg    1200
gactccgacg gctccttctt cctctacagc aggctaaccg tggacaagag caggtggcag    1260
gaggggaatg tcttctcatg ctccgtgatg catgaggctc tgcacaacca ctacacacag    1320
aagagcctct ccctgtctct gggtaaatga                                     1350

<210> SEQ ID NO 38
<211> LENGTH: 366
<212> TYPE: DNA
<213> ORGANISM: Homo sapiens

<400> SEQUENCE: 38
caggtgcagc tggtgcagtc tggggctgag gtgaagaagc ctggggcctc agtgaaggtt      60
tcctgcaagg catctggata caccttcacc agctactata tgcactggat acgacaggcc    120
cctggacaag gcttgagtg gatgggaatg atcaaccctaa gtggtggtag cacaacctac    180
gcacagaagt tccagggcag agtcaccttg accaggggaca cgtccacgag cacagtctac    240
atggacctga gcagcctgag atctgaggac acggccgtat attactgtgc gagagagaga    300
tggtataagt ggaacttcga tgttttgat atctggggcc aagggacaat ggtcaccgtc    360
tcttca                                                              366

<210> SEQ ID NO 39
<211> LENGTH: 15
<212> TYPE: DNA
<213> ORGANISM: Homo sapiens

<400> SEQUENCE: 39
agctactata tgcac                                                     15

<210> SEQ ID NO 40
<211> LENGTH: 51
<212> TYPE: DNA
<213> ORGANISM: Homo sapiens

<400> SEQUENCE: 40
atgatcaacc ctagtggtgg tagcacaacc tacgcacaga gttccaggg c              51

<210> SEQ ID NO 41
<211> LENGTH: 39
<212> TYPE: DNA
<213> ORGANISM: Homo sapiens

<400> SEQUENCE: 41
gagagatggt ataagtggaa cttcgatgtt tttgatatc                           39

<210> SEQ ID NO 42
<211> LENGTH: 90
<212> TYPE: DNA
<213> ORGANISM: Homo sapiens

<400> SEQUENCE: 42
caggtgcagc tggtgcagtc tggggctgag gtgaagaagc ctggggcctc agtgaaggtt     60
tcctgcaagg catctggata caccttcacc                                     90

<210> SEQ ID NO 43
<211> LENGTH: 42
<212> TYPE: DNA
```

<213> ORGANISM: Homo sapiens

<400> SEQUENCE: 43
tggatacgac aggcccctgg acaagggctt gagtggatgg ga       42

<210> SEQ ID NO 44
<211> LENGTH: 96
<212> TYPE: DNA
<213> ORGANISM: Homo sapiens

<400> SEQUENCE: 44
agagtcacct tgaccaggga cacgtccacg agcacagtct acatggacct gagcagcctg       60
agatctgagg acacggccgt atattactgt gcgaga       96

<210> SEQ ID NO 45
<211> LENGTH: 33
<212> TYPE: DNA
<213> ORGANISM: Homo sapiens

<400> SEQUENCE: 45
tggggccaag ggacaatggt caccgtctct tca       33

<210> SEQ ID NO 46
<211> LENGTH: 449
<212> TYPE: PRT
<213> ORGANISM: Homo sapiens

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Ile Arg Gln Ala Pro Gly Gln Gly Leu Glu Trp Met
        35                  40                  45

Gly Met Ile Asn Pro Ser Gly Gly Ser Thr Thr Tyr Ala Gln Lys Phe
    50                  55                  60

Gln Gly Arg Val Thr Leu Thr Arg Asp Thr Ser Thr Ser Thr Val Tyr
65                  70                  75                  80

Met Asp Leu Ser Ser Leu Arg Ser Glu Asp Thr Ala Val Tyr Tyr Cys
                85                  90                  95

Ala Arg Glu Arg Trp Tyr Lys Trp Asn Phe Asp Val Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240

-continued

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 47
<211> LENGTH: 122
<212> TYPE: PRT
<213> ORGANISM: Homo sapiens

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Ile Arg Gln Ala Pro Gly Gln Gly Leu Glu Trp Met
        35                  40                  45

Gly Met Ile Asn Pro Ser Gly Gly Ser Thr Thr Tyr Ala Gln Lys Phe
    50                  55                  60

Gln Gly Arg Val Thr Leu Thr Arg Asp Thr Ser Thr Ser Thr Val Tyr
65                  70                  75                  80

Met Asp Leu Ser Ser Leu Arg Ser Glu Asp Thr Ala Val Tyr Tyr Cys
                85                  90                  95

Ala Arg Glu Arg Trp Tyr Lys Trp Asn Phe Asp Val Phe Asp Ile Trp
            100                 105                 110

Gly Gln Gly Thr Met Val Thr Val Ser Ser
        115                 120

<210> SEQ ID NO 48
<211> LENGTH: 5
<212> TYPE: PRT
<213> ORGANISM: Homo sapiens

```
<400> SEQUENCE: 48

Ser Tyr Tyr Met His
1               5

<210> SEQ ID NO 49
<211> LENGTH: 17
<212> TYPE: PRT
<213> ORGANISM: Homo sapiens

<400> SEQUENCE: 49

Met Ile Asn Pro Ser Gly Gly Ser Thr Thr Tyr Ala Gln Lys Phe Gln
1               5                   10                  15

Gly

<210> SEQ ID NO 50
<211> LENGTH: 13
<212> TYPE: PRT
<213> ORGANISM: Homo sapiens

<400> SEQUENCE: 50

Glu Arg Trp Tyr Lys Trp Asn Phe Asp Val Phe Asp Ile
1               5                   10

<210> SEQ ID NO 51
<211> LENGTH: 30
<212> TYPE: PRT
<213> ORGANISM: Homo sapiens

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 52
<211> LENGTH: 14
<212> TYPE: PRT
<213> ORGANISM: Homo sapiens

<400> SEQUENCE: 52

Trp Ile Arg Gln Ala Pro Gly Gln Gly Leu Glu Trp Met Gly
1               5                   10

<210> SEQ ID NO 53
<211> LENGTH: 32
<212> TYPE: PRT
<213> ORGANISM: Homo sapiens

<400> SEQUENCE: 53

Arg Val Thr Leu Thr Arg Asp Thr Ser Thr Ser Thr Val Tyr Met Asp
1               5                   10                  15

Leu Ser Ser Leu Arg Ser Glu Asp Thr Ala Val Tyr Tyr Cys Ala Arg
            20                  25                  30

<210> SEQ ID NO 54
<211> LENGTH: 11
<212> TYPE: PRT
<213> ORGANISM: Homo sapiens

<400> SEQUENCE: 54

Trp Gly Gln Gly Thr Met Val Thr Val Ser Ser
1               5                   10
```

```
<210> SEQ ID NO 55
<211> LENGTH: 648
<212> TYPE: DNA
<213> ORGANISM: Homo sapiens

<400> SEQUENCE: 55
gatgttgtga tgactcagtc tccactctcc ctgcccgtca cccttggaca gccggcctcc      60
atctcctgca ggtctagtca aagccccgta tacagtgatg gaaacaccta cttgaattgg     120
cttcagcaga ggccaggcca atctccaagg cgcctaattt ataaggtttc taactgggac     180
gctggggtcc cagacagatt cagcggcagt gggtcaggca ctgatttcac actgaaaatc     240
agcagggtgg aggctgagga tgttgggttt tattacactg gccgatcgat caccgtcggc     300
caagggacac gactggagat taaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgttag                  648

<210> SEQ ID NO 56
<211> LENGTH: 324
<212> TYPE: DNA
<213> ORGANISM: Homo sapiens

<400> SEQUENCE: 56
gatgttgtga tgactcagtc tccactctcc ctgcccgtca cccttggaca gccggcctcc      60
atctcctgca ggtctagtca aagccccgta tacagtgatg gaaacaccta cttgaattgg     120
cttcagcaga ggccaggcca atctccaagg cgcctaattt ataaggtttc taactgggac     180
gctggggtcc cagacagatt cagcggcagt gggtcaggca ctgatttcac actgaaaatc     240
agcagggtgg aggctgagga tgttgggttt tattacactg gccgatcgat caccgtcggc     300
caagggacac gactggagat taaa                                            324

<210> SEQ ID NO 57
<211> LENGTH: 48
<212> TYPE: DNA
<213> ORGANISM: Homo sapiens

<400> SEQUENCE: 57
aggtctagtc aaagcccgt atacagtgat ggaaacacct acttgaat                    48

<210> SEQ ID NO 58
<211> LENGTH: 21
<212> TYPE: DNA
<213> ORGANISM: Homo sapiens

<400> SEQUENCE: 58
aaggtttcta actgggacgc t                                                21

<210> SEQ ID NO 59
<211> LENGTH: 18
<212> TYPE: DNA
<213> ORGANISM: Homo sapiens

<400> SEQUENCE: 59
actggccgat cgatcacc                                                    18
```

<210> SEQ ID NO 60
<211> LENGTH: 69
<212> TYPE: DNA
<213> ORGANISM: Homo sapiens

<400> SEQUENCE: 60
gatgttgtga tgactcagtc tccactctcc ctgcccgtca cccttggaca gccggcctcc    60
atctcctgc                                                            69

<210> SEQ ID NO 61
<211> LENGTH: 45
<212> TYPE: DNA
<213> ORGANISM: Homo sapiens

<400> SEQUENCE: 61
tggcttcagc agaggccagg ccaatctcca aggcgcctaa tttat                    45

<210> SEQ ID NO 62
<211> LENGTH: 93
<212> TYPE: DNA
<213> ORGANISM: Homo sapiens

<400> SEQUENCE: 62
ggggtcccag acagattcag cggcagtggg tcaggcactg atttcacact gaaaatcagc    60
agggtggagg ctgaggatgt tgggttttat tac                                 93

<210> SEQ ID NO 63
<211> LENGTH: 30
<212> TYPE: DNA
<213> ORGANISM: Homo sapiens

<400> SEQUENCE: 63
gtcggccaag ggacacgact ggagattaaa                                     30

<210> SEQ ID NO 64
<211> LENGTH: 215
<212> TYPE: PRT
<213> ORGANISM: Homo sapiens

<400> SEQUENCE: 64

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Pro Val Tyr Ser
            20                  25                  30

Asp Gly Asn Thr Tyr Leu Asn Trp Leu Gln Gln Arg Pro Gly Gln Ser
        35                  40                  45

Pro Arg Arg Leu Ile Tyr Lys Val Ser Asn Trp Asp Ala Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Thr Arg Ser
                85                  90                  95

Ile Thr Val Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 65
<211> LENGTH: 108
<212> TYPE: PRT
<213> ORGANISM: Homo sapiens

<400> SEQUENCE: 65

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Pro Val Tyr Ser
            20                  25                  30

Asp Gly Asn Thr Tyr Leu Asn Trp Leu Gln Arg Pro Gly Gln Ser
        35                  40                  45

Pro Arg Arg Leu Ile Tyr Lys Val Ser Asn Trp Asp Ala Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Thr Gly Arg Ser
                85                  90                  95

Ile Thr Val Gly Gln Gly Thr Arg Leu Glu Ile Lys
            100                 105

<210> SEQ ID NO 66
<211> LENGTH: 16
<212> TYPE: PRT
<213> ORGANISM: Homo sapiens

<400> SEQUENCE: 66

Arg Ser Ser Gln Ser Pro Val Tyr Ser Asp Gly Asn Thr Tyr Leu Asn
1               5                   10                  15

<210> SEQ ID NO 67
<211> LENGTH: 7
<212> TYPE: PRT
<213> ORGANISM: Homo sapiens

<400> SEQUENCE: 67

Lys Val Ser Asn Trp Asp Ala
1               5

<210> SEQ ID NO 68
<211> LENGTH: 6
<212> TYPE: PRT
<213> ORGANISM: Homo sapiens

<400> SEQUENCE: 68

Thr Gly Arg Ser Ile Thr
1               5

<210> SEQ ID NO 69
<211> LENGTH: 23
<212> TYPE: PRT
<213> ORGANISM: Homo sapiens

```
<400> SEQUENCE: 69

Asp Val Val Met Thr Gln Ser Pro Leu Ser Leu Pro Val Thr Leu Gly
1               5                   10                  15
Gln Pro Ala Ser Ile Ser Cys
            20

<210> SEQ ID NO 70
<211> LENGTH: 15
<212> TYPE: PRT
<213> ORGANISM: Homo sapiens

<400> SEQUENCE: 70

Trp Leu Gln Gln Arg Pro Gly Gln Ser Pro Arg Arg Leu Ile Tyr
1               5                   10                  15

<210> SEQ ID NO 71
<211> LENGTH: 31
<212> TYPE: PRT
<213> ORGANISM: Homo sapiens

<400> SEQUENCE: 71

Gly Val Pro Asp Arg Phe Ser Gly Ser Gly Ser Gly Thr Asp Phe Thr
1               5                   10                  15
Leu Lys Ile Ser Arg Val Glu Ala Glu Asp Val Gly Phe Tyr Tyr
            20                  25                  30

<210> SEQ ID NO 72
<211> LENGTH: 10
<212> TYPE: PRT
<213> ORGANISM: Homo sapiens

<400> SEQUENCE: 72

Val Gly Gln Gly Thr Arg Leu Glu Ile Lys
1               5                   10

<210> SEQ ID NO 73
<211> LENGTH: 1350
<212> TYPE: DNA
<213> ORGANISM: Homo sapiens

<400> SEQUENCE: 73
caggtgcagc tggtggagtc tgggggaggc gtggtccagc ctgggaggtc cctgagactc    60
tcctgtgcag cctctggact caccttcagt agctatggca tgcactgggt ccgccaggct   120
ccaggcaagg ggctggagtg ggtggcagtt atattatatg atggaaagaa taaatactat   180
gcagactccg tgaagggccg attcaccatc tccagagaca attccaagaa cacgctgtat   240
ctgcaaatga acagcctgag agctgaggac acggctgtgt attactgtgc gagagatcag   300
gcgtactgga cctactttga tgcttttgat atctggggcc aagggacaat ggtcaccgtc   360
tcttcagctt ccaccaaggg cccatccgtc ttccccctgg cgccctgctc caggagcacc   420
tccgagagca cagccgccct gggctgcctg gtcaaggact acttccccga accggtgacg   480
gtgtcgtgga actcaggcgc cctgaccagc ggcgtgcaca ccttcccggc tgtcctacag   540
tcctcaggac tctactccct cagcagcgtg gtgaccgtgc cctccagcag cttgggcacg   600
aagacctaca cctgcaacgt agatcacaag cccagcaaca ccaaggtgga caagagagtt   660
gagtccaaat atggtccccc atgcccatca tgcccagcac ctgagttcct ggggggacca   720
tcagtcttcc tgttcccccc aaaacccaag gacactctca tgatctcccg gacccctgag   780
gtcacgtgcg tggtggtgga cgtgagccag gaagaccccg aggtccagtt caactggtac   840
```

```
gtggatggcg tggaggtgca taatgccaag acaaagccgc gggaggagca gttcaacagc        900
acgtaccgtg tggtcagcgt cctcaccgtc ctgcaccagg actggctgaa cggcaaggag        960
tacaagtgca aggtctccaa caaaggcctc ccgtcctcca tcgagaaaac catctccaaa       1020
gccaaagggc agccccgaga gccacaggtg tacaccctgc ccccatccca ggaggagatg       1080
accaagaacc aggtcagcct gacctgcctg gtcaaaggct tctacccag cgacatcgcc        1140 gtggagtggg agagcaatgg gcagccggag aacaactaca agaccacgcc tcccgtgctg       1200
gactccgacg gctccttctt cctctacagc aggctaaccg tggacaagag caggtggcag       1260 gagggaatg tcttctcatg ctccgtgatg catgaggctc tgcacaacca ctacacacag        1320
aagagcctct ccctgtctct gggtaaatga                                       1350

<210> SEQ ID NO 74
<211> LENGTH: 366
<212> TYPE: DNA
<213> ORGANISM: Homo sapiens

<400> SEQUENCE: 74
caggtgcagc tggtggagtc tgggggaggc gtggtccagc ctgggaggtc cctgagactc         60
tcctgtgcag cctctggact caccttcagt agctatggca tgcactgggt ccgccaggct        120
ccaggcaagg ggctggagtg ggtggcagtt atattatatg atggaaagaa taaatactat        180
gcagactccg tgaagggccg attcaccatc tccagagaca attccaagaa cacgctgtat        240
ctgcaaatga acagcctgag agctgaggac acggctgtgt attactgtgc gagagatcag        300
gcgtactgga cctactttga tgcttttgat atctggggcc aagggacaat ggtcaccgtc        360
tcttca                                                                  366

<210> SEQ ID NO 75
<211> LENGTH: 15
<212> TYPE: DNA
<213> ORGANISM: Homo sapiens

<400> SEQUENCE: 75
agctatggca tgcac                                                         15

<210> SEQ ID NO 76
<211> LENGTH: 51
<212> TYPE: DNA
<213> ORGANISM: Homo sapiens

<400> SEQUENCE: 76
gttatattat atgatggaaa gaataaatac tatgcagact ccgtgaaggg c                 51

<210> SEQ ID NO 77
<211> LENGTH: 39
<212> TYPE: DNA
<213> ORGANISM: Homo sapiens

<400> SEQUENCE: 77
gatcaggcgt actggaccta ctttgatgct tttgatatc                               39

<210> SEQ ID NO 78
<211> LENGTH: 90
<212> TYPE: DNA
<213> ORGANISM: Homo sapiens

<400> SEQUENCE: 78
caggtgcagc tggtggagtc tgggggaggc gtggtccagc ctgggaggtc cctgagactc         60
```

```
tcctgtgcag cctctggact caccttcagt                                         90

<210> SEQ ID NO 79
<211> LENGTH: 42
<212> TYPE: DNA
<213> ORGANISM: Homo sapiens

<400> SEQUENCE: 79
tgggtccgcc aggctccagg caaggggctg gagtgggtgg ca                           42

<210> SEQ ID NO 80
<211> LENGTH: 96
<212> TYPE: DNA
<213> ORGANISM: Homo sapiens

<400> SEQUENCE: 80
cgattcacca tctccagaga caattccaag aacacgctgt atctgcaaat gaacagcctg       60
agagctgagg acacggctgt gtattactgt gcgaga                                 96

<210> SEQ ID NO 81
<211> LENGTH: 33
<212> TYPE: DNA
<213> ORGANISM: Homo sapiens

<400> SEQUENCE: 81
tggggccaag ggacaatggt caccgtctct tca                                    33

<210> SEQ ID NO 82
<211> LENGTH: 449
<212> TYPE: PRT
<213> ORGANISM: Homo sapiens

<400> SEQUENCE: 82
```

Gln Val Gln Leu Val Glu Ser Gly Gly Gly Val Val Gln Pro Gly Arg
1               5                   10                  15

Ser Leu Arg Leu Ser Cys Ala Ala Ser Gly Leu Thr Phe Ser Ser Tyr
            20                  25                  30

Gly Met His Trp Val Arg Gln Ala Pro Gly Lys Gly Leu Glu Trp Val
        35                  40                  45

Ala Val Ile Leu Tyr Asp Gly Lys Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Ala Tyr Trp Thr Tyr Phe Asp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp

```
                195                 200                 205
His Lys Pro Ser Asn Thr Lys Val Asp Lys Arg Val Glu Ser Lys Tyr
210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

Lys

<210> SEQ ID NO 83
<211> LENGTH: 122
<212> TYPE: PRT
<213> ORGANISM: Homo sapiens

<400> SEQUENCE: 83

Gln Val Gln Leu Val Glu Ser Gly Gly Gly Val Val Gln Pro Gly Arg
1               5                   10                  15

Ser Leu Arg Leu Ser Cys Ala Ala Ser Gly Leu Thr Phe Ser Ser Tyr
                20                  25                  30

Gly Met His Trp Val Arg Gln Ala Pro Gly Lys Gly Leu Glu Trp Val
                35                  40                  45

Ala Val Ile Leu Tyr Asp Gly Lys Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Ala Tyr Trp Thr Tyr Phe Asp Ala Phe Asp Ile Trp
                100                 105                 110

Gly Gln Gly Thr Met Val Thr Val Ser Ser
                115                 120
```

<210> SEQ ID NO 84
<211> LENGTH: 5
<212> TYPE: PRT
<213> ORGANISM: Homo sapiens

<400> SEQUENCE: 84

Ser Tyr Gly Met His
1               5

<210> SEQ ID NO 85
<211> LENGTH: 17
<212> TYPE: PRT
<213> ORGANISM: Homo sapiens

<400> SEQUENCE: 85

Val Ile Leu Tyr Asp Gly Lys Asn Lys Tyr Tyr Ala Asp Ser Val Lys
1               5                   10                  15

Gly

<210> SEQ ID NO 86
<211> LENGTH: 13
<212> TYPE: PRT
<213> ORGANISM: Homo sapiens

<400> SEQUENCE: 86

Asp Gln Ala Tyr Trp Thr Tyr Phe Asp Ala Phe Asp Ile
1               5                   10

<210> SEQ ID NO 87
<211> LENGTH: 30
<212> TYPE: PRT
<213> ORGANISM: Homo sapiens

<400> SEQUENCE: 87

Gln Val Gln Leu Val Glu Ser Gly Gly Gly Val Val Gln Pro Gly Arg
1               5                   10                  15

Ser Leu Arg Leu Ser Cys Ala Ala Ser Gly Leu Thr Phe Ser
            20                  25                  30

<210> SEQ ID NO 88
<211> LENGTH: 14
<212> TYPE: PRT
<213> ORGANISM: Homo sapiens

<400> SEQUENCE: 88

Trp Val Arg Gln Ala Pro Gly Lys Gly Leu Glu Trp Val Ala
1               5                   10

<210> SEQ ID NO 89
<211> LENGTH: 32
<212> TYPE: PRT
<213> ORGANISM: Homo sapiens

<400> SEQUENCE: 89

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 90
<211> LENGTH: 11
<212> TYPE: PRT
<213> ORGANISM: Homo sapiens

<400> SEQUENCE: 90

Trp Gly Gln Gly Thr Met Val Thr Val Ser Ser
1               5                   10

<210> SEQ ID NO 91
<211> LENGTH: 645
<212> TYPE: DNA
<213> ORGANISM: Homo sapiens

<400> SEQUENCE: 91

| | | | | |
|---|---|---|---|---|
| gaaattgtgc | tgactcagtc | tccagacttt | cagtctgtga | ctccaaagga gaaagtcacc | 60 |
| atcacctgcc | gggccagtca | gagcattggt | agtagcttac | actggtacca gcagaaacca | 120 |
| gatcagtctc | caaagctcct | catcaagtat | gcttcccagt | ccttctcagg ggtcccctcg | 180 |
| aggttcagtg | gcagtggatc | tgcgacagat | ttcaccctca | ccatcaatag cctggaagct | 240 |
| gaagatgctg | caacgtatta | ctgtcatcag | agtagtagtt | taccgctcac tttcggcgga | 300 |
| gggaccaagg | tggagatcaa | acgaactgtg | gctgcaccat | ctgtcttcat cttcccgcca | 360 |
| tctgatgagc | agttgaaatc | tggaactgcc | tctgttgtgt | gcctgctgaa taacttctat | 420 |
| cccagagagg | ccaaagtaca | gtggaaggtg | gataacgccc | tccaatcggg taactcccag | 480 |
| gagagtgtca | cagagcagga | cagcaaggac | agcacctaca | gcctcagcag caccctgacg | 540 |
| ctgagcaaag | cagactacga | gaaacacaaa | gtctacgcct | gcgaagtcac ccatcagggc | 600 |
| ctgagctcgc | ccgtcacaaa | gagcttcaac | aggggagagt | gttag | 645 |

<210> SEQ ID NO 92
<211> LENGTH: 321
<212> TYPE: DNA
<213> ORGANISM: Homo sapiens

<400> SEQUENCE: 92

| | | | | |
|---|---|---|---|---|
| gaaattgtgc | tgactcagtc | tccagacttt | cagtctgtga | ctccaaagga gaaagtcacc | 60 |
| atcacctgcc | gggccagtca | gagcattggt | agtagcttac | actggtacca gcagaaacca | 120 |
| gatcagtctc | caaagctcct | catcaagtat | gcttcccagt | ccttctcagg ggtcccctcg | 180 |
| aggttcagtg | gcagtggatc | tgcgacagat | ttcaccctca | ccatcaatag cctggaagct | 240 |
| gaagatgctg | caacgtatta | ctgtcatcag | agtagtagtt | taccgctcac tttcggcgga | 300 |
| gggaccaagg | tggagatcaa | a | | | 321 |

<210> SEQ ID NO 93
<211> LENGTH: 33
<212> TYPE: DNA
<213> ORGANISM: Homo sapiens

<400> SEQUENCE: 93
cgggccagtc agagcattgg tagtagctta cac       33

<210> SEQ ID NO 94
<211> LENGTH: 21
<212> TYPE: DNA
<213> ORGANISM: Homo sapiens

<400> SEQUENCE: 94
tatgcttccc agtccttctc a       21

<210> SEQ ID NO 95
<211> LENGTH: 27
<212> TYPE: DNA

<210> SEQ ID NO 95
<211> LENGTH: 27
<212> TYPE: DNA
<213> ORGANISM: Homo sapiens

<400> SEQUENCE: 95
catcagagta gtagtttacc gctcact                                        27

<210> SEQ ID NO 96
<211> LENGTH: 69
<212> TYPE: DNA
<213> ORGANISM: Homo sapiens

<400> SEQUENCE: 96
gaaattgtgc tgactcagtc tccagacttt cagtctgtga ctccaaagga gaaagtcacc   60
atcacctgc                                                           69

<210> SEQ ID NO 97
<211> LENGTH: 45
<212> TYPE: DNA
<213> ORGANISM: Homo sapiens

<400> SEQUENCE: 97
tggtaccagc agaaaccaga tcagtctcca aagctcctca tcaag                   45

<210> SEQ ID NO 98
<211> LENGTH: 96
<212> TYPE: DNA
<213> ORGANISM: Homo sapiens

<400> SEQUENCE: 98
ggggtcccct cgaggttcag tggcagtgga tctgcgacag atttcaccct caccatcaat   60
agcctggaag ctgaagatgc tgcaacgtat tactgt                             96

<210> SEQ ID NO 99
<211> LENGTH: 30
<212> TYPE: DNA
<213> ORGANISM: Homo sapiens

<400> SEQUENCE: 99
ttcggcggag ggaccaaggt ggagatcaaa                                    30

<210> SEQ ID NO 100
<211> LENGTH: 214
<212> TYPE: PRT
<213> ORGANISM: Homo sapiens

<400> SEQUENCE: 100

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Ala Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly

```
                115                 120                 125
Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 101
<211> LENGTH: 107
<212> TYPE: PRT
<213> ORGANISM: Homo sapiens

<400> SEQUENCE: 101

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Ala Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro Leu
                85                  90                  95

Thr Phe Gly Gly Gly Thr Lys Val Glu Ile Lys
            100                 105

<210> SEQ ID NO 102
<211> LENGTH: 11
<212> TYPE: PRT
<213> ORGANISM: Homo sapiens

<400> SEQUENCE: 102

Arg Ala Ser Gln Ser Ile Gly Ser Ser Leu His
1               5                   10

<210> SEQ ID NO 103
<211> LENGTH: 7
<212> TYPE: PRT
<213> ORGANISM: Homo sapiens

<400> SEQUENCE: 103

Tyr Ala Ser Gln Ser Phe Ser
1               5

<210> SEQ ID NO 104
<211> LENGTH: 9
<212> TYPE: PRT
<213> ORGANISM: Homo sapiens

<400> SEQUENCE: 104

His Gln Ser Ser Ser Leu Pro Leu Thr
```

<210> SEQ ID NO 105
<211> LENGTH: 23
<212> TYPE: PRT
<213> ORGANISM: Homo sapiens

<400> SEQUENCE: 105

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 106
<211> LENGTH: 15
<212> TYPE: PRT
<213> ORGANISM: Homo sapiens

<400> SEQUENCE: 106

Trp Tyr Gln Gln Lys Pro Asp Gln Ser Pro Lys Leu Leu Ile Lys
1               5                   10                  15

<210> SEQ ID NO 107
<211> LENGTH: 32
<212> TYPE: PRT
<213> ORGANISM: Homo sapiens

<400> SEQUENCE: 107

Gly Val Pro Ser Arg Phe Ser Gly Ser Gly Ser Ala Thr Asp Phe Thr
1               5                   10                  15

Leu Thr Ile Asn Ser Leu Glu Ala Glu Asp Ala Ala Thr Tyr Tyr Cys
            20                  25                  30

<210> SEQ ID NO 108
<211> LENGTH: 10
<212> TYPE: PRT
<213> ORGANISM: Homo sapiens

<400> SEQUENCE: 108

Phe Gly Gly Gly Thr Lys Val Glu Ile Lys
1               5                   10

<210> SEQ ID NO 109
<211> LENGTH: 645
<212> TYPE: DNA
<213> ORGANISM: Homo sapiens

<400> SEQUENCE: 109
gaaattgtgc tgactcagtc tccagacttt cagtctgtga ctccaaagga gaaagtcacc      60
atcacctgcc gggccagtca gagcattggt agtagcttac actggtacca gcagaaacca     120
gatcagtctc caaagctcct catcaagtat gcttcccagt ccttctcagg ggtcccctcg     180
aggttcagtg gcagtggatc tgggacagat ttcacccctca ccatcaatag cctggaagct     240
gaagatgctg caacgtatta ctgtcatcag agtagtagtt accgctcac tttcggcgga      300 gggaccaagg tggagatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacccctgacg     540 ctgagcaaag cagactacga gaaacacaaa gtctacgcct gcgaagtcac ccatcagggc     600
ctgagctcgc ccgtcacaaa gagcttcaac aggggagagt gttag     645

<210> SEQ ID NO 110
<211> LENGTH: 321
<212> TYPE: DNA
<213> ORGANISM: Homo sapiens

<400> SEQUENCE: 110
gaaattgtgc tgactcagtc tccagacttt cagtctgtga ctccaaagga gaaagtcacc     60
atcacctgcc gggccagtca gagcattggt agtagcttac actggtacca gcagaaacca    120
gatcagtctc caaagctcct catcaagtat gcttcccagt ccttctcagg ggtcccctcg    180
aggttcagtg gcagtggatc tgggacagat ttcaccctca ccatcaatag cctggaagct    240
gaagatgctg caacgtatta ctgtcatcag agtagtagtt taccgctcac tttcggcgga    300
gggaccaagg tggagatcaa a                                              321

<210> SEQ ID NO 111
<211> LENGTH: 96
<212> TYPE: DNA
<213> ORGANISM: Homo sapiens

<400> SEQUENCE: 111
ggggtcccct cgaggttcag tggcagtgga tctgggacag atttcaccct caccatcaat     60
agcctggaag ctgaagatgc tgcaacgtat tactgt                               96

<210> SEQ ID NO 112
<211> LENGTH: 214
<212> TYPE: PRT
<213> ORGANISM: Homo sapiens

<400> SEQUENCE: 112

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 113
<211> LENGTH: 107
<212> TYPE: PRT
<213> ORGANISM: Homo sapiens

<400> SEQUENCE: 113

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro Leu
                85                  90                  95

Thr Phe Gly Gly Gly Thr Lys Val Glu Ile Lys
            100                 105

<210> SEQ ID NO 114
<211> LENGTH: 32
<212> TYPE: PRT
<213> ORGANISM: Homo sapiens

<400> SEQUENCE: 114

Gly Val Pro Ser Arg Phe Ser Gly Ser Gly Ser Gly Thr Asp Phe Thr
1               5                   10                  15

Leu Thr Ile Asn Ser Leu Glu Ala Glu Asp Ala Ala Thr Tyr Tyr Cys
            20                  25                  30

<210> SEQ ID NO 115
<211> LENGTH: 1350
<212> TYPE: DNA
<213> ORGANISM: Homo sapiens

<400> SEQUENCE: 115
caggtgcagc tggtggagtc tgggggaggc gtggtccagc ctgggaggtc cctgagactc      60
tcctgtgcag cctctggact caccttcagt agctatggca tgcactgggt ccgccaggct     120
ccaggcaagg ggctggagtg ggtggcagtt atattatatg atggaaagaa taaatactat     180
gcagactccg tgaagggccg attcaccatc tccagagaca attccaagaa cacgctgtat     240
ctgcaaatga acagcctgag agctgaggac acggctgtgt attactgtgc gagagatcag     300
gcgtactgga cctactttga tcttttgat atctggggcc aagggacaat ggtcaccgtc     360
tcttcagctt ccaccaaggg cccatccgtc ttccccctgg cgccctgctc caggagcacc     420
tccgagagca cagccgccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660
gagtccaaat atggtccccc atgcccacca tgcccagcac ctgagttcct ggggggacca     720
tcagtcttcc tgttcccccc aaaacccaag gacactctca tgatctcccg gacccctgag     780

```
gtcacgtgcg tggtggtgga cgtgagccag gaagacccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa   1020
gccaaagggc agccccgaga gccacaggtg tacaccctgc ccccatccca ggaggagatg   1080
accaagaacc aggtcagcct gacctgcctg gtcaaaggct tctaccccag cgacatcgcc   1140
gtggagtggg agagcaatgg gcagccggag aacaactaca agaccacgcc tcccgtgctg   1200
gactccgacg gctccttctt cctctacagc aggctaaccg tggacaagag caggtggcag   1260 gagggaatg tcttctcatg ctccgtgatg catgaggctc tgcacaacca ctacacacag   1320
aagagcctct ccctgtctct gggtaaatga                                    1350
```

<210> SEQ ID NO 116
<211> LENGTH: 449
<212> TYPE: PRT
<213> ORGANISM: Homo sapiens

<400> SEQUENCE: 116

```
Gln Val Gln Leu Val Glu Ser Gly Gly Gly Val Val Gln Pro Gly Arg
1               5                   10                  15

Ser Leu Arg Leu Ser Cys Ala Ala Ser Gly Leu Thr Phe Ser Ser Tyr
            20                  25                  30

Gly Met His Trp Val Arg Gln Ala Pro Gly Lys Gly Leu Glu Trp Val
        35                  40                  45

Ala Val Ile Leu Tyr Asp Gly Lys Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Ala Tyr Trp Thr Tyr Phe Asp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270
```

```
Pro Glu Val Gln Phe Asn Trp Tyr Val Asp Gly Val Glu Val His Asn
    275                 280                 285
Ala Lys Thr Lys Pro Arg Glu Glu Gln Phe Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Gln Glu Glu Met Thr Lys Asn Gln Val Ser Leu Thr
                355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
                420                 425                 430
Ala Leu His Asn His Tyr Thr Gln Lys Ser Leu Ser Leu Ser Leu Gly
                435                 440                 445
Lys

<210> SEQ ID NO 117
<211> LENGTH: 389
<212> TYPE: PRT
<213> ORGANISM: Homo sapiens

<400> SEQUENCE: 117

Met Asp Ser Lys Gly Ser Ser Gln Lys Gly Ser Arg Leu Leu Leu Leu
1               5                   10                  15
Leu Val Val Ser Asn Leu Leu Leu Cys Gln Gly Val Val Ser Asp Tyr
                20                  25                  30
Lys Asp Asp Asp Asp Val Asp Glu Thr Pro Asn Thr Thr Glu Asp Tyr
                35                  40                  45
Asp Thr Thr Thr Glu Phe Asp Tyr Gly Asp Ala Thr Pro Cys Gln Lys
    50                  55                  60
Val Asn Glu Arg Ala Phe Gly Ala Gln Leu Leu Pro Pro Leu Tyr Ser
65                  70                  75                  80
Leu Val Phe Ile Phe Gly Phe Val Gly Asn Met Leu Val Val Leu Ile
                85                  90                  95
Leu Ile Asn Cys Lys Lys Leu Lys Cys Leu Thr Asp Ile Tyr Leu Leu
                100                 105                 110
Asn Leu Ala Ile Ser Asp Leu Leu Phe Leu Ile Thr Leu Pro Leu Trp
            115                 120                 125
Ala His Ser Ala Ala Asn Glu Trp Val Phe Gly Asn Ala Met Cys Lys
    130                 135                 140
Leu Phe Thr Gly Leu Tyr His Ile Gly Tyr Phe Gly Gly Ile Phe Phe
145                 150                 155                 160
Ile Ile Leu Leu Thr Ile Asp Arg Tyr Leu Ala Ile Val His Ala Val
                165                 170                 175
Phe Ala Leu Lys Ala Arg Thr Val Thr Phe Gly Val Val Thr Ser Val
                180                 185                 190
Ile Thr Trp Leu Val Ala Val Phe Ala Ser Val Pro Gly Ile Ile Phe
```

```
              195                 200                 205
Thr Lys Cys Gln Lys Glu Asp Ser Val Tyr Val Cys Gly Pro Tyr Phe
210                 215                 220

Pro Arg Gly Trp Asn Asn Phe His Thr Ile Met Arg Asn Ile Leu Gly
225                 230                 235                 240

Leu Val Leu Pro Leu Leu Ile Met Val Ile Cys Tyr Ser Gly Ile Leu
                245                 250                 255

Lys Thr Leu Leu Arg Cys Arg Asn Glu Lys Lys Arg His Arg Ala Val
                260                 265                 270

Arg Val Ile Phe Thr Ile Met Ile Val Tyr Phe Leu Phe Trp Thr Pro
                275                 280                 285

Tyr Asn Ile Val Ile Leu Leu Asn Thr Phe Gln Asp Phe Leu Phe Thr
290                 295                 300

His Glu Cys Glu Gln Ser Arg His Leu Asp Leu Ala Val Gln Val Thr
305                 310                 315                 320

Glu Val Ile Ala Tyr Thr His Cys Cys Val Asn Pro Val Ile Tyr Ala
                325                 330                 335

Phe Val Gly Glu Arg Phe Arg Lys Tyr Leu Arg Gln Leu Phe His Arg
                340                 345                 350

Arg Val Ala Val His Leu Val Lys Trp Leu Pro Phe Leu Ser Val Asp
                355                 360                 365

Arg Leu Glu Arg Val Ser Ser Thr Ser Pro Ser Thr Gly Glu His Glu
    370                 375                 380

Leu Ser Ala Gly Phe
385

<210> SEQ ID NO 118
<211> LENGTH: 1167
<212> TYPE: DNA
<213> ORGANISM: Homo sapiens

<400> SEQUENCE: 118
atggacagca aaggttcgtc gcagaaaggg tcccgcctgc tcctgctgct ggtggtgtca      60
aatctactct tgtgccaggg tgtggtctcc gattacaaag atgatgatga tgtcgacgaa     120
actccaaaca ccacagagga ctatgacacg accacagagt ttgactatgg ggatgcaact     180
ccgtgccaga aggtgaacga gagggccttt ggggcccaac tcctgcctcc gctctactcg     240
ctggtgttca tctttggttt tgtgggcaac atgctggtcg tcctcatctt aataaactgc     300
aaaaagctga agtgcttgac tgacatttac ctgctcaacc tggccatctc tgatctgctt     360
tttcttatta ctctcccatt gtgggctcac tctgctgcaa atgagtgggt ctttgggaat     420
gcaatgtgca attattcac agggctgtat cacatcggtt attttggcgg aatcttcttc     480
atcatcctcc tgacaatcga tagatacctg gctattgtcc atgctgtgtt tgctttaaaa     540
gccaggacgg tcacctttgg ggtggtgaca agtgtgatca cctggttggt ggctgtgttt     600
gcttctgtcc caggaatcat ctttactaaa tgccagaaag aagattctgt ttatgtctgt     660
ggcccttatt ttccacgagg atggaataat ttccacacaa taatgaggaa cattttgggg     720
ctggtcctgc cgctgctcat catggtcatc tgctactcgg gaatcctgaa aaccctgctt     780
cggtgtcgaa acgagaagaa gaggcatagg gcagtgagag tcatcttcac catcatgatt     840 gtttacttc tcttctggac tccctataac attgtcattc tcctgaacac cttccaagac     900
ttcctgttca cccatgagtg tgagcagagc agacatttgg acctggctgt gcaagtgacg     960
gaggtgatcg cctacacgca ctgctgtgtc aacccagtga tctacgcctt cgttggtgag    1020
```

```
aggttccgga agtacctgcg gcagttgttc cacaggcgtg tggctgtgca cctggttaaa    1080
tggctcccct tcctctccgt ggacaggctg gagagggtca gctccacatc tccctccaca    1140
ggggagcatg aactctctgc tgggttc                                         1167
```

<210> SEQ ID NO 119
<211> LENGTH: 394
<212> TYPE: PRT
<213> ORGANISM: Homo sapiens

<400> SEQUENCE: 119

```
Met Asp Ser Lys Gly Ser Ser Gln Lys Gly Ser Arg Leu Leu Leu Leu
1               5                   10                  15

Leu Val Val Ser Asn Leu Leu Leu Cys Gln Gly Val Val Ser Asp Tyr
            20                  25                  30

Lys Asp Asp Asp Val Asp Glu Thr Pro Asn Thr Thr Glu Asp Tyr
        35                  40                  45

Asp Thr Thr Thr Glu Phe Asp Tyr Gly Asp Ala Thr Pro Cys Gln Lys
    50                  55                  60

Val Asn Glu Arg Ala Phe Gly Ala Gln Leu Leu Pro Pro Leu Tyr Ser
65                  70                  75                  80

Leu Val Phe Val Ile Gly Leu Val Gly Asn Ile Leu Val Val Leu Val
                85                  90                  95

Leu Val Gln Tyr Lys Arg Leu Lys Asn Met Thr Ser Ile Tyr Leu Leu
            100                 105                 110

Asn Leu Ala Ile Ser Asp Leu Leu Phe Leu Phe Thr Leu Pro Phe Trp
        115                 120                 125

Ile Asp Tyr Lys Leu Lys Asp Asp Trp Val Phe Gly Asp Ala Met Cys
    130                 135                 140

Lys Ile Leu Ser Gly Phe Tyr Tyr Thr Gly Leu Tyr Ser Glu Ile Phe
145                 150                 155                 160

Phe Ile Ile Leu Leu Thr Ile Asp Arg Tyr Leu Ala Ile Val His Ala
                165                 170                 175

Val Phe Ala Leu Arg Ala Arg Thr Val Thr Phe Gly Val Ile Thr Ser
            180                 185                 190

Ile Ile Ile Trp Ala Leu Ala Ile Leu Ala Ser Met Pro Gly Leu Tyr
        195                 200                 205

Phe Ser Lys Thr Gln Trp Glu Phe Thr His His Thr Cys Ser Leu His
    210                 215                 220

Phe Pro His Glu Ser Leu Arg Glu Trp Lys Leu Phe Gln Ala Leu Lys
225                 230                 235                 240

Leu Asn Leu Phe Gly Leu Val Leu Pro Leu Leu Val Met Ile Ile Cys
                245                 250                 255

Tyr Thr Gly Ile Ile Lys Ile Leu Leu Arg Arg Pro Asn Glu Lys Lys
            260                 265                 270

Ser Lys Ala Val Arg Leu Ile Phe Val Ile Met Ile Ile Phe Phe Leu
        275                 280                 285

Phe Trp Thr Pro Tyr Asn Leu Thr Ile Leu Ile Ser Val Phe Gln Glu
    290                 295                 300

Phe Phe Gly Leu Ser Asn Cys Glu Ser Thr Ser Gln Leu Asp Gln Ala
305                 310                 315                 320

Thr Gln Val Thr Glu Thr Leu Gly Met Thr His Cys Cys Ile Asn Pro
                325                 330                 335

Ile Ile Tyr Ala Phe Val Gly Glu Lys Phe Arg Arg Tyr Leu Ser Val
            340                 345                 350
```

Phe Phe Arg Lys His Ile Thr Lys Arg Phe Cys Lys Gln Cys Pro Val
        355                 360                 365

Phe Tyr Arg Glu Thr Val Asp Gly Val Thr Ser Thr Asn Thr Pro Ser
        370                 375                 380

Thr Gly Glu Gln Glu Val Ser Ala Gly Leu
385                 390

<210> SEQ ID NO 120
<211> LENGTH: 1182
<212> TYPE: DNA
<213> ORGANISM: Homo sapiens

<400> SEQUENCE: 120

| | | | | | |
|---|---|---|---|---|---|
| atggacagca | aaggttcgtc | gcagaaaggg | tcccgcctgc | tcctgctgct | ggtggtgtca | 60 |
| aatctactct | tgtgccaggg | tgtggtctcc | gattacaaag | atgatgatga | tgtcgacgaa | 120 |
| actccaaaca | ccacagagga | ctatgacacg | accacagagt | ttgactatgg | ggatgcaact | 180 |
| ccgtgccaga | aggtgaacga | gagggccttt | ggggcccaac | tgctgccccc | tctgtactcc | 240 |
| ttggtatttg | tcattggcct | ggttggaaac | atcctggtgg | tcctggtcct | tgtgcaatac | 300 |
| aagaggctaa | aaacatgac | cagcatctac | ctcctgaacc | tggccatttc | tgacctgctc | 360 |
| ttcctgttca | cgcttccctt | ctggatcgac | tacaagttga | aggatgactg | gttttttggt | 420 |
| gatgccatgt | gtaagatcct | ctctgggttt | tattacacag | gcttgtacag | cgagatcttt | 480 |
| ttcatcatcc | tgctgacgat | tgacaggtac | ctggccatcg | tccacgccgt | gtttgccttg | 540 |
| cgggcacgga | ccgtcacttt | tggtgtcatc | accagcatca | tcatttgggc | cctggccatc | 600 |
| ttggcttcca | tgccaggctt | atactttttc | caagacccaa | tgggaattca | ctcaccacac | 660 |
| tgcagccttc | actttcctca | cgaaagccta | cgagagtgga | agctgttttca | ggctctgaaa | 720 |
| ctgaacctct | ttgggctggt | attgccttg | ttggtcatga | tcatctgcta | cacagggatt | 780 |
| ataaagattc | tgctaagacg | accaaatgag | aagaaatcca | agctgtccg | tttgattttt | 840 |
| gtcatcatga | tcatcttttt | tctctttttgg | accccctaca | atttgactat | acttatttct | 900 |
| gttttccagg | aattcttcgg | cctgagtaac | tgtgaaagca | ccagtcaact | ggaccaagcc | 960 |
| acgcaggtga | cagagactct | tgggatgact | cactgctgca | tcaatcccat | catctatgcc | 1020 |
| ttcgttgggg | agaagttcag | aaggtatctc | tcggtgttct | tccgaaagca | catcaccaag | 1080 |
| cgcttctgca | acaatgtcc | agttttctac | agggagacag | tggatggagt | gacttcaaca | 1140 |
| aacacgcctt | ccactgggga | gcaggaagtc | tcggctggtt | ta | | 1182 |

<210> SEQ ID NO 121
<211> LENGTH: 390
<212> TYPE: PRT
<213> ORGANISM: Homo sapiens

<400> SEQUENCE: 121

Met Asp Ser Lys Gly Ser Ser Gln Lys Gly Ser Arg Leu Leu Leu Leu
1               5                   10                  15

Leu Val Val Ser Asn Leu Leu Leu Cys Gln Gly Val Val Ser Asp Tyr
                20                  25                  30

Lys Asp Asp Asp Asp Val Asp Glu Thr Pro Asn Thr Thr Glu Asp Tyr
            35                  40                  45

Asp Thr Thr Thr Glu Phe Asp Tyr Gly Asp Ala Thr Pro Cys Gln Lys
        50                  55                  60

Val Asn Glu Arg Ala Phe Gly Ala Gln Leu Leu Pro Pro Leu Tyr Ser
65                  70                  75                  80

```
Leu Val Phe Ile Phe Gly Phe Val Gly Asn Met Leu Val Val Leu Ile
                 85                  90                  95

Leu Ile Asn Cys Lys Lys Leu Lys Cys Leu Thr Asp Ile Tyr Leu Leu
            100                 105                 110

Asn Leu Ala Ile Ser Asp Leu Leu Phe Leu Ile Thr Leu Pro Leu Trp
        115                 120                 125

Ala His Ser Ala Ala Asn Glu Trp Val Phe Gly Asn Ala Met Cys Lys
    130                 135                 140

Leu Phe Thr Gly Leu Tyr His Ile Gly Tyr Phe Gly Gly Ile Phe Phe
145                 150                 155                 160

Ile Ile Leu Leu Thr Ile Asp Arg Tyr Leu Ala Ile Val His Ala Val
            165                 170                 175

Phe Ala Leu Lys Ala Arg Thr Val Thr Phe Gly Val Val Thr Ser Val
        180                 185                 190

Ile Thr Trp Leu Val Ala Val Phe Ala Ser Val Pro Gly Ile Ile Phe
    195                 200                 205

Thr Lys Cys Gln Lys Glu Asp Ser Val Tyr Val Cys Gly Pro Tyr Phe
210                 215                 220

Pro Arg Gly Trp Asn Asn Phe His Thr Ile Met Arg Asn Ile Leu Gly
225                 230                 235                 240

Leu Val Leu Pro Leu Leu Ile Met Val Ile Cys Tyr Ser Gly Ile Leu
            245                 250                 255

Lys Thr Leu Leu Arg Cys Arg Asn Glu Lys Lys Arg His Arg Ala Val
        260                 265                 270

Arg Val Ile Phe Thr Ile Met Ile Val Tyr Phe Leu Phe Trp Thr Pro
    275                 280                 285

Tyr Asn Ile Val Ile Leu Leu Asn Thr Phe Gln Glu Phe Phe Gly Leu
290                 295                 300

Ser Asn Cys Glu Ser Thr Ser Gln Leu Asp Gln Ala Thr Gln Val Thr
305                 310                 315                 320

Glu Thr Leu Gly Met Thr His Cys Cys Ile Asn Pro Ile Ile Tyr Ala
            325                 330                 335

Phe Val Gly Glu Lys Phe Arg Arg Tyr Leu Ser Val Phe Phe Arg Lys
        340                 345                 350

His Ile Thr Lys Arg Phe Cys Lys Gln Cys Pro Val Phe Tyr Arg Glu
    355                 360                 365

Thr Val Asp Gly Val Thr Ser Thr Asn Thr Pro Ser Thr Gly Glu Gln
370                 375                 380

Glu Val Ser Ala Gly Leu
385                 390

<210> SEQ ID NO 122
<211> LENGTH: 1170
<212> TYPE: DNA
<213> ORGANISM: Homo sapiens

<400> SEQUENCE: 122
atggacagca aaggttcgtc gcagaaaggg tcccgcctgc tcctgctgct ggtggtgtca      60
aatctactct tgtgccaggg tgtggtctcc gattacaaag atgatgatga tgtcgacgaa     120
actccaaaca ccacagagga ctatgacacg accacagagt tgactatgg ggatgcaact     180 ccgtgccaga aggtgaacga gagggccttt ggggcccaac tcctgcctcc gctctactcg     240
ctggtgttca tctttggttt tgtgggcaac atgctggtcg tcctcatctt aataaaactgc    300 aaaaagctga agtgcttgac tgacatttac ctgctcaacc tggccatctc tgatctgctt    360
```

```
tttcttatta ctctcccatt gtgggctcac tctgctgcaa atgagtgggt ctttgggaat      420
gcaatgtgca aattattcac agggctgtat cacatcggtt attttggcgg aatcttcttc      480
atcatcctcc tgacaatcga tagatacctg gctattgtcc atgctgtgtt tgctttaaaa      540
gccaggacgg tcacctttgg ggtggtgaca agtgtgatca cctggttggt ggctgtgttt      600
gcttctgtcc caggaatcat ctttactaaa tgccagaaag aagattctgt ttatgtctgt      660
ggcccttatt ttccacgagg atggaataat ttccacacaa taatgaggaa catttttgggg     720 ctggtcctgc cgctgctcat catggtcatc tgctactcgg gaatcctgaa aaccctgctt      780
cggtgtcgaa acgagaagaa gaggcatagg gcagtgagag tcatcttcac catcatgatt      840
gtttactttc tcttctggac tccctataac attgtcattc tcctgaacac cttccaggaa      900
ttcttcggcc tgagtaactg tgaaagcacc agtcaactgg accaagccac gcaggtgaca      960
gagactcttg ggatgactca ctgctgcatc aatcccatca tctatgcctt cgttggggag     1020
aagttcagaa ggtatctctc ggtgttcttc cgaaagcaca tcaccaagcg cttctgcaaa     1080
caatgtccag ttttctacag ggagacagtg gatggagtga cttcaacaaa cacgccttcc     1140
actggggagc aggaagtctc ggctggttta                                     1170

<210> SEQ ID NO 123
<211> LENGTH: 400
<212> TYPE: PRT
<213> ORGANISM: Homo sapiens

<400> SEQUENCE: 123

Met Asp Ser Lys Gly Ser Ser Gln Lys Gly Ser Arg Leu Leu Leu Leu
1               5                   10                  15

Leu Val Val Ser Asn Leu Leu Leu Cys Gln Gly Val Val Ser Asp Tyr
            20                  25                  30

Lys Asp Asp Asp Val Asp Leu Ser Thr Ser Arg Ser Arg Phe Ile
        35                  40                  45

Arg Asn Thr Asn Glu Ser Gly Glu Glu Val Thr Thr Phe Phe Asp Tyr
    50                  55                  60

Asp Tyr Gly Ala Pro Cys His Lys Phe Asp Val Lys Gln Ile Gly Ala
65                  70                  75                  80

Gln Leu Leu Pro Pro Leu Tyr Ser Leu Val Phe Ile Phe Gly Phe Val
                85                  90                  95

Gly Asn Met Leu Val Val Leu Ile Leu Ile Asn Cys Lys Lys Leu Lys
            100                 105                 110

Cys Leu Thr Asp Ile Tyr Leu Leu Asn Leu Ala Ile Ser Asp Leu Leu
        115                 120                 125

Phe Leu Ile Thr Leu Pro Leu Trp Ala His Ser Ala Ala Asn Glu Trp
    130                 135                 140

Val Phe Gly Asn Ala Met Cys Lys Leu Phe Thr Gly Leu Tyr His Ile
145                 150                 155                 160

Gly Tyr Phe Gly Gly Ile Phe Phe Ile Ile Leu Thr Ile Asp Arg
                165                 170                 175

Tyr Leu Ala Ile Val His Ala Val Phe Ala Leu Arg Ala Arg Thr Val
            180                 185                 190

Thr Phe Gly Val Ile Thr Ser Ile Ile Ile Trp Ala Leu Ala Ile Leu
        195                 200                 205

Ala Ser Met Pro Gly Leu Tyr Phe Ser Lys Thr Gln Trp Glu Phe Thr
    210                 215                 220

His His Thr Cys Ser Leu His Phe Pro His Glu Ser Leu Arg Glu Trp
225                 230                 235                 240
```

```
Lys Leu Phe Gln Ala Leu Lys Leu Asn Leu Phe Gly Leu Val Leu Pro
                245                 250                 255
Leu Leu Val Met Ile Ile Cys Tyr Thr Gly Ile Ile Lys Ile Leu Leu
            260                 265                 270
Arg Arg Pro Asn Glu Lys Lys Ser Lys Ala Val Arg Leu Ile Phe Val
        275                 280                 285
Ile Met Ile Ile Phe Phe Leu Phe Trp Thr Pro Tyr Asn Leu Thr Ile
    290                 295                 300
Leu Ile Ser Val Phe Gln Asp Phe Leu Phe Thr His Glu Cys Glu Gln
305                 310                 315                 320
Ser Arg His Leu Asp Leu Ala Val Gln Val Thr Glu Val Ile Ala Tyr
                325                 330                 335
Thr His Cys Cys Val Asn Pro Val Ile Tyr Ala Phe Val Gly Glu Arg
            340                 345                 350
Phe Arg Lys Tyr Leu Arg Gln Leu Phe His Arg Val Ala Val His
        355                 360                 365
Leu Val Lys Trp Leu Pro Phe Leu Ser Val Asp Arg Leu Glu Arg Val
    370                 375                 380
Ser Ser Thr Ser Pro Ser Thr Gly Glu His Glu Leu Ser Ala Gly Phe
385                 390                 395                 400
```

<210> SEQ ID NO 124
<211> LENGTH: 1200
<212> TYPE: DNA
<213> ORGANISM: Homo sapiens

<400> SEQUENCE: 124

```
atggacagca aaggttcgtc gcagaaaggg tcccgcctgc tcctgctgct ggtggtgtca      60
aatctactct tgtgccaggg tgtggtctcc gattacaaag atgatgatga tgtcgacctg     120
tccacatctc gttctcggtt tatcagaaat accaacgaga gcggtgaaga agtcaccacc     180
tttttttgatt atgattacgg tgctccctgt cataaatttg acgtgaagca aattggggcc     240
caactcctgc ctccgctcta ctcgctggtg ttcatctttg gttttgtggg caacatgctg     300
gtcgtcctca tcttaataaa ctgcaaaaag ctgaagtgct tgactgacat ttacctgctc     360
aacctggcca tctctgatct gcttttttctt attactctcc cattgtgggc tcactctgct     420
gcaaatgagt gggtctttgg gaatgcaatg tgcaaattat tcacagggct gtatcacatc     480
ggttattttg cggaatcttt ttcatcatc ctgctgacga ttgacaggta cctggccatc     540
gtccacgccg tgtttgcctt gcgggcacgg accgtcactt ttggtgtcat caccagcatc     600
atcatttggg ccctggccat cttggcttcc atgccaggct atactttttc caagacccaa     660
tgggaattca ctcaccacac ctgcagcctt cactttcctc acgaaagcct acgagagtgg     720
aagctgtttc aggctctgaa actgaacctc tttgggctgg tattgccttt gttggtcatg     780
atcatctgct acacagggat tataaagatt ctgctaagac gaccaaatga aagaaatcc     840
aaagctgtcc gtttgatttt tgtcatcatg atcatctttt ttctcttttg gacccctac     900
aatttgacta tacttatttc tgttttccaa gacttcctgt tcacccatga gtgtgagcag     960
agcagacatt tggacctggc tgtgcaagtg acggaggtga tcgcctacac gcactgctgt    1020
gtcaacccag tgatctacgc cttcgttggt gagaggttcc ggaagtacct gcggcagttg    1080
ttccacaggc gtgtggctgt gcacctggtt aaatggctcc ccttcctctc cgtggacagg    1140
ctggagaggg tcagctccac atctccctcc acaggggagc atgaactctc tgctgggttc    1200
```

```
<210> SEQ ID NO 125
<211> LENGTH: 374
<212> TYPE: PRT
<213> ORGANISM: Homo sapiens

<400> SEQUENCE: 125

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
            20                  25                  30

His Lys Phe Asp Val Lys Gln Ile Gly Ala Gln Leu Leu Pro Pro Leu
        35                  40                  45

Tyr Ser Leu Val Phe Ile Phe Gly Phe Val Gly Asn Met Leu Val Val
    50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
    130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
        195                 200                 205

Leu Gly Leu Val Leu Pro Leu Leu Ile Met Val Ile Cys Tyr Ser Gly
    210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Ser Gln Leu Asp Gln Ala Thr Gln
        275                 280                 285

Val Thr Glu Thr Leu Gly Met Thr His Cys Cys Ile Asn Pro Ile Ile
    290                 295                 300

Tyr Ala Phe Val Gly Glu Lys Phe Arg Ser Leu Phe His Ile Ala Leu
305                 310                 315                 320

Gly Cys Arg Ile Ala Pro Leu Gln Lys Pro Val Cys Gly Gly Pro Gly
                325                 330                 335

Val Arg Pro Gly Lys Asn Val Lys Val Thr Thr Gln Gly Leu Leu Asp
            340                 345                 350

Gly Arg Gly Lys Gly Lys Ser Ile Gly Arg Ala Pro Glu Ala Ser Leu
        355                 360                 365

Gln Asp Lys Glu Gly Ala
    370
```

```
<210> SEQ ID NO 126
<211> LENGTH: 360
<212> TYPE: PRT
<213> ORGANISM: Homo sapiens

<400> SEQUENCE: 126

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
            20                  25                  30

His Lys Phe Asp Val Lys Gln Ile Gly Ala Gln Leu Leu Pro Pro Leu
        35                  40                  45

Tyr Ser Leu Val Phe Ile Phe Gly Phe Val Gly Asn Met Leu Val Val
    50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
    130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
        195                 200                 205

Leu Gly Leu Val Leu Pro Leu Leu Ile Met Val Ile Cys Tyr Ser Gly
    210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Ser Gln Leu Asp Gln Ala Thr Gln
        275                 280                 285

Val Thr Glu Thr Leu Gly Met Thr His Cys Cys Ile Asn Pro Ile Ile
    290                 295                 300

Tyr Ala Phe Val Gly Glu Lys Phe Arg Arg Tyr Leu Ser Val Phe Phe
305                 310                 315                 320

Arg Lys His Ile Thr Lys Arg Phe Cys Lys Gln Cys Pro Val Phe Tyr
                325                 330                 335

Arg Glu Thr Val Asp Gly Val Thr Ser Thr Asn Thr Pro Ser Thr Gly
            340                 345                 350

Glu Gln Glu Val Ser Ala Gly Leu
        355                 360

<210> SEQ ID NO 127
<211> LENGTH: 42
<212> TYPE: PRT
```

<213> ORGANISM: Homo sapiens

<400> SEQUENCE: 127

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
            20                  25                  30

His Lys Phe Asp Val Lys Gln Ile Gly Ala
        35                  40

<210> SEQ ID NO 128
<211> LENGTH: 14
<212> TYPE: PRT
<213> ORGANISM: Homo sapiens

<400> SEQUENCE: 128

Ser Ala Ala Asn Glu Trp Val Phe Gly Asn Ala Met Cys Lys
1               5                   10

<210> SEQ ID NO 129
<211> LENGTH: 28
<212> TYPE: PRT
<213> ORGANISM: Homo sapiens

<400> SEQUENCE: 129

Thr Lys Cys Gln Lys Glu Asp Ser Val Tyr Val Cys Gly Pro Tyr Phe
1               5                   10                  15

Pro Arg Gly Trp Asn Asn Phe His Thr Ile Met Arg
            20                  25

<210> SEQ ID NO 130
<211> LENGTH: 17
<212> TYPE: PRT
<213> ORGANISM: Homo sapiens

<400> SEQUENCE: 130

Gln Glu Phe Phe Gly Leu Ser Asn Cys Glu Ser Thr Ser Gln Leu Asp
1               5                   10                  15

Gln

<210> SEQ ID NO 131
<211> LENGTH: 352
<212> TYPE: PRT
<213> ORGANISM: Homo sapiens

<400> SEQUENCE: 131

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

```
Phe Ser Gly Ile Phe Phe Ile Ile Leu Leu Thr Ile Asp Arg Tyr Leu
            115                 120                 125
Ala Val Val His Ala Val Phe Ala Leu Lys Ala Arg Thr Val Thr Phe
        130                 135                 140
Gly Val Val Thr Ser Val Ile Thr Trp Val Val Ala Val Phe Ala Ser
145                 150                 155                 160
Leu Pro Gly Ile Ile Phe Thr Arg Ser Gln Lys Glu Gly Leu His Tyr
                165                 170                 175
Thr Cys Ser Ser His Phe Pro Tyr Ser Gln Tyr Gln Phe Trp Lys Asn
            180                 185                 190
Phe Gln Thr Leu Lys Ile Val Ile Leu Gly Leu Val Leu Pro Leu Leu
        195                 200                 205
Val Met Val Ile Cys Tyr Ser Gly Ile Leu Lys Thr Leu Leu Arg Cys
210                 215                 220
Arg Asn Glu Lys Lys Arg His Arg Ala Val Arg Leu Ile Phe Thr Ile
225                 230                 235                 240
Met Ile Val Tyr Phe Leu Phe Trp Ala Pro Tyr Asn Ile Val Leu Leu
                245                 250                 255
Leu Asn Thr Phe Gln Glu Phe Phe Gly Leu Asn Asn Cys Ser Ser Ser
            260                 265                 270
Asn Arg Leu Asp Gln Ala Met Gln Val Thr Glu Thr Leu Gly Met Thr
        275                 280                 285
His Cys Cys Ile Asn Pro Ile Ile Tyr Ala Phe Val Gly Glu Lys Phe
290                 295                 300
Arg Asn Tyr Leu Leu Val Phe Phe Gln Lys His Ile Ala Lys Arg Phe
305                 310                 315                 320
Cys Lys Cys Cys Ser Ile Phe Gln Gln Glu Ala Pro Glu Arg Ala Ser
                325                 330                 335
Ser Val Tyr Thr Arg Ser Thr Gly Glu Gln Glu Ile Ser Val Gly Leu
            340                 345                 350

<210> SEQ ID NO 132
<211> LENGTH: 30
<212> TYPE: DNA
<213> ORGANISM: Homo sapiens

<400> SEQUENCE: 132
cgagagggcc tttgggatcc aactgctgcc                                        30

<210> SEQ ID NO 133
<211> LENGTH: 30
<212> TYPE: DNA
<213> ORGANISM: Homo sapiens

<400> SEQUENCE: 133
ggcagcagtt ggatcccaaa ggccctctcg                                        30

<210> SEQ ID NO 134
<211> LENGTH: 24
<212> TYPE: DNA
<213> ORGANISM: Homo sapiens

<400> SEQUENCE: 134
gcaaattggg atccaactcc tgcc                                              24

<210> SEQ ID NO 135

<400> SEQUENCE: 135
```

<210> SEQ ID NO 136
<211> LENGTH: 24
<212> TYPE: DNA
<213> ORGANISM: Homo sapiens

<400> SEQUENCE: 136
gcaaattggg gcccaactgc tgcc                                          24

<210> SEQ ID NO 137
<211> LENGTH: 24
<212> TYPE: DNA
<213> ORGANISM: Homo sapiens

<400> SEQUENCE: 137
ggcagcagtt gggccccaat ttgc                                          24

<210> SEQ ID NO 138
<211> LENGTH: 26
<212> TYPE: DNA
<213> ORGANISM: Homo sapiens

<400> SEQUENCE: 138
ctcttgtgcc agggtgtggt ctccga                                        26

<210> SEQ ID NO 139
<211> LENGTH: 35
<212> TYPE: DNA
<213> ORGANISM: Homo sapiens

<400> SEQUENCE: 139
gatcgaagct ttcagaaccc agcagagagt tcatg                              35

<210> SEQ ID NO 140
<211> LENGTH: 43
<212> TYPE: DNA
<213> ORGANISM: Homo sapiens

<400> SEQUENCE: 140
gactatactt atttctgttt tcattgtcat tctcctgaac acc                     43

<210> SEQ ID NO 141
<211> LENGTH: 29
<212> TYPE: DNA
<213> ORGANISM: Homo sapiens

<400> SEQUENCE: 141
cgccaagctt cattataaac cagccgaga                                     29

<210> SEQ ID NO 142
<211> LENGTH: 31
<212> TYPE: DNA
<213> ORGANISM: Homo sapiens

<400> SEQUENCE: 142
acgcgtcgac gaaactccaa acaccacaga g                                  31

<210> SEQ ID NO 143
<211> LENGTH: 40
<212> TYPE: DNA
<213> ORGANISM: Homo sapiens

<400> SEQUENCE: 143

```
gttcaggaga atgacaatga aaacagaaat aagtatagtc                              40

<210> SEQ ID NO 144
<211> LENGTH: 39
<212> TYPE: DNA
<213> ORGANISM: Homo sapiens

<400> SEQUENCE: 144
cattctcctg aacaccttcc aagacttcct gttcaccca                               39

<210> SEQ ID NO 145
<211> LENGTH: 29
<212> TYPE: DNA
<213> ORGANISM: Homo sapiens

<400> SEQUENCE: 145
gccaagcttc cagtgtgatg gatatctga                                          29

<210> SEQ ID NO 146
<211> LENGTH: 40
<212> TYPE: DNA
<213> ORGANISM: Homo sapiens

<400> SEQUENCE: 146
tgggtgaaca ggaagtcttg gaaggtgttc aggagaatga                              40

<210> SEQ ID NO 147
<211> LENGTH: 23
<212> TYPE: DNA
<213> ORGANISM: Homo sapiens

<400> SEQUENCE: 147
caggtgcagc tggtggagtc tgg                                                23

<210> SEQ ID NO 148
<211> LENGTH: 25
<212> TYPE: DNA
<213> ORGANISM: Homo sapiens

<400> SEQUENCE: 148
gaagagacgg tgaccattgt ccctt                                              25

<210> SEQ ID NO 149
<211> LENGTH: 27
<212> TYPE: DNA
<213> ORGANISM: Homo sapiens

<400> SEQUENCE: 149
gaaattgtgc tgactcagtc tccagac                                            27

<210> SEQ ID NO 150
<211> LENGTH: 24
<212> TYPE: DNA
<213> ORGANISM: Homo sapiens

<400> SEQUENCE: 150
gtttgatctc caccttggtc cctc                                               24

<210> SEQ ID NO 151
<211> LENGTH: 27
<212> TYPE: DNA
<213> ORGANISM: Homo sapiens

<400> SEQUENCE: 151
```

-continued

| | |
|---|---|
| ggcagtggat ctgggacaga tttcacc | 27 |

<210> SEQ ID NO 152
<211> LENGTH: 27
<212> TYPE: DNA
<213> ORGANISM: Homo sapiens

<400> SEQUENCE: 152

| | |
|---|---|
| ggtgaaatct gtcccagatc cactgcc | 27 |

<210> SEQ ID NO 153
<211> LENGTH: 88
<212> TYPE: DNA
<213> ORGANISM: Homo sapiens

<400> SEQUENCE: 153

| | |
|---|---|
| ttatgctggg cccagctctg tcccacaccg cggtcacatg gcaccacctc tcttgcagct | 60 |
| tccaccaaag gcccatccgt cttccccc | 88 |

<210> SEQ ID NO 154
<211> LENGTH: 39
<212> TYPE: DNA
<213> ORGANISM: Homo sapiens

<400> SEQUENCE: 154

| | |
|---|---|
| tcatattctc tagatcattt acccagagac agggagagg | 39 |

<210> SEQ ID NO 155
<211> LENGTH: 27
<212> TYPE: DNA
<213> ORGANISM: Homo sapiens

<400> SEQUENCE: 155

| | |
|---|---|
| cagcgtggtg acagtgccct ccagcag | 27 |

<210> SEQ ID NO 156
<211> LENGTH: 27
<212> TYPE: DNA
<213> ORGANISM: Homo sapiens

<400> SEQUENCE: 156

| | |
|---|---|
| ctgctggagg gcactgtcac cacgctg | 27 |

<210> SEQ ID NO 157
<211> LENGTH: 12754
<212> TYPE: DNA
<213> ORGANISM: Homo sapiens

<400> SEQUENCE: 157

| | |
|---|---|
| ccccacctgt aggtttggca agctagctta agtaacgcca ttttgcaagg catggaaaat | 60 |
| acataactga gaatagagaa gttcagatca aggttaggaa ggggtggaca tccaaaccgt | 120 |
| tcgatcgaat tcattgcggt aaaacgttcc gtacctttta tgtattgact cttatctctt | 180 |
| caagtctagt tccaatcctt cagagagaca gcagaatatg ggccaaacag gatatctgtg | 240 |
| gtaagcagtt cctgccccgg ctcagggcca agaacagatg gtccccagat gcggtcccgc | 300 |
| gtctctctgt cgtcttatac ccggtttgtc ctatagacac cattcgtcaa ggacggggcc | 360 |
| gagtcccggt tcttgtctac caggggtcta cgccagggcg cctcagcagt ttctagagaa | 420 |
| ccatcagatg tttccagggt gccccaagga cctgaaaatg accctgtgcc ttatttgaac | 480 |
| taaccaatca gttcgcttct ggagtcgtca aagatctctt ggtagtctac aaaggtccca | 540 |

```
cgggggttcct ggacttttac tgggacacgg aataaacttg attggttagt caagcgaaga      600
cgcttctgtt cgcgcgcttc tgctccccga gctcaataaa agagcccaca acccctcact      660
cggcgcgcca gtcctccgat agactgcgtc gcccgggtac gcgaagacaa gcgcgcgaag      720
acgaggggct cgagttattt tctcgggtgt tggggagtga gccgcgcggt caggaggcta      780
tctgacgcag cgggcccatg ccccccccccc cccgtattcc caataaagcc tcttgctgtt      840
tgcatccgaa tcgtggactc gctgatcctt ggagggtct cctcagattg attgactgcc       900
gggggggggg gggcataagg gttatttcgg agaacgacaa acgtaggctt agcacctgag      960
cgactaggaa ccctcccaga ggagtctaac taactgacgg cacctcgggg gtctttcatt     1020
tggaggttcc accgagattt ggagacccct gcctagggac caccgacccc ccgccggga     1080 ggtaagctgg ccagcggtcg gtggagcccc cagaaagtaa acctccaagg tggctctaaa    1140
cctctgggga cggatccctg gtggctgggg gggcggccct ccattcgacc ggtcgccagc    1200
tttcgtgtct gtctctgtct ttgtgcgtgt tgtgccggc atctaatgtt tgcgcctgcg      1260
tctgtactag ttagctaact agctctgtat ctggcggacc aaagcacaga cagagacaga    1320
aacacgcaca aacacggccg tagattacaa acgcggacgc agacatgatc aatcgattga    1380
tcgagacata daccgcctgg cgtggtggaa ctgacgagtt ctgaacaccc ggccgcaacc    1440
ctgggagacg tcccagggac tttgggggcc gttttttgtgg cccgacctga ggaagggagt   1500
gcaccacctt gactgctcaa gacttgtggg ccggcgttgg gaccctctgc agggtccctg    1560
aaaccccggg caaaaacacc gggctggact ccttccctca cgatgtggaa tccgaccccg     1620
tcaggatatg tggttctggt aggagacgag aacctaaaac agttcccgcc tccgtctgaa    1680
tttttgcttt cggtttggaa gctacaccttt aggctgggc agtcctatac accaagacca    1740
tcctctgctc ttggattttg tcaagggcgg aggcagactt aaaaacgaaa gccaaacctt    1800
ccgaagccgc gcgtcttgtc tgctgcagcg ctgcagcatc gttctgtgtt gtctctgtct    1860
gactgtgttt ctgtatttgt ctgaaaatta gggccagact ggcttcggcg cgcagaacag    1920
acgacgtcgc gacgtcgtag caagacacaa cagagacaga ctgacacaaa gacataaaca    1980
gacttttaat cccggtctga gttaccactc ccttaagttt gaccttaggt cactggaaag    2040
atgtcgagcg gatcgctcac aaccagtcgg tagatgtcaa gaagagacgt tgggttacct    2100
caatggtgag ggaattcaaa ctggaatcca gtgacctttc tacagctcgc ctagcgagtg    2160
ttggtcagcc atctacagtt cttctctgca acccaatgga tctgctctgc agaatggcca    2220
acctttaacg tcggatggcc gcgagacggc acctttaacc gagacctcat cacccaggtt    2280
aagatcaagg tcttttcacc agacgagacg tcttaccggt tggaaattgc agcctaccgg    2340
cgctctgccg tggaaattgg ctctggagta gtgggtccaa ttctagttcc agaaaagtgg    2400
tggcccgcat ggacacccag accaggtccc ctacatcgtg acctgggaag ccttggcttt    2460 tgaccccccct ccctgggtca agccctttgt acacctaag accgggcgta cctgtgggtc    2520
tggtccaggg gatgtagcac tggacccttc ggaaccgaaa actgggggga gggacccagt    2580
tcggaaaaca tgtgggattc cctccgcctc ctcttcctcc atccgccccg tctctccccc    2640
ttgaacctcc tcgttcgacc ccgcctcgat cctcccttta tccagccctc actccttctc    2700
ggaggcggag gagaaggagg taggcgggc agagagggg aacttggagg agcaagctgg      2760
ggcggagcta ggagggaaat aggtcgggag tgaggaagag taggcgccga gatctctcga    2820
ggttaaactt aagctatgga cagcaaaggt tcgtcgcaga aagggtcccg cctgctcctg    2880
ctgctggtgg tgtcaaatct atccgcggct ctagagagct ccaatttgaa ttcgatacct    2940
```

```
gtcgtttcca agcagcgtct ttcccagggc ggacgaggac gacgaccacc acagtttaga    3000
actcttgtgc cagggtgtgg tctccgatta caaagatgat gatgatagcg ctgaagacaa    3060
taatatgtta cctcagttca tccacggcat actatcaaca tgagaacacg gtcccacacc    3120
agaggctaat gtttctacta ctactatcgc gacttctgtt attatacaat ggagtcaagt    3180
aggtgccgta tgatagttgt tctcattctc tatttacacg aagtatccaa gagcttgatg    3240
aaggggccac cacaccgtat gactacgatg atggtgagcc ttgtcataaa accagtgtga    3300
agagtaagag ataaatgtgc ttcataggtt ctcgaactac ttccccggtg gtgtggcata    3360
ctgatgctac taccactcgg aacagtattt tggtcacact agcaaattgg agcttggatc    3420
ctgcctccgc tctactcgct ggtgttcatc tttggttttg tgggcaacat gctggtcgtc    3480
ctcatcttaa taaactgcaa tcgtttaacc tcgaacctag gacggaggcg agatgagcga    3540
ccacaagtag aaaccaaaac acccgttgta cgaccagcag gagtagaatt atttgacgtt    3600
aaagctgaag tgcttgactg acatttacct gctcaacctg gccatctctg atctgctttt    3660
tcttattact ctcccattgt gggctcactc tgctgcaaat tttcgacttc acgaactgac    3720
tgtaaatgga cgagttggac cggtagagac tagacgaaaa agaataatga gagggtaaca    3780
cccgagtgag acgacgttta gagtgggtct ttgggaatgc aatgtgcaaa ttattcacag    3840
ggctgtatca catcggttat tttggcggaa tcttcttcat catcctcctg acaatcgata    3900
ctcacccaga aacccttacg ttacacgttt aataagtgtc ccgacatagt gtagccaata    3960
aaaccgcctt agaagaagta gtaggaggac tgttagctat gatacctggc tattgtccat    4020
gctgtgtttg ctttaaaagc caggacggtc acctttgggg tggtgacaag tgtgatcacc    4080
tggttggtgg ctgtgtttgc ctatggaccg ataacaggta cgacacaaac gaaattttcg    4140
gtcctgccag tggaaacccc accactgttc acactagtgg accaaccacc gacacaaacg    4200
ttctgtccca ggaatcatct ttactaaatg ccagaaagaa gattctgttt atgtctgtgg    4260
cccttatttt ccacgaggat ggaataattt ccacacaata aagacagggt ccttagtaga    4320
aatgatttac ggtctttctt ctaagacaaa tacagacacc gggaataaaa ggtgctccta    4380
ccttattaaa ggtgtgttat atgaggaaca ttttggggct ggtcctgccg ctgctcatca    4440
tggtcatctg ctactcggga atcctgaaaa ccctgcttcg gtgtcgaaac gagaagaaga    4500
tactccttgt aaaccccga ccaggacggc gacgagtagt accagtagac gatgagccct    4560
taggactttt gggacgaagc cacagctttg ctcttcttct ggcatagggc agtgagagtc    4620 atcttccacca tcatgattgt ttactttctc ttctggactc cctataatat tgtcattctc    4680
ctgaacacct tccaggaatt ccgtatcccg tcactctcag tagaagtggt agtactaaca    4740
aatgaaagag aagacctgag ggatattata acagtaagag gacttgtgga aggtccttaa    4800
cttcggcctg agtaactgtg aaagcaccag tcaactggac caagccacgc aggtgacaga    4860
gactcttggg atgactcact gctgcatcaa tccatcatc gaagccggac tcattgacac    4920
tttcgtggtc agttgacctg gttcggtgcg tccactgtct ctgagaaccc tactgagtga    4980
cgacgtagtc agggtagtag tatgccttcg ttggggagaa gttcagaagg tatctctcgg    5040
tgttcttccg aaagcacatc accaagcgct tctgcaaaca atgtccagtt ttctacaggg    5100
atacggaagc aaccctctt caagtcttcc atagagagcc acaagaaggc tttcgtgtag    5160
tggttcgcga agacgtttgt tacaggtcaa aagatgtccc agacagtgga tggagtgact    5220
tcaacaaaca cgccttccac tggggagcag gaagtctcgg ctggtttata atgactcgag    5280
ctctctagag ggcccgtttg tctgtcacct acctcactga agttgtttgt gcggaaggtg    5340
```

```
accccctcgtc cttcagagcc gaccaaatat tactgagctc gagagatctc ccgggcaaac    5400
acctgcagcc aagcttatcg ataaaataaa agatttatt tagtctccag aaaaaggggg     5460
gaatgaaaga ccccacctgt aggtttggca agctagctta tggacgtcgg ttcgaatagc    5520
tatttattt tctaaaataa atcagaggtc ttttttccccc cttactttct ggggtggaca    5580
tccaaaccgt tcgatcgaat agtaacgcca ttttgcaagg catggaaaat acataactga    5640
gaatagagaa gttcagatca aggttaggaa cagagagaca gcagaatatg ggccaaacag    5700
tcattgcggt aaaacgttcc gtaccttta tgtattgact cttatctctt caagtctagt     5760
tccaatcctt gtctctctgt cgtcttatac ccggtttgtc gatatctgtg gtaagcagtt    5820
cctgccccgg ctcagggcca agaacagatg gtccccagat gcggtcccgc cctcagcagt    5880
ttctagagaa ccatcagatg ctatagacac cattcgtcaa ggacggggcc gagtcccggt    5940
tcttgtctac caggggtcta cgccagggcg ggagtcgtca agatctcttt ggtagtctac    6000
tttccagggt gccccaagga cctgaaaatg accctgtgcc ttatttgaac taaccaatca    6060
gttcgcttct cgcttctgtt cgcgcgcttc tgctccccga aaaggtccca cggggttcct    6120
ggactttac tgggacacgg aataaacttg attggttagt caagcgaaga gcgaagacaa     6180
gcgcgcgaag acgaggggct gctcaataaa agagcccaca acccctcact cggcgcgcca    6240
gtcctccgat agactgcgtc gcccgggtac ccgtgtatcc aataaaccct cttgcagttg    6300
cgagttattt tctcgggtgt tggggagtga gccgcgcggt caggaggcta tctgacgcag    6360
cgggcccatg ggcacatagg ttatttggga gaacgtcaac catccgactt gtggtctcgc    6420
tgttccttgg gagggtctcc tctgagtgat tgactacccg tcagcggggg tctttcatgg    6480
gtaacagttt cttgaagttg gtaggctgaa caccagagcg acaaggaacc ctcccagagg    6540
agactcacta actgatgggc agtcgccccc agaaagtacc cattgtcaaa gaacttcaac    6600
gagaacaaca ttctgagggt aggagtcgaa tattaagtaa tcctgactca attagccact    6660
gttttgaatc cacatactcc aatactcctg aaatagttca ctcttgttgt aagactccca    6720
tcctcagctt ataattcatt aggactgagt taatcggtga caaaacttag gtgtatgagg    6780
ttatgaggac tttatcaagt ttatggacag cgcagaaaga gctggggaga attgtgaaat    6840
tgttatccgc tcacaattcc acacaacata cgagccggaa gcataaagtg taaagcctgg    6900
aatacctgtc gcgtctttct cgacccctct taacacttta acaataggcg agtgttaagg    6960
tgtgttgtat gctcggcctt cgtatttcac atttcggacc ggtgcctaat gagtgagcta    7020
actcacatta attgcgttgc gctcactgcc cgctttccag tcgggaaacc tgtcgtgcca    7080
gctgcattaa tgaatcggcc cacggatta ctcactcgat tgagtgtaat taacgcaacg     7140
cgagtgacgg gcgaaaggtc agcccttggg acagcacggt cgacgtaatt acttagccgg    7200
aacgcgcggg gagaggcggt ttgcgtattg ggcgctcttc cgcttcctcg ctcactgact    7260
cgctgcgctc ggtcgttcgg ctgcggcgag cggtatcagc ttgcgcgccc ctctccgcca    7320
aacgcataac ccgcgagaag gcgaaggagc gagtgactga gcgacgcgag ccagcaagcc    7380
gacgccgctc gccatagtcg tcactcaaag gcggtaatac ggttatccac agaatcaggg    7440
gataacgcag gaaagaacat gtgagcaaaa ggccagcaaa aggccaggaa ccgtaaaaag    7500
agtgagtttc cgccattatg ccaataggtg tcttagtccc ctattgcgtc ctttcttgta    7560
cactcgtttt ccggtcgttt tccggtcctt ggcatttttc gccgcgttgc tggcgttttt    7620
ccataggctc cgcccccctg acgagcatca caaaaatcga cgctcaagtc agaggtggcg    7680
aaacccgaca ggactataaa cggcgcaacg accgcaaaaa ggtatccgag gcgggggac     7740
```

```
tgctcgtagt gttttagct gcgagttcag tctccaccgc tttgggctgt cctgatattt    7800
gataccaggc gtttccccct ggaagctccc tcgtgcgctc tcctgttccg accctgccgc    7860
ttaccggata cctgtccgcc tttctccctt cgggaagcgt ctatggtccg caaaggggga    7920
ccttcgaggg agcacgcgag aggacaaggc tgggacggcg aatggcctat ggacaggcgg    7980
aaagagggaa gcccttcgca ggcgctttct catagctcac gctgtaggta tctcagttcg    8040
gtgtaggtcg ttcgctccaa gctgggctgt gtgcacgaac cccccgttca gcccgaccgc    8100
ccgcgaaaga gtatcgagtg cgacatccat agagtcaagc cacatccagc aagcgaggtt    8160
cgacccgaca cacgtgcttg gggggcaagt cgggctggcg tgcgccttat ccggtaacta    8220
tcgtcttgag tccaacccgg taagacacga cttatcgcca ctggcagcag ccactggtaa    8280
caggattagc agagcgaggt acgcggaata ggccattgat agcagaactc aggttgggcc    8340
attctgtgct gaatagcggt gaccgtcgtc ggtgaccatt gtcctaatcg tctcgctcca    8400
atgtaggcgg tgctacagag ttcttgaagt ggtggcctaa ctacggctac actagaagga    8460
cagtatttgg tatctgcgct ctgctgaagc cagttacctt tacatccgcc acgatgtctc    8520
aagaacttca ccaccggatt gatgccgatg tgatcttcct gtcataaacc atagacgcga    8580
gacgacttcg gtcaatggaa cggaaaaaga gttggtagct cttgatccgg caaacaaacc    8640
accgctggta gcggtggttt ttttgtttgc aagcagcaga ttacgcgcag aaaaaaagga    8700
gccttttcct caaccatcga gaactaggcc gtttgtttgg tggcgaccat cgccaccaaa    8760
aaaacaaacg ttcgtcgtct aatgcgcgtc ttttttcct tctcaagaag atcctttgat    8820
cttttctacg gggtctgacg ctcagtggaa cgaaaactca cgttaaggga ttttggtcat    8880
gagattatca aaaaggatct agagttcttc taggaaacta aaaagatgc cccagactgc    8940
gagtcacctt gcttttgagt gcaattccct aaaaccagta ctctaatagt ttttcctaga    9000
tcacctagat cctttaaat taaaaatgaa gttttaaatc aatctaaagt atatatgagt    9060
aaacttggtc tgacagttac caatgcttaa tcagtgaggc agtggatcta ggaaaattta    9120
atttttactt caaatttag ttagatttca tatatactca tttgaaccag actgtcaatg    9180
gttacgaatt agtcactccg acctatctca gcgatctgtc tatttcgttc atccatagtt    9240
gcctgactcc ccgtcgtgta gataactacg atacgggagg gcttaccatc tggccccagt    9300
tggatagagt cgctagacag ataaagcaag taggtatcaa cggactgagg ggcagcacat    9360
ctattgatgc tatgccctcc cgaatggtag accggggtca gctgcaatga taccgcgaga    9420
cccacgctca ccgctccag atttatcagc aataaaccag ccagccggaa gggccgagcg    9480
cagaagtggt cctgcaactt cgacgttact atggcgctct gggtgcgagt ggccgaggtc    9540
taaatagtcg ttatttggtc ggtcggcctt cccggctcgc gtcttcacca ggacgttgaa    9600
tatccgcctc catccagtct attaattgtt gccgggaagc tagagtaagt agttcgccag    9660
ttaatagttt gcgcaacgtt gttgccattg ctacaggcat ataggcggag gtaggtcaga    9720
taattaacaa cggcccttcg atctcattca tcaagcggtc aattatcaaa cgcgttgcaa    9780
caacggtaac gatgtccgta cgtggtgtca cgctcgtcgt ttggtatggc ttcattcagc    9840
tccggttccc aacgatcaag gcgagttaca tgatccccca tgttgtgcaa aaaagcggtt    9900
gcaccacagt gcgagcagca aaccataccg aagtaagtcg aggccaaggg ttgctagttc    9960
cgctcaatgt actaggggt acaacacgtt ttttcgccaa agctccttcg gtcctccgat    10020
cgttgtcaga agtaagttgg ccgcagtgtt atcactcatg gttatggcag cactgcataa    10080
ttctcttact gtcatgccat tcgaggaagc caggaggcta gcaacagtct tcattcaacc    10140
```

```
ggcgtcacaa tagtgagtac caataccgtc gtgacgtatt aagagaatga cagtacggta    10200
ccgtaagatg cttttctgtg actggtgagt actcaaccaa gtcattctga aatagtgta     10260 tgcggcgacc gagttgctct tgcccggcgt caatacggga ggcattctac gaaaagacac    10320
tgaccactca tgagttggtt cagtaagact cttatcacat acgccgctgg ctcaacgaga    10380
acgggccgca gttatgccct taataccgcg ccacatagca gaactttaaa agtgctcatc    10440
attggaaaac gttcttcggg gcgaaaactc tcaaggatct taccgctgtt gagatccagt    10500
attatggcgc ggtgtatcgt cttgaaattt tcacgagtag taaccttttg caagaagccc    10560
cgcttttgag agttcctaga atggcgacaa ctctaggtca tcgatgtaac ccactcgtgc    10620
acccaactga tcttcagcat cttttacttt caccagcgtt tctgggtgag caaaaacagg    10680
aaggcaaaat gccgcaaaaa agctacattg ggtgagcacg tgggttgact agaagtcgta    10740
gaaaatgaaa gtggtcgcaa agacccactc gttttttgtcc ttccgtttta cggcgttttt    10800
agggaataag ggcgacacgg aaatgttgaa tactcatact cttccttttt caatattatt    10860
gaagcattta tcagggttat tgtctcatga gcggatacat tcccttattc ccgctgtgcc    10920
tttacaactt atgagtatga gaaggaaaaa gttataataa cttcgtaaat agtcccaata    10980
acagagtact cgcctatgta atttgaatgt atttagaaaa ataaacaaat aggggttccg    11040
cgcacatttc cccgaaaagt gccacctgac gtctaagaaa ccattattat catgacatta    11100
taaacttaca taaatctttt tatttgttta tccccaaggc gcgtgtaaag gggcttttca    11160
cggtggactg cagattcttt ggtaataata gtactgtaat acctataaaa ataggcgtat    11220
cacgaggccc tttcgtctcg cgcgtttcgg tgatgacggt gaaaacctct gacacatgca    11280
gctcccggag acgtcacag tggatatttt tatccgcata gtgctccggg aaagcagagc     11340
gcgcaaagcc actactgcca cttttggaga ctgtgtacgt cgagggcctc tgccagtgtc    11400
cttgtctgta agcggatgcc gggagcagac aagcccgtca gggcgcgtca gcgggtgttg    11460
gcgggtgtcg gggctggctt aactatgcgg catcagagca gaacagacat tcgcctacgg    11520
ccctcgtctg ttcgggcagt cccgcgcagt cgcccacaac cgcccacagc cccgaccgaa    11580
ttgatacgcc gtagtctcgt gattgtactg agagtgcacc atatgcggtg tgaaataccg    11640
cacagatgcg taaggagaaa ataccgcatc aggcgccatt cgccattcag gctgcgcaac    11700
ctaacatgac tctcacgtgg tatacgccac actttatggc gtgtctacgc attcctcttt    11760
tatggcgtag tccgcggtaa gcggtaagtc cgacgcgttg tgttgggaag ggcgatcggt    11820
gcgggcctct tcgctattac gccagctggc gaaaggggga tgtgctgcaa ggcgattaag    11880
ttgggtaacg ccagggtttt acaacccttc ccgctagcca cgcccggaga agcgataatg    11940
cggtcgaccc ctttcccccct acacgacgtt ccgctaattc aacccattgc ggtcccaaaa    12000
cccagtcacg acgttgtaaa acgacggcgc aaggaatggt gcatgcaagg agatggcgcc    12060
caacagtccc ccgccacgg ggcctgccac catacccacg gggtcagtgc tgcaacattt      12120
tgctgccgcg ttccttacca cgtacgttcc tctaccgcgg gttgtcaggg ggccggtgcc    12180
ccggacggtg gtatgggtgc ccgaaacaag cgctcatgag cccgaagtgg cgagcccgat    12240
cttccccatc ggtgatgtcg gcgatatagg cgccagcaac cgcacctgtg cgccggtga     12300 ggctttgttc gcgagtactc gggcttcacc gctcgggcta gaagggggtag ccactacagc   12360 cgctatatcc gcggtcgttg gcgtggacac cgcggccact tgccggccac gatgcgtccg    12420
gcgtagaggc gattagtcca atttgttaaa gacaggatat cagtggtcca ggctctagtt    12480
ttgactcaac aatatcacca acggccggtg ctacgcaggc cgcatctccg ctaatcaggt    12540
```

```
taaacaattt ctgtcctata gtcaccaggt ccgagatcaa aactgagttg ttatagtggt    12600
gctgaagcct atagagtacg agccatagat aaaataaaag attttattta gtctccagaa    12660
aaagggggga tgaaagacga cttcggatat ctcatgctcg gtatctattt tattttctaa    12720
aataaatcag aggtcttttt cccccctact ttct                                12754
```

<210> SEQ ID NO 158
<211> LENGTH: 119
<212> TYPE: PRT
<213> ORGANISM: Homo sapiens

<400> SEQUENCE: 158

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Tyr Asn Trp Asn Tyr Ala Phe Asp Ile Trp Gly Gln Gly
            100                 105                 110

Thr Met Val Thr Val Ser Ser
        115

<210> SEQ ID NO 159
<211> LENGTH: 112
<212> TYPE: PRT
<213> ORGANISM: Homo sapiens

<400> SEQUENCE: 159

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Ile Thr Phe Gly Gln Gly Thr Arg Leu Glu Ile Lys
            100                 105                 110

<210> SEQ ID NO 160
<211> LENGTH: 118
<212> TYPE: PRT
<213> ORGANISM: Homo sapiens

<400> SEQUENCE: 160

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Trp Asn Tyr Ala Phe Asp Ile Trp Gly Gln Gly Thr
            100                 105                 110

Met Val Thr Val Ser Ser
            115

<210> SEQ ID NO 161
<211> LENGTH: 107
<212> TYPE: PRT
<213> ORGANISM: Homo sapiens

<400> SEQUENCE: 161

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
                20                  25                  30

Leu His Trp Tyr Gln Gln Lys Pro Asp Gln Ser Pro Lys Leu Leu Ile
            35                  40                  45

Lys Tyr Ala Ser Gln Ser Phe Ser Gly Val Pro Ser Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro Leu
                85                  90                  95

Thr Phe Gly Gly Gly Thr Lys Val Glu Ile Lys
            100                 105

<210> SEQ ID NO 162
<211> LENGTH: 117
<212> TYPE: PRT
<213> ORGANISM: Homo sapiens

<400> SEQUENCE: 162

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Met His Trp Val Arg Gln Ala Pro Gly Lys Gly Leu Glu Trp Val Ala
            35                  40                  45

Val Ile Ser Tyr Asp Gly Ser Asn Lys Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Asn Trp Asn Tyr Ala Phe Asp Ile Trp Gly Gln Gly Thr Met
            100                 105                 110

Val Thr Val Ser Ser

<210> SEQ ID NO 163
<211> LENGTH: 107
<212> TYPE: PRT
<213> ORGANISM: Homo sapiens

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 164
<211> LENGTH: 118
<212> TYPE: PRT
<213> ORGANISM: Homo sapiens

<400> SEQUENCE: 164

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Asn Trp Asn Tyr Ala Phe Asp Ile Trp Gly Gln Gly Thr
            100                 105                 110

Met Val Thr Val Ser Ser
        115

<210> SEQ ID NO 165
<211> LENGTH: 113
<212> TYPE: PRT
<213> ORGANISM: Homo sapiens

<400> SEQUENCE: 165

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

```
Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Trp Thr Phe Gly Gln Gly Thr Lys Val Glu Ile
            100                 105                 110

Lys

<210> SEQ ID NO 166
<211> LENGTH: 1350
<212> TYPE: DNA
<213> ORGANISM: Homo sapiens

<400> SEQUENCE: 166
caggtgcagc tggtgcagtc tggggctgag gtgaagaagc ctggggcctc agtgaaggtt      60
tcctgcaagg catctggata caccttcacc agctactata cattgggt gcgacaggcc     120 cctggacaag gcttgagtg gatgggaatg atcaatccta gtggtggtcg cacaagctac     180
gcacagaagt tccagggcag agtcaccatg accagggaca cgtccacgag cacagtctac     240
atggacctga gcagcctgag atctgaggac acggccgtgt tttactgtgc gagagagaga     300
tggtataagt ggaacttcga tgcttttgat atctggggcc aagggacaat ggtcaccgtc     360
tcctcagctt ccaccaaggg cccatccgtc ttccccctgg cgccctgctc caggagcacc     420
tccgagagca cagccgccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660
gagtccaaat atggtccccc atgcccatca tgcccagcac ctgagttcct ggggggacca     720
tcagtcttcc tgttcccccc aaaacccaag gacactctca tgatctcccg gacccctgag     780
gtcacgtgcg tggtggtgga cgtgagccag gaagaccccg aggtccagtt caactggtac     840
gtggatggcg tggaggtgca taatgccaag acaaagccgc gggaggagca gttcaacagc     900
acgtaccgtg tggtcagcgt cctcaccgtc ctgcaccagg actggctgaa cggcaaggag     960
tacaagtgca aggtctccaa caaaggcctc ccgtcctcca tcgagaaaac catctccaaa    1020
gccaaagggc agccccgaga gccacaggtg tacaccctgc cccatccca ggaggagatg    1080 accaagaacc aggtcagcct gacctgcctg gtcaaaggct tctacccag cgacatcgcc    1140 gtggagtggg agagcaatgg gcagccggag aacaactaca agaccacgcc tcccgtgctg    1200
gactccgacg gctccttctt cctctacagc aggctaaccg tggacaagag caggtggcag    1260
gaggggaatg tcttctcatg ctccgtgatg catgaggctc tgcacaacca ctacacacag    1320
aagagcctct ccctgtctct gggtaaatga                                    1350

<210> SEQ ID NO 167
<211> LENGTH: 366
<212> TYPE: DNA
<213> ORGANISM: Homo sapiens

<400> SEQUENCE: 167
caggtgcagc tggtgcagtc tggggctgag gtgaagaagc ctggggcctc agtgaaggtt      60
tcctgcaagg catctggata caccttcacc agctactata cattgggt gcgacaggcc     120
```

```
cctggacaag ggcttgagtg gatgggaatg atcaatccta gtggtggtcg cacaagctac    180
gcacagaagt tccagggcag agtcaccatg accagggaca cgtccacgag cacagtctac    240
atggacctga gcagcctgag atctgaggac acggccgtgt tttactgtgc gagagagaga    300
tggtataagt ggaacttcga tgcttttgat atctggggcc aagggacaat ggtcaccgtc    360
tcctca                                                                366

<210> SEQ ID NO 168
<211> LENGTH: 15
<212> TYPE: DNA
<213> ORGANISM: Homo sapiens

<400> SEQUENCE: 168
agctactata tacat                                                      15

<210> SEQ ID NO 169
<211> LENGTH: 51
<212> TYPE: DNA
<213> ORGANISM: Homo sapiens

<400> SEQUENCE: 169
atgatcaatc ctagtggtgg tcgcacaagc tacgcacaga agttccaggg c              51

<210> SEQ ID NO 170
<211> LENGTH: 39
<212> TYPE: DNA
<213> ORGANISM: Homo sapiens

<400> SEQUENCE: 170
gagagatggt ataagtggaa cttcgatgct tttgatatc                            39

<210> SEQ ID NO 171
<211> LENGTH: 90
<212> TYPE: DNA
<213> ORGANISM: Homo sapiens

<400> SEQUENCE: 171
caggtgcagc tggtgcagtc tggggctgag gtgaagaagc ctggggcctc agtgaaggtt    60
tcctgcaagg catctggata caccttcacc                                      90

<210> SEQ ID NO 172
<211> LENGTH: 42
<212> TYPE: DNA
<213> ORGANISM: Homo sapiens

<400> SEQUENCE: 172
tgggtgcgac aggcccctgg acaagggctt gagtggatgg ga                        42

<210> SEQ ID NO 173
<211> LENGTH: 96
<212> TYPE: DNA
<213> ORGANISM: Homo sapiens

<400> SEQUENCE: 173
agagtcacca tgaccaggga cacgtccacg agcacagtct acatggacct gagcagcctg    60
agatctgagg acacggccgt gttttactgt gcgaga                              96

<210> SEQ ID NO 174
<211> LENGTH: 33
<212> TYPE: DNA
<213> ORGANISM: Homo sapiens
```

-continued

<400> SEQUENCE: 174
tggggccaag ggacaatggt caccgtctcc tca                                   33

<210> SEQ ID NO 175
<211> LENGTH: 449
<212> TYPE: PRT
<213> ORGANISM: Homo sapiens

<400> SEQUENCE: 175

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Met Ile Asn Pro Ser Gly Gly Pro Thr Tyr Ala Gln Lys Phe
    50                  55                  60

Gln Gly Arg Val Thr Met Thr Arg Asp Thr Ser Thr Ser Thr Val Tyr
65                  70                  75                  80

Met Asp Leu Ser Ser Leu Arg Ser Glu Asp Thr Ala Val Phe Tyr Cys
                85                  90                  95

Ala Arg Glu Arg Trp Tyr Lys Trp Asn Phe Asp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 176
<211> LENGTH: 122
<212> TYPE: PRT
<213> ORGANISM: Homo sapiens

<400> SEQUENCE: 176

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Met Ile Asn Pro Ser Gly Gly Pro Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Asp Leu Ser Ser Leu Arg Ser Glu Asp Thr Ala Val Phe Tyr Cys
                85                  90                  95

Ala Arg Glu Arg Trp Tyr Lys Trp Asn Phe Asp Ala Phe Asp Ile Trp
            100                 105                 110

Gly Gln Gly Thr Met Val Thr Val Ser Ser
        115                 120

<210> SEQ ID NO 177
<211> LENGTH: 5
<212> TYPE: PRT
<213> ORGANISM: Homo sapiens

<400> SEQUENCE: 177

Ser Tyr Tyr Ile His
1               5

<210> SEQ ID NO 178
<211> LENGTH: 17
<212> TYPE: PRT
<213> ORGANISM: Homo sapiens

<400> SEQUENCE: 178

Met Ile Asn Pro Ser Gly Gly Pro Thr Ser Tyr Ala Gln Lys Phe Gln
1               5                   10                  15

Gly

<210> SEQ ID NO 179
<211> LENGTH: 13
<212> TYPE: PRT
<213> ORGANISM: Homo sapiens

```
<400> SEQUENCE: 179

Glu Arg Trp Tyr Lys Trp Asn Phe Asp Ala Phe Asp Ile
1               5                   10

<210> SEQ ID NO 180
<211> LENGTH: 30
<212> TYPE: PRT
<213> ORGANISM: Homo sapiens

<400> SEQUENCE: 180

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 181
<211> LENGTH: 14
<212> TYPE: PRT
<213> ORGANISM: Homo sapiens

<400> SEQUENCE: 181

Trp Val Arg Gln Ala Pro Gly Gln Gly Leu Glu Trp Met Gly
1               5                   10

<210> SEQ ID NO 182
<211> LENGTH: 32
<212> TYPE: PRT
<213> ORGANISM: Homo sapiens

<400> SEQUENCE: 182

Arg Val Thr Met Thr Arg Asp Thr Ser Thr Ser Thr Val Tyr Met Asp
1               5                   10                  15

Leu Ser Ser Leu Arg Ser Glu Asp Thr Ala Val Phe Tyr Cys Ala Arg
            20                  25                  30

<210> SEQ ID NO 183
<211> LENGTH: 11
<212> TYPE: PRT
<213> ORGANISM: Homo sapiens

<400> SEQUENCE: 183

Trp Gly Gln Gly Thr Met Val Thr Val Ser Ser
1               5                   10

<210> SEQ ID NO 184
<211> LENGTH: 663
<212> TYPE: DNA
<213> ORGANISM: Homo sapiens

<400> SEQUENCE: 184
gacatcgtga tgacccagtc tccagactcc ctggctgtgt ctctgggcga gagggccacc      60
atcaactgca agtccagcca gagtgtttta tacagctcca acaataagaa ctacttagct     120
tggtaccaac agaaaccagg acagcctcct aagctgctca tttactgggc atctacacgg     180
gaatccgggg tccctgaccg attcagtggc agcgggtctg ggacagattt cactctcacc     240
atcagcagcc agcaggctga agatgtggca gtttattact gtcagcaata ttacagtact     300
cctcggacgt tcggccaagg gaccaaggtg gaaatcaaac gaactgtggc tgcaccatct     360
gtcttcatct tcccgccatc tgatgagcag ttgaaatctg gaactgcctc tgttgtgtgc     420
ctgctgaaga acttctatcc cagagaggcc aaagtacagt ggaaggtgga taacgccctc     480
caatcgggta actcccagga gagtgtcaca gagcaggaca gcaaggacag cacctacagc     540
```

```
ctcagcagca cccgacgct gagcaaagca gactacgaga aacacaaagt ctacgcctgc    600
gaagtcaccc atcagggcct gagctcgccc gtcacaaaga gcttcaacag gggagagtgt    660
tag                                                                  663

<210> SEQ ID NO 185
<211> LENGTH: 339
<212> TYPE: DNA
<213> ORGANISM: Homo sapiens

<400> SEQUENCE: 185
gacatcgtga tgacccagtc tccagactcc ctggctgtgt ctctgggcga gagggccacc     60
atcaactgca gtccagcca gagtgtttta tacagctcca acaataagaa ctacttagct    120
tggtaccaac agaaaccagg acagcctcct aagctgctca tttactgggc atctacacgg    180
gaatccgggg tccctgaccg attcagtggc agcgggtctg ggacagattt cactctcacc    240
atcagcagcc agcaggctga gatgtggca gtttattact gtcagcaata ttacagtact    300
cctcggacgt tcggccaagg gaccaaggtg gaaatcaaa                           339

<210> SEQ ID NO 186
<211> LENGTH: 51
<212> TYPE: DNA
<213> ORGANISM: Homo sapiens

<400> SEQUENCE: 186
aagtccagcc agagtgtttt atacagctcc aacaataaga actacttagc t              51

<210> SEQ ID NO 187
<211> LENGTH: 21
<212> TYPE: DNA
<213> ORGANISM: Homo sapiens

<400> SEQUENCE: 187
tgggcatcta cacgggaatc c                                               21

<210> SEQ ID NO 188
<211> LENGTH: 27
<212> TYPE: DNA
<213> ORGANISM: Homo sapiens

<400> SEQUENCE: 188
cagcaatatt acagtactcc tcggacg                                         27

<210> SEQ ID NO 189
<211> LENGTH: 69
<212> TYPE: DNA
<213> ORGANISM: Homo sapiens

<400> SEQUENCE: 189
gacatcgtga tgacccagtc tccagactcc ctggctgtgt ctctgggcga gagggccacc     60
atcaactgc                                                             69

<210> SEQ ID NO 190
<211> LENGTH: 45
<212> TYPE: DNA
<213> ORGANISM: Homo sapiens

<400> SEQUENCE: 190
tggtaccaac agaaaccagg acagcctcct aagctgctca tttac                     45
```

<210> SEQ ID NO 191
<211> LENGTH: 96
<212> TYPE: DNA
<213> ORGANISM: Homo sapiens

<400> SEQUENCE: 191
ggggtccctg accgattcag tggcagcggg tctgggacag atttcactct caccatcagc    60
agccagcagg ctgaagatgt ggcagtttat tactgt                              96

<210> SEQ ID NO 192
<211> LENGTH: 30
<212> TYPE: DNA
<213> ORGANISM: Homo sapiens

<400> SEQUENCE: 192
ttcggccaag ggaccaaggt ggaaatcaaa                                     30

<210> SEQ ID NO 193
<211> LENGTH: 220
<212> TYPE: PRT
<213> ORGANISM: Homo sapiens

<400> SEQUENCE: 193

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Gln Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 194
<211> LENGTH: 113
<212> TYPE: PRT
<213> ORGANISM: Homo sapiens -continued

<400> SEQUENCE: 194

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Gln Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys

<210> SEQ ID NO 195
<211> LENGTH: 17
<212> TYPE: PRT
<213> ORGANISM: Homo sapiens

<400> SEQUENCE: 195

Lys Ser Ser Gln Ser Val Leu Tyr Ser Ser Asn Asn Lys Asn Tyr Leu
1               5                   10                  15

Ala

<210> SEQ ID NO 196
<211> LENGTH: 7
<212> TYPE: PRT
<213> ORGANISM: Homo sapiens

<400> SEQUENCE: 196

Trp Ala Ser Thr Arg Glu Ser
1               5

<210> SEQ ID NO 197
<211> LENGTH: 9
<212> TYPE: PRT
<213> ORGANISM: Homo sapiens

<400> SEQUENCE: 197

Gln Gln Tyr Tyr Ser Thr Pro Arg Thr
1               5

<210> SEQ ID NO 198
<211> LENGTH: 23
<212> TYPE: PRT
<213> ORGANISM: Homo sapiens

<400> SEQUENCE: 198

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 199
<211> LENGTH: 15
<212> TYPE: PRT

```
<400> SEQUENCE: 199

Trp Tyr Gln Gln Lys Pro Gly Gln Pro Pro Lys Leu Leu Ile Tyr
1               5                   10                  15

<210> SEQ ID NO 200
<211> LENGTH: 32
<212> TYPE: PRT
<213> ORGANISM: Homo sapiens

<400> SEQUENCE: 200

Gly Val Pro Asp Arg Phe Ser Gly Ser Gly Ser Gly Thr Asp Phe Thr
1               5                   10                  15

Leu Thr Ile Ser Ser Gln Gln Ala Glu Asp Val Ala Val Tyr Tyr Cys
            20                  25                  30

<210> SEQ ID NO 201
<211> LENGTH: 10
<212> TYPE: PRT
<213> ORGANISM: Homo sapiens

<400> SEQUENCE: 201

Phe Gly Gln Gly Thr Lys Val Glu Ile Lys
1               5                   10

<210> SEQ ID NO 202
<211> LENGTH: 13
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = E or D
<220> FEATURE:
<221> NAME/KEY: MISC_FEATURE
<222> LOCATION: (2)..(2)
<223> OTHER INFORMATION: X = Q, N, R, K or H
<220> FEATURE:
<221> NAME/KEY: MISC_FEATURE
<222> LOCATION: (3)..(3)
<223> OTHER INFORMATION: X = A, G, W or Y
<220> FEATURE:
<221> NAME/KEY: MISC_FEATURE
<222> LOCATION: (5)..(5)
<223> OTHER INFORMATION: X = W, Y, K, R or H
<220> FEATURE:
<221> NAME/KEY: MISC_FEATURE
<222> LOCATION: (6)..(6)
<223> OTHER INFORMATION: X = K, R, H, W, Y, T or S
<220> FEATURE:
<221> NAME/KEY: MISC_FEATURE
<222> LOCATION: (7)..(7)
<223> OTHER INFORMATION: X = Y, W, N or Q
<220> FEATURE:
<221> NAME/KEY: MISC_FEATURE
<222> LOCATION: (10)..(10)
<223> OTHER INFORMATION: X = A, G or V

<400> SEQUENCE: 202

Xaa Xaa Xaa Tyr Xaa Xaa Xaa Phe Asp Xaa Phe Asp Ile
1               5                   10

<210> SEQ ID NO 203
<211> LENGTH: 13
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = D or E
```

-continued

```
<220> FEATURE:
<221> NAME/KEY: MISC_FEATURE
<222> LOCATION: (2)..(2)
<223> OTHER INFORMATION: X = Q or R
<220> FEATURE:
<221> NAME/KEY: MISC_FEATURE
<222> LOCATION: (3)..(3)
<223> OTHER INFORMATION: X = A or W
<220> FEATURE:
<221> NAME/KEY: MISC_FEATURE
<222> LOCATION: (5)..(5)
<223> OTHER INFORMATION: X = W or K
<220> FEATURE:
<221> NAME/KEY: MISC_FEATURE
<222> LOCATION: (6)..(6)
<223> OTHER INFORMATION: X = W or K
<220> FEATURE:
<221> NAME/KEY: MISC_FEATURE
<222> LOCATION: (7)..(7)
<223> OTHER INFORMATION: X = Y or N
<220> FEATURE:
<221> NAME/KEY: MISC_FEATURE
<222> LOCATION: (10)..(10)
<223> OTHER INFORMATION: X = A or V

<400> SEQUENCE: 203

Xaa Xaa Xaa Tyr Xaa Xaa Xaa Phe Asp Xaa Phe Asp Ile
1               5                   10
```